US012195547B2

(12) United States Patent
Lechner et al.

(10) Patent No.: US 12,195,547 B2
(45) Date of Patent: Jan. 14, 2025

(54) DOSING FOR COMBINATION TREATMENT WITH ANTI-CD20/ANTI-CD3 BISPECIFIC ANTIBODY AND ANTI-CD79B ANTIBODY DRUG CONJUGATE

(71) Applicant: Hoffmann-La Roche Inc., Little Falls, NJ (US)

(72) Inventors: Katharina Lechner, Munich (DE); Thomas Francis Moore, Starnberg (DE); Martin Weisser, Penzberg (DE); Natalie Dimier, Welwyn Garden City (GB); David John Carlile, Princes Riborough (GB); Nassim Djebli, Rixheim (FR); Peter Nabil Morcos, Marlboro, NJ (US); Linda Maria Lundberg, Binningen (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 17/733,918

(22) Filed: Apr. 29, 2022

(65) Prior Publication Data
US 2022/0380480 A1 Dec. 1, 2022

Related U.S. Application Data

(60) Provisional application No. 63/182,749, filed on Apr. 30, 2021.

(30) Foreign Application Priority Data

Nov. 2, 2021 (WO) .................. PCT/EP2021/080293

(51) Int. Cl.
| | |
|---|---|
| C07K 16/28 | (2006.01) |
| A61K 47/68 | (2017.01) |
| A61P 35/00 | (2006.01) |
| A61K 39/00 | (2006.01) |

(52) U.S. Cl.
CPC .... *C07K 16/2887* (2013.01); *A61K 47/68031* (2023.08); *A61K 47/6849* (2017.08); *A61P 35/00* (2018.01); *C07K 16/2803* (2013.01); *C07K 16/2809* (2013.01); *A61K 2039/507* (2013.01); *A61K 2039/545* (2013.01); *C07K 2317/24* (2013.01); *C07K 2317/31* (2013.01); *C07K 2317/35* (2013.01); *C07K 2317/55* (2013.01)

(58) Field of Classification Search
CPC ............ C07K 16/2887; C07K 16/2803; C07K 16/2809; C07K 2317/24; C07K 2317/31; C07K 2317/35; C07K 2317/55; A61K 47/6803; A61K 47/6849; A61K 2039/507; A61K 2039/545; A61K 47/6867; A61K 2039/505; A61P 35/00
See application file for complete search history.

(56) References Cited

U.S. PATENT DOCUMENTS

| | | |
|---|---|---|
| 5,571,894 A | 11/1996 | Wels et al. |
| 5,587,458 A | 12/1996 | King et al. |
| 5,591,828 A | 1/1997 | Bosslet et al. |
| 5,731,168 A | 3/1998 | Carter et al. |
| 5,821,337 A | 10/1998 | Carter et al. |
| 5,869,046 A | 2/1999 | Presta et al. |
| 6,248,516 B1 | 6/2001 | Winter et al. |
| 6,737,056 B1 | 5/2004 | Presta |
| 6,809,185 B1 | 10/2004 | Schoonjans et al. |
| 7,332,581 B2 | 2/2008 | Presta |
| 7,695,936 B2 | 4/2010 | Carter et al. |
| 8,227,577 B2 | 7/2012 | Klein et al. |
| 8,236,308 B2 | 8/2012 | Kischel et al. |
| 8,242,247 B2 | 8/2012 | Klein et al. |
| 8,642,742 B2 | 2/2014 | Hofer et al. |
| 8,703,132 B2 | 4/2014 | Imhof-Jung et al. |
| 8,709,421 B2 | 4/2014 | Heiss et al. |
| 8,796,424 B2 | 8/2014 | Croasdale et al. |
| 8,846,042 B2 | 9/2014 | Zhou |
| 8,895,702 B2 | 11/2014 | Williams et al. |
| 8,969,526 B2 | 3/2015 | Baehner et al. |
| 9,068,008 B2 | 6/2015 | Mossner et al. |
| 9,206,260 B2 | 12/2015 | Hofer et al. |
| 9,266,938 B2 | 2/2016 | Ast et al. |
| 9,266,967 B2 | 2/2016 | Klein et al. |
| 9,382,323 B2 | 7/2016 | Brinkmann et al. |

(Continued)

FOREIGN PATENT DOCUMENTS

| | | |
|---|---|---|
| CA | 2853230 A1 | 5/2013 |
| CA | 2884307 A1 | 3/2014 |

(Continued)

OTHER PUBLICATIONS

Hutchings et al. (Blood, 136: 46-48, Nov. 5, 2020).*
Djebli et al. (Blood, 136 (Supplement 1), 2020).*
"Purified Mouse Anti-Human CD3-epsilon Clone SP34," BD Biosciences, <https://www.bdbiosciences.com/us/reagents/research/antibodies-buffers/immunology-reagents/anti-non-human-primate-antibodies/cell-surface-antigens/purified-mouse-anti-human-cd3-sp34/p/556610>, retrieved on Jan. 4, 2021 (4 pages).
Atwell et al., "Stable Heterodimers from Remodeling the Domain Interface of a Homodimer using a Phage Display Library," J Mol Biol. 270(1):26-35 (1997).

(Continued)

*Primary Examiner* — Nelson B Moseley, II
(74) *Attorney, Agent, or Firm* — Clark & Elbing LLP; Karen L. Elbing

(57) ABSTRACT

The present invention relates to the treatment of subjects having CD20-positive cell proliferative disorders (e.g., B cell proliferative disorders, such as non-Hodgkin's lymphomas). More specifically, the invention pertains to the treatment of subjects having a CD20-positive cell proliferative disorder (e.g., B cell proliferative disorder) by administering a combination of an anti-CD20/anti-CD3 bispecific antibody and an anti-CD79b antibody drug conjugate.

28 Claims, 10 Drawing Sheets

Specification includes a Sequence Listing.

(56) References Cited

U.S. PATENT DOCUMENTS

| | | | |
|---|---|---|---|
| 9,447,159 B2 | 9/2016 | Ast et al. |
| 9,526,797 B2 | 12/2016 | Gerdes et al. |
| 9,714,291 B2 | 7/2017 | Niwa et al. |
| 9,914,776 B2 | 3/2018 | Ast et al. |
| 10,357,571 B2 | 7/2019 | Williams et al. |
| 10,611,840 B2 | 4/2020 | Ast et al. |
| 10,611,841 B2 | 4/2020 | Ast et al. |
| 2002/0004587 A1 | 1/2002 | Miller et al. |
| 2007/0071675 A1 | 3/2007 | Wu et al. |
| 2007/0111281 A1 | 5/2007 | Sondermann et al. |
| 2007/0219133 A1 | 9/2007 | Lazar et al. |
| 2008/0241152 A1 | 10/2008 | Alitalo et al. |
| 2009/0252683 A1 | 10/2009 | Kischel et al. |
| 2009/0304719 A1 | 12/2009 | Daugherty et al. |
| 2010/0015133 A1 | 1/2010 | Igawa et al. |
| 2010/0150918 A1 | 6/2010 | Kufer et al. |
| 2010/0316645 A1 | 12/2010 | Imhof-Jung et al. |
| 2011/0178279 A1 | 7/2011 | Williams et al. |
| 2011/0293613 A1 | 12/2011 | Brinkmann et al. |
| 2012/0225071 A1 | 9/2012 | Klein et al. |
| 2012/0276125 A1 | 11/2012 | Ast et al. |
| 2013/0022601 A1 | 1/2013 | Brinkmann et al. |
| 2013/0058936 A1 | 3/2013 | Bruenker et al. |
| 2013/0058937 A1 | 3/2013 | Auer et al. |
| 2013/0060011 A1 | 3/2013 | Bruenker et al. |
| 2013/0078249 A1 | 3/2013 | Ast et al. |
| 2013/0171095 A1 | 7/2013 | Bernett et al. |
| 2013/0266568 A1 | 10/2013 | Brinkmann et al. |
| 2014/0088295 A1 | 3/2014 | Smith et al. |
| 2014/0112914 A1 | 4/2014 | Nezu et al. |
| 2014/0154254 A1 | 6/2014 | Kannan et al. |
| 2014/0242079 A1 | 8/2014 | Bacac et al. |
| 2014/0242080 A1 | 8/2014 | Jaeger et al. |
| 2014/0288275 A1 | 9/2014 | Moore et al. |
| 2014/0294823 A1 | 10/2014 | Moore et al. |
| 2014/0294833 A1 | 10/2014 | Desjarlais et al. |
| 2014/0302064 A1 | 10/2014 | Moore |
| 2014/0322217 A1 | 10/2014 | Moore et al. |
| 2014/0363426 A1 | 12/2014 | Moore et al. |
| 2014/0370013 A1 | 12/2014 | Desjarlais et al. |
| 2014/0377270 A1 | 12/2014 | Moore et al. |
| 2015/0166661 A1 | 6/2015 | Chen et al. |
| 2015/0266966 A1 | 9/2015 | Smith et al. |
| 2015/0274845 A1 | 10/2015 | Bruenker et al. |
| 2015/0315296 A1 | 11/2015 | Schaefer et al. |
| 2015/0368351 A1 | 12/2015 | Vu et al. |
| 2015/0376287 A1 | 12/2015 | Vu et al. |
| 2016/0075785 A1 | 3/2016 | Ast et al. |
| 2016/0130347 A1 | 5/2016 | Bruenker et al. |
| 2016/0145354 A1 | 5/2016 | Bacac et al. |
| 2016/0152711 A1 | 6/2016 | Williams et al. |
| 2016/0159906 A1* | 6/2016 | Sun ................. A61P 37/02 424/139.1 |
| 2016/0175397 A1 | 6/2016 | Umana et al. |
| 2016/0194399 A1 | 7/2016 | Irving et al. |
| 2016/0208017 A1 | 7/2016 | Ast et al. |
| 2016/0208019 A1 | 7/2016 | Bacac et al. |
| 2016/0263240 A1 | 9/2016 | Ast et al. |
| 2016/0297881 A1 | 10/2016 | Vu et al. |
| 2016/0368985 A1 | 12/2016 | Hotzel et al. |
| 2017/0008971 A1 | 1/2017 | Dennis et al. |
| 2017/0096485 A1 | 4/2017 | Bacac et al. |
| 2017/0096495 A1 | 4/2017 | Bacac et al. |
| 2017/0114146 A1 | 4/2017 | Klein et al. |
| 2017/0174786 A1 | 6/2017 | Bacac et al. |
| 2017/0190783 A1 | 7/2017 | Bacac et al. |
| 2017/0209573 A1 | 7/2017 | Bacac et al. |
| 2017/0218074 A1 | 8/2017 | Williams et al. |
| 2017/0253670 A1 | 9/2017 | Klein et al. |
| 2017/0267783 A1 | 9/2017 | Nezu et al. |
| 2017/0306018 A1 | 10/2017 | Vu et al. |
| 2017/0306036 A1 | 10/2017 | Vu et al. |
| 2017/0306044 A1 | 10/2017 | Vu et al. |
| 2017/0327579 A1 | 11/2017 | Vu et al. |
| 2017/0327580 A1 | 11/2017 | Vu et al. |
| 2018/0134798 A1* | 5/2018 | Chu .................. C07K 16/2809 |
| 2018/0148508 A1 | 5/2018 | Wang et al. |
| 2018/0193479 A1 | 7/2018 | Williams et al. |
| 2020/0164077 A1 | 5/2020 | Williams et al. |
| 2020/0172627 A1* | 6/2020 | Bacac ................ C07K 16/2827 |
| 2020/0199578 A1 | 6/2020 | Short et al. |
| 2020/0325238 A1 | 10/2020 | Bacac et al. |
| 2024/0132613 A1 | 4/2024 | Chu et al. |

FOREIGN PATENT DOCUMENTS

| | | |
|---|---|---|
| CN | 102369218 A | 3/2012 |
| CN | 102373214 A | 3/2012 |
| CN | 102892779 A | 1/2013 |
| CN | 103429737 A | 12/2013 |
| CN | 103748114 A | 4/2014 |
| CN | 103764681 A | 4/2014 |
| CN | 103889452 A | 6/2014 |
| CN | 104245738 A | 12/2014 |
| CN | 104640881 A | 5/2015 |
| CN | 105143258 A | 12/2015 |
| CN | 105934253 A | 9/2016 |
| CN | 106029696 A | 10/2016 |
| CN | 106164095 A | 11/2016 |
| EP | 0404097 B1 | 9/1996 |
| EP | 1870459 A1 | 12/2007 |
| EP | 1870459 A4 | 9/2010 |
| EP | 2578230 A1 | 4/2013 |
| EP | 2647707 A1 | 10/2013 |
| EP | 2647707 A4 | 4/2014 |
| EP | 1870459 B1 | 6/2016 |
| EP | 3177643 B1 | 5/2019 |
| JP | 2011-508604 A | 3/2011 |
| JP | 2015-509951 A | 4/2015 |
| JP | 2015-509952 A | 4/2015 |
| JP | 2018-527887 A | 9/2018 |
| RU | 2539112 C2 | 1/2015 |
| SG | 10201803384 T | 6/2018 |
| TW | 201508008 A | 3/2015 |
| WO | WO-91/03493 A1 | 3/1991 |
| WO | WO-93/01161 A1 | 1/1993 |
| WO | WO-93/16185 A2 | 8/1993 |
| WO | WO-96/01126 A1 | 1/1996 |
| WO | WO-96/27011 A1 | 9/1996 |
| WO | WO-96/40210 A1 | 12/1996 |
| WO | WO-98/50431 A2 | 11/1998 |
| WO | WO-98/50431 A3 | 1/1999 |
| WO | WO-02/09573 A2 | 2/2002 |
| WO | WO-03/074679 A2 | 9/2003 |
| WO | WO-2005/044859 A2 | 5/2005 |
| WO | WO-2005/083431 A2 | 9/2005 |
| WO | WO-2006/082515 A2 | 8/2006 |
| WO | WO-2007/005874 A2 | 1/2007 |
| WO | WO-2007/024715 A2 | 3/2007 |
| WO | WO-2007/042261 A1 | 4/2007 |
| WO | WO-2007/075270 A2 | 7/2007 |
| WO | WO-2007/110205 A2 | 10/2007 |
| WO | WO-2007/146968 A2 | 12/2007 |
| WO | WO-2007/147901 A1 | 12/2007 |
| WO | WO-2007/024715 A3 | 10/2008 |
| WO | WO-2008/119566 A2 | 10/2008 |
| WO | WO-2008/119567 A2 | 10/2008 |
| WO | WO-2007/024715 A9 | 4/2009 |
| WO | WO-2009/070642 A1 | 6/2009 |
| WO | WO-2009/080251 A1 | 7/2009 |
| WO | WO-2009/080252 A1 | 7/2009 |
| WO | WO-2009/080253 A1 | 7/2009 |
| WO | WO-2009/080254 A1 | 7/2009 |
| WO | WO-2009/089004 A1 | 7/2009 |
| WO | WO-2009/106321 A1 | 9/2009 |
| WO | WO-2010/115589 A1 | 10/2010 |
| WO | WO-2010/129304 A2 | 11/2010 |
| WO | WO-2010/136172 A1 | 12/2010 |
| WO | WO-2010/145792 A1 | 12/2010 |
| WO | WO-2010/145793 A1 | 12/2010 |
| WO | WO-2010/129304 A3 | 2/2011 |
| WO | WO-2011/028945 A1 | 3/2011 |
| WO | WO-2011/028952 A1 | 3/2011 |
| WO | WO-2011/090754 A1 | 7/2011 |

(56) References Cited

FOREIGN PATENT DOCUMENTS

| | | |
|---|---|---|
| WO | WO-2011/090762 A1 | 7/2011 |
| WO | WO-2011/103242 A1 | 8/2011 |
| WO | WO-2011/121110 A1 | 10/2011 |
| WO | WO-2011/143545 A1 | 11/2011 |
| WO | WO-2012/025525 A1 | 3/2012 |
| WO | WO-2012/058768 A1 | 5/2012 |
| WO | WO-2012/058768 A8 | 6/2012 |
| WO | WO-2012/073985 A1 | 6/2012 |
| WO | WO-2012/117002 A1 | 9/2012 |
| WO | WO-2012/130831 A1 | 10/2012 |
| WO | WO-2012/143524 A2 | 10/2012 |
| WO | WO-2012/158818 A2 | 11/2012 |
| WO | WO-2012/162067 A2 | 11/2012 |
| WO | WO-2013/012414 A1 | 1/2013 |
| WO | WO-2013/026831 A1 | 2/2013 |
| WO | WO-2013/026832 A1 | 2/2013 |
| WO | WO-2013/026833 A1 | 2/2013 |
| WO | WO-2013/026837 A1 | 2/2013 |
| WO | WO-2013/026839 A1 | 2/2013 |
| WO | WO-2013/096291 A2 | 6/2013 |
| WO | WO-2013/128027 A1 | 9/2013 |
| WO | WO-2013/128194 A1 | 9/2013 |
| WO | WO-2013/150043 A1 | 10/2013 |
| WO | WO-2013/157953 A1 | 10/2013 |
| WO | WO-2013/157954 A1 | 10/2013 |
| WO | WO-2014/022540 A1 | 2/2014 |
| WO | WO-2014/028560 A2 | 2/2014 |
| WO | WO-2014/039855 A1 | 3/2014 |
| WO | WO-2014/047231 A1 | 3/2014 |
| WO | WO-2014/054804 A1 | 4/2014 |
| WO | WO-2014/056783 A1 | 4/2014 |
| WO | WO-2014/028560 A3 | 5/2014 |
| WO | WO-2014/081955 A1 | 5/2014 |
| WO | WO-2014/122143 A1 | 8/2014 |
| WO | WO-2014/122144 A1 | 8/2014 |
| WO | WO-2014/122251 A2 | 8/2014 |
| WO | WO-2014/141152 A2 | 9/2014 |
| WO | WO-2014/144722 A2 | 9/2014 |
| WO | WO-2014/150877 A1 | 9/2014 |
| WO | WO-2014/153002 A1 | 9/2014 |
| WO | WO-2014/122251 A3 | 10/2014 |
| WO | WO-2014/167022 A1 | 10/2014 |
| WO | WO-2014/141152 A3 | 12/2014 |
| WO | WO-2014/191113 A1 | 12/2014 |
| WO | WO-2014/210064 A1 | 12/2014 |
| WO | WO-2014/191113 A8 | 2/2015 |
| WO | WO-2015/095392 A1 | 6/2015 |
| WO | WO-2015/095418 A1 | 6/2015 |
| WO | WO-2015/150447 A1 | 10/2015 |
| WO | WO-2016/019969 A1 | 2/2016 |
| WO | WO-2016/020065 A1 | 2/2016 |
| WO | WO-2016/020309 A1 | 2/2016 |
| WO | WO-2016/020332 A1 | 2/2016 |
| WO | WO-2016/036678 A1 | 3/2016 |
| WO | WO-2016/055592 A1 | 4/2016 |
| WO | WO-2016/055593 A1 | 4/2016 |
| WO | WO-2016/079081 A1 | 5/2016 |
| WO | WO-2016/079177 A1 | 5/2016 |
| WO | WO-2016/081490 A1 | 5/2016 |
| WO | WO-2016/087531 A1 | 6/2016 |
| WO | WO-2016/090210 A1 | 6/2016 |
| WO | WO-2016/110576 A1 | 7/2016 |
| WO | WO-2016/179003 A1 | 11/2016 |
| WO | WO-2016/205520 A1 | 12/2016 |
| WO | WO-2017/021450 A1 | 2/2017 |
| WO | WO-2018/093821 A1 | 5/2018 |
| WO | WO-2019/095641 A1 | 5/2019 |
| WO | WO-2022/098648 A2 | 5/2022 |

OTHER PUBLICATIONS

BBE23702, GenomeQuest Keyword Search Report, dated May 1, 2017 (2 pages).

BBE23705, GenomeQuest Keyword Search Report, dated May 1, 2017 (2 pages).

BBF28771, GenomeQuest Keyword Search Report, dated May 1, 2017 (2 pages).

BBF28775, GenomeQuest Keyword Search Report, dated May 1, 2017 (2 pages).

Beckman et al., "Antibody constructs in cancer therapy: protein engineering strategies to improve exposure in solid tumors," Cancer. 109(2):170-9 (2007).

Booy et al., "Monoclonal and bispecific antibodies as novel therapeutics," Arch Immunol Ther Exp (Warsz). 54(2):85-101 (2006).

Bosch et al., "MCSP/CD3-bispecific single-chain antibody construct engages CD4+ and CD8+ T cells for lysis of MCSP-expressing human uveal melanoma cells," AACR 101st Annual Meeting. Apr. 17-21, Washington, DC. 70(8 Suppl) Abstract 5621 (2010) (1 page).

Budde et al., "Mosunetuzumab, a Full-Length Bispecific CD20/CD3 Antibody, Displays Clinical Activity in Relapsed/Refractory B-Cell Non-Hodgkin Lymphoma (NHL): Interim Safety and Efficacy Results from a Phase 1 Study," Blood. 132(Supplement 1):399 (2018) (6 pages).

Budde et al., "Ongoing Phase 1B/2 Trials of Mosunetuzumab Investigating Novel Treatment Regimens for Patients with B-Call Non-Hodgkin Lymphoma (NHL)," Hematol Oncol. 37(52):564-566 (2019) (4 pages).

Buhmann et al., "Immunotherapy of recurrent B-cell malignancies after allo-SCT with Bi20 (FBTA05), a trifunctional anti-CD3 x anti-CD20 antibody and donor lymphocyte infusion," Bone Marrow Transplant. 43(5):383-97 (2009).

Buhmann et al., "Immunotherapy with FBTA05 (Bi20), a trifunctional bispecific anti-CD3 x anti-CD20 antibody and donor lymphocyte infusion (DLI) in relapsed or refractory B-cell lymphoma after allogeneic stem cell transplantation: study protocol of an investigator-driven, open-label, non-randomized, uncontrolled, dose-escalating Phase I/II-trial," J Transl Med. 11:160 (2013) (9 pages).

Carter, "Bispecific human IgG by design," J Immunol Methods. 248(1-2):7-15 (2001).

Chan et al., "Variable region domain exchange in human IgGs promotes antibody complex formation with accompanying structural changes and altered effector functions," Mol Immunol. 41(5):527-38 (2004).

Conaghan et al., "Targeted killing of colorectal cancer cell lines by a humanised IgG1 monoclonal antibody that binds to membrane-bound carcinoembryonic antigen," Br J Cancer. 98(7):1217-25 (2008).

Desnoyers et al., "Tumor-specific activation of an EGFR-targeting probody enhances therapeutic index," Sci Transl Med. 5(207):207ra144 (2013) (2 pages) (Abstract only).

Diefenbach et al., "An individualized risk mitigation approach for safety: experience from the mosunetuzumab (CD20/CD3 bispecific antibody) development program in relation to neurotoxicity risk," 61st Ash Annual Meeting & Exposition 10 (2019) (1 page).

Donaldson et al., "Design and development of masked therapeutic antibodies to limit off-target effects: application to anti-EGFR antibodies," available in PMC Jan. 16, 2013, published in final edited form as: Cancer Biol Ther. 8(22): 2147-52 (2009) (12 pages).

Edelman et al., "The covalent structure of an entire gammaG immunoglobulin molecule," Proc Natl Acad Sci U S A. 63(1):78-85 (1969).

Edwards et al., "The remarkable flexibility of the human antibody repertoire; isolation of over one thousand different antibodies to a single protein, BLyS," J Mol Biol. 334(1):103-18 (2003).

Erster et al., "Site-specific targeting of antibody activity in vivo mediated by disease-associated proteases," J Control Release. 161(3): 804-12 (2012) (2 pages) (Abstract only).

Gaston et al., "Intracellular delivery of therapeutic antibodies into specific cells using antibody-peptide fusions," Sci Rep. 9(1):18688 (2019) (12 pages).

Ghosh et al., "Glofitamab Plus R-CHOP Induces High Response Rates with Minimal Cytokine Release Syndrome (CRS) in Patients (pts) with Relapsed/Refractory (R/R) Non-Hodgkin Lymphoma (NHL) and Previously Untreated (1L) Diffuse Large B-Cell Lymphoma (DLBCL): Preliminary Results from a Dose-Escalation and

(56) References Cited

OTHER PUBLICATIONS

Safety Run-in Phase Ib Study," Blood. 138(Supplement 1):2479 (Nov. 23, 2021) (Abstract only) (5 pages).
Gonzales et al., "Minimizing the Immunogenicity of Antibodies for Clinical Application," Tumor Biol. 26(1):31-43 (2005) (Abstract only) (1 page).
Haile et al., "Soluble CD80 Restores T Cell Activation and Overcomes Tumor Cell Programmed Death Ligand 1-Mediated Immune Suppression," J Immunol. 191(5):2829-36 (2013) (9 pages).
Han et al., "Masked Chimeric Antigen Receptor for Tumor-Specific Activation," Mol Ther. 25(1):274-84 (2017).
Hernandez et al., "Pharmacodynamic Effects and Immune Correlates of Response to the CD20/CD3 Bispecific Antibody Mosunetuzumab in Relapsed or Refractory Non-Hodgkin Lymphoma," Blood. 134(Supplement 1):1585 (2019) (4 pages).
Holliger et al., "Diabodies': small bivalent and bispecific antibody fragments," Proc Natl Acad Sci U S A. 90(14):6444-8 (1993).
Holliger et al., "Specific killing of lymphoma cells by cytotoxic T-cells mediated by a bispecific diabody," Protein Eng. 9(3):299-305 (1996).
Honeychurch et al., "Bispecific Ab therapy of B-cell lymphoma: target cell specificity of antibody derivatives appears critical in determining therapeutic outcome," Cancer Immunol Immunother. 45(3-4):171-3 (1997).
Hosseini et al., "Abstract B043: Systems pharmacology modeling of anti-CD20/CD3 T-cell dependent bispecific antibody and its application to clinical trial design," Proceedings of the Second CRI-CIMT-EATI-AACR International Cancer Immunotherapy Conference: Translating Science into Survival, New York USA (2016) (4 pages).
Hosseini et al., "Mitigating The Risk Of Cytokine Release Syndrome In A Phase I Trial Of CD20/CD3 Bispecific Antibody Mosunetuzumab In NHL: Impact Of Translational System Modeling," NPJ Syst Biol Appl. 6(1):28 (2020) (11 pages).
Huang, "Structural chemistry and therapeutic intervention of protein-protein interactions in immune response, human immunodeficiency virus entry, and apoptosis," Pharmacol Ther. 86(3):201-215 (2000).
Hudson et al., "Engineered antibodies," Nat Med. 9(1):129-34 (2003).
Hutchings et al., "Glofitamab (Glofit) in Combination with Polatuzumab Vedotin (Pola): Phase Ib/II Preliminary Data Support Manageable Safety and Encouraging Efficacy in Relapsed/Refractory (R/R) Diffuse Large B-Cell Lymphoma (DLBCL)" Blood. 138(Supplement 1):525 (Nov. 5, 2021) (Abstract only) (4 pages).
Hutchings et al., "Glofitamab, a Novel, Bivalent CD20-Targeting T-Cell-Engaging Bispecific Antibody, Induces Durable Complete Remissions in Relapsed or Refractory B-Cell Lymphoma: A Phase I Trial," J Clin Oncol. 39(18):1959-70 (Mar. 19, 2021) (13 pages).
Jaksic et al., "High Dose Chlorambucil versus Binet's Modified Cyclophosphamide Doxorubicin, Vincristine, and Prednisone Regimen in the Treatment of Patients with Advanced B-Cell Chronic Lymphocytic Leukemia. Results of an International Multicenter Randomized Trial," Cancer. 79(11):2107-14 (1997).
Kipriyanov et al., "Bispecific Tandem Diabody for Tumor Therapy with Improved Antigen Binding and Pharmacokinetics," J Mol Biol. 293(1):41-56 (1999).
Klein et al., "Progress in overcoming the chain association issue in bispecific heterodimeric IgG antibodies," MAbs. 4(6):653-63 (2012).
Kontermann, "Dual targeting strategies with bispecific antibodies," MAbs. 4(2):182-97 (2012).
Leabman et al., "Effects of altered FcgammaR binding on antibody pharmacokinetics in cynomolgus monkeys," MAbs. 5(6):896-903 (2013).
Lee et al., "Current concepts in the diagnosis and management of cytokine release syndrome," Blood. 124(2):188-95 (2014) (18 pages).
Li et al., "Exposure-response analyses indicate a promising benefit/risk profile of mosunetuzumab in relapsed and refractory non-Hodgkin lymphoma," 61st Ash Annual Meeting & Exposition (2019) (1 page).
Lloyd et al., "Modelling the human immune response: performance of a 1011 human antibody repertoire against a broad panel of therapeutically relevant antigens". Protein Eng Des Sel. 22(3):159-68 (2009).
Lord et al., "Structure-based engineering to restore high affinity binding of an isoform-selective anti-TGFß1 antibody," MAbs. 10(3):444-452 (2018) (10 pages).
Lu et al., "Tetravalent anti-CD20/CD3 bispecific antibody for the treatment of B cell lymphoma," Biochem Biophys Res Commun. 473(4):808-813 (2016) (Abstract only) (3 pages).
Lund et al., "Multiple interactions of IgG with its core oligosaccharide can modulate recognition by complement and human Fc gamma receptor I and influence the synthesis of its oligosaccharide chains," J Immunol. 157(11):4963-9 (1996) (8 pages).
MacLean et al., "Anti-CD3:anti-IL-2 receptor-bispecific mAb-mediated immunomodulation. Low systemic toxicity, differential effect on lymphoid tissue, and inhibition of cell-mediated hypersensitivity," J Immunol. 155(7):3674-82 (1995).
Mariuzza et al., "The structural basis of antigen-antibody recognition," Annu Rev Biophys Biophys Chem. 16:139-159 (1987) (2 pages) (Abstract only).
Merchant et al., "An efficient route to human bispecific IgG," Nat Biotechnol. 16(7):677-81 (1998).
Miller et al., "Design, construction, and in vitro analyses of multivalent antibodies," J Immunol. 170(9):4854-61 (2003).
Milne et al., "Systematic Analysis of Immune Infiltrates in High-Grade Serous Ovarian Cancer Reveals CD20, FoxP3 and TIA-1 as Positive Prognostic Factors," PLoS One. 4(7):e6412 (2009) (14 pages).
Minson et al., "Trial in Progress: A Multicentre, Parallel Arm, Open-Label Trial of Frontline R-CHOP/Polatuzumab Vedotin-RCHP and Glofitamab in Younger Patients with Higher Risk Diffuse Large B Cell Lymphoma (Coalition)," Blood. 138(Supplement 1):3571 (Nov. 5, 2021) (3 pages).
Montoto et al., "Risk and Clinical Implications of Transformation of Follicular Lymphoma to Diffuse Large B-Cell Lymphoma," J Clin Oncol. 25(17):2426-33 (2007) (9 pages).
Moore et al., "A novel bispecific antibody format enables simultaneous bivalent and monovalent co-engagement of distinct target antigens," MAbs. 3(6):546-57 (2011).
Moore et al., "Application of dual affinity retargeting molecules to achieve optimal redirected T-cell killing of B-cell lymphoma," Blood. 117(17):4542-51 (2011) (11 pages).
Nagorsen et al., "Immunomodulatory therapy of cancer with T cell-engaging BiTE antibody blinatumomab," Exp Cell Res. 317(9):1255-60 (2011).
NIH/NCI, "anti-PD-1 fusion protein AMP-224," dated Jul. 10, 2015, accessed Jul. 31, 2019 (1 page).
Nishimoto et al., "Toxicity, pharmacokinetics, and dose-finding study of repetitive treatment with the humanized anti-interleukin 6 receptor antibody MRA in rheumatoid arthritis. Phase I/II clinical study," J Rheumatol. 30(7):1426-35 (2003).
Oshimi et al., "Increased lysis of patient CD10-positive leukemic cells by T cells coated with anti-CD3 Fab' antibody cross-linked to anti-CD10 Fab' antibody," Blood. 77(5):1044-9 (1991) (7 pages).
Paino et al., "Reply to 'Response to 'CD20 Positive Cells Are Undetectable in the Majority of Multiple Myeloma Cell Lines and Are Not Associated With a Cancer Stem Cell Phenotype," Haematologica. 97(7):1110-1114 (2012) (1 page).
Peng et al., "The CEA/CD3-bispecific antibody MEDI-565 (MT111) binds a nonlinear epitope in the full-length but not a short splice variant of CEA," PLoS One. 7(5):e36412 (2012) (14 pages).
Pessano et al., "The T3/T cell receptor complex: antigenic distinction between the two 20-kd T3 (T3-delta and T3-epsilon) subunits," EMBO J. 4(2):337-44 (1985).
Plückthun, Chapter 11: Antibodies from *Escherichia coli. The Pharmacology of Monoclonal Antibodies*. Martin Rosenberg & Gordon P. Moore (eds.), 269-315 (1994) (26 pages).
Polu et al., "Probody therapeutics for targeting antibodies to diseased tissue," Expert Opin Biol Ther. 14(8):1049-53 (2014).
Reusch et al., "Anti-CD3 x anti-epidermal growth factor receptor (EGFR) bispecific antibody redirects T-cell cytolytic activity to

(56) References Cited

OTHER PUBLICATIONS

EGFR-positive cancers in vitro and in an animal model," Clin Cancer Res. 12(1):183-90 (2006) (9 pages).
Ridgway et al., "'Knobs-into-holes' engineering of antibody CH3 domains for heavy chain heterodimerization," Protein Eng. 9(7):617-21 (1996).
Riedle et al., "In vivo activation and expansion of T cells by a bi-specific antibody abolishes metastasis formation of human melanoma cells in SCID mice," Int J Cancer. 75(6):908-18 (1998).
Rudnick et al., "Affinity and avidity in antibody-based tumor targeting," Cancer Biother Radiopharm. 24(2):155-61 (2009).
Salmerón et al., "A conformational epitope expressed upon association of CD3-epsilon with either CD3-delta or CD3-gamma is the main target for recognition by anti-CD3 monoclonal antibodies," J Immunol. 147(9): 3047-52 (1991) (2 pages) (Abstract only).
Schaefer et al., "Immunoglobulin domain crossover as a generic approach for the production of bispecific IgG antibodies," Proc Natl Acad Sci U S A. 108(27):11187-92 (2011).
Schuster et al., "Immunotherapy with the trifunctional anti-CD20 x anti-CD3 antibody FBTA05 (Lymphomun) in paediatric high-risk patients with recurrent CD20-positive B cell malignancies," Br J Haematol. 169:90-102 (2015) (13 pages).
Seimetz et al., "Development and approval of the trifunctional antibody catumaxomab (anti-EpCAM x anti-CD3) as a targeted cancer immunotherapy," Cancer Treat Rev. 36(6):458-67 (2010).
Sen et al., "Use of Anti-CD3 x Anti-HER2/neu Bispecific Antibody for Redirecting Cytotoxicity of Activated T Cells Toward HER2/neu$^+$ Tumors," J Hematother Stem Cell Res. 10(2):247-60 (2001).
Seung et al., "Immunotherapy with long-lived anti-CD20 x anti-CD3 bispecific antibodies stimulates potent t cell-mediated killing of human b cell lines and of circulating and lymphoid b cells in monkeys: a potential therapy for b cell lymphomas and leukemias," 56th ASH Annual Meeting and Exposition, Dec. 6-9, San Francisco, CA. 124(21):3111 (2014) (1 page).
Shi et al., "Margin-Infiltrating CD20$^+$ B Cells Display an Atypical Memory Phenotype and Correlate with Favorable Prognosis in Hepatocellular Carcinoma," Clin Cancer Res. 19(21):5994-6005 (2013) (13 pages).
Somasundaram et al., "Will Engineered T Cells Expressing CD20 scFv Eradicate Melanoma?" Mol Ther. 19(4):638-40 (2011).
Stein et al., "Novel and Emerging Drugs for Acute Myeloid Leukemia," available in PMC May 22, 2014, published in final edited form as: Curr Cancer Drug Targets. 12(5):522-530 (2012) (19 pages).
Stewart et al., "Humanisation and characterisation of PR1A3, a monoclonal antibody specific for cell-bound carcinoembryonic antigen," Cancer Immunol Immunother. 47(6):299-306 (1999).
Stieglmaier et al., "Utilizing the BiTE (bispecific T-cell engager) platform for immunotherapy of cancer," Expert Opin Biol Ther. 15(8):1093-1099 (2015) (8 pages).
Stubenrauch et al., "Impact of molecular processing in the hinge region of therapeutic IgG4 antibodies on disposition profiles in cynomolgus monkeys," Drug Metab Dispos. 38(1):84-91 (2010).
Sun et al., "Anti-CD20/CD3 T cell-dependent bispecific antibody for the treatment of B cell malignancies," Sci Transl Med. 7(287):287ra70 (2015) (11 pages).
Torisu-Itakura et al., "Redirected lysis of human melanoma cells by a MCSP/CD3-bispecific BiTE antibody that engages patient-derived T cells," J Immunother. 34(8):597-605 (2011).
Trabolsi et al., "T Cell-Activating Bispecific Antibodies in Cancer Therapy," J Immunol. 203(3):585-592 (2019) (9 pages).

Tutt et al., "Trispecific F(ab')$_3$ derivatives that use cooperative signaling via the TCR/CD3 complex and CD2 to activate and redirect resting cytotoxic T cells," J Immunol. 147(1):60-9 (1991).
Wakefield et al., "Addition of a C-terminal extension sequence to transforming growth factor-beta 1 interferes with biosynthetic processing and abolishes biological activity," Growth Factors. 5(3):243-53 (1991) (2 pages) (Abstract only).
Wells et al., "Reaching for high-hanging fruit in drug discovery at protein-protein interfaces," Nature. 450(7172):1001-9 (2007).
Wolf et al., "BiTEs: bispecific antibody constructs with unique anti-tumor activity," Drug Discov Today. 10(18):1237-44 (2005).
Wu et al., "Humanization of a Murine Monoclonal Antibody by Simultaneous Optimization of Framework and CDR Residues," J Mol Biol. 294(1):151-162 (1999).
Yang et al., "Generation and characterization of a target-selectively activated antibody against epidermal growth factor receptor with enhanced anti-tumor potency," MAbs. 7(2):440-50 (2015).
Yu et al., "Interaction between bevacizumab and murine VEGF-A: a reassessment," Invest Ophthalmol Vis Sci. 49(2):522-7 (2008).
Zhu et al., "Identification of heavy chain residues in a humanized anti-CD3 antibody important for efficient antigen binding and T cell activation," J Immunol. 155(4):1903-10 (1995).
Communication Pursuant to Article 94(3) EPC for European Patent Application No. 17808689.8, dated Apr. 30, 2020 (8 pages).
International Search Report and Written Opinion for International Patent Application No. PCT/EP2021/080293, dated Feb. 10, 2022 (65 pages).
"History of Changes for Study: NCT02500407: A Safety, Efficacy and Pharmacokinetic Study of BTCT4465A (Mosunetuzumab) as a Single Agent and Combined With Atezolizumab in Non-Hodgkin's Lymphoma (NHL) and Chronic Lymphocytic Leukemia (CLL) ," ClinicalTrials.gov, last updated Mar. 17, 2022, retrieved Jul. 17, 2023, from <https://classic.clinicaltrials.gov/ct2/history/NCT02500407?V_74=View#StudyPageTop> (10 pages).
Chu et al., "Immunotherapy with long-lived anti-CD20 x anti-CD3 bispecific antibodies stimulates potent T cell-mediated killing of Human B cell lines and of circulating and lymphoid B cells in monkeys: a potential therapy for B cell lymphomas and leukemias," Xencor poster (2014) (1 page).
Heini et al., "Experiences with Glofitamab Administration following CAR T Therapy in Patients with Relapsed Mantle Cell Lymphoma," Cells 11(17):2747 (Sep. 2022) (12 pages).
Hutchings et al., "Glofitamab Plus Polatuzumab Vedotin Continues to Demonstrate Frequent and Durable Responses and Has a Manageable Safety Profile in Patients with ≥2L Relapsed/Refractory DLBCL, Including HGBCL, and in Patients with Prior CAR T-Cell Therapy: Updated Results from a Phase Ib/II Study," Blood. 142(Supplement 1): 4460, Nov. 2, 2023, (6 pages).
Hutchings et al., "Glofitamab Step-up Dosing Induces High Response Rates in Patients with Hard-to-Treat Refractory or Relapsed Non-Hodgkin Lymphoma" Blood. 136(Supplement 1):46, Nov. 5, 2020, (6 pages).
Xiong et al., "Study of specific targeting cytotoxicity mediated by anti-CD3/anti-CD$_{20}$ Diabody," Chin J Hematol. 22(7):359-362 (2001) (8 pages).
Xu et al., "Production of bispecific antibodies in 'knobs-into-holes' using a cell-free expression system," *MAbs*. 7(1):231-42 (Nov. 26, 2014) (13 pages).
Yuraszeck et al., "A quantitative systems pharmacology (QSP) model to assess the action of blinatumomab in NHL patients (pts)," Journal of Clinical Oncology 34(15_suppl) Abstract e14511 (May 20, 2016) (3 pages).

* cited by examiner

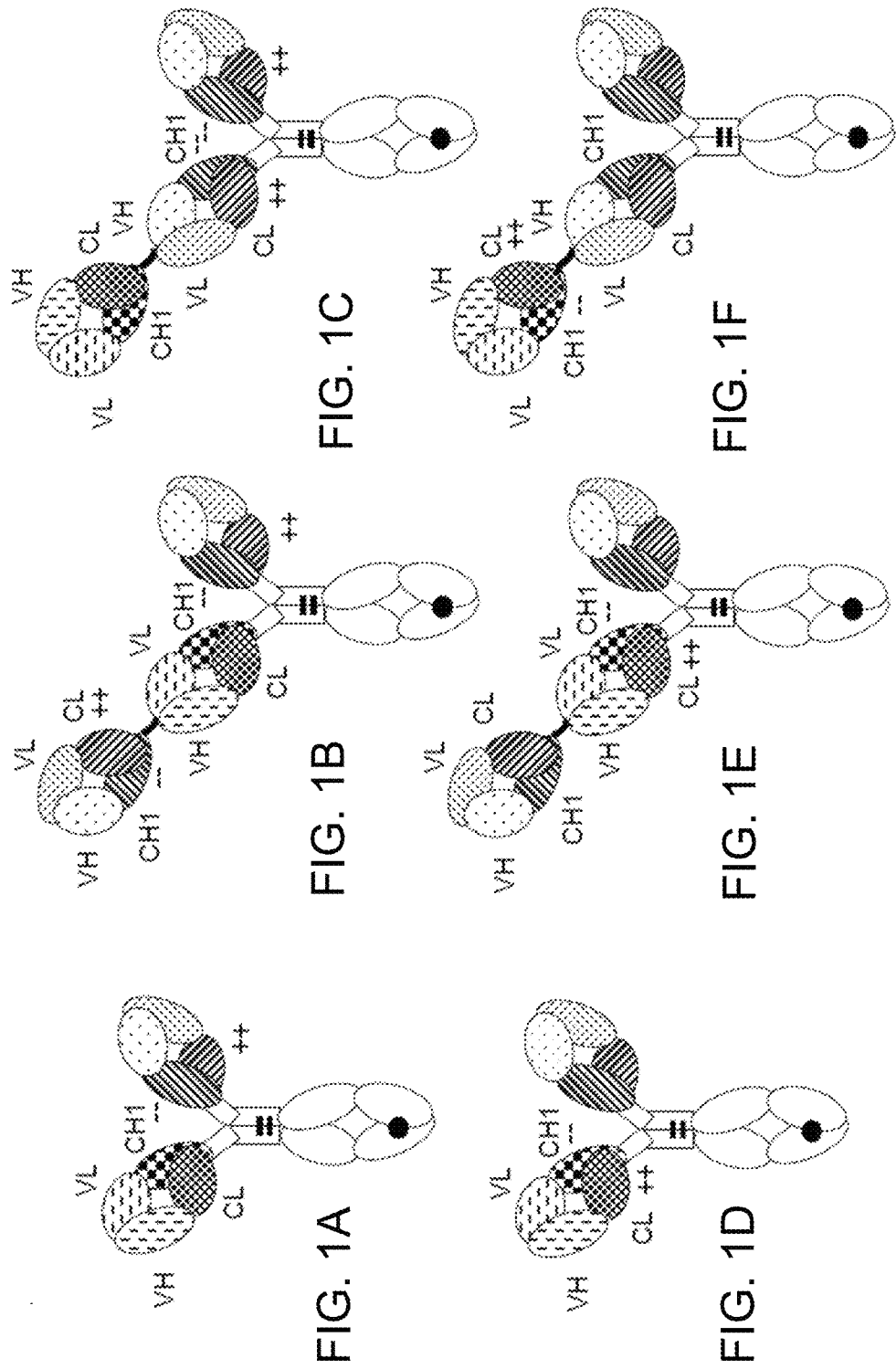

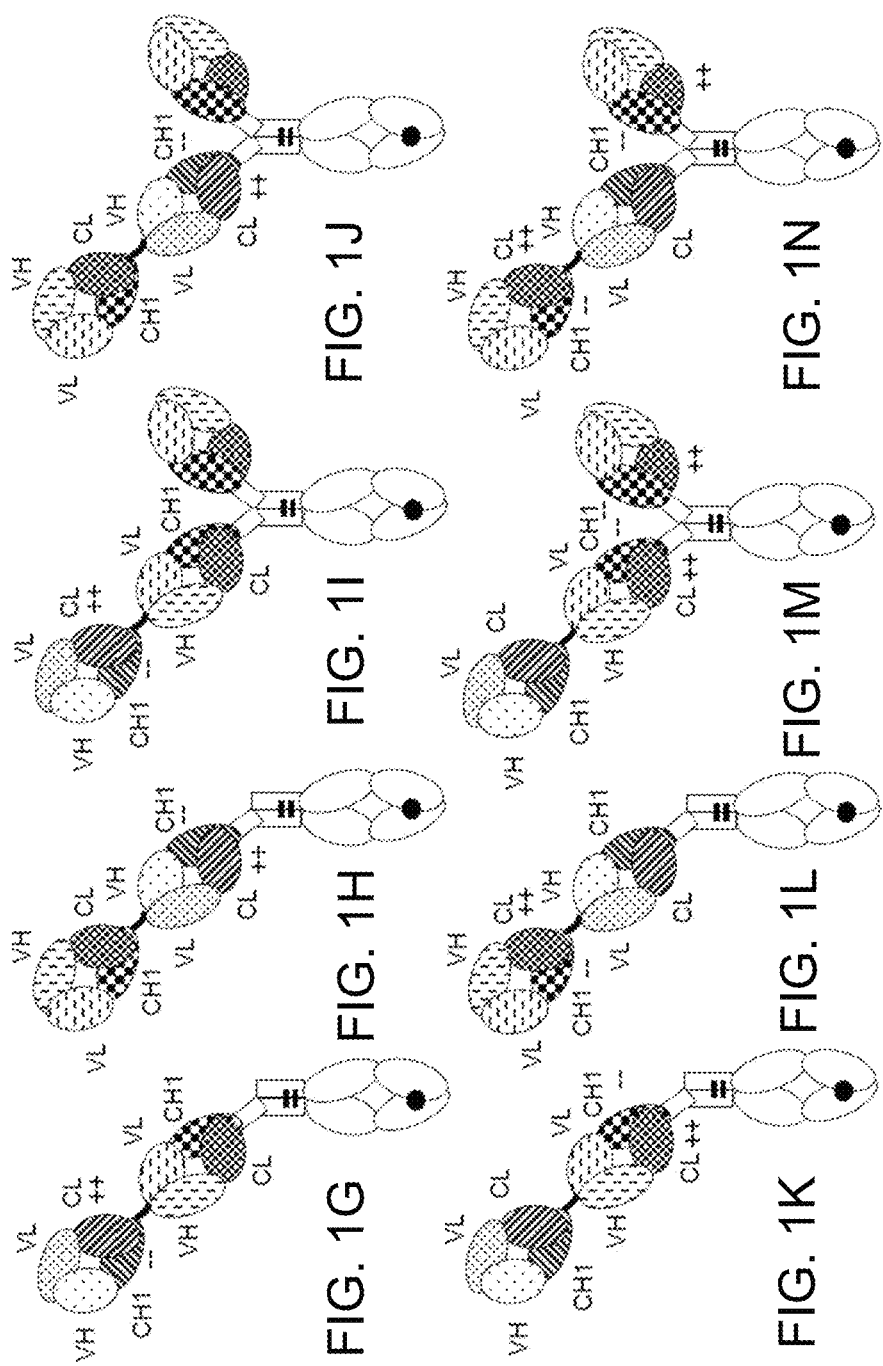

Part I: Dose-escalation until MTD and/or RP2D in NHL patients
Part II: Expansion with RP2D in about 40 pts with r/r FL and 40 pts with r/r DLBCL

Current Study Design (pts enrolled in DE cohorts)
Part I: Dose-escalation with at least 2 pre-defined dose-groups in r/r NHL patients

Study Design-Expansion
Part II: Expansion with RP2D in Approx. 40 pts with r/r DLBCL

[# DOSING FOR COMBINATION TREATMENT WITH ANTI-CD20/ANTI-CD3 BISPECIFIC ANTIBODY AND ANTI-CD79B ANTIBODY DRUG CONJUGATE

CROSS-REFERENCE TO RELATED APPLICATIONS

This application claims benefit of priority to U.S. Provisional Application No. 63/182,749, filed on Apr. 30, 2021, and PCT Application No. PCT/EP2021/080293, filed on Nov. 2, 2021, the contents of which are hereby incorporated by reference in their entirety.

SEQUENCE LISTING

The instant application contains a Sequence Listing which has been submitted electronically in ASCII format and is hereby incorporated by reference in its entirety. Said ASCII copy, created on Apr. 25, 2022, is named 51177-033003_Sequence_Listing_4_25_22_ST25 and is 43,014 bytes in size.

FIELD OF THE INVENTION

The present invention relates to methods of treating a disease, particularly a B-cell proliferative disorder, by administering an anti-CD20/anti-CD3 bispecific antibody and an anti-CD79b antibody drug conjugate, and methods for reduction of adverse effects in response to the administration of the anti-CD20/anti-CD3 bispecific antibody and the anti-CD79b antibody drug conjugate.

BACKGROUND OF THE INVENTION

B-cell proliferative disorders describe a heterogeneous group of malignancies that include both leukemias and lymphomas. Lymphomas develop from lymphatic cells and include two main categories: Hodgkin lymphomas (HL) and the non-Hodgkin lymphomas (NHL). In the United States, lymphomas of B cell origin constitute approximately 80-85% of all non-Hodgkin lymphoma cases, and there is considerable heterogeneity within the B-cell subset, based upon genotypic and phenotypic expression patterns in the B-cell of origin. For example, B cell lymphoma subsets include the slow-growing indolent and incurable diseases, such as Follicular lymphoma (FL) or chronic lymphocytic leukemia (CLL), as well as the more aggressive subtypes, mantle cell lymphoma (MCL) and diffuse large B cell lymphoma (DLBCL). Diffuse large B-cell lymphoma (DLBCL) is the most common type of NHL accounting for approximately 30%-40% of all NHL diagnosis, followed by follicular lymphoma (FL; 20%-25% of all NHL diagnosis) and mantle cell lymphoma (MCL; 6%-10% of all NHL diagnosis). B-cell chronic lymphocytic leukemia (CLL) is the most common leukemia in adults, with approximately 15,000 new cases per year in the United States (American Cancer Society 2015).

Bispecific antibodies are capable of simultaneously binding cell surface antigens on cytotoxic cells (e.g., T cells, via binding to cluster of differentiation 3 (CD3)) and cancer cells (e.g., B cells, via binding to CD20), with the intent that the bound cytotoxic cell will destroy the bound cancer cell. Glofitamab is a T-cell-engaging bispecific (TCB) antibody targeting CD20 expressed on B cells and CD3 epsilon chain (CD3ε) present on T cells.

However, immunotherapies with anti-CD20/anti-CD3 bispecific antibodies like glofitamab can be limited by unwanted effects, including cytokine driven toxicities (e.g., cytokine release syndrome (CRS)), infusion-related reactions (IRRs), severe tumor lysis syndrome (TLS), and central nervous system (CNS) toxicities.

Thus, there is an unmet need in the field for the development of efficacious methods of dosing of an anti-CD20/anti-CD3 bispecific antibody (e.g., glofitamab) for the treatment of CD20-positive B cell proliferative disorders (e.g., non-Hodgkin's lymphoma, NHL) that achieve a more favorable benefit-risk profile.

SUMMARY OF THE INVENTION

In one aspect, the invention features a method of treating a subject having a CD20-positive cell proliferative disorder comprising administering to the subject an anti-CD79b antibody drug conjugate and an anti-CD20/anti-CD3 bispecific antibody in a dosing regimen comprising at least a first dosing cycle and a second dosing cycle, wherein: (a) the first dosing cycle comprises a first dose (C1D1) of the anti-CD20/anti-CD3 bispecific antibody and a second dose (C1D2) of the anti-CD20/anti-CD3 bispecific antibody, wherein the C1D1 of the anti-CD20/anti-CD3 bispecific antibody is about 2.5 mg, and the C1D2 of the anti-CD20/anti-CD3 bispecific antibody is about 10 mg; and (b) the second dosing cycle comprises a single dose (C2D1) of the anti-CD20/anti-CD3 bispecific antibody, wherein the C2D1 of the anti-CD20/anti-CD3 bispecific antibody is about 10 mg, about 16 mg, or about 30 mg.

In another aspect, the invention features an anti-CD79b antibody drug conjugate and an anti-CD20/anti-CD3 bispecific antibody for use in a method of treating a subject having a CD20-positive cell proliferative disorder, wherein the anti-CD79b antibody drug conjugate and the anti-CD20/anti-CD3 bispecific antibody are administered in a dosing regimen comprising at least a first dosing cycle and a second dosing cycle, wherein: (a) the first dosing cycle comprises a first dose (C1D1) of the anti-CD20/anti-CD3 bispecific antibody and a second dose (C1D2) of the anti-CD20/anti-CD3 bispecific antibody, wherein the C1D1 of the anti-CD20/anti-CD3 bispecific antibody is about 2.5 mg, and the C1D2 of the anti-CD20/anti-CD3 bispecific antibody is about 10 mg; and (b) the second dosing cycle comprises a single dose (C2D1) of the anti-CD20/anti-CD3 bispecific antibody, wherein the C2D1 of the anti-CD20/anti-CD3 bispecific antibody is about 10 mg, about 16 mg, or about 30 mg.

In another aspect, the invention features use of an anti-CD79b antibody drug conjugate and an anti-CD20/anti-CD3 bispecific antibody in treating a subject having a CD20-positive cell proliferative disorder, wherein the anti-CD79b antibody drug conjugate and the anti-CD20/anti-CD3 bispecific antibody are administered in a dosing regimen comprising at least a first dosing cycle and a second dosing cycle, wherein: (a) the first dosing cycle comprises a first dose (C1D1) of the anti-CD20/anti-CD3 bispecific antibody and a second dose (C1D2) of the anti-CD20/anti-CD3 bispecific antibody, wherein the C1D1 of the anti-CD20/anti-CD3 bispecific antibody is about 2.5 mg, and the C1D2 of the anti-CD20/anti-CD3 bispecific antibody is about 10 mg; and (b) the second dosing cycle comprises a single dose (C2D1) of the anti-CD20/anti-CD3 bispecific antibody, wherein the C2D1 of the anti-CD20/anti-CD3 bispecific antibody is about 10 mg, about 16 mg, or about 30 mg.

In another aspect, the invention features use of an anti-CD79b antibody drug conjugate and an anti-CD20/anti-CD3 bispecific antibody in the manufacture of a medicament for treating a subject having a CD20-positive cell proliferative disorder, wherein the anti-CD79b antibody drug conjugate and the anti-CD20/anti-CD3 bispecific antibody are administered in a dosing regimen comprising at least a first dosing cycle and a second dosing cycle, wherein: (a) the first dosing cycle comprises a first dose (C1D1) of the anti-CD20/anti-CD3 bispecific antibody and a second dose (C1D2) of the anti-CD20/anti-CD3 bispecific antibody, wherein the C1D1 of the anti-CD20/anti-CD3 bispecific antibody is about 2.5 mg, and the C1D2 of the anti-CD20/anti-CD3 bispecific antibody is about 10 mg; and (b) the second dosing cycle comprises a single dose (C2D1) of the anti-CD20/anti-CD3 bispecific antibody, wherein the C2D1 of the anti-CD20/anti-CD3 bispecific antibody is about 10 mg, about 16 mg, or about 30 mg.

In some embodiments, the C2D1 of the anti-CD20/anti-CD3 bispecific antibody is about 10 mg. In some embodiments, the C2D1 of the anti-CD20/anti-CD3 bispecific antibody is about 16 mg. In some embodiments, the C2D1 of the anti-CD20/anti-CD3 bispecific antibody is about 30 mg.

In some embodiments, the first dosing cycle comprises a single dose C1D1 of the anti-CD79b antibody drug conjugate. In some embodiments, the single dose C1D1 of the anti-CD79b antibody drug conjugate is from about 0.1 mg/kg to about 2.4 mg/kg (e.g., from about 0.1 mg/kg to about 2.2 mg/kg, from about 0.1 mg/kg to about 2.0 mg/kg, from about 0.5 mg/kg to about 2.2 mg/kg, from about 0.8 mg/kg to about 2.2 mg/kg, from about 1 mg/kg to about 2.2 mg/kg, from about 1.2 mg/kg to about 2.2 mg/kg, from about 1.4 mg/kg to about 2.2 mg/kg, from about 1.6 mg/kg to about 2.2 mg/kg, from about 1.8 mg/kg to about 2.0 mg/kg, from about 0.1 mg/kg to about 1.6 mg/kg, from about 0.5 mg/kg to about 1.6 mg/kg, or from about 1 mg/kg to about 1.8 mg/kg; e.g., about 1 mg/kg, about 1.2 mg/kg, about 1.6 mg/kg, or about 1.8 mg/kg). In some embodiments, the single dose C1D1 of the anti-CD79b antibody drug conjugate is about 1.8 mg/kg. In some embodiments, the C1D1 of the anti-CD79b antibody drug conjugate is administered or is to be administered on or about Day 2 (±1 day) of the dosing cycles. In some embodiments, the second dosing cycle comprises a single dose C2D1 of the anti-CD79b antibody drug conjugate. In some embodiments, the single dose C2D1 of the anti-CD79b antibody drug conjugate is from about 0.1 mg/kg to about 2.4 mg/kg (e.g., from about 0.1 mg/kg to about 2.2 mg/kg, from about 0.1 mg/kg to about 2.0 mg/kg, from about 0.5 mg/kg to about 2.2 mg/kg, from about 0.8 mg/kg to about 2.2 mg/kg, from about 1 mg/kg to about 2.2 mg/kg, from about 1.2 mg/kg to about 2.2 mg/kg, from about 1.4 mg/kg to about 2.2 mg/kg, from about 1.6 mg/kg to about 2.2 mg/kg, from about 1.8 mg/kg to about 2.0 mg/kg, from about 0.1 mg/kg to about 1.6 mg/kg, from about 0.5 mg/kg to about 1.6 mg/kg, or from about 1 mg/kg to about 1.8 mg/kg; e.g., about 1 mg/kg, about 1.2 mg/kg, about 1.6 mg/kg, or about 1.8 mg/kg). In some embodiments, the single dose C2D1 of the anti-CD79b antibody drug conjugate is about 1.8 mg/kg.

In some embodiments, the C1D1 of the anti-CD20/anti-CD3 bispecific antibody and the C1D2 of the anti-CD20/anti-CD3 bispecific antibody are administered or are to be administered to the subject on or about Days 8 (±1 day) and 15 (±1 day), respectively, of the first dosing cycle. In some embodiments, the C2D1 of the anti-CD20/anti-CD3 bispecific antibody is administered or is to be administered to the subject on or about Day 1 (±1 day) of the second dosing cycle. In some embodiments, the C2D1 of the anti-CD20/anti-CD3 bispecific antibody is administered or is to be administered after the administration of the C2D1 of the anti-CD79b antibody drug conjugate has completed. In some embodiments, the C2D1 of the anti-CD20/anti-CD3 bispecific antibody is administered or is to be administered between about 60-120 minutes (e.g., between about 60-100 minutes, between about 60-90 minutes, between about 60-80 minutes, between about 90-120 minutes, between about 80-100 minutes, between about 80-120 minutes, between about 75-105 minutes, or between about 85-95 minutes; e.g., about 60 minutes, about 70 minutes, about 80 minutes, about 85 minutes, about 88 minutes, about 90 minutes, about 92 minutes, about 95 minutes, about 100 minutes, about 110 minutes, or about 120 minutes) after the administration of the C2D1 of the anti-CD79b antibody drug conjugate has completed. In some embodiments, the C2D1 of the anti-CD20/anti-CD3 bispecific antibody is administered or is to be administered about 90 minutes after the administration of the C2D1 of the anti-CD79b antibody drug conjugate has completed. In some embodiments, the C1D1 of the anti-CD79b antibody drug conjugate is administered or is to be administered to the subject on or about Day 2 (±1 day) of the first dosing cycle and the C2D1 of the anti-CD79b antibody drug conjugate is administered or is to be administered to the subject on or about Day 1 (±1 day) of the second dosing cycle. In some embodiments, the first and second dosing cycles are 14-day (e.g., 14±3 days) dosing cycles. In some embodiments, the first and second dosing cycles are 21-day (e.g., 21±3 days) dosing cycles.

In some embodiments, the dosing regimen comprises one or more additional dosing cycles. In some embodiments, the dosing regimen comprises six to ten additional dosing cycles (e.g., six additional dosing cycles, seven additional dosing cycles, eight additional dosing cycles, nine additional dosing cycles, or ten additional dosing cycles). In some embodiments, the dosing regimen comprises ten additional dosing cycles. In some embodiments, the additional dosing cycles are 14-day (e.g., 14±3 days) dosing cycles. In some embodiments, the additional dosing cycles are 21-day (e.g., 21±3 days) dosing cycles.

In some embodiments, one or more of the additional dosing cycles comprise an additional single dose of the anti-CD20/anti-CD3 bispecific antibody and an additional single dose of the anti-CD79b antibody drug conjugate. In some embodiments, the additional single dose of the anti-CD79b antibody drug conjugate is about equivalent in amount to the C2D1 of the anti-CD79b antibody drug conjugate. In some embodiments, the additional single dose of the anti-CD79b antibody drug conjugate is about 1.8 mg/kg. In some embodiments, the additional single dose of the anti-CD79b antibody drug conjugate is administered or is to be administered to the subject on or about Day 1 (±1 day) of each additional dosing cycle comprising an additional dose of the anti-CD79b antibody drug conjugate.

In some embodiments, the additional single dose of the anti-CD20/anti-CD3 bispecific antibody of each additional dosing cycle comprising an additional dose of the anti-CD79b antibody drug conjugate is administered or is to be administered after the administration of the additional single dose of the anti-CD79b antibody drug conjugate has completed. In some embodiments, the additional single dose of the anti-CD20/anti-CD3 bispecific antibody of each additional dosing cycle comprising an additional dose of the anti-CD79b antibody drug conjugate is administered or is to be administered between about 60-120 minutes (e.g., between about 60-100 minutes, between about 60-90 minutes, between about 60-80 minutes, between about 90-120 minutes, between about 80-100 minutes, between about 80-120 minutes, between about 75-105 minutes, or between about 85-95 minutes; e.g., about 60 minutes, about 70 minutes, about 80 minutes, about 85 minutes, about 88 minutes, about 90 minutes, about 92 minutes, about 95 minutes, about 100 minutes, about 110 minutes, or about 120 minutes) after the administration of the additional single dose of the anti-CD79b antibody drug conjugate has completed. In some embodiments, the additional single dose of the anti-CD20/anti-CD3 bispecific antibody of each additional dosing cycle comprising an additional dose of the anti-CD79b antibody drug conjugate is administered or is to be administered about 90 minutes after the administration of the additional single dose of the anti-CD79b antibody drug conjugate has completed.

In some embodiments, the dosing regimen comprises at least four additional dosing cycles comprising an additional single dose of the anti-CD79b antibody drug conjugate. In some embodiments, the dosing regimen comprises between four to ten additional dosing cycles (e.g., four additional dosing cycles, five additional dosing cycles, six additional dosing cycles, seven additional dosing cycles, eight additional dosing cycles, nine additional dosing cycles, or ten additional dosing cycles) comprising an additional single dose of the anti-CD79b antibody drug conjugate.

In some embodiments, one or more of the additional dosing cycles comprise an additional single dose of the anti-CD20/anti-CD3 bispecific antibody and do not comprise administration of the anti-CD79b antibody drug conjugate. In some embodiments, the dosing regimen comprises at least two additional dosing cycles comprising an additional single dose of the anti-CD20/anti-CD3 bispecific antibody and not comprising administration of the anti-CD79b antibody drug conjugate. In some embodiments, the dosing regimen comprises between two and ten additional dosing cycles comprising an additional single dose of the anti-CD20/anti-CD3 bispecific antibody and not comprising administration of the anti-CD79b antibody drug conjugate (e.g., two additional dosing cycles, three additional dosing cycles, four additional dosing cycles, five additional dosing cycles, six additional dosing cycles, seven additional dosing cycles, eight additional dosing cycles, nine additional dosing cycles, or ten additional dosing cycles).

In some embodiments, the additional single dose of the anti-CD20/anti-CD3 bispecific antibody is about equivalent in amount to the C2D1 of the anti-CD20/anti-CD3 bispecific antibody. In some embodiments, the additional single dose of the anti-CD20/anti-CD3 bispecific antibody is about 30 mg. In some embodiments, the additional single dose of the anti-CD20/anti-CD3 bispecific antibody is administered or is to be administered to the subject on or about Day 1 (±1 day) of each additional dosing cycle comprising an additional dose of the anti-CD20/anti-CD3 bispecific antibody.

In some embodiments, the dosing regimen comprises six or more additional dosing cycles (e.g., six additional dosing cycles, seven additional dosing cycles, eight additional dosing cycles, nine additional dosing cycles, or ten additional dosing cycles), wherein each of the six or more additional dosing cycles comprises a single dose of the anti-CD20/anti-CD3 bispecific antibody, and wherein no more than four (e.g., none, no more than one, no more than two, no more than three, or no more than four; e.g., none, one, two, three, or four) of the six or more additional dosing cycles comprise administration of the anti-CD79b antibody drug conjugate. In some embodiments, the dosing regimen comprises six additional dosing cycles, wherein each of the six or more additional dosing cycles comprises a single dose of the anti-CD20/anti-CD3 bispecific antibody, and wherein no more than four (e.g., none, no more than one, no more than two, no more than three, or no more than four; e.g., none, one, two, three, or four) of the six additional dosing cycles comprise administration of the anti-CD79b antibody drug conjugate.

In one aspect, the invention features a method of treating a subject having a CD20-positive cell proliferative disorder comprising administering to the subject an anti-CD79b antibody drug conjugate and an anti-CD20/anti-CD3 bispecific antibody in a dosing regimen comprising at least a first dosing cycle and a second dosing cycle, wherein: (a) the first dosing cycle comprises: (i) a single dose (C1D1) of the anti-CD79b antibody drug conjugate; and (ii) a first dose (C1D1) of the anti-CD20/anti-CD3 bispecific antibody and a second dose (C1D2) of the anti-CD20/anti-CD3 bispecific antibody, wherein the C1D1 and the C1D2 of the anti-CD20/anti-CD3 bispecific antibody are each administered to the subject after the C1D1 of the anti-CD79b antibody drug conjugate, wherein the C1D1 of the anti-CD20/anti-CD3 bispecific antibody is about 2.5 mg, and the C1D2 of the anti-CD20/anti-CD3 bispecific antibody is about 10 mg; and (b) the second dosing cycle comprises: (i) a single dose (C2D1) of the anti-CD79b antibody drug conjugate; and (ii) a single dose (C2D1) of the anti-CD20/anti-CD3 bispecific antibody, wherein the C2D1 of the anti-CD20/anti-CD3 bispecific antibody is about 10 mg, about 16 mg, or about 30 mg.

In another aspect, the invention features an anti-CD79b antibody drug conjugate and an anti-CD20/anti-CD3 bispecific antibody for use in a method of treating a subject having a CD20-positive cell proliferative disorder comprising, wherein the anti-CD79b antibody drug conjugate and the anti-CD20/anti-CD3 bispecific antibody are administered to the subject in a dosing regimen comprising at least a first dosing cycle and a second dosing cycle, wherein: (a) the first dosing cycle comprises: (i) a single dose (C1D1) of the anti-CD79b antibody drug conjugate; and (ii) a first dose (C1D1) of the anti-CD20/anti-CD3 bispecific antibody and a second dose (C1D2) of the anti-CD20/anti-CD3 bispecific antibody, wherein the C1D1 and the C1D2 of the anti-CD20/anti-CD3 bispecific antibody are each to be administered to the subject after the C1D1 of the anti-CD79b antibody drug conjugate, wherein the C1D1 of the anti-CD20/anti-CD3 bispecific antibody is about 2.5 mg, and the C1D2 of the anti-CD20/anti-CD3 bispecific antibody is about 10 mg; and (b) the second dosing cycle comprises: (i) a single dose (C2D1) of the anti-CD79b antibody drug conjugate; and (ii) a single dose (C2D1) of the anti-CD20/anti-CD3 bispecific antibody, wherein the C2D1 of the anti-CD20/anti-CD3 bispecific antibody is about 10 mg, about 16 mg, or about 30 mg.

In another aspect, the invention features use of an anti-CD79b antibody drug conjugate and an anti-CD20/anti-CD3 bispecific antibody for treating a subject having a CD20-positive cell proliferative disorder, wherein the anti-CD79b antibody drug conjugate and the anti-CD20/anti-CD3 bispecific antibody are administered to the subject in a dosing regimen comprising at least a first dosing cycle and a second dosing cycle, wherein: (a) the first dosing cycle comprises: (i) a single dose (C1D1) of the anti-CD79b antibody drug conjugate; and (ii) a first dose (C1D1) of the anti-CD20/anti-CD3 bispecific antibody and a second dose (C1D2) of the anti-CD20/anti-CD3 bispecific antibody, wherein the C1D1 and the C1D2 of the anti-CD20/anti-CD3 bispecific antibody are each to be administered to the subject after the C1D1 of the anti-CD79b antibody drug conjugate, wherein the C1D1 of the anti-CD20/anti-CD3 bispecific antibody is about 2.5 mg, and the C1D2 of the anti-CD20/anti-CD3 bispecific antibody is about 10 mg; and (b) the second dosing cycle comprises: (i) a single dose (C2D1) of the anti-CD79b antibody drug conjugate; and (ii) a single dose (C2D1) of the anti-CD20/anti-CD3 bispecific antibody, wherein the C2D1 of the anti-CD20/anti-CD3 bispecific antibody is about 10 mg, about 16 mg, or about 30 mg.

In another aspect, the invention features use of an anti-CD79b antibody drug conjugate and an anti-CD20/anti-CD3 bispecific antibody in the manufacture of a medicament for treating a subject having a CD20-positive cell proliferative disorder, wherein the anti-CD79b antibody drug conjugate and the anti-CD20/anti-CD3 bispecific antibody are administered to the subject in a dosing regimen comprising at least a first dosing cycle and a second dosing cycle, wherein: (a) the first dosing cycle comprises: (i) a single dose (C1D1) of the anti-CD79b antibody drug conjugate; and (ii) a first dose (C1D1) of the anti-CD20/anti-CD3 bispecific antibody and a second dose (C1D2) of the anti-CD20/anti-CD3 bispecific antibody, wherein the C1D1 and the C1D2 of the anti-CD20/anti-CD3 bispecific antibody are each to be administered to the subject after the C1D1 of the anti-CD79b antibody drug conjugate, wherein the C1D1 of the anti-CD20/anti-CD3 bispecific antibody is about 2.5 mg, and the C1D2 of the anti-CD20/anti-CD3 bispecific antibody is about 10 mg; and (b) the second dosing cycle comprises: (i) a single dose (C2D1) of the anti-CD79b antibody drug conjugate; and (ii) a single dose (C2D1) of the anti-CD20/anti-CD3 bispecific antibody, wherein the C2D1 of the anti-CD20/anti-CD3 bispecific antibody is about 10 mg, about 16 mg, or about 30 mg.

In some embodiments, the single dose C1D1 of the anti-CD79b antibody drug conjugate is from about 0.1 mg/kg to about 2.4 mg/kg (e.g., from about 0.1 mg/kg to about 2.2 mg/kg, from about 0.1 mg/kg to about 2.0 mg/kg, from about 0.5 mg/kg to about 2.2 mg/kg, from about 0.8 mg/kg to about 2.2 mg/kg, from about 1 mg/kg to about 2.2 mg/kg, from about 1.2 mg/kg to about 2.2 mg/kg, from about 1.4 mg/kg to about 2.2 mg/kg, from about 1.6 mg/kg to about 2.2 mg/kg, from about 1.8 mg/kg to about 2.0 mg/kg, from about 0.1 mg/kg to about 1.6 mg/kg, from about 0.5 mg/kg to about 1.6 mg/kg, or from about 1 mg/kg to about 1.8 mg/kg; e.g., about 1 mg/kg, about 1.2 mg/kg, about 1.6 mg/kg, or about 1.8 mg/kg) and the single dose C2D1 of the anti-CD79b antibody drug conjugate is from about 0.1 mg/kg to about 2.4 mg/kg (e.g., from about 0.1 mg/kg to about 2.2 mg/kg, from about 0.1 mg/kg to about 2.0 mg/kg, from about 0.5 mg/kg to about 2.2 mg/kg, from about 0.8 mg/kg to about 2.2 mg/kg, from about 1 mg/kg to about 2.2 mg/kg, from about 1.2 mg/kg to about 2.2 mg/kg, from about 1.4 mg/kg to about 2.2 mg/kg, from about 1.6 mg/kg to about 2.2 mg/kg, from about 1.8 mg/kg to about 2.0 mg/kg, from about 0.1 mg/kg to about 1.6 mg/kg, from about 0.5 mg/kg to about 1.6 mg/kg, or from about 1 mg/kg to about 1.8 mg/kg; e.g., about 1 mg/kg, about 1.2 mg/kg, about 1.6 mg/kg, or about 1.8 mg/kg). In some embodiments, the single dose C1D1 of the anti-CD79b antibody drug conjugate is about 1.8 mg/kg and the single dose C2D1 of the anti-CD79b antibody drug conjugate is about 1.8 mg/kg.

In some embodiments, the C1D1 of the anti-CD20/anti-CD3 bispecific antibody and the C1D2 of the anti-CD20/anti-CD3 bispecific antibody are administered or are to be administered to the subject on or about Days 8 (±1 day) and 15 (±1 day), respectively, of the first dosing cycle.

In some embodiments, the C2D1 of the anti-CD20/anti-CD3 bispecific antibody is administered or is to be administered to the subject on or about Day 1 (±1 day) of the second dosing cycle. In some embodiments, the C1D1 of the anti-CD79b antibody drug conjugate is administered or is to be administered to the subject on or about Day 2 (±1 day) of the first dosing cycle and the C2D1 of the anti-CD79b antibody drug conjugate is administered or is to be administered to the subject on or about Day 1 (±1 day) of the second dosing cycle.

In some embodiments, the first and second dosing cycles are 14-day (e.g., 14±3 days) dosing cycles. In some embodiments, the first and second dosing cycles are 21-day (e.g., 21±3 days) dosing cycles.

In some embodiments, the dosing regimen comprises one or more additional dosing cycles. In some embodiments, the dosing regimen comprises six to ten additional dosing cycles (e.g., six additional dosing cycles, seven additional dosing cycles, eight additional dosing cycles, nine additional dosing cycles, or ten additional dosing cycles).

In some embodiments, the dosing regimen comprises ten additional dosing cycles. In some embodiments, the additional dosing cycles are 21-day (e.g., 21±3 days) dosing cycles. In some embodiments, the dosing regimen comprises one or more additional dosing cycles. In some embodiments, the dosing regimen comprises six to ten additional dosing cycles. In some embodiments, the dosing regimen comprises ten additional dosing cycles.

In some embodiments, the additional dosing cycles are 14-day (e.g., 14±3 days) dosing cycles.

In some embodiments, one or more of the additional dosing cycles comprise an additional single dose of the anti-CD20/anti-CD3 bispecific antibody and an additional single dose of the anti-CD79b antibody drug conjugate. In some embodiments, the additional single dose of the anti-CD79b antibody drug conjugate is about equivalent in amount to the C2D1 of the anti-CD79b antibody drug conjugate. In some embodiments, the additional single dose of the anti-CD79b antibody drug conjugate is administered or is to be administered to the subject on or about Day 1 (±1 day) of each additional dosing cycle comprising an additional dose of the anti-CD79b antibody drug conjugate.

In some embodiments, the additional single dose of the anti-CD20/anti-CD3 bispecific antibody of each additional dosing cycle comprising an additional dose of the anti-CD79b antibody drug conjugate is administered or is to be administered after the administration of the additional single dose of the anti-CD79b antibody drug conjugate has completed. In some embodiments, the additional single dose of the anti-CD20/anti-CD3 bispecific antibody of each additional dosing cycle comprising an additional dose of the anti-CD79b antibody drug conjugate is administered or is to be administered between about 60-120 minutes (e.g., between about 60-100 minutes, between about 60-90 minutes, between about 60-80 minutes, between about 90-120 minutes, between about 80-100 minutes, between about 80-120 minutes, between about 75-105 minutes, or between about 85-95 minutes; e.g., about 60 minutes, about 70 minutes, about 80 minutes, about 85 minutes, about 88 minutes, about 90 minutes, about 92 minutes, about 95 minutes, about 100 minutes, about 110 minutes, or about 120 minutes) after the administration of the additional single dose of the anti-CD79b antibody drug conjugate has completed. In some embodiments, the additional single dose of the anti-CD20/anti-CD3 bispecific antibody of each additional dosing cycle comprising an additional dose of the anti-CD79b antibody drug conjugate is administered or is to be administered about 90 minutes after the administration of the additional single dose of the anti-CD79b antibody drug conjugate has completed.

In some embodiments, the dosing regimen comprises at least four additional dosing cycles comprising an additional single dose of the anti-CD20/anti-CD3 bispecific antibody and an additional single dose of the anti-CD79b antibody drug conjugate. In some embodiments, the dosing regimen comprises between four to ten additional dosing cycles (e.g., four additional dosing cycles, five additional dosing cycles, six additional dosing cycles, seven additional dosing cycles, eight additional dosing cycles, nine additional dosing cycles, or ten additional dosing cycles) comprising an additional single dose of the anti-CD20/anti-CD3 bispecific antibody and an additional single dose of the anti-CD79b antibody drug conjugate. In some embodiments, one or more of the additional dosing cycles comprise an additional single dose of the anti-CD20/anti-CD3 bispecific antibody and do not comprise administration of the anti-CD79b antibody drug conjugate.

In some embodiments, the dosing regimen comprises at least two additional dosing cycles comprising an additional single dose of the anti-CD20/anti-CD3 bispecific antibody and not comprising administration of the anti-CD79b antibody drug conjugate. In some embodiments, the dosing regimen comprises between two and ten additional dosing cycles (e.g., two additional dosing cycles, three additional dosing cycles, four additional dosing cycles, five additional dosing cycles, six additional dosing cycles, seven additional dosing cycles, eight additional dosing cycles, nine additional dosing cycles, or ten additional dosing cycles) comprising an additional single dose of the anti-CD20/anti-CD3 bispecific antibody and not comprising administration of the anti-CD79b antibody drug conjugate.

In some embodiments, the additional single dose of the anti-CD20/anti-CD3 bispecific antibody is about equivalent in amount to the C2D1 of the anti-CD20/anti-CD3 bispecific antibody. In some embodiments, the additional single dose of the anti-CD20/anti-CD3 bispecific antibody is about 30 mg. In some embodiments, the additional single dose of the anti-CD20/anti-CD3 bispecific antibody is administered or is to be administered to the subject on or about Day 1 (±1 day) of each additional dosing cycle comprising an additional dose of the anti-CD20/anti-CD3 bispecific antibody.

In some embodiments, the dosing regimen comprises six or more additional dosing cycles (e.g., six additional dosing cycles, seven additional dosing cycles, eight additional dosing cycles, nine additional dosing cycles, or ten additional dosing cycles), wherein each of the six or more additional dosing cycles comprises a single dose of the anti-CD20/anti-CD3 bispecific antibody, and wherein no more than four (e.g., none, no more than one, no more than two, no more than three, or no more than four; e.g., none, one, two, three, or four) of the six or more additional dosing cycles comprise administration of the anti-CD79b antibody drug conjugate. In some embodiments, the dosing regimen comprises six to ten additional dosing cycles (e.g., six additional dosing cycles, seven additional dosing cycles, eight additional dosing cycles, nine additional dosing cycles, or ten additional dosing cycles), wherein each of the six to ten additional dosing cycles comprises a single dose of the anti-CD20/anti-CD3 bispecific antibody, and wherein no more than four (e.g., none, no more than one, no more than two, no more than three, or no more than four; e.g., none, one, two, three, or four) of the six additional dosing cycles comprise administration of the anti-CD79b antibody drug conjugate. In some embodiments, the dosing regimen comprises ten additional dosing cycles, wherein each of the ten additional dosing cycles comprises a single dose of the anti-CD20/anti-CD3 bispecific antibody, and wherein no more than four (e.g., none, no more than one, no more than two, no more than three, or no more than four; e.g., none, one, two, three, or four) of the ten additional dosing cycles comprise administration of the anti-CD79b antibody drug conjugate. In some embodiments, the dosing regimen comprises ten additional dosing cycles, wherein each of the ten additional dosing cycles comprises a single dose of the anti-CD20/anti-CD3 bispecific antibody, and wherein each of the ten additional dosing cycles comprises administration of the anti-CD79b antibody drug conjugate.

In one aspect, the invention features a method of treating a subject having a CD20-positive cell proliferative disorder comprising administering to the subject an anti-CD79b antibody drug conjugate and an anti-CD20/anti-CD3 bispecific antibody in a dosing regimen comprising 12 dosing cycles, wherein: (a) the first dosing cycle comprises: (i) a first dose (C1D1) of the anti-CD20/anti-CD3 bispecific antibody and a second dose (C1D2) of the anti-CD20/anti-CD3 bispecific antibody, wherein the C1D1 of the anti-CD20/anti-CD3 bispecific antibody is about 2.5 mg, and the C1D2 of the anti-CD20/anti-CD3 bispecific antibody is about 10 mg; and (ii) a single dose (C1D1) of the anti-CD79b antibody drug conjugate; (b) the second to sixth dosing cycles each comprises a single dose (C2D1-C6D1) of the anti-CD20/anti-CD3 bispecific antibody and a single dose (C2D1-C6D1) of the anti-CD79b antibody drug conjugate; and (c) the seventh to $12^{th}$ dosing cycles each comprises a single dose (C7D1-C12D1) of the anti-CD20/anti-CD3 bispecific antibody and does not comprise administration of the anti-CD79b antibody drug conjugate, and wherein each single dose C2D1-C12D1 of the anti-CD20/anti-CD3 bispecific antibody is about 10 mg, about 16 mg, or about 30 mg.

In another aspect, the invention features an anti-CD79b antibody drug conjugate and an anti-CD20/anti-CD3 bispecific antibody for use in a method of treating a subject having a CD20-positive cell proliferative disorder, wherein the anti-CD79b antibody drug conjugate and the anti-CD20/anti-CD3 bispecific antibody are administered in a dosing regimen comprising 12 dosing cycles, wherein: (a) the first dosing cycle comprises: (i) a first dose (C1D1) of the anti-CD20/anti-CD3 bispecific antibody and a second dose (C1D2) of the anti-CD20/anti-CD3 bispecific antibody, wherein the C1D1 of the anti-CD20/anti-CD3 bispecific antibody is about 2.5 mg, and the C1D2 of the anti-CD20/anti-CD3 bispecific antibody is about 10 mg; and (ii) a single dose (C1D1) of the anti-CD79b antibody drug conjugate; (b) the second to sixth dosing cycles each comprises a single dose (C2D1-C6D1) of the anti-CD20/anti-CD3 bispecific antibody and a single dose (C2D1-C6D1) of the anti-CD79b antibody drug conjugate; and (c) the seventh to $12^{th}$ dosing cycles each comprises a single dose (C7D1-C12D1) of the anti-CD20/anti-CD3 bispecific antibody and does not comprise administration of the anti-CD79b antibody drug conjugate, and wherein each single dose C2D1-C12D1 of the anti-CD20/anti-CD3 bispecific antibody is about 10 mg, about 16 mg, or about 30 mg.

In another aspect, the invention features use of an anti-CD79b antibody drug conjugate and an anti-CD20/anti-CD3 bispecific antibody in treating a subject having a CD20-positive cell proliferative disorder, wherein the anti-CD79b antibody drug conjugate and the anti-CD20/anti-CD3 bispecific antibody are administered in a dosing regimen comprising 12 dosing cycles, wherein: (a) the first dosing cycle comprises: (i) a first dose (C1D1) of the anti-CD20/anti-CD3 bispecific antibody and a second dose (C1D2) of the anti-CD20/anti-CD3 bispecific antibody, wherein the C1D1 of the anti-CD20/anti-CD3 bispecific antibody is about 2.5 mg, and the C1D2 of the anti-CD20/anti-CD3 bispecific antibody is about 10 mg; and (ii) a single dose (C1D1) of the anti-CD79b antibody drug conjugate; (b) the second to sixth dosing cycles each comprises a single dose (C2D1-C6D1) of the anti-CD20/anti-CD3 bispecific antibody and a single dose (C2D1-C6D1) of the anti-CD79b antibody drug conjugate; and (c) the seventh to $12^{th}$ dosing cycles each comprises a single dose (C7D1-C12D1) of the anti-CD20/anti-CD3 bispecific antibody and does not comprise administration of the anti-CD79b antibody drug conjugate, and wherein each single dose C2D1-C12D1 of the anti-CD20/anti-CD3 bispecific antibody is about 10 mg, about 16 mg, or about 30 mg.

In another aspect, the invention features use of an anti-CD79b antibody drug conjugate and an anti-CD20/anti-CD3 bispecific antibody in the manufacture of a medicament for treating a subject having a CD20-positive cell proliferative disorder, wherein the anti-CD79b antibody drug conjugate and the anti-CD20/anti-CD3 bispecific antibody are administered in a dosing regimen comprising 12 dosing cycles, wherein: (a) the first dosing cycle comprises: (i) a first dose (C1D1) of the anti-CD20/anti-CD3 bispecific antibody and a second dose (C1D2) of the anti-CD20/anti-CD3 bispecific antibody, wherein the C1D1 of the anti-CD20/anti-CD3 bispecific antibody is about 2.5 mg, and the C1D2 of the anti-CD20/anti-CD3 bispecific antibody is about 10 mg; and (ii) a single dose (C1D1) of the anti-CD79b antibody drug conjugate; (b) the second to sixth dosing cycles each comprises a single dose (C2D1-C6D1) of the anti-CD20/anti-CD3 bispecific antibody and a single dose (C2D1-C6D1) of the anti-CD79b antibody drug conjugate; and (c) the seventh to $12^{th}$ dosing cycles each comprises a single dose (C7D1-C12D1) of the anti-CD20/anti-CD3 bispecific antibody and does not comprise administration of the anti-CD79b antibody drug conjugate, and wherein each single dose C2D1-C12D1 of the anti-CD20/anti-CD3 bispecific antibody is about 10 mg, about 16 mg, or about 30 mg.

In some embodiments, the C2D1-C12D1 of the anti-CD20/anti-CD3 bispecific antibody are about equivalent in amount. In some embodiments, the C2D1 of the anti-CD20/anti-CD3 bispecific antibody is about 30 mg.

In some embodiments, the C1D1-C6D1 of the anti-CD79b antibody drug conjugate are about equivalent in amount. In some embodiments, each of the C1D1-C6D1 of the anti-CD79b antibody drug conjugate is from about 0.1 mg/kg to about 2.4 mg/kg (e.g., from about 0.1 mg/kg to about 2.2 mg/kg, from about 0.1 mg/kg to about 2.0 mg/kg, from about 0.5 mg/kg to about 2.2 mg/kg, from about 0.8 mg/kg to about 2.2 mg/kg, from about 1 mg/kg to about 2.2 mg/kg, from about 1.2 mg/kg to about 2.2 mg/kg, from about 1.4 mg/kg to about 2.2 mg/kg, from about 1.6 mg/kg to about 2.2 mg/kg, from about 1.8 mg/kg to about 2.0 mg/kg, from about 0.1 mg/kg to about 1.6 mg/kg, from about 0.5 mg/kg to about 1.6 mg/kg, or from about 1 mg/kg to about 1.8 mg/kg; e.g., about 1 mg/kg, about 1.2 mg/kg, about 1.6 mg/kg, or about 1.8 mg/kg). In some embodiments, each of the C1D1-C6D1 of the anti-CD79b antibody drug conjugate is about 1.8 mg/kg.

In some embodiments, the C1D1 of the anti-CD20/anti-CD3 bispecific antibody and the C1D2 of the anti-CD20/anti-CD3 bispecific antibody are administered or are to be administered to the subject on or about Days 8 (±1 day) and 15 (±1 day), respectively, of the first dosing cycle. In some embodiments, the C2D1-C12D1 of the anti-CD20/anti-CD3 bispecific antibody is administered or is to be administered to the subject on or about Day 1 of each dosing cycle. In some embodiments, the C1D1 of the anti-CD79b antibody drug conjugate is administered or is to be administered to the subject on or about Day 2 (±1 day) of the first dosing cycle and the C2D1-C6D1 of the anti-CD79b antibody drug conjugate is administered or is to be administered to the subject on or about Day 1 of each dosing cycle comprising administration of the anti-CD79b antibody drug conjugate.

In some embodiments, the C2D1-C6D1 of the anti-CD20/anti-CD3 bispecific antibody is administered or is to be administered after the administration the C2D1-C6D1 of the anti-CD79b antibody drug conjugate has completed. In some embodiments, the C2D1-C6D1 of the anti-CD20/anti-CD3 bispecific antibody is administered or is to be administered between about 60-120 minutes (e.g., between about 60-100 minutes, between about 60-90 minutes, between about 60-80 minutes, between about 90-120 minutes, between about 80-100 minutes, between about 80-120 minutes, between about 75-105 minutes, or between about 85-95 minutes; e.g., about 60 minutes, about 70 minutes, about 80 minutes, about 85 minutes, about 88 minutes, about 90 minutes, about 92 minutes, about 95 minutes, about 100 minutes, about 110 minutes, or about 120 minutes) after the administration of the C2D1-C6D1 of the anti-CD79b antibody drug conjugate has completed. In some embodiments, the C2D1-C6D1 of the anti-CD20/anti-CD3 bispecific antibody is administered or is to be administered about 90 minutes after the administration of the C2D1-C6D1 anti-CD79b antibody drug conjugate has completed.

In some embodiments, each dosing cycle is a 14-day (e.g., 14±3 days) dosing cycle. In some embodiments, each dosing cycle is a 21-day (e.g., 21±3 days) dosing cycle.

In some embodiments, the dosing regimen comprises an additional re-treatment regimen after the completion of the 12 dosing cycles of the dosing regimen. In some embodiments, the additional re-treatment regimen comprises 12 additional dosing cycles, wherein: (a) the first additional dosing cycle comprises: (i) a first dose (C13D1) of the anti-CD20/anti-CD3 bispecific antibody and a second dose (C13D2) of the anti-CD20/anti-CD3 bispecific antibody, wherein the C13D1 of the anti-CD20/anti-CD3 bispecific antibody is about 2.5 mg, and the C13D2 of the anti-CD20/anti-CD3 bispecific antibody is about 10 mg; and (ii) a single dose (C13D1) of the anti-CD79b antibody drug conjugate; (b) the second to sixth additional dosing cycles each comprises a single dose (C14D1-C18D1) of the anti-CD20/anti-CD3 bispecific antibody and a single dose (C14D1-C18D1) of the anti-CD79b antibody drug conjugate; and (c) the seventh to $12^{th}$ additional dosing cycles each comprises a single dose (C19D1-C24D1) of the anti-CD20/anti-CD3 bispecific antibody and does not comprise administration of the anti-CD79b antibody drug conjugate, and wherein each single dose C14D1-C24D1 of the anti-CD20/anti-CD3 bispecific antibody is about 10 mg, about 16 mg, or about 30 mg. In some embodiments, (a) the first additional dosing cycle comprises: (i) a first dose (C13D1) of the anti-CD20/anti-CD3 bispecific antibody administered or to be administered on Day 8 (±1 day) of the first additional dosing cycle and a second dose (C13D2) of the anti-CD20/anti-CD3 bispecific antibody administered or to be administered on Day 15 (±1 day) of the first additional dosing cycle, wherein the C13D1 of the anti-CD20/anti-CD3 bispecific antibody is about 2.5 mg, and the C13D2 of the anti-CD20/anti-CD3 bispecific antibody is about 10 mg; and (ii) a single dose (C13D1) of the anti-CD79b antibody drug conjugate administered or to be administered on Day 2 (±1 day) of the first additional dosing cycle; (b) the second to sixth additional dosing cycles each comprises a single dose (C14D1-C18D1) of the anti-CD20/anti-CD3 bispecific antibody and a single dose (C14D1-C18D1) of the anti-CD79b antibody drug conjugate; and (c) the seventh to 12$^{th}$ additional dosing cycles each comprises a single dose (C19D1-C24D1) of the anti-CD20/anti-CD3 bispecific antibody and does not comprise administration of the anti-CD79b antibody drug conjugate, and wherein the C14D1-C24D1 of the anti-CD20/anti-CD3 bispecific antibody are administered or are to be administered on Day 1 of (±1 day) each additional dosing cycle and the C14D1-C18D1 of the anti-CD79b antibody drug conjugate are administered or are to be administered on Day 1 (±1 day) of each additional dosing cycle, and wherein each single dose C14D1-C24D1 of the anti-CD20/anti-CD3 bispecific antibody is about 30 mg and each single dose C13D1-C18D1 of the anti-CD79b antibody drug conjugate is about 1.8 mg/kg. In some embodiments, there is a waiting period between the completion of the 12 dosing cycles of the dosing regimen and the start of the 12 additional dosing cycles of the additional re-treatment regimen. In some embodiments, the waiting period is between about one to about eight weeks. In some embodiments, each additional dosing cycle of the additional re-treatment regimen is a 14-day (e.g., 14±3 days) dosing cycle. In some embodiments, each additional dosing cycle of the additional re-treatment regimen is a 21-day (e.g., 21±3 days) dosing cycle.

In some embodiments, the method further comprises administering to the subject one or more additional therapeutic agents. In some embodiments, the anti-CD79b antibody drug conjugate and bispecific antibody are administered with one or more additional therapeutic agents.

In some embodiments, the one or more additional therapeutic agents comprise one or more chemotherapeutic agents. In some embodiments, the one or more chemotherapeutic agents comprise cyclophosphamide, doxorubicin, and rituximab.

In some embodiments, the one or more additional therapeutic agents is tocilizumab. In some embodiments, the one or more additional therapeutic agents is a corticosteroid. In some embodiments, the corticosteroid comprises prednisone, prednisolone, methylprednisolone and dexamethasone.

In some embodiments, the method further comprises administering to the subject rituximab, cyclophosphamide, doxorubicin, and prednisone (R-CHP). In some embodiments, the anti-CD79b antibody drug conjugate and bispecific antibody are administered with rituximab, cyclophosphamide, doxorubicin, and prednisone (R-CHP).

In some embodiments, the one or more additional therapeutic agents is an antihistamine. In some embodiments, the antihistamine is diphenhydramine. In some embodiments, the one or more additional therapeutic agents comprises allopurinol and rasburicase. In some embodiments, the one or more additional therapeutic agents is an antipyretic.

In some embodiments, the one or more additional therapeutic agents is obinutuzumab. In some embodiments, obinutuzumab is administered or is to be administered prior to administration of the anti-CD20/anti-CD3 bispecific antibody. In some embodiments, obinutuzumab is administered or is to be administered about seven days (±1 day) prior to administration of the anti-CD20/anti-CD3 bispecific antibody. In some embodiments, obinutuzumab is administered or is to be administered as a single dose of about 1000 mg. In some embodiments, obinutuzumab is administered at a first dose of about 1000 mg and a second dose of about 1000 mg. In some embodiments, the first dose of obinutuzumab is administered about seven days (±1 day) prior to administration of the C1D1 of the anti-CD20/anti-CD3 bispecific antibody. In some embodiments, the second dose of obinutuzumab is administered about one day (±1 day) prior to administration of the C1D1 of the anti-CD20/anti-CD3 bispecific antibody.

In some embodiments, the anti-CD79b antibody drug conjugate is polatuzumab vedotin or anti-CD79b-MC-vc-PAB-MMAE. In some embodiments, the anti-CD79b antibody drug conjugate is polatuzumab vedotin.

In some embodiments, the anti-CD20/anti-CD3 bispecific antibody comprises at least one Fab molecule which specifically binds to CD20 comprising the following six hypervariable regions (HVRs): (a) an HVR-H1 comprising the amino acid sequence of YSWIN (SEQ ID NO: 1); (b) an HVR-H2 comprising the amino acid sequence of RIFPGDGDTDYNGKFKG (SEQ ID NO: 2); (c) an HVR-H3 comprising the amino acid sequence of NVFDGYWLVY (SEQ ID NO:3); (d) an HVR-L1 comprising the amino acid sequence of RSSKSLLHSNGITYLY (SEQ ID NO: 4); (e) an HVR-L2 comprising the amino acid sequence of QMSNLVS (SEQ ID NO: 5); and (f) an HVR-L3 comprising the amino acid sequence of AQNLELPYT (SEQ ID NO: 6). In some embodiments, the anti-CD20/anti-CD3 bispecific antibody comprises at least one Fab molecule which specifically binds to CD20 comprising (a) a heavy chain variable VH domain comprising an amino acid sequence having at least 95% (e.g., at least 95%, at least 96%, at least 97%, at least 98%, or at least 99%; e.g., 95%, 96%, 97%, 98%, 99%, or 100%) sequence identity to the amino acid sequence of SEQ ID NO: 7; (b) a variable light (VL) domain comprising an amino acid sequence having at least 95% (e.g., at least 95%, at least 96%, at least 97%, at least 98%, or at least 99%; e.g., 95%, 96%, 97%, 98%, 99%, or 100%) sequence identity to the amino acid sequence of SEQ ID NO: 8; or (c) a VH domain as in (a) and a VL domain as in (b). In some embodiments, the Fab molecule which specifically binds to CD20 comprises (a) a VH domain comprising an amino acid sequence of SEQ ID NO: 7 and (b) a VL domain comprising an amino acid sequence of SEQ ID NO: 8.

In some embodiments, the anti-CD20/anti-CD3 bispecific antibody comprises at least one Fab molecule which specifically binds to CD3 comprising the following six HVRs: (a) an HVR-H1 comprising the amino acid sequence of TYAMN (SEQ ID NO: 9); (b) an HVR-H2 comprising the amino acid sequence of RIRSKYNNYATYYADSVKG (SEQ ID NO: 10); (c) an HVR-H3 comprising the amino acid sequence of HGNFGNSYVSWFAY (SEQ ID NO: 11); (d) an HVR-L1 comprising the amino acid sequence of GSSTGAVTTSNYAN (SEQ ID NO: 12); (e) an HVR-L2 comprising the amino acid sequence of GTNKRAP (SEQ ID NO: 13); and (f) an HVR-L3 comprising the amino acid sequence of ALWYSNLWV (SEQ ID NO: 14). In some embodiments, the anti-CD20/anti-CD3 bispecific antibody comprises at least one Fab molecule which specifically binds to CD3 comprising (a) a heavy chain variable VH domain comprising an amino acid sequence having at least 95% (e.g., at least 95%, at least 96%, at least 97%, at least 98%, or at least 99%; e.g., 95%, 96%, 97%, 98%, 99%, or 100%) sequence identity to the amino acid sequence of SEQ ID NO: 15; (b) a variable light (VL) domain comprising an amino acid sequence having at least 95% (e.g., at least 95%, at least 96%, at least 97%, at least 98%, or at least 99%; e.g., 95%, 96%, 97%, 98%, 99%, or 100%) sequence identity to the amino acid sequence of SEQ ID NO: 16; or (c) a VH domain as in (a) and a VL domain as in (b). In some embodiments, the Fab molecule which specifically binds to CD3 comprises (a) a VH domain comprising an amino acid sequence of SEQ ID NO: 15 and (b) a VL domain comprising an amino acid sequence of SEQ ID NO: 16.

In some embodiments, the anti-CD20/anti-CD3 bispecific antibody comprises a Fab molecule which specifically binds to CD3, wherein (a) the variable domains of the Fab heavy and light chain are exchanged or (b) the constant domains of the Fab heavy and light chain are exchanged. In some embodiments, the anti-CD20/anti-CD3 bispecific antibody comprises at least one Fab molecule which specifically binds to CD20, wherein in the constant domain CL of the Fab molecule the amino acid at position 124 is substituted by lysine (K) (numbering according to Kabat) and the amino acid at position 123 is substituted by arginine (R) or lysine (K) (numbering according to Kabat), and wherein in the constant domain CH1 of the Fab molecule the amino acid at position 147 is substituted by glutamic acid (E) (EU numbering) and the amino acid at position 213 is substituted by glutamic acid (E) (EU numbering). In some embodiments, the anti-CD20/anti-CD3 bispecific antibody is bivalent for CD20 and monovalent for CD3. In some embodiments, the anti-CD20/anti-CD3 bispecific antibody comprises two Fab molecule which specifically bind to CD20 and one Fab molecule which specifically binds to CD3.

In some embodiments, the anti-CD20/anti-CD3 bispecific antibody comprises (a) a first Fab molecule which specifically binds to CD20; (b) a second Fab molecule which specifically binds to CD3; (c) a third Fab molecule which specifically binds to CD20; and (d) an Fc domain composed of a first and a second subunit capable of stable association; wherein the third Fab molecule under (c) is identical to the first Fab molecule under (a); wherein in the constant domain CL of the first Fab molecule under (a) and the third Fab molecule under (c) the amino acid at position 124 is substituted by lysine (K) (numbering according to Kabat) and the amino acid at position 123 is substituted by arginine (R) or lysine (K) (numbering according to Kabat); and wherein in the constant domain CH1 of the first Fab molecule under (a) and the third Fab molecule under (c) the amino acid at position 147 is substituted by glutamic acid (E) (EU numbering) and the amino acid at position 213 is substituted by glutamic acid (E) (EU numbering); and wherein the first Fab molecule under (a) is fused at the C-terminus of the Fab heavy chain to the N-terminus of the Fab heavy chain of the second Fab molecule under (b), and the second Fab molecule under (b) and the third Fab molecule under (c) are each fused at the C-terminus of the Fab heavy chain to the N-terminus of one of the subunits of the Fc domain under (d).

In some embodiments, the anti-CD20/anti-CD3 bispecific antibody is a humanized antibody. In some embodiments, the anti-CD20/anti-CD3 bispecific antibody is a chimeric antibody.

In some embodiments, the anti-CD20/anti-CD3 bispecific antibody comprises an Fc domain, wherein the Fc domain is an IgG Fc domain. In some embodiments, the IgG Fc domain is an IgG1 Fc domain. In some embodiments, the IgG Fc domain comprises a mutation at amino acid residue N297 (EU numbering) that results in the absence of glycosylation. In some embodiments, the mutation at amino acid residue N297 is a substitution mutation. In some embodiments, the mutation at amino acid residue N297 reduces effector function of the Fc region. In some embodiments, the mutation is an N297G or N297A mutation. In some embodiments, the anti-CD20/anti-CD3 bispecific antibody comprises a mutation in the Fc region that reduces effector function. In some embodiments, the mutation is a substitution mutation. In some embodiments, the substitution mutation is at amino acid residue L234, L235, D265, and/or P329 (EU numbering). In some embodiments, mutation is selected from the group consisting of L234A, L235A, D265A, and P329G.

In some embodiments, the anti-CD20/anti-CD3 bispecific antibody comprises one or more heavy chain constant domains, wherein the one or more heavy chain constant domains are selected from a first CH1 ($CH1_1$) domain, a first CH2 ($CH2_1$) domain, a first CH3 ($CH3_1$) domain, a second CH1 ($CH1_2$) domain, second CH2 ($CH2_2$) domain, and a second CH3 ($CH3_2$) domain. In some embodiments, at least one of the one or more heavy chain constant domains is paired with another heavy chain constant domain. In some embodiments, the $CH3_1$ and $CH3_2$ domains each comprise a protuberance or cavity, and wherein the protuberance or cavity in the $CH3_1$ domain is positionable in the cavity or protuberance, respectively, in the $CH3_2$ domain. In some embodiments, the $CH3_1$ and $CH3_2$ domains meet at an interface between the protuberance and cavity. In some embodiments, the $CH2_1$ and $CH2_2$ domains each comprise a protuberance or cavity, and wherein the protuberance or cavity in the $CH2_1$ domain is positionable in the cavity or protuberance, respectively, in the $CH2_2$ domain. In some embodiments, the $CH2_1$ and $CH2_2$ domains meet at an interface between said protuberance and cavity.

In some embodiments, the anti-CD20/anti-CD3 bispecific antibody is glofitamab.

In some embodiments, the anti-CD20/anti-CD3 bispecific antibody is administered or is administered intravenously. In some embodiments, the anti-CD79b antibody drug conjugate is administered or is administered intravenously. In some embodiments, if the anti-CD20/anti-CD3 bispecific antibody and the anti-CD79b antibody drug conjugate are administered or are to be administered on the same day, then the anti-CD20/anti-CD3 bispecific antibody is administered or is to be administered after the administration of the anti-CD79b antibody drug conjugate has completed. In some embodiments, the anti-CD20/anti-CD3 bispecific antibody is administered or is to be administered between about 60-120 minutes (e.g., between about 60-100 minutes, between about 60-90 minutes, between about 60-80 minutes, between about 90-120 minutes, between about 80-100 minutes, between about 80-120 minutes, between about 75-105 minutes, or between about 85-95 minutes; e.g., about 60 minutes, about 70 minutes, about 80 minutes, about 85 minutes, about 88 minutes, about 90 minutes, about 92 minutes, about 95 minutes, about 100 minutes, about 110 minutes, or about 120 minutes) after the administration of the anti-CD79b antibody drug conjugate has completed. In some embodiments, the anti-CD20/anti-CD3 bispecific antibody is administered or is to be administered about 90 minutes after the administration of the anti-CD79b antibody drug conjugate has completed.

In one aspect, the invention features a method of treating a subject having a CD20-positive cell proliferative disorder comprising administering to the subject polatuzumab vedotin and glofitamab in a dosing regimen comprising at least a first dosing cycle and a second dosing cycle, wherein: (a) the first dosing cycle comprises a first dose (C1D1) of glofitamab administered on Day 8 (±1 day) of the first dosing cycle and a second dose (C1D2) of glofitamab administered on Day 15 (±1 day) of the first dosing cycle, wherein the C1D1 of glofitamab is about 2.5 mg, the C1D2 of glofitamab is about 10 mg; and (b) the second dosing cycle comprises a single dose (C2D1) of glofitamab administered on Day 1 (±1 day) of the second dosing cycle and a single dose (C2D1) of polatuzumab vedotin administered on Day 1 (±1 day) of the second dosing cycle, wherein the C2D1 of glofitamab is about 10 mg, about 16 mg, or about 30 mg.

In another aspect, the invention features polatuzumab vedotin and glofitamab for use in a method of treating a subject having a CD20-positive cell proliferative disorder, wherein polatuzumab vedotin and glofitamab are administered in a dosing regimen comprising at least a first dosing cycle and a second dosing cycle, wherein: (a) the first dosing cycle comprises a first dose (C1D1) of glofitamab to be administered on Day 8 (±1 day) of the first dosing cycle and a second dose (C1D2) of glofitamab to be administered on Day 15 (±1 day) of the first dosing cycle, wherein the C1D1 of glofitamab is about 2.5 mg, the C1D2 of glofitamab is about 10 mg; and (b) the second dosing cycle comprises a single dose (C2D1) of glofitamab to be administered on Day 1 (±1 day) of the second dosing cycle and a single dose (C2D1) of polatuzumab vedotin to be administered on Day 1 (±1 day) of the second dosing cycle, wherein the C2D1 of glofitamab is about 10 mg, about 16 mg, or about 30 mg.

In another aspect, the invention features use of polatuzumab vedotin and glofitamab for treating a subject having a CD20-positive cell proliferative disorder, wherein polatuzumab vedotin and glofitamab are administered in a dosing regimen comprising at least a first dosing cycle and a second dosing cycle, wherein: (a) the first dosing cycle comprises a first dose (C1D1) of glofitamab to be administered on Day 8 (±1 day) of the first dosing cycle and a second dose (C1D2) of glofitamab to be administered on Day 15 (±1 day) of the first dosing cycle, wherein the C1D1 of glofitamab is about 2.5 mg, the C1D2 of glofitamab is about 10 mg; and (b) the second dosing cycle comprises a single dose (C2D1) of glofitamab to be administered on Day 1 (±1 day) of the second dosing cycle and a single dose (C2D1) of polatuzumab vedotin to be administered on Day 1 (±1 day) of the second dosing cycle, wherein the C2D1 of glofitamab is about 10 mg, about 16 mg, or about 30 mg.

In another aspect, the invention features use of polatuzumab vedotin and glofitamab in the manufacture of a medicament for treating a subject having a CD20-positive cell proliferative disorder, wherein polatuzumab vedotin and glofitamab are administered in a dosing regimen comprising at least a first dosing cycle and a second dosing cycle, wherein: (a) the first dosing cycle comprises a first dose (C1D1) of glofitamab to be administered on Day 8 (±1 day) of the first dosing cycle and a second dose (C1D2) of glofitamab to be administered on Day 15 (±1 day) of the first dosing cycle, wherein the C1D1 of glofitamab is about 2.5 mg, the C1D2 of glofitamab is about 10 mg; and (b) the second dosing cycle comprises a single dose (C2D1) of glofitamab to be administered on Day 1 (±1 day) of the second dosing cycle and a single dose (C2D1) of polatuzumab vedotin to be administered on Day 1 (±1 day) of the second dosing cycle, wherein the C2D1 of glofitamab is about 10 mg, about 16 mg, or about 30 mg.

In one aspect, the invention features a method of treating a subject having a CD20-positive cell proliferative disorder comprising administering to the subject polatuzumab vedotin and glofitamab in a dosing regimen comprising at least a first dosing cycle and a second dosing cycle, wherein: (a) the first dosing cycle comprises: (i) a single dose (C1D1) of polatuzumab vedotin administered on Day 2 (±1 day) of the first dosing cycle; and (ii) a first dose (C1D1) of glofitamab administered on Day 8 (±1 day) of the first dosing cycle and a second dose (C1D2) of glofitamab administered on Day 15 (±1 day) of the first dosing cycle, wherein the C1D1 of glofitamab is about 2.5 mg, and the C1D2 of glofitamab is about 10 mg; and (b) the second dosing cycle comprises: (i) a single dose (C2D1) of polatuzumab vedotin administered on Day 1 (±1 day) of the second dosing cycle; and (ii) a single dose (C2D1) of glofitamab administered on Day 1 (±1 day) of the second dosing cycle, wherein the C2D1 of glofitamab is about 10 mg, about 16 mg, or about 30 mg, and the C1D1 and C2D1 of polatuzumab vedotin are each about 1.8 mg/kg.

In another aspect, the invention features polatuzumab vedotin and glofitamab for use in a method of treating a subject having a CD20-positive cell proliferative disorder, wherein polatuzumab vedotin and glofitamab are administered in a dosing regimen comprising at least a first dosing cycle and a second dosing cycle, wherein: (a) the first dosing cycle comprises: (i) a single dose (C1D1) of polatuzumab vedotin to be administered on Day 2 (±1 day) of the first dosing cycle; and (ii) a first dose (C1D1) of glofitamab to be administered on Day 8 (±1 day) of the first dosing cycle and a second dose (C1D2) of glofitamab to be administered on Day 15 (±1 day) of the first dosing cycle, wherein the C1D1 of glofitamab is about 2.5 mg, and the C1D2 of glofitamab is about 10 mg; and (b) the second dosing cycle comprises: (i) a single dose (C2D1) of polatuzumab vedotin to be administered on Day 1 (±1 day) of the second dosing cycle; and (ii) a single dose (C2D1) of glofitamab to be administered on Day 1 (±1 day) of the second dosing cycle, wherein the C2D1 of glofitamab is about 10 mg, about 16 mg, or about 30 mg, and the C1D1 and C2D1 of polatuzumab vedotin are each about 1.8 mg/kg.

In another aspect, the invention features use of polatuzumab vedotin and glofitamab in treating a subject having a CD20-positive cell proliferative disorder, wherein polatuzumab vedotin and glofitamab are administered in a dosing regimen comprising at least a first dosing cycle and a second dosing cycle, wherein: (a) the first dosing cycle comprises: (i) a single dose (C1D1) of polatuzumab vedotin to be administered on Day 2 (±1 day) of the first dosing cycle; and (ii) a first dose (C1D1) of glofitamab to be administered on Day 8 (±1 day) of the first dosing cycle and a second dose (C1D2) of glofitamab to be administered on Day 15 (±1 day) of the first dosing cycle, wherein the C1D1 of glofitamab is about 2.5 mg, and the C1D2 of glofitamab is about 10 mg; and (b) the second dosing cycle comprises: (i) a single dose (C2D1) of polatuzumab vedotin to be administered on Day 1 (±1 day) of the second dosing cycle; and (ii) a single dose (C2D1) of glofitamab to be administered on Day 1 (±1 day) of the second dosing cycle, wherein the C2D1 of glofitamab is about 10 mg, about 16 mg, or about 30 mg, and the C1D1 and C2D1 of polatuzumab vedotin are each about 1.8 mg/kg.

In another aspect, the invention features use of polatuzumab vedotin and glofitamab in the manufacture of a medicament for treating a subject having a CD20-positive cell proliferative disorder, wherein polatuzumab vedotin and glofitamab are administered in a dosing regimen comprising at least a first dosing cycle and a second dosing cycle, wherein: (a) the first dosing cycle comprises: (i) a single dose (C1D1) of polatuzumab vedotin to be administered on Day 2 (±1 day) of the first dosing cycle; and (ii) a first dose (C1D1) of glofitamab to be administered on Day 8 (±1 day) of the first dosing cycle and a second dose (C1D2) of glofitamab to be administered on Day 15 (±1 day) of the first dosing cycle, wherein the C1D1 of glofitamab is about 2.5 mg, and the C1D2 of glofitamab is about 10 mg; and (b) the second dosing cycle comprises: (i) a single dose (C2D1) of polatuzumab vedotin to be administered on Day 1 (±1 day) of the second dosing cycle; and (ii) a single dose (C2D1) of glofitamab to be administered on Day 1 (±1 day) of the second dosing cycle, wherein the C2D1 of glofitamab is about 10 mg, about 16 mg, or about 30 mg, and the C1D1 and C2D1 of polatuzumab vedotin are each about 1.8 mg/kg.

In one aspect, the invention features a method of treating a subject having a CD20-positive cell proliferative disorder comprising administering to the subject polatuzumab vedotin and glofitamab in a dosing regimen comprising 12 dosing cycles, wherein: (a) the first dosing cycle comprises a first dose (C1D1) of glofitamab administered on Day 8 (±1 day) of the first dosing cycle, a second dose (C1D2) of glofitamab administered on Day 15 (±1 day) of the first dosing cycle, and a single dose (C1D1) of polatuzumab vedotin administered on Day 2 (±1 day) of the first dosing cycle, wherein the C1D1 of glofitamab is between about 1 mg to about 5 mg, and the C1D2 of glofitamab is about 10 mg; (b) the second to sixth dosing cycles each comprises a single dose (C2D1-C6D1) of glofitamab and a single dose (C2D1-C6D1) of polatuzumab vedotin, wherein the C2D1 of glofitamab is about 10 mg, about 16 mg, or about 30 mg; and (c) the seventh to $12^{th}$ dosing cycles each comprises a single dose (C7D1-C12D1) of glofitamab and does not comprise administration of polatuzumab vedotin, and wherein each single dose C2D1-C12D1 of glofitamab is administered on Day 1 (±1 day) of each dosing cycle, and each single dose C2D1-C6D1 of polatuzumab vedotin is administered on Day 1 (±1 day) of each dosing cycle, and wherein each single dose C3D1-C12D1 of glofitamab is about equal in amount to the C2D1 of glofitamab, and each single dose C1D1-C6D1 of polatuzumab vedotin is about 1.8 mg/kg.

In another aspect, the invention features polatuzumab vedotin and glofitamab for use in a method of treating a subject having a CD20-positive cell proliferative disorder, wherein polatuzumab vedotin and glofitamab are administered in a dosing regimen comprising 12 dosing cycles, wherein: (a) the first dosing cycle comprises a first dose (C1D1) of glofitamab to be administered on Day 8 (±1 day) of the first dosing cycle, a second dose (C1D2) of glofitamab to be administered on Day 15 (±1 day) of the first dosing cycle, and a single dose (C1D1) of polatuzumab vedotin to be administered on Day 2 (±1 day) of the first dosing cycle, wherein the C1D1 of glofitamab is about 2.5 mg, and the C1D2 of glofitamab is about 10 mg; (b) the second to sixth dosing cycles each comprises a single dose (C2D1-C6D1) of glofitamab and a single dose (C2D1-C6D1) of polatuzumab vedotin, wherein the C2D1 of glofitamab is about 10 mg, about 16 mg, or about 30 mg; and (c) the seventh to $12^{th}$ dosing cycles each comprises a single dose (C7D1-C12D1) of glofitamab and does not comprise administration of polatuzumab vedotin, and wherein each single dose C2D1-C12D1 of glofitamab is to be administered on Day 1 (±1 day) of each dosing cycle, and each single dose C2D1-C6D1 of polatuzumab vedotin is to be administered on Day 1 (±1 day) of each dosing cycle, and wherein each single dose C3D1-C12D1 of glofitamab is about equal in amount to the C2D1 of glofitamab, and each single dose C1D1-C6D1 of polatuzumab vedotin is about 1.8 mg/kg.

In another aspect, the invention features use of polatuzumab vedotin and glofitamab in treating a subject having a CD20-positive cell proliferative disorder, wherein polatuzumab vedotin and glofitamab are administered in a dosing regimen comprising 12 dosing cycles, wherein: (a) the first dosing cycle comprises a first dose (C1D1) of glofitamab to be administered on Day 8 (±1 day) of the first dosing cycle, a second dose (C1D2) of glofitamab to be administered on Day 15 (±1 day) of the first dosing cycle, and a single dose (C1D1) of polatuzumab vedotin to be administered on Day 2 (±1 day) of the first dosing cycle, wherein the C1D1 of glofitamab is about 2.5 mg, and the C1D2 of glofitamab is about 10 mg; (b) the second to sixth dosing cycles each comprises a single dose (C2D1-C6D1) of glofitamab and a single dose (C2D1-C6D1) of polatuzumab vedotin, wherein the C2D1 of glofitamab is about 10 mg, about 16 mg, or about 30 mg; and (c) the seventh to $12^{th}$ dosing cycles each comprises a single dose (C7D1-C12D1) of glofitamab and does not comprise administration of polatuzumab vedotin, and wherein each single dose C2D1-C12D1 of glofitamab is to be administered on Day 1 (±1 day) of each dosing cycle, and each single dose C2D1-C6D1 of polatuzumab vedotin is to be administered on Day 1 (±1 day) of each dosing cycle, and wherein each single dose C3D1-C12D1 of glofitamab is about equal in amount to the C2D1 of glofitamab, and each single dose C1D1-C6D1 of polatuzumab vedotin is about 1.8 mg/kg.

In another aspect, the invention features use of polatuzumab vedotin and glofitamab in the manufacture of a medicament for treating a subject having a CD20-positive cell proliferative disorder, wherein polatuzumab vedotin and glofitamab are administered in a dosing regimen comprising 12 dosing cycles, wherein: (a) the first dosing cycle comprises a first dose (C1D1) of glofitamab to be administered on Day 8 (±1 day) of the first dosing cycle, a second dose (C1D2) of glofitamab to be administered on Day 15 (±1 day) of the first dosing cycle, and a single dose (C1D1) of polatuzumab vedotin to be administered on Day 2 (±1 day) of the first dosing cycle, wherein the C1D1 of glofitamab is about 2.5 mg, and the C1D2 of glofitamab is about 10 mg; (b) the second to sixth dosing cycles each comprises a single dose (C2D1-C6D1) of glofitamab and a single dose (C2D1-C6D1) of polatuzumab vedotin, wherein the C2D1 of glofitamab is about 10 mg, about 16 mg, or about 30 mg; and (c) the seventh to $12^{th}$ dosing cycles each comprises a single dose (C7D1-C12D1) of glofitamab and does not comprise administration of polatuzumab vedotin, and wherein each single dose C2D1-C12D1 of glofitamab is to be administered on Day 1 (±1 day) of each dosing cycle, and each single dose C2D1-C6D1 of polatuzumab vedotin is to be administered on Day 1 (±1 day) of each dosing cycle, and wherein each single dose C3D1-C12D1 of glofitamab is about equal in amount to the C2D1 of glofitamab, and each single dose C1D1-C6D1 of polatuzumab vedotin is about 1.8 mg/kg.

In one aspect, the invention features a method of treating a subject having a CD20-positive cell proliferative disorder comprising administering to the subject polatuzumab vedotin and glofitamab in a dosing regimen comprising 12 dosing cycles, wherein: (a) the first dosing cycle comprises: (i) a first dose (C1D1) of glofitamab administered on Day 8 (±1 day) of the first dosing cycle and a second dose (C1D2) of glofitamab administered on Day 15 (±1 day) of the first dosing cycle, wherein the C1D1 of glofitamab is about 2.5 mg and the C1D2 of glofitamab is about 10 mg; and (ii) a single dose (C1D1) of polatuzumab vedotin administered on Day 2 (±1 day) of the first dosing cycle; (b) the second to sixth dosing cycles each comprises a single dose (C2D1-C6D1) of glofitamab and a single dose (C2D1-C6D1) of polatuzumab vedotin, wherein the C2D1 of glofitamab is about 10 mg, about 16 mg, or about 30 mg; and (c) the seventh to $12^{th}$ dosing cycles each comprises a single dose (C7D1-C12D1) of glofitamab and does not comprise administration of polatuzumab vedotin, and wherein each single dose C2D1-C12D1 of glofitamab is administered on Day 1 (±1 day) of each dosing cycle, and each single dose C2D1-C6D1 of polatuzumab vedotin is administered on Day 1 (±1 day) of each dosing cycle, and wherein each single dose C3D1-C12D1 of glofitamab is about equal in amount to the C2D1 of glofitamab, and each single dose C1D1-C6D1 of polatuzumab vedotin is about 1.8 mg/kg.

In another aspect, the invention features polatuzumab vedotin and glofitamab for use in a method of treating a subject having a CD20-positive cell proliferative disorder, wherein polatuzumab vedotin and glofitamab are administered in a dosing regimen comprising 12 dosing cycles, wherein: (a) the first dosing cycle comprises: (i) a first dose (C1D1) of glofitamab to be administered on Day 8 (±1 day) of the first dosing cycle and a second dose (C1D2) of glofitamab to be administered on Day 15 (±1 day) of the first dosing cycle, wherein the C1D1 of glofitamab is about 2.5 mg and the C1D2 of glofitamab is about 10 mg; and (ii) a single dose (C1D1) of polatuzumab vedotin to be administered on Day 2 (±1 day) of the first dosing cycle; (b) the second to sixth dosing cycles each comprises a single dose (C2D1-C6D1) of glofitamab and a single dose (C2D1-C6D1) of polatuzumab vedotin, wherein the C2D1 of glofitamab is about 10 mg, about 16 mg, or about 30 mg; and (c) the seventh to $12^{th}$ dosing cycles each comprises a single dose (C7D1-C12D1) of glofitamab and does not comprise administration of polatuzumab vedotin, and wherein each single dose C2D1-C12D1 of glofitamab is to be administered on Day 1 (±1 day) of each dosing cycle, and each single dose C2D1-C6D1 of polatuzumab vedotin is to be administered on Day 1 (±1 day) of each dosing cycle, and wherein each single dose C3D1-C12D1 of glofitamab is about equal in amount to the C2D1 of glofitamab, and each single dose C1D1-C6D1 of polatuzumab vedotin is about 1.8 mg/kg.

In another aspect, the invention features use of polatuzumab vedotin and glofitamab in treating a subject having a CD20-positive cell proliferative disorder, wherein polatuzumab vedotin and glofitamab are administered in a dosing regimen comprising 12 dosing cycles, wherein: (a) the first dosing cycle comprises: (i) a first dose (C1D1) of glofitamab to be administered on Day 8 (±1 day) of the first dosing cycle and a second dose (C1D2) of glofitamab to be administered on Day 15 (±1 day) of the first dosing cycle, wherein the C1D1 of glofitamab is about 2.5 mg and the C1D2 of glofitamab is about 10 mg; and (ii) a single dose (C1D1) of polatuzumab vedotin to be administered on Day 2 (±1 day) of the first dosing cycle; (b) the second to sixth dosing cycles each comprises a single dose (C2D1-C6D1) of glofitamab and a single dose (C2D1-C6D1) of polatuzumab vedotin, wherein the C2D1 of glofitamab is about 10 mg, about 16 mg, or about 30 mg; and (c) the seventh to $12^{th}$ dosing cycles each comprises a single dose (C7D1-C12D1) of glofitamab and does not comprise administration of polatuzumab vedotin, and wherein each single dose C2D1-C12D1 of glofitamab is to be administered on Day 1 (±1 day) of each dosing cycle, and each single dose C2D1-C6D1 of polatuzumab vedotin is to be administered on Day 1 (±1 day) of each dosing cycle, and wherein each single dose C3D1-C12D1 of glofitamab is about equal in amount to the C2D1 of glofitamab, and each single dose C1D1-C6D1 of polatuzumab vedotin is about 1.8 mg/kg.

In another aspect, the invention features use of polatuzumab vedotin and glofitamab in the manufacture of a medicament for treating a subject having a CD20-positive cell proliferative disorder, wherein polatuzumab vedotin and glofitamab are administered in a dosing regimen comprising 12 dosing cycles, wherein: (a) the first dosing cycle comprises: (i) a first dose (C1D1) of glofitamab to be administered on Day 8 (±1 day) of the first dosing cycle and a second dose (C1D2) of glofitamab to be administered on Day 15 (±1 day) of the first dosing cycle, wherein the C1D1 of glofitamab is about 2.5 mg and the C1D2 of glofitamab is about 10 mg; and (ii) a single dose (C1D1) of polatuzumab vedotin to be administered on Day 2 (±1 day) of the first dosing cycle; (b) the second to sixth dosing cycles each comprises a single dose (C2D1-C6D1) of glofitamab and a single dose (C2D1-C6D1) of polatuzumab vedotin, wherein the C2D1 of glofitamab is about 10 mg, about 16 mg, or about 30 mg; and (c) the seventh to $12^{th}$ dosing cycles each comprises a single dose (C7D1-C12D1) of glofitamab and does not comprise administration of polatuzumab vedotin, and wherein each single dose C2D1-C12D1 of glofitamab is to be administered on Day 1 (±1 day) of each dosing cycle, and each single dose C2D1-C6D1 of polatuzumab vedotin is to be administered on Day 1 (±1 day) of each dosing cycle, and wherein each single dose C3D1-C12D1 of glofitamab is about equal in amount to the C2D1, and each single dose C1D1-C6D1 of polatuzumab vedotin is about 1.8 mg/kg.

In one aspect, the invention features a method of treating a subject having a CD20-positive cell proliferative disorder comprising administering to the subject polatuzumab vedotin and glofitamab in a dosing regimen comprising 12 dosing cycles, wherein: (a) the first dosing cycle comprises: (i) a first dose (C1D1) of glofitamab administered on Day 8 (±1 day) of the first dosing cycle and a second dose (C1D2) of glofitamab administered on Day 15 (±1 day) of the first dosing cycle, wherein the C1D1 of glofitamab is about 2.5 mg and the C1D2 of glofitamab is about 10 mg; and (ii) a single dose (C1D1) of polatuzumab vedotin administered on Day 2 (±1 day) of the first dosing cycle; (b) the second to sixth dosing cycles each comprises a single dose (C2D1-C6D1) of glofitamab and a single dose (C2D1-C6D1) of polatuzumab vedotin, wherein the C2D1 of glofitamab is about 30 mg; and (c) the seventh to $12^{th}$ dosing cycles each comprises a single dose (C7D1-C12D1) of glofitamab and does not comprise administration of polatuzumab vedotin, and wherein each single dose C2D1-C12D1 of glofitamab is administered on Day 1 (±1 day) of each dosing cycle, and each single dose C2D1-C6D1 of polatuzumab vedotin is administered on Day 1 (±1 day) of each dosing cycle, and wherein each single dose C3D1-C12D1 of glofitamab is about equal in amount to the C2D1 of glofitamab, and each single dose C1D1-C6D1 of polatuzumab vedotin is about 1.8 mg/kg.

In another aspect, the invention features polatuzumab vedotin and glofitamab for use in a method of treating a subject having a CD20-positive cell proliferative disorder, wherein polatuzumab vedotin and glofitamab are administered in a dosing regimen comprising 12 dosing cycles, wherein: (a) the first dosing cycle comprises: (i) a first dose (C1D1) of glofitamab to be administered on Day 8 (±1 day) of the first dosing cycle and a second dose (C1D2) of glofitamab to be administered on Day 15 (±1 day) of the first dosing cycle, wherein the C1D1 of glofitamab is about 2.5 mg and the C1D2 of glofitamab is about 10 mg; and (ii) a single dose (C1D1) of polatuzumab vedotin to be administered on Day 2 (±1 day) of the first dosing cycle; (b) the second to sixth dosing cycles each comprises a single dose (C2D1-C6D1) of glofitamab and a single dose (C2D1-C6D1) of polatuzumab vedotin, wherein the C2D1 of glofitamab is about 30 mg; and (c) the seventh to $12^{th}$ dosing cycles each comprises a single dose (C7D1-C12D1) of glofitamab and does not comprise administration of polatuzumab vedotin, and wherein each single dose C2D1-C12D1 of glofitamab is to be administered on Day 1 (±1 day) of each dosing cycle, and each single dose C2D1-C6D1 of polatuzumab vedotin is to be administered on Day 1 (±1 day) of each dosing cycle, and wherein each single dose C3D1-C12D1 of glofitamab is about equal in amount to the C2D1 of glofitamab, and each single dose C1D1-C6D1 of polatuzumab vedotin is about 1.8 mg/kg.

In another aspect, the invention features use of polatuzumab vedotin and glofitamab in treating a subject having a CD20-positive cell proliferative disorder, wherein polatuzumab vedotin and glofitamab are administered in a dosing regimen comprising 12 dosing cycles, wherein: (a) the first dosing cycle comprises: (i) a first dose (C1D1) of glofitamab to be administered on Day 8 (±1 day) of the first dosing cycle and a second dose (C1D2) of glofitamab to be administered on Day 15 (±1 day) of the first dosing cycle, wherein the C1D1 of glofitamab is about 2.5 mg and the C1D2 of glofitamab is about 10 mg; and (ii) a single dose (C1D1) of polatuzumab vedotin to be administered on Day 2 (±1 day) of the first dosing cycle; (b) the second to sixth dosing cycles each comprises a single dose (C2D1-C6D1) of glofitamab and a single dose (C2D1-C6D1) of polatuzumab vedotin, wherein the C2D1 of glofitamab is about 30 mg; and (c) the seventh to $12^{th}$ dosing cycles each comprises a single dose (C7D1-C12D1) of glofitamab and does not comprise administration of polatuzumab vedotin, and wherein each single dose C2D1-C12D1 of glofitamab is to be administered on Day 1 (±1 day) of each dosing cycle, and each single dose C2D1-C6D1 of polatuzumab vedotin is to be administered on Day 1 (±1 day) of each dosing cycle, and wherein each single dose C3D1-C12D1 of glofitamab is about equal in amount to the C2D1 of glofitamab, and each single dose C1D1-C6D1 of polatuzumab vedotin is about 1.8 mg/kg.

In another aspect, the invention features use of polatuzumab vedotin and glofitamab in the manufacture of a medicament for treating a subject having a CD20-positive cell proliferative disorder, wherein polatuzumab vedotin and glofitamab are administered in a dosing regimen comprising 12 dosing cycles, wherein: (a) the first dosing cycle comprises: (i) a first dose (C1D1) of glofitamab to be administered on Day 8 (±1 day) of the first dosing cycle and a second dose (C1D2) of glofitamab to be administered on Day 15 (±1 day) of the first dosing cycle, wherein the C1D1 of glofitamab is about 2.5 mg and the C1D2 of glofitamab is about 10 mg; and (ii) a single dose (C1D1) of polatuzumab vedotin to be administered on Day 2 (±1 day) of the first dosing cycle; (b) the second to sixth dosing cycles each comprises a single dose (C2D1-C6D1) of glofitamab and a single dose (C2D1-C6D1) of polatuzumab vedotin, wherein the C2D1 of glofitamab is about 30 mg; and (c) the seventh to $12^{th}$ dosing cycles each comprises a single dose (C7D1-C12D1) of glofitamab and does not comprise administration of polatuzumab vedotin, and wherein each single dose C2D1-C12D1 of glofitamab is to be administered on Day 1 (±1 day) of each dosing cycle, and each single dose C2D1-C6D1 of polatuzumab vedotin is to be administered on Day 1 (±1 day) of each dosing cycle, and wherein each single dose C3D1-C12D1 of glofitamab is about equal in amount to the C2D1, and each single dose C1D1-C6D1 of polatuzumab vedotin is about 1.8 mg/kg.

In some embodiments, the dosing cycles are 14-day (e.g., 14±3 days) dosing cycles. In some embodiments, the dosing cycles are 21-day (e.g., 21±3 days) dosing cycles.

In some embodiments, glofitamab is administered intravenously. In some embodiments, polatuzumab vedotin is administered intravenously. In some embodiments, if glofitamab and polatuzumab vedotin are administered or are to be administered on the same day, then glofitamab is administered or is to be administered after the administration of polatuzumab vedotin has completed. In some embodiments, glofitamab is administered or is to be administered between about 60-120 minutes (e.g., between about 60-100 minutes, between about 60-90 minutes, between about 60-80 minutes, between about 90-120 minutes, between about 80-100 minutes, between about 80-120 minutes, between about 75-105 minutes, or between about 85-95 minutes; e.g., about 60 minutes, about 70 minutes, about 80 minutes, about 85 minutes, about 88 minutes, about 90 minutes, about 92 minutes, about 95 minutes, about 100 minutes, about 110 minutes, or about 120 minutes) after the administration of polatuzumab has completed. In some embodiments, glofitamab is administered or is to be administered about 90 minutes after the administration of polatuzumab vedotin has completed.

In some embodiments, the method further comprises administering to the subject obinutuzumab. In some embodiments, polatuzumab vedotin and glofitamab are administered with obinutuzumab. In some embodiments, obinutuzumab is administered or is to be administered prior to administration of glofitamab. In some embodiments, obinutuzumab is administered or is to be administered about seven days (±1 day) prior to administration of glofitamab. In some embodiments, obinutuzumab is administered or is to be administered as a single dose of about 1000 mg.

In some embodiments, the CD20-positive cell proliferative disorder is a B cell proliferative disorder. In some embodiments, the B cell proliferative disorder is a non-Hodgkin's lymphoma (NHL) or a central nervous system lymphoma (CNSL). In some embodiments, the NHL is relapsed and/or refractory. In some embodiments, the NHL is a diffuse-large B cell lymphoma (DLBCL), a follicular lymphoma (FL), a mantle cell lymphoma (MCL), a marginal zone lymphoma (MZL), a high-grade B cell lymphoma, a primary mediastinal (thymic) large B cell lymphoma (PMLBCL), a diffuse B cell lymphoma, or a small lymphocytic lymphoma.

In some embodiments, the NHL is a DLBCL. In some embodiments, the DLBCL is a relapsed or refractory DLBCL.

In some embodiments, the NHL is an FL. In some embodiments, the FL is a relapsed or refractory FL. In some embodiments, the FL is a transformed FL.

In some embodiments, the NHL is an MCL. In some embodiments, the MCL is a relapsed or refractory MCL.

In some embodiments, the CD20-positive cell proliferative disorder is not a chronic lymphoid leukemia (CLL), an acute lymphoblastic leukemia (ALL), a Richter's transformation, a Burkitt lymphoma, or a lymphoplasmacytic lymphoma.

In one aspect, the invention features a method of treating a population of subjects having a R/R NHL comprising administering to the subjects an anti-CD79b antibody drug conjugate and an anti-CD20/anti-CD3 bispecific antibody in a dosing regimen comprising at least a first dosing cycle and a second dosing cycle, wherein: (a) the first dosing cycle comprises a first dose (C1D1) of the anti-CD20/anti-CD3 bispecific antibody administered on Day 8 (±1 day) of the first dosing cycle, a second dose (C1D2) of the anti-CD20/anti-CD3 bispecific antibody administered on Day 15 (±1 day) of the first dosing cycle, and a single dose (C1D1) of polatuzumab vedotin administered on Day 2 (±1 day) of the first dosing cycle, wherein the C1D1 of the anti-CD20/anti- CD3 bispecific antibody is about 2.5 mg, and the C1D2 of the anti-CD20/anti-CD3 bispecific antibody is about 10 mg; and (b) the second dosing cycle comprises a single dose (C2D1) of the anti-CD20/anti-CD3 bispecific antibody administered on Day 1 (±1 day) of the second dosing cycle and a single dose (C2D1) of polatuzumab vedotin administered on Day 1 (±1 day) of the second dosing cycle, wherein the C2D1 of the anti-CD20/anti-CD3 bispecific antibody is about 30 mg, and wherein the C1D1 and the C1D2 of the anti-CD79b antibody drug conjugate are each about 1.8 mg/kg.

In another aspect, the invention features an anti-CD79b antibody drug conjugate and an anti-CD20/anti-CD3 bispecific antibody for use in a method of treating a population of subjects having a R/R NHL, wherein the anti-CD79b antibody drug conjugate and the anti-CD20/anti-CD3 bispecific antibody are administered in a dosing regimen comprising at least a first dosing cycle and a second dosing cycle, wherein: (a) the first dosing cycle comprises a first dose (C1D1) of the anti-CD20/anti-CD3 bispecific antibody to be administered on Day 8 (±1 day) of the first dosing cycle, a second dose (C1D2) of the anti-CD20/anti-CD3 bispecific antibody to be administered on Day 15 (±1 day) of the first dosing cycle, and a single dose (C1D1) of polatuzumab vedotin to be administered on Day 2 (±1 day) of the first dosing cycle, wherein the C1D1 of the anti-CD20/anti-CD3 bispecific antibody is about 2.5 mg, and the C1D2 of the anti-CD20/anti-CD3 bispecific antibody is about 10 mg; and (b) the second dosing cycle comprises a single dose (C2D1) of the anti-CD20/anti-CD3 bispecific antibody to be administered on Day 1 (±1 day) of the second dosing cycle and a single dose (C2D1) of polatuzumab vedotin to be administered on Day 1 (±1 day) of the second dosing cycle, wherein the C2D1 of the anti-CD20/anti-CD3 bispecific antibody is about 30 mg, and wherein the C1D1 and the C1D2 of the anti-CD79b antibody drug conjugate are each about 1.8 mg/kg.

In another aspect, the invention features use of an anti-CD79b antibody drug conjugate and an anti-CD20/anti-CD3 bispecific antibody for treating a population of subjects having a R/R NHL, wherein the anti-CD79b antibody drug conjugate and the anti-CD20/anti-CD3 bispecific antibody are administered in a dosing regimen comprising at least a first dosing cycle and a second dosing cycle, wherein: (a) the first dosing cycle comprises a first dose (C1D1) of the anti-CD20/anti-CD3 bispecific antibody to be administered on Day 8 (±1 day) of the first dosing cycle, a second dose (C1D2) of the anti-CD20/anti-CD3 bispecific antibody to be administered on Day 15 (±1 day) of the first dosing cycle, and a single dose (C1D1) of polatuzumab vedotin to be administered on Day 2 (±1 day) of the first dosing cycle, wherein the C1D1 of the anti-CD20/anti-CD3 bispecific antibody is about 2.5 mg, and the C1D2 of the anti-CD20/anti-CD3 bispecific antibody is about 10 mg; and (b) the second dosing cycle comprises a single dose (C2D1) of the anti-CD20/anti-CD3 bispecific antibody to be administered on Day 1 (±1 day) of the second dosing cycle and a single dose (C2D1) of polatuzumab vedotin to be administered on Day 1 (±1 day) of the second dosing cycle, wherein the C2D1 of the anti-CD20/anti-CD3 bispecific antibody is about 30 mg, and wherein the C1D1 and the C1D2 of the anti-CD79b antibody drug conjugate are each about 1.8 mg/kg.

In another aspect, the invention features use of an anti-CD79b antibody drug conjugate and an anti-CD20/anti-CD3 bispecific antibody in the manufacture of a medicament for treating a population of subjects having a R/R NHL, wherein the anti-CD79b antibody drug conjugate and the anti-CD20/anti-CD3 bispecific antibody are administered in a dosing regimen comprising at least a first dosing cycle and a second dosing cycle, wherein: (a) the first dosing cycle comprises a first dose (C1D1) of the anti-CD20/anti-CD3 bispecific antibody to be administered on Day 8 (±1 day) of the first dosing cycle, a second dose (C1D2) of the anti-CD20/anti-CD3 bispecific antibody to be administered on Day 15 (±1 day) of the first dosing cycle, and a single dose (C1D1) of polatuzumab vedotin to be administered on Day 2 (±1 day) of the first dosing cycle, wherein the C1D1 of the anti-CD20/anti-CD3 bispecific antibody is about 2.5 mg, and the C1D2 of the anti-CD20/anti-CD3 bispecific antibody is about 10 mg; and (b) the second dosing cycle comprises a single dose (C2D1) of the anti-CD20/anti-CD3 bispecific antibody to be administered on Day 1 (±1 day) of the second dosing cycle and a single dose (C2D1) of polatuzumab vedotin to be administered on Day 1 (±1 day) of the second dosing cycle, wherein the C2D1 of the anti-CD20/anti-CD3 bispecific antibody is about 30 mg, and wherein the C1D1 and the C1D2 of the anti-CD79b antibody drug conjugate are each about 1.8 mg/kg.

In one aspect, the invention features a method of treating a population of subjects having a R/R NHL comprising administering to the subjects an anti-CD79b antibody drug conjugate and an anti-CD20/anti-CD3 bispecific antibody in a dosing regimen comprising 12 dosing cycles, wherein: (a) the first dosing cycle comprises: (i) a first dose (C1D1) of the anti-CD20/anti-CD3 bispecific antibody administered on Day 8 (±1 day) of the first dosing cycle and a second dose (C1D2) of the anti-CD20/anti-CD3 bispecific antibody to be administered on Day 15 (±1 day) of the first dosing cycle, wherein the C1D1 of the anti-CD20/anti-CD3 bispecific antibody is about 2.5 mg, and the C1D2 of the anti-CD20/anti-CD3 bispecific antibody is about 10 mg; and (ii) a single dose (C1D1) of the anti-CD79b antibody drug conjugate administered on Day 2 (±1 day) of the first dosing cycle; (b) the second to sixth dosing cycles each comprises a single dose (C2D1-C6D1) of the anti-CD20/anti-CD3 bispecific antibody and a single dose (C2D1-C6D1) of the anti-CD79b antibody drug conjugate; and (c) the seventh to $12^{th}$ dosing cycles each comprises a single dose (C7D1-C12D1) of the anti-CD20/anti-CD3 bispecific antibody and does not comprise administration of the anti-CD79b antibody drug conjugate, and wherein each single dose C2D1-C12D1 of the anti-CD20/anti-CD3 bispecific antibody is administered on Day 1 (±1 day) of each dosing cycle, and each single dose C2D1-C6D1 of the anti-CD79b antibody drug conjugate is administered on Day 1 (±1 day) of each dosing cycle, and wherein each single dose C2D1-C12D1 of the anti-CD20/anti-CD3 bispecific antibody is about 30 mg and each single dose C1D1-C6D1 of the anti-CD79b antibody drug conjugate is about 1.8 mg/kg.

In another aspect, the invention features an anti-CD79b antibody drug conjugate and an anti-CD20/anti-CD3 bispecific antibody for use in a method of treating a population of subjects having a R/R NHL, wherein the anti-CD79b antibody drug conjugate and the anti-CD20/anti-CD3 bispecific antibody are administered in a dosing regimen comprising 12 dosing cycles, wherein: (a) the first dosing cycle comprises: (i) a first dose (C1D1) of the anti-CD20/anti-CD3 bispecific antibody to be administered on Day 8 (±1 day) of the first dosing cycle and a second dose (C1D2) of the anti-CD20/anti-CD3 bispecific antibody to be administered on Day 15 (±1 day) of the first dosing cycle, wherein the C1D1 of the anti-CD20/anti-CD3 bispecific antibody is about 2.5 mg, and the C1D2 of the anti-CD20/anti-CD3 bispecific antibody is about 10 mg; and (ii) a single dose (C1D1) of the anti-CD79b antibody drug conjugate to be administered on Day 2 (±1 day) of the first dosing cycle; (b) the second to sixth dosing cycles each comprises a single dose (C2D1-C6D1) of the anti-CD20/anti-CD3 bispecific antibody and a single dose (C2D1-C6D1) of the anti-CD79b antibody drug conjugate; and (c) the seventh to $12^{th}$ dosing cycles each comprises a single dose (C7D1-C12D1) of the anti-CD20/anti-CD3 bispecific antibody and does not comprise administration of the anti-CD79b antibody drug conjugate, and wherein each single dose C2D1-C12D1 of the anti-CD20/anti-CD3 bispecific antibody is to be administered on Day 1 (±1 day) of each dosing cycle, and each single dose C2D1-C6D1 of the anti-CD79b antibody drug conjugate is to be administered on Day 1 (±1 day) of each dosing cycle, and wherein each single dose C2D1-C12D1 of the anti-CD20/anti-CD3 bispecific antibody is about 30 mg and each single dose C1D1-C6D1 of the anti-CD79b antibody drug conjugate is about 1.8 mg/kg.

In another aspect, the invention features use of an anti-CD79b antibody drug conjugate and an anti-CD20/anti-CD3 bispecific antibody for treating a population of subjects having a R/R NHL, wherein the anti-CD79b antibody drug conjugate and the anti-CD20/anti-CD3 bispecific antibody are administered in a dosing regimen comprising 12 dosing cycles, wherein: (a) the first dosing cycle comprises: (i) a first dose (C1D1) of the anti-CD20/anti-CD3 bispecific antibody to be administered on Day 8 (±1 day) of the first dosing cycle and a second dose (C1D2) of the anti-CD20/anti-CD3 bispecific antibody to be administered on Day 15 (±1 day) of the first dosing cycle, wherein the C1D1 of the anti-CD20/anti-CD3 bispecific antibody is about 2.5 mg, and the C1D2 of the anti-CD20/anti-CD3 bispecific antibody is about 10 mg; and (ii) a single dose (C1D1) of the anti-CD79b antibody drug conjugate to be administered on Day 2 (±1 day) of the first dosing cycle; (b) the second to sixth dosing cycles each comprises a single dose (C2D1-C6D1) of the anti-CD20/anti-CD3 bispecific antibody and a single dose (C2D1-C6D1) of the anti-CD79b antibody drug conjugate; and (c) the seventh to $12^{th}$ dosing cycles each comprises a single dose (C7D1-C12D1) of the anti-CD20/anti-CD3 bispecific antibody and does not comprise administration of the anti-CD79b antibody drug conjugate, and wherein each single dose C2D1-C12D1 of the anti-CD20/anti-CD3 bispecific antibody is to be administered on Day 1 (±1 day) of each dosing cycle, and each single dose C2D1-C6D1 of the anti-CD79b antibody drug conjugate is to be administered on Day 1 (±1 day) of each dosing cycle, and wherein each single dose C2D1-C12D1 of the anti-CD20/anti-CD3 bispecific antibody is about 30 mg and each single dose C1D1-C6D1 of the anti-CD79b antibody drug conjugate is about 1.8 mg/kg.

In another aspect, the invention features use of an anti-CD79b antibody drug conjugate and an anti-CD20/anti-CD3 bispecific antibody in the manufacture of a medicament for treating a population of subjects having a R/R NHL, wherein the anti-CD79b antibody drug conjugate and the anti-CD20/anti-CD3 bispecific antibody are administered in a dosing regimen comprising 12 dosing cycles, wherein: (a) the first dosing cycle comprises: (i) a first dose (C1D1) of the anti-CD20/anti-CD3 bispecific antibody to be administered on Day 8 (±1 day) of the first dosing cycle and a second dose (C1D2) of the anti-CD20/anti-CD3 bispecific antibody to be administered on Day 15 (±1 day) of the first dosing cycle, wherein the C1D1 of the anti-CD20/anti-CD3 bispecific antibody is about 2.5 mg, and the C1D2 of the anti-CD20/anti-CD3 bispecific antibody is about 10 mg; and (ii) a single dose (C1D1) of the anti-CD79b antibody drug conjugate to be administered on Day 2 (±1 day) of the first dosing cycle; (b) the second to sixth dosing cycles each comprises a single dose (C2D1-C6D1) of the anti-CD20/anti-CD3 bispecific antibody and a single dose (C2D1-C6D1) of the anti-CD79b antibody drug conjugate; and (c) the seventh to $12^{th}$ dosing cycles each comprises a single dose (C7D1-C12D1) of the anti-CD20/anti-CD3 bispecific antibody and does not comprise administration of the anti-CD79b antibody drug conjugate, and wherein each single dose C2D1-C12D1 of the anti-CD20/anti-CD3 bispecific antibody is to be administered on Day 1 (±1 day) of each dosing cycle, and each single dose C2D1-C6D1 of the anti-CD79b antibody drug conjugate is to be administered on Day 1 (±1 day) of each dosing cycle, and wherein each single dose C2D1-C12D1 of the anti-CD20/anti-CD3 bispecific antibody is about 30 mg and each single dose C1D1-C6D1 of the anti-CD79b antibody drug conjugate is about 1.8 mg/kg.

In one aspect, the invention features a method of treating a population of subjects having a R/R NHL comprising administering to the subjects polatuzumab vedotin and glofitamab in a dosing regimen comprising at least a first dosing cycle and a second dosing cycle, wherein: (a) the first dosing cycle comprises a first dose (C1D1) of glofitamab administered on Day 8 (±1 day) of the first dosing cycle, a second dose (C1D2) of glofitamab administered on Day 15 (±1 day) of the first dosing cycle, and a single dose (C1D1) of polatuzumab vedotin administered on Day 2 (±1 day) of the first dosing cycle, wherein the C1D1 of glofitamab is about 2.5 mg, and the C1D2 of glofitamab is about 10 mg; and (b) the second dosing cycle comprises a single dose (C2D1) of glofitamab administered on Day 1 (±1 day) of the second dosing cycle and a single dose (C2D1) of polatuzumab vedotin administered on Day 1 (±1 day) of the second dosing cycle, wherein the C2D1 of glofitamab is about 30 mg, and wherein the C1D1 and the C2D1 of polatuzumab vedotin are each about 1.8 mg/kg.

In another aspect, the invention features polatuzumab vedotin and glofitamab for use in a method of treating a population of subjects having a R/R NHL, wherein polatuzumab vedotin and glofitamab are administered in a dosing regimen comprising at least a first dosing cycle and a second dosing cycle, wherein: (a) the first dosing cycle comprises a first dose (C1D1) of glofitamab to be administered on Day 8 (±1 day) of the first dosing cycle, a second dose (C1D2) of glofitamab to be administered on Day 15 (±1 day) of the first dosing cycle, and a single dose (C1D1) of polatuzumab vedotin to be administered on Day 2 (±1 day) of the first dosing cycle, wherein the C1D1 of glofitamab is about 2.5 mg, and the C1D2 of glofitamab is about 10 mg; and (b) the second dosing cycle comprises a single dose (C2D1) of glofitamab to be administered on Day 1 (±1 day) of the second dosing cycle and a single dose (C2D1) of polatuzumab vedotin to be administered on Day 1 (±1 day) of the second dosing cycle, wherein the C2D1 of glofitamab is about 30 mg, and wherein the C1D1 and the C2D1 of polatuzumab vedotin are each about 1.8 mg/kg.

In another aspect, the invention features use of polatuzumab vedotin and glofitamab in treating a population of subjects having a R/R NHL, wherein polatuzumab vedotin and glofitamab are administered in a dosing regimen comprising at least a first dosing cycle and a second dosing cycle, wherein: (a) the first dosing cycle comprises a first dose (C1D1) of glofitamab to be administered on Day 8 (±1 day) of the first dosing cycle, a second dose (C1D2) of glofitamab to be administered on Day 15 (±1 day) of the first dosing cycle, and a single dose (C1D1) of polatuzumab vedotin to be administered on Day 2 (±1 day) of the first dosing cycle, wherein the C1D1 of glofitamab is about 2.5 mg, and the C1D2 of glofitamab is about 10 mg; and (b) the second dosing cycle comprises a single dose (C2D1) of glofitamab to be administered on Day 1 (±1 day) of the second dosing cycle and a single dose (C2D1) of polatuzumab vedotin to be administered on Day 1 (±1 day) of the second dosing cycle, wherein the C2D1 of glofitamab is about 30 mg, and wherein the C1D1 and the C2D1 of polatuzumab vedotin are each about 1.8 mg/kg.

In another aspect, the invention features use of polatuzumab vedotin and glofitamab in the manufacture of a medicament for treating a population of subjects having a R/R NHL, wherein polatuzumab vedotin and glofitamab are administered in a dosing regimen comprising at least a first dosing cycle and a second dosing cycle, wherein: (a) the first dosing cycle comprises a first dose (C1D1) of glofitamab to be administered on Day 8 (±1 day) of the first dosing cycle, a second dose (C1D2) of glofitamab to be administered on Day 15 (±1 day) of the first dosing cycle, and a single dose (C1D1) of polatuzumab vedotin to be administered on Day 2 (±1 day) of the first dosing cycle, wherein the C1D1 of glofitamab is about 2.5 mg, and the C1D2 of glofitamab is about 10 mg; and (b) the second dosing cycle comprises a single dose (C2D1) of glofitamab to be administered on Day 1 (±1 day) of the second dosing cycle and a single dose (C2D1) of polatuzumab vedotin to be administered on Day 1 (±1 day) of the second dosing cycle, wherein the C2D1 of glofitamab is about 30 mg, and wherein the C1D1 and the C2D1 of polatuzumab vedotin are each about 1.8 mg/kg.

In one aspect, the invention features a method of treating a population of subjects having a R/R NHL comprising administering to the subjects polatuzumab vedotin and glofitamab in a dosing regimen comprising 12 dosing cycles, wherein: (a) the first dosing cycle comprises: (i) a first dose (C1D1) of glofitamab administered on Day 8 (±1 day) of the first dosing cycle and a second dose (C1D2) of glofitamab administered on Day 15 (±1 day) of the first dosing cycle, wherein the C1D1 of glofitamab is about 2.5 mg, and the C1D2 of glofitamab is about 10 mg; and (ii) a single dose (C1D1) of polatuzumab vedotin administered on Day 2 (±1 day) of the first dosing cycle; (b) the second to sixth dosing cycles each comprises a single dose (C2D1-C6D1) of glofitamab and a single dose (C2D1-C6D1) of polatuzumab vedotin; and (c) the seventh to 12$^{th}$ dosing cycles each comprises a single dose (C7D1-C12D1) of glofitamab and does not comprise administration of polatuzumab vedotin, and wherein each single dose C2D1-C12D1 of glofitamab is administered on Day 1 (±1 day) of each dosing cycle, and each single dose C2D1-C6D1 of polatuzumab vedotin is administered on Day 1 (±1 day) of each dosing cycle, and wherein each single dose C2D1-C12D1 of glofitamab is about 30 mg and each single dose C1D1-C6D1 of polatuzumab vedotin is about 1.8 mg/kg.

In another aspect, the invention features polatuzumab vedotin and glofitamab for use in a method of treating a population of subjects having a R/R NHL, wherein polatuzumab vedotin and glofitamab are administered in a dosing regimen comprising 12 dosing cycles, wherein: (a) the first dosing cycle comprises: (i) a first dose (C1D1) of glofitamab to be administered on Day 8 (±1 day) of the first dosing cycle and a second dose (C1D2) of glofitamab to be administered on Day 15 (±1 day) of the first dosing cycle, wherein the C1D1 of glofitamab is about 2.5 mg, and the C1D2 of glofitamab is about 10 mg; and (ii) a single dose (C1D1) of polatuzumab vedotin to be administered on Day 2 (±1 day) of the first dosing cycle; (b) the second to sixth dosing cycles each comprises a single dose (C2D1-C6D1) of glofitamab and a single dose (C2D1-C6D1) of polatuzumab vedotin; and (c) the seventh to 12$^{th}$ dosing cycles each comprises a single dose (C7D1-C12D1) of glofitamab and does not comprise administration of polatuzumab vedotin, and wherein each single dose C2D1-C12D1 of glofitamab is to be administered on Day 1 (±1 day) of each dosing cycle, and each single dose C2D1-C6D1 of polatuzumab vedotin is to be administered on Day 1 (±1 day) of each dosing cycle, and wherein each single dose C2D1-C12D1 of glofitamab is about 30 mg and each single dose C1D1-C6D1 of polatuzumab vedotin is about 1.8 mg/kg.

In another aspect, the invention features use of polatuzumab vedotin and glofitamab in treating a population of subjects having a R/R NHL, wherein polatuzumab vedotin and glofitamab are administered in a dosing regimen comprising 12 dosing cycles, wherein: (a) the first dosing cycle comprises: (i) a first dose (C1D1) of glofitamab to be administered on Day 8 (±1 day) of the first dosing cycle and a second dose (C1D2) of glofitamab to be administered on Day 15 (±1 day) of the first dosing cycle, wherein the C1D1 of glofitamab is about 2.5 mg, and the C1D2 of glofitamab is about 10 mg; and (ii) a single dose (C1D1) of polatuzumab vedotin to be administered on Day 2 (±1 day) of the first dosing cycle; (b) the second to sixth dosing cycles each comprises a single dose (C2D1-C6D1) of glofitamab and a single dose (C2D1-C6D1) of polatuzumab vedotin; and (c) the seventh to 12$^{th}$ dosing cycles each comprises a single dose (C7D1) of glofitamab and does not comprise administration of polatuzumab vedotin, and wherein each single dose C2D1-C12D1 of glofitamab is to be administered on Day 1 (±1 day) of each dosing cycle, and each single dose C2D1-C6D1 of polatuzumab vedotin is to be administered on Day 1 (±1 day) of each dosing cycle, and wherein each single dose C2D1-C12D1 of glofitamab is about 30 mg and each single dose C1D1-C6D1 of polatuzumab vedotin is about 1.8 mg/kg.

In another aspect, the invention features use of polatuzumab vedotin and glofitamab in the manufacture of a medicament for treating a population of subjects having a R/R NHL, wherein polatuzumab vedotin and glofitamab are administered in a dosing regimen comprising 12 dosing cycles, wherein: (a) the first dosing cycle comprises: (i) a first dose (C1D1) of glofitamab to be administered on Day 8 (±1 day) of the first dosing cycle and a second dose (C1D2) of glofitamab to be administered on Day 15 (±1 day) of the first dosing cycle, wherein the C1D1 of glofitamab is about 2.5 mg, and the C1D2 of glofitamab is about 10 mg; and (ii) a single dose (C1D1) of polatuzumab vedotin to be administered on Day 2 (±1 day) of the first dosing cycle; (b) the second to sixth dosing cycles each comprises a single dose (C2D1-C6D1) of glofitamab and a single dose (C2D1-C6D1) of polatuzumab vedotin; and (c) the seventh to 12$^{th}$ dosing cycles each comprises a single dose (C7D1) of glofitamab and does not comprise administration of polatuzumab vedotin, and wherein each single dose C2D1-C12D1 of glofitamab is to be administered on Day 1 (±1 day) of each dosing cycle, and each single dose C2D1-C6D1 of polatuzumab vedotin is to be administered on Day 1 (±1 day) of each dosing cycle, and wherein each single dose C2D1-C12D1 of glofitamab is about 30 mg and each single dose C1D1-C6D1 of polatuzumab vedotin is about 1.8 mg/kg.

In some embodiments, the complete response rate is at least 20% (e.g., at least 25%, at least 40%, at least 50%, at least 60%, at least 70%, at least 80%, or at least 90%; e.g., between 20-100%, between 40-100%, between 60-100%, between 80-100%, between 20-80%, between 20-60%, between 20-40%, between 40-80%, between 40-60%, between 30-50%, or between 35-45%; e.g., about 20%, about 25%, about 30%, about 35%, about 40%, about 41%, about 42%, about 43%, about 44%, about 45%, about 50%, about 60%, or more). In some embodiments, the complete response rate is at least 40%. In particular embodiments, the complete response rate in the population of subjects having a R/R NHL is about 42%. In some embodiments, the overall response rate is at least 30% (e.g., at least 35%, at least 40%, at least 50%, at least 60%, at least 70%, at least 80%, or at least 90%; e.g., between 30-100%, between 50-100%, between 70-100%, between 30-90%, between 30-70%, between 30-50%, between 40-80%, between 40-60%, between 45-55%, or between 35-45%; e.g., about 30%, about 35%, about 40%, about 45%, about 48%, about 49%, about 50%, about 51%, about 52%, about 55%, about 60%, about 70%, or more). In some embodiments, the overall response rate is at least 50%. In particular embodiments, the overall response rate in the population of subjects having a R/R NHL is about 50%.

In some embodiments, the B cell proliferative disorder is a R/R MCL. In some embodiments, the R/R NHL is a R/R MCL. In some embodiments, the complete response rate is at least 60% (e.g., at least 60%, at least 70%, at least 80%, or at least 90%; e.g., between 60-100%, between 70-100%, between 80-100%, between 90-100%, between 60-90%, between 60-80%, between 60-70%, between 70-90%, between 80-90%, between 80-100%, or between 90-100%; e.g., about 60%, about 70%, about 75%, about 80%, about 83%, about 85%, about 87%, about 90%, about 95%, about 97%, about 98%, about 99%, or more). In some embodiments, the complete response rate is at least 80%. In particular embodiments, the complete response rate in the population of subjects having a R/R NHL is at least about 85%. In particular embodiments, the complete response rate in the population of subjects having a R/R MCL is at least about 85%. In particular embodiments, the complete response rate in the population of subjects having a R/R MCL is about 100%. In some embodiments, the overall response rate is at least 60% (e.g., at least 60%, at least 70%, at least 80%, or at least 90%; e.g., between 60-100%, between 70-100%, between 80-100%, between 90-100%, between 60-90%, between 60-80%, between 60-70%, between 70-90%, between 80-90%, between 80-100%, or between 90-100%; e.g., about 60%, about 70%, about 75%, about 80%, about 83%, about 85%, about 87%, about 90%, about 95%, about 97%, about 98%, about 99%, or more). In particular embodiments, the overall response rate in the population of subjects having a R/R NHL is at least about 85%. In particular embodiments, the overall response rate in the population of subjects having a R/R MCL is at least about 85%. In particular embodiments, the overall response rate in the population of subjects having a R/R MCL is about 100%. In some embodiments, the overall response rate is at least 80%.

In some embodiments, the B cell proliferative disorder is a R/R DLBCL. In some embodiments, the R/R NHL is a R/R MCL. In some embodiments, the R/R NHL is a R/R DLBCL. In some embodiments, the complete response rate is at least 60% (e.g., at least 60%, at least 70%, at least 80%, or at least 90%; e.g., between 60-100%, between 70-100%, between 80-100%, between 90-100%, between 60-90%, between 60-80%, between 60-70%, between 60-65%, between 65-75%, or between 75-85%; e.g., about 60%, about 61%, about 62%, about 65%, about 68%, about 69%, about 70%, about 71%, about 72%, about 73%, about 74%, about 75%, about 76%, about 77%, about 80%, about 85%, about 90%, or more). In some embodiments, the complete response rate is at least 65%. In some embodiments, the complete response rate is at least 70%. In particular embodiments, the complete response rate in the population of subjects having a R/R DLBCL is about 60%. In particular embodiments, the complete response rate in the population of subjects having a R/R DLBCL is about 65%. In particular embodiments, the complete response rate in the population of subjects having a R/R DLBCL is about 70%. In particular embodiments, the complete response rate in the population of subjects having a R/R DLBCL is about 75%. In some embodiments, the overall response rate is at least 60% (e.g., at least 60%, at least 70%, at least 80%, or at least 90%; e.g., between 60-100%, between 70-100%, between 80-100%, between 90-100%, between 60-90%, between 60-80%, between 60-70%, between 60-65%, between 65-75%, between 70-90%, or between 75-85%; e.g., about 60%, about 63%, about 64%, about 65%, about 66%, about 67%, about 70%, about 73%, about 74%, about 75%, about 76%, about 77%, about 80%, about 83%, about 84%, about 85%, about 86%, about 87%, about 90%, or more). In some embodiments, the overall response rate is at least 70%. In some embodiments, the overall response rate is at least 80%. In particular embodiments, the overall response rate in the population of subjects having a R/R DLBCL is about 65%. In particular embodiments, the overall response rate in the population of subjects having a R/R DLBCL is about 73%. In particular embodiments, the overall response rate in the population of subjects having a R/R DLBCL is about 75%. In particular embodiments, the overall response rate in the population of subjects having a R/R DLBCL is about 85%.

In some embodiments, the B cell proliferative disorder is a R/R DLBCL. In some embodiments, the R/R NHL is a R/R DLBCL. In some embodiments, the complete response rate is at least 35% (e.g., least 40%, at least 50%, at least 60%, at least 70%, at least 80%, at least 90%, or more; e.g., between 30-100%, between 50-100%, between 70-100%, between 35-90%, between 45-90%, between 35-70%, between 35-50%, between 40-80%, between 40-60%, between 45-55%, or between 35-45%; e.g., about 35%, about 40%, about 45%, about 48%, about 49%, about 50%, about 51%, about 52%, about 55%, about 60%, about 70%, about 75%, about 80%, about 85%, or more). In some embodiments, the complete response rate is at least 45%. In some embodiments, the complete response rate is at least 55%. In some embodiments, the complete response rate is at least 75%. In some embodiments, the complete response rate is at least 85%. In some embodiments, the complete response rate is at least 90%. In particular embodiments, the complete response rate in the population of subjects having a R/R DLBCL is about 46%. In particular embodiments, the complete response rate in the population of subjects having a R/R DLBCL is about 52%. In particular embodiments, the complete response rate in the population of subjects having a R/R DLBCL is about 86%. In some embodiments, the overall response rate is at least 85% (e.g., at least 86%, at least 87%, at least 88%, at least 89%, at least 90%, at least 91%, at least 92%, at least 93%, at least 94%, at least 95%, at least 96%, at least 97%, at least 98%, at least 99%, or more; e.g., between 85-100%, between 87-100%, between 90-100%, between 95-100%, between 85-97%, between 85-95%, between 85-90%, between 85-87%, between 90-95%, or between 93-97%; e.g., about 85%, about 86%, about 87%, about 88%, about 89%, about 90%, about 91%, about 92%, about 93%, about 94%, about 95%, about 96%, about 97%, about 98%, about 99%, or more). In some embodiments, the overall response rate is at least 85%. In some embodiments, the overall response rate is at least 90%. In particular embodiments, the overall response rate in the population of subjects having a R/R DLBCL is about 86%.

In some embodiments, the complete response rate is higher than a reference complete response rate in a reference population of subjects treated with a combination therapy comprising an anti-CD20/anti-CD3 bispecific antibody and an anti-PD-L1 antagonist antibody and not comprising an anti-CD79b antibody drug conjugate. In some embodiments, the objective response rate is higher than a reference objective response rate in a reference population of subjects treated with a combination therapy comprising an anti-CD20/anti-CD3 bispecific antibody and an anti-PD-L1 antagonist antibody and not comprising an anti-CD79b antibody drug conjugate. In some embodiments, the complete response rate is higher than a reference complete response rate in a reference population of subjects treated with a combination therapy comprising glofitamab and atezolizumab and not comprising polatuzumab vedotin. In some embodiments, the objective response rate is higher than a reference objective response rate in a reference population of subjects treated with a combination therapy comprising glofitamab and atezolizumab and not comprising polatuzumab vedotin.

In some embodiments, the subject is human. In some embodiments, each subject in a population of subjects is human. In some embodiments, each subject in a reference population of subjects is human. In some embodiments, the subject or population of subjects has received at least two prior systemic therapies (e.g., two, three, four, five, six, or more prior systemic therapies). In some embodiments, the subject or population of subjects is ineligible for autologous stem cell transplant (SCT).

BRIEF DESCRIPTION OF THE DRAWINGS

FIG. 1A-FIG. 1N are schematic diagrams showing configurations of exemplary anti-CD20/anti-CD3 bispecific antibodies.

DETAILED DESCRIPTION OF THE INVENTION

Figure 2:
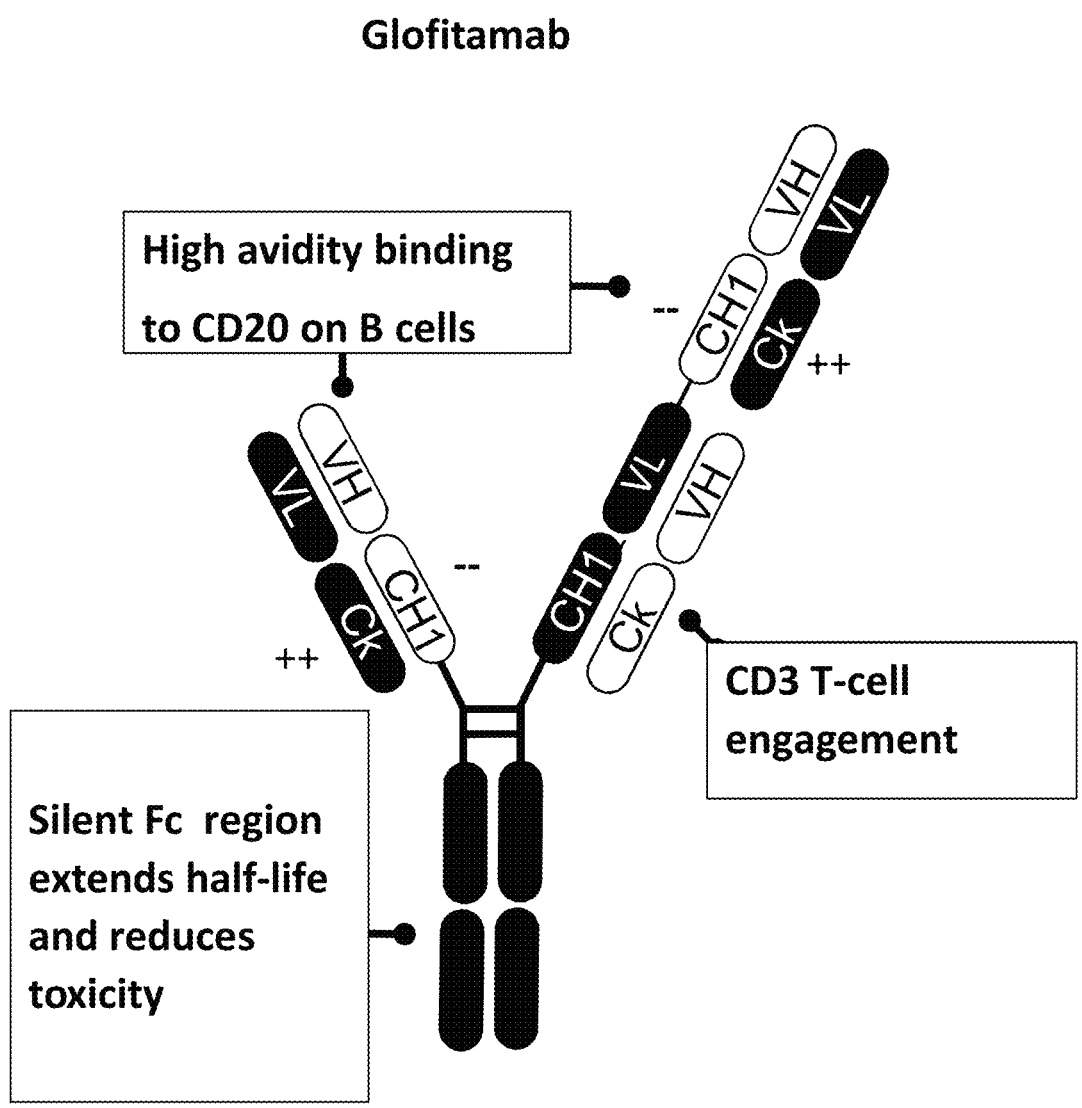
FIG. 2 is a schematic diagram showing the structure of glofitamab.

The invention provides methods for treating a subject having a CD20-positive cell proliferative disorder (e.g., a B cell proliferative disorder (e.g., non-Hodgkin's lymphoma (NHL) (e.g., a relapsed and/or refractory NHL, a diffuse-large B cell lymphoma (DLBCL) (e.g., a relapsed and/or refractory DLBCL), a follicular lymphoma (FL) (e.g., a relapsed and/or refractory FL or a transformed FL), or a mantle cell lymphoma (MCL) (e.g., a relapsed or refractory MCL)), or a central nervous system lymphoma (CNSL))) that includes administering to the subject an anti-CD79b antibody drug conjugate and/or an anti-CD20/anti-CD3 bispecific antibody, e.g., in a fractionated, dose-escalation dosing regimen. The method comprises at least a first dosing cycle and a second dosing cycle, wherein: (a) the first dosing cycle comprises a first dose (C1D1) of the anti-CD20/anti-CD3 bispecific antibody and a second dose (C1D2) of the anti-CD20/anti-CD3 bispecific antibody, wherein the C1D1 of the anti-CD20/anti-CD3 bispecific antibody is about 2.5 mg and the C1D2 of the anti-CD20/anti-CD3 bispecific antibody is about 10 mg; and (b) the second dosing cycle comprises a single dose (C2D1) of the anti-CD20/anti-CD3 bispecific antibody, wherein the C2D1 of the anti-CD20/anti-CD3 bispecific antibody is about 10 mg, about 16 mg, or about 30 mg.

The invention is based, in part, on the discovery that a fractionated, dose-escalation dosing regimen involving administration of an anti-CD20/anti-CD3 bispecific antibody (e.g., glofitamab) over multiple dosing cycles (e.g., wherein the first dosing cycle is a step-up, fractionated dosing cycle) can very effectively treat subjects having a CD20-positive cell proliferative disorder (e.g., B cell proliferative disorder) and with an acceptable safety profile (e.g., with respect to cytokine release syndrome).

I. General Techniques

The practice of the present invention will employ, unless otherwise indicated, conventional techniques of molecular biology (including recombinant techniques), microbiology, cell biology, biochemistry, and immunology, which are within the skill of the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Current Protocols in Molecular Biology" (F. M. Ausubel et al., eds., 1987, and periodic updates); "PCR: The Polymerase Chain Reaction", (Mullis et al., ed., 1994); "A Practical Guide to Molecular Cloning" (Perbal Bernard V., 1988); "Phage Display: A Laboratory Manual" (Barbas et al., 2001).

II. Definitions

Terms are used herein as generally used in the art, unless otherwise defined in the following.

The term "cluster of differentiation 20" or "CD20" as used herein, refers to any native CD20 from any vertebrate source, including mammals such as primates (e.g., humans) and rodents (e.g., mice and rats), unless otherwise indicated. CD20 (also known as B-lymphocyte antigen CD20, B-lymphocyte surface antigen B1, Leu-16, Bp35, BM5, and LF5; the human protein is characterized in UniProt database entry P11836) is a hydrophobic transmembrane protein with a molecular weight of approximately 35 kD expressed on pre-B and mature B lymphocytes (Valentine, M. A. et al., *J. Biol. Chem.* 264 (1989) 11282-11287; Tedder, T. F., et al., *Proc. Natl. Acad. Sci. U.S.A.* 85 (1988) 208-212; Stamenkovic, I., et al., *J. Exp. Med.* 167 (1988) 1975-1980; Einfeld, D. A., et al., EMBO J. 7 (1988) 711-717; Tedder, T. F., et al., *J. Immunol.* 142 (1989) 2560-2568). The corresponding human gene is Membrane-spanning 4-domains, subfamily A, member 1, also known as MS4A1. This gene encodes a member of the membrane-spanning 4A gene family. Members of this nascent protein family are characterized by common structural features and similar intron/exon splice boundaries and display unique expression patterns among hematopoietic cells and nonlymphoid tissues. This gene encodes the B-lymphocyte surface molecule which plays a role in the development and differentiation of B-cells into plasma cells. This family member is localized to 11q12, among a cluster of family members. The term encompasses "full-length," unprocessed CD20 as well as any form of CD20 that results from processing in the cell. The term also encompasses naturally occurring variants of CD20, e.g., splice variants or allelic variants. Alternative splicing of this gene results in two transcript variants which encode the same protein. In one embodiment, CD20 is human CD20.

The terms "anti-CD20 antibody" and "an antibody that binds to CD20" refer to an antibody that is capable of binding CD20 with sufficient affinity such that the antibody is useful as a diagnostic and/or therapeutic agent in targeting CD20. In one embodiment, the extent of binding of an anti-CD20 antibody to an unrelated, non-CD20 protein is less than about 10% of the binding of the antibody to CD20 as measured, e.g., by a radioimmunoassay (RIA). In certain embodiments, an antibody that binds to CD20 has a dissociation constant ($K_D$) of ≤1 µM, ≤100 nM, ≤10 nM, ≤1 nM, ≤0.1 nM, ≤0.01 nM, or ≤0.001 nM (e.g., $10^{-8}$ M or less, e.g., from $10^{-8}$ M to $10^{-13}$ M, e.g., from $10^{-9}$ M to $10^{-13}$ M). In certain embodiments, an anti-CD20 antibody binds to an epitope of CD20 that is conserved among CD20 from different species.

By "Type II anti-CD20 antibody" is meant an anti-CD20 antibody having binding properties and biological activities of Type II anti-CD20 antibodies as described in Cragg et al., *Blood* 103 (2004) 2738-2743; Cragg et al., *Blood* 101 (2003) 1045-1052, Klein et al., mAbs 5 (2013), 22-33, and summarized in Table 1 below.

TABLE 1

Properties of type I and type II anti-CD20 antibodies

| type I anti-CD20 antibodies | type II anti-CD20 antibodies |
| --- | --- |
| Bind class I CD20 epitope | Bind class II CD20 epitope |
| Localize CD20 to lipid rafts | Do not localize CD20 to lipid rafts |
| High CDC * | Low CDC * |
| ADCC activity * | ADCC activity * |
| Full binding capacity to B cells | Approx. half binding capacity to B cells |
| Weak homotypic aggregation | Homotypic aggregation |
| Low cell death induction | Strong cell death induction |

* if $IgG_1$ isotype

Examples of type II anti-CD20 antibodies include, e.g., obinutuzumab (GA101), tositumumab (B1), humanized B-Ly1 antibody IgG1 (a chimeric humanized IgG1 antibody as disclosed in WO 2005/044859), 11B8 IgG1 (as disclosed in WO 2004/035607) and AT80 IgG1.

Examples of type I anti-CD20 antibodies include, e.g., rituximab, ofatumumab, veltuzumab, ocaratuzumab, ocrelizumab, PRO131921, ublituximab, HI47 IgG3 (ECACC, hybridoma), 2C6 IgG1 (as disclosed in WO 2005/103081), 2F2 IgG1 (as disclosed in WO 2004/035607 and WO 2005/103081) and 2H7 IgG1 (as disclosed in WO 2004/056312).

"CD3" refers to any native CD3 from any vertebrate source, including mammals such as primates (e.g., humans), non-human primates (e.g., cynomolgus monkeys) and rodents (e.g., mice and rats), unless otherwise indicated. The term encompasses "full-length," unprocessed CD3 as well as any form of CD3 that results from processing in the cell. The term also encompasses naturally occurring variants of CD3, e.g., splice variants or allelic variants. In one embodiment, CD3 is human CD3, particularly the epsilon subunit of human CD3 (CD3ε). The amino acid sequence of human CD3ε is shown in UniProt (www.uniprot.org) accession no. P07766 (version 144), or NCBI (www.ncbi.nlm.nih.gov/) RefSeq NP_000724.1. The amino acid sequence of cynomolgus monkey [*Macaca fascicularis*] CD3ε is shown in NCBI GenBank no. BAB71849.1.

The terms "anti-CD20/anti-CD3 bispecific antibody" and "a bispecific antibody that binds to CD20 and CD3" refer to a bispecific antibody that is capable of binding both CD20 and CD3 with sufficient affinity such that the antibody is useful as a diagnostic and/or therapeutic agent in targeting CD20 and/or CD3. In one embodiment, the extent of binding of an anti-CD20/anti-CD3 bispecific antibody to an unrelated, non-CD3 protein and/or non-CD20 protein is less than about 10% of the binding of the antibody to CD3 and/or CD20 as measured, e.g., by a radioimmunoassay (RIA). In certain embodiments, an anti-CD20/anti-CD3 bispecific antibody has a dissociation constant ($K_D$) of ≤1 µM, ≤100 nM, ≤10 nM, ≤1 nM, ≤0.1 nM, ≤0.01 nM, or ≤0.001 nM (e.g., $10^{-8}$ M or less, e.g., from $10^{-8}$ M to $10^{-13}$ M, e.g., from $10^{-9}$ M to $10^{-13}$ M) to CD3 and/or CD20. In certain embodiments, an anti-CD20/anti-CD3 bispecific antibody binds to an epitope of CD3 that is conserved among CD3 from different species and/or an epitope of CD20 that is conserved among CD20 from different species. One example of an anti-CD20/anti-CD3 bispecific antibody is glofitamab (WHO Drug Information (International Nonproprietary Names for Pharmaceutical Substances), Recommended INN: List 83, 2020, vol. 34, no. 1, p. 39; also known as CD20-TCB, R07082859, or RG6026; CAS #: 2229047-91-8).

The term "cluster of differentiation 79b" or "CD79b," as used herein, refers to any native CD79b from any vertebrate source, including mammals such as primates (e.g., humans) and rodents (e.g., mice and rats), unless otherwise indicated. The term encompasses "full-length," unprocessed CD79b, as well as any form of CD79b that results from processing in the cell. The term also encompasses naturally occurring variants of CD79b, including, for example, splice variants or allelic variants. CD79b includes, for example, human CD79b protein (NCBI RefSeq No. NP_000617), which is 229 amino acids in length.

The terms "anti-CD79b antibody" and "an antibody that binds to CD79b" refer to an antibody that is capable of binding CD79b with sufficient affinity such that the antibody is useful as a diagnostic and/or therapeutic agent in targeting CD79b. In one embodiment, the extent of binding of an anti-CD79b antibody to an unrelated, non-CD79b protein is less than about 10% of the binding of the antibody to CD79b as measured, e.g., by a radioimmunoassay (RIA). In certain embodiments, an antibody that binds to CD79b has a dissociation constant (KD) of $\leq 1$ μM, $\leq 100$ nM, $\leq 10$ nM, $\leq 1$ nM, $\leq 0.1$ nM, $\leq 0.01$ nM, or $\leq 0.001$ nM (e.g., $10^{-8}$ M or less, e.g., from $10^{-8}$ M to $10^{-13}$ M, or e.g., from $10^{-9}$ M to $10^{-13}$ M). In certain embodiments, an anti-CD79b antibody binds to an epitope of CD79b that is conserved among CD79b from different species.

As used herein, the term "release of cytokines" or "cytokine release" is synonymous with "cytokine storm" or "cytokine release syndrome" (abbreviated as "CRS"), and refers to an increase in the levels of cytokines, particularly tumor necrosis factor alpha (TNF-α), interferon gamma (IFN-γ), interleukin-6 (IL-6), interleukin-10 (IL-10), interleukin-2 (IL-2) and/or interleukin-8 (IL-8), in the blood of a subject during or shortly after (e.g., within 1 day of) administration of a therapeutic agent, resulting in adverse symptoms. Cytokine release is defined as a supraphysiologic response following administration of any immune therapy that results in activation or engagement of endogenous or infused T cells and/or other immune effector cells. Symptoms can be progressive, always include fever at the onset, and may include hypotension, capillary leak (hypoxia), and end-organ dysfunction (Lee et al. 2019). In some instances, e.g., after the administration of CAR-T cells, CRS can also occur several days after administration upon expansion of the CAR-T cells. The incidence and severity typically decrease with subsequent infusions. Symptoms may range from symptomatic discomfort to fatal events, and may include fever, chills, dizziness, hypertension, hypotension, dyspnea, restlessness, sweating, flushing, skin rash, tachycardia, tachypnea, headache, tumor pain, nausea, vomiting and/or organ failure.

The term "amino acid mutation" as used herein is meant to encompass amino acid substitutions, deletions, insertions, and modifications. Any combination of substitution, deletion, insertion, and modification can be made to arrive at the final construct, provided that the final construct possesses the desired characteristics, e.g., reduced binding to an Fc receptor. Amino acid sequence deletions and insertions include amino- and/or carboxy-terminal deletions and insertions of amino acids. Particular amino acid mutations are amino acid substitutions. For the purpose of altering, e.g., the binding characteristics of an Fc region, non-conservative amino acid substitutions, i.e., replacing one amino acid with another amino acid having different structural and/or chemical properties, are particularly preferred. Amino acid substitutions include replacement by non-naturally occurring amino acids or by naturally occurring amino acid derivatives of the twenty standard amino acids (e.g., 4-hydroxyproline, 3-methylhistidine, ornithine, homoserine, 5-hydroxylysine). Amino acid mutations can be generated using genetic or chemical methods well known in the art. Genetic methods may include site-directed mutagenesis, PCR, gene synthesis and the like. It is contemplated that methods of altering the side chain group of an amino acid by methods other than genetic engineering, such as chemical modification, may also be useful. Various designations may be used herein to indicate the same amino acid mutation. For example, a substitution from proline at position 329 of the Fc region to glycine can be indicated as 329G, G329, $G_{329}$, P329G, or Pro329Gly.

"Affinity" refers to the strength of the sum total of non-covalent interactions between a single binding site of a molecule (e.g., a receptor) and its binding partner (e.g., a ligand). Unless indicated otherwise, as used herein, "binding affinity" refers to intrinsic binding affinity which reflects a 1:1 interaction between members of a binding pair (e.g., receptor and a ligand). The affinity of a molecule X for its partner Y can generally be represented by the dissociation constant ($K_D$), which is the ratio of dissociation and association rate constants ($k_{off}$ and $k_{on}$, respectively). Thus, equivalent affinities may comprise different rate constants, as long as the ratio of the rate constants remains the same. Affinity can be measured by well-established methods known in the art. A particular method for measuring affinity is Surface Plasmon Resonance (SPR).

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

As used herein, the term "antigen binding moiety" refers to a polypeptide molecule that specifically binds to an antigenic determinant. In one embodiment, an antigen binding moiety is able to direct the entity to which it is attached (e.g., a cytokine or a second antigen binding moiety) to a target site, for example to a specific type of tumor cell or tumor stroma bearing the antigenic determinant. Antigen binding moieties include antibodies and fragments thereof as further defined herein. Preferred antigen binding moieties include an antigen binding domain of an antibody, comprising an antibody heavy chain variable region and an antibody light chain variable region. In certain embodiments, the antigen binding moieties may include antibody constant regions as further defined herein and known in the art. Useful heavy chain constant regions include any of the five isotypes: α, δ, ε, γ, or μ. Useful light chain constant regions include any of the two isotypes: κ and λ.

By "binds," "specifically binds," or is "specific for" is meant that the binding is selective for the antigen and can be discriminated from unwanted or non-specific interactions. The ability of an antigen binding moiety to bind to a specific antigenic determinant can be measured either through an enzyme-linked immunosorbent assay (ELISA) or other techniques familiar to one of skill in the art, e.g., surface plasmon resonance technique (analyzed on a BIACORE® instrument) (Liljeblad et al., *Glyco J.* 17, 323-329 (2000)), and traditional binding assays (Heeley, *Endocr Res.* 28, 217-229 (2002)). In one embodiment, the extent of binding of an antigen binding moiety to an unrelated protein is less than about 10% of the binding of the antigen binding moiety to the antigen as measured, e.g., by SPR. In certain embodiments, an antigen binding moiety that binds to the antigen, or an antigen binding molecule comprising that antigen binding moiety, has a dissociation constant ($K_D$) of $\leq 1$ μM, ≤100 nM, ≤10 nM, ≤1 nM, ≤0.1 nM, ≤0.01 nM, or ≤0.001 nM (e.g., $10^{-8}$ M or less, e.g., from $10^{-8}$ M to $10^{-13}$ M, e.g., from $10^{-9}$ M to $10^{-13}$ M).

"Reduced binding," for example reduced binding to an Fc receptor, refers to a decrease in affinity for the respective interaction, as measured for example by SPR. For clarity the term includes also reduction of the affinity to zero (or below the detection limit of the analytic method), i.e., complete abolishment of the interaction. Conversely, "increased binding" refers to an increase in binding affinity for the respective interaction.

As used herein, the term "antigen binding molecule" refers in its broadest sense to a molecule that specifically binds an antigenic determinant. Examples of antigen binding molecules are immunoglobulins and derivatives, e.g., fragments, thereof.

As used herein, the term "antigenic determinant" is synonymous with "antigen" and "epitope," and refers to a site (e.g., a contiguous stretch of amino acids or a conformational configuration made up of different regions of non-contiguous amino acids) on a polypeptide macromolecule to which an antigen binding moiety binds, forming an antigen binding moiety-antigen complex. Useful antigenic determinants can be found, for example, on the surfaces of tumor cells, on the surfaces of virus-infected cells, on the surfaces of other diseased cells, free in blood serum, and/or in the extracellular matrix (ECM). The proteins referred to as antigens herein (e.g., CD3) can be any native form the proteins from any vertebrate source, including mammals such as primates (e.g., humans) and rodents (e.g., mice and rats), unless otherwise indicated. In a particular embodiment the antigen is a human protein. Where reference is made to a specific protein herein, the term encompasses the "full-length", unprocessed protein as well as any form of the protein that results from processing in the cell. The term also encompasses naturally occurring variants of the protein, e.g., splice variants or allelic variants. An exemplary human protein useful as antigen is CD3, particularly the epsilon subunit of CD3 (see UniProt no. P07766 (version 130), NCBI RefSeq no. NP_000724.1, for the human sequence; or UniProt no. Q95II5 (version 49), NCBI GenBank no. BAB71849.1, for the cynomolgus [*Macaca fascicularis*] sequence). In certain embodiments a T cell activating bispecific antigen binding molecule described herein binds to an epitope of CD3 or a target cell antigen that is conserved among the CD3 or target cell antigen from different species.

As used herein, term "polypeptide" refers to a molecule composed of monomers (amino acids) linearly linked by amide bonds (also known as peptide bonds). The term "polypeptide" refers to any chain of two or more amino acids, and does not refer to a specific length of the product. Thus, peptides, dipeptides, tripeptides, oligopeptides, "protein," "amino acid chain," or any other term used to refer to a chain of two or more amino acids, are included within the definition of "polypeptide," and the term "polypeptide" may be used instead of, or interchangeably with any of these terms. The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-naturally occurring amino acids. A polypeptide may be derived from a natural biological source or produced by recombinant technology, but is not necessarily translated from a designated nucleic acid sequence. It may be generated in any manner, including by chemical synthesis. A polypeptide of the invention may be of a size of about 3 or more, 5 or more, 10 or more, 20 or more, 25 or more, 50 or more, 75 or more, 100 or more, 200 or more, 500 or more, 1,000 or more, or 2,000 or more amino acids. Polypeptides may have a defined three-dimensional structure, although they do not necessarily have such structure. Polypeptides with a defined three-dimensional structure are referred to as folded, and polypeptides which do not possess a defined three-dimensional structure, but rather can adopt a large number of different conformations, and are referred to as unfolded.

By an "isolated" polypeptide or a variant, or derivative thereof is intended a polypeptide that is not in its natural milieu. No particular level of purification is required. For example, an isolated polypeptide can be removed from its native or natural environment. Recombinantly produced polypeptides and proteins expressed in host cells are considered isolated for the purpose of the invention, as are native or recombinant polypeptides which have been separated, fractionated, or partially or substantially purified by any suitable technique.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or MEGALIGN® (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, California, or may be compiled from the source code. The ALIGN-2 program should be compiled for use on a UNIX® operating system, including digital UNIX® V4.0D. All sequence comparison parameters are set by the ALIGN-2 program and do not vary. In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

$$100 \text{ times the fraction } X/Y$$

where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen binding activity.

The terms "full length antibody," "intact antibody," and "whole antibody" are used herein interchangeably to refer to an antibody having a structure substantially similar to a native antibody structure or having heavy chains that contain an Fc region as defined herein.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$, diabodies, linear antibodies, single-chain antibody molecules (e.g., scFv), and multispecific antibodies formed from antibody fragments. The term "antibody fragment" as used herein also encompasses single-domain antibodies.

The term "immunoglobulin molecule" refers to a protein having the structure of a naturally occurring antibody. For example, immunoglobulins of the IgG class are heterotetrameric glycoproteins of about 150,000 Daltons, composed of two light chains and two heavy chains that are disulfide-bonded. From N- to C-terminus, each heavy chain has a variable region (VH), also called a variable heavy domain or a heavy chain variable domain, followed by three constant domains (CH1, CH2, and CH3), also called a heavy chain constant region. Similarly, from N- to C-terminus, each light chain has a variable region (VL), also called a variable light domain or a light chain variable domain, followed by a constant light (CL) domain, also called a light chain constant region. The heavy chain of an immunoglobulin may be assigned to one of five classes, called α (IgA), δ (IgD), ε(IgE), γ (IgG), or μ(IgM), some of which may be further divided into subclasses, e.g., $γ_1$ (IgG$_1$), $γ_2$ (IgG$_2$), $γ_3$ (IgG$_3$), $γ_4$ (IgG$_4$), $α_1$ (IgA$_1$) and $α_2$ (IgA$_2$). The light chain of an immunoglobulin may be assigned to one of two types, called kappa (κ) and lambda (λ), based on the amino acid sequence of its constant domain. An immunoglobulin essentially consists of two Fab molecules and an Fc domain, linked via the immunoglobulin hinge region.

The term "antigen binding domain" refers to the part of an antibody that comprises the area which specifically binds to and is complementary to part or all of an antigen. An antigen binding domain may be provided by, for example, one or more antibody variable domains (also called antibody variable regions). Preferably, an antigen binding domain comprises an antibody light chain variable region (VL) and an antibody heavy chain variable region (VH).

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). See, e.g., Kindt et al., *Kuby Immunology*, 6$^{th}$ ed., W.H. Freeman and Co., page 91 (2007). A single VH or VL domain may be sufficient to confer antigen binding specificity.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR" as used herein refers to each of the regions of an antibody variable domain which are hypervariable in sequence ("complementarity determining regions" or "CDRs") and/or form structurally defined loops ("hypervariable loops") and/or contain the antigen-contacting residues ("antigen contacts"). Generally, antibodies comprise six HVRs: three in the VH (H1, H2, H3), and three in the VL (L1, L2, L3). Exemplary HVRs herein include:

(a) hypervariable loops occurring at amino acid residues 26-32 (L1), 50-52 (L2), 91-96 (L3), 26-32 (H1), 53-55 (H2), and 96-101 (H3) (Chothia and Lesk, *J. Mol. Biol.* 196:901-917 (1987)); (b) CDRs occurring at amino acid residues 24-34 (L1), 50-56 (L2), 89-97 (L3), 31-35b (H1), 50-65 (H2), and 95-102 (H3) (Kabat et al., *Sequences of Proteins of Immunological Interest*, 5th Ed. Public Health Service, National Institutes of Health, Bethesda, MD (1991));

(c) antigen contacts occurring at amino acid residues 27c-36 (L1), 46-55 (L2), 89-96 (L3), 30-35b (H1), 47-58 (H2), and 93-101 (H3) (MacCallum et al. *J. Mol. Biol.* 262: 732-745 (1996)); and (d) combinations of (a), (b), and/or (c), including HVR amino acid residues 46-56 (L2), 47-56 (L2), 48-56 (L2), 49-56 (L2), 26-35 (H1), 26-35b (H1), 49-65 (H2), 93-102 (H3), and 94-102 (H3).

Unless otherwise indicated, HVR residues and other residues in the variable domain (e.g., FR residues) are numbered herein according to Kabat et al., supra.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., Sequences of Proteins of Immunological Interest, Fifth Edition, NIH Publication 91-3242, Bethesda MD (1991), vols. 1-3. In one embodiment, for the VL, the subgroup is subgroup kappa I as in Kabat et al., supra. In one embodiment, for the VH, the subgroup is subgroup III as in Kabat et al., supra.

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called α, δ, ε, γ, and μ, respectively.

The term IgG "isotype" or "subclass" as used herein is meant any of the subclasses of immunoglobulins defined by the chemical and antigenic characteristics of their constant regions.

The term "Fc domain" or "Fc region" herein is used to define a C-terminal region of an immunoglobulin heavy chain that contains at least a portion of the constant region. The term includes native sequence Fc regions and variant Fc regions. Although the boundaries of the Fc region of an IgG heavy chain might vary slightly, the human IgG heavy chain Fc region is usually defined to extend from Cys226, or from Pro230, to the carboxyl-terminus of the heavy chain. However, antibodies produced by host cells may undergo post-translational cleavage of one or more, particularly one or two, amino acids from the C-terminus of the heavy chain. Therefore an antibody produced by a host cell by expression of a specific nucleic acid molecule encoding a full-length heavy chain may include the full-length heavy chain, or it may include a cleaved variant of the full-length heavy chain (also referred to herein as a "cleaved variant heavy chain"). This may be the case where the final two C-terminal amino acids of the heavy chain are glycine (G446) and lysine (K447, EU numbering). Therefore, the C-terminal lysine (Lys447), or the C-terminal glycine (Gly446) and lysine (K447), of the Fc region may or may not be present. Unless otherwise specified herein, numbering of amino acid residues in the Fc region or constant region is according to the EU numbering system, also called the EU index, as described in Kabat et al., *Sequences of Proteins of Immunological Interest*, 5th Ed. Public Health Service, National Institutes of Health, Bethesda, MD, 1991 (see also above). A "subunit" of an Fc domain as used herein refers to one of the two polypeptides forming the dimeric Fc domain, i.e., a polypeptide comprising C-terminal constant regions of an immunoglobulin heavy chain, capable of stable self-association. For example, a subunit of an IgG Fc domain comprises an IgG CH2 and an IgG CH3 constant domain.

A "modification promoting the association of the first and the second subunit of the Fc domain" is a manipulation of the peptide backbone or the post-translational modifications of an Fc domain subunit that reduces or prevents the association of a polypeptide comprising the Fc domain subunit with an identical polypeptide to form a homodimer. A modification promoting association as used herein particularly includes separate modifications made to each of the two Fc domain subunits desired to associate (i.e., the first and the second subunit of the Fc domain), wherein the modifications are complementary to each other so as to promote association of the two Fc domain subunits. For example, a modification promoting association may alter the structure or charge of one or both of the Fc domain subunits so as to make their association sterically or electrostatically favorable, respectively. Thus, (hetero)dimerization occurs between a polypeptide comprising the first Fc domain subunit and a polypeptide comprising the second Fc domain subunit, which might be non-identical in the sense that further components fused to each of the subunits (e.g., antigen binding moieties) are not the same. In some embodiments the modification promoting association comprises an amino acid mutation in the Fc domain, specifically an amino acid substitution. In a particular embodiment, the modification promoting association comprises a separate amino acid mutation, specifically an amino acid substitution, in each of the two subunits of the Fc domain.

An "activating Fc receptor" is an Fc receptor that following engagement by an Fc region of an antibody elicits signaling events that stimulate the receptor-bearing cell to perform effector functions. Activating Fc receptors include FcγRIIIa (CD16a), FcγRI (CD64), FcγRIIa (CD32), and FcαRI (CD89).

The term "effector functions" when used in reference to antibodies refer to those biological activities attributable to the Fc region of an antibody, which vary with the antibody isotype. Examples of antibody effector functions include: C1q binding and complement dependent cytotoxicity (CDC), Fc receptor binding, antibody-dependent cell-mediated cytotoxicity (ADCC), antibody-dependent cellular phagocytosis (ADCP), cytokine secretion, immune complex-mediated antigen uptake by antigen presenting cells, down regulation of cell surface receptors (e.g., B cell receptor), and B cell activation.

As used herein, the term "effector cells" refers to a population of lymphocytes that display effector moiety receptors, e.g., cytokine receptors, and/or Fc receptors on their surface through which they bind an effector moiety, e.g., a cytokine, and/or an Fc region of an antibody and contribute to the destruction of target cells, e.g., tumor cells. Effector cells may for example mediate cytotoxic or phagocytic effects. Effector cells include, but are not limited to, effector T cells such as $CD8^+$ cytotoxic T cells, $CD4^+$ helper T cells, γδ T cells, NK cells, lymphokine-activated killer (LAK) cells and macrophages/monocytes.

As used herein, the terms "engineer," "engineered," and "engineering," are considered to include any manipulation of the peptide backbone or the post-translational modifications of a naturally occurring or recombinant polypeptide or fragment thereof. Engineering includes modifications of the amino acid sequence, of the glycosylation pattern, or of the side chain group of individual amino acids, as well as combinations of these approaches. "Engineering", particularly with the prefix "glyco-", as well as the term "glycosylation engineering," includes metabolic engineering of the glycosylation machinery of a cell, including genetic manipulations of the oligosaccharide synthesis pathways to achieve altered glycosylation of glycoproteins expressed in cells. Furthermore, glycosylation engineering includes the effects of mutations and cell environment on glycosylation. In one embodiment, the glycosylation engineering is an alteration in glycosyltransferase activity. In a particular embodiment, the engineering results in altered glucosaminyltransferase activity and/or fucosyltransferase activity. Glycosylation engineering can be used to obtain a "host cell having increased GnTIII activity" (e.g., a host cell that has been manipulated to express increased levels of one or more polypeptides having β(1,4)-N-acetylglucosaminyltransferase III (GnTIII) activity), a "host cell having increased ManII activity" (e.g., a host cell that has been manipulated to express increased levels of one or more polypeptides having α-mannosidase II (ManII) activity), or a "host cell having decreased α(1,6) fucosyltransferase activity" (e.g., a host cell that has been manipulated to express decreased levels of α(1,6) fucosyltransferase).

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein. A host cell is any type of cellular system that can be used to generate proteins used for the present invention. In one embodiment, the host cell is engineered to allow the production of an antibody with modified oligosaccharides. In certain embodiments, the host cells have been manipulated to express increased levels of one or more polypeptides having β(1,4)-N-acetylglucosaminyltransferase III (GnTIII) activity. In certain embodiments the host cells have been further manipulated to express increased levels of one or more polypeptides having α-mannosidase II (ManII) activity. Host cells include cultured cells, e.g., mammalian cultured cells, such as CHO cells, BHK cells, NS0 cells, SP2/0 cells, YO myeloma cells, P3X63 mouse myeloma cells, PER cells, PER.C6 cells or hybridoma cells, yeast cells, insect cells, and plant cells, to name only a few, but also cells comprised within a transgenic animal, transgenic plant or cultured plant or animal tissue.

As used herein, the term "polypeptide having GnTIII activity" refers to a polypeptide that is able to catalyze the addition of a N-acetylglucosamine (GlcNAc) residue in β-1,4 linkage to the β-linked mannoside of the trimannosyl core of N-linked oligosaccharides. This includes fusion polypeptides exhibiting enzymatic activity similar to, but not necessarily identical to, an activity of β(1,4)-N-acetylglucosaminyltransferase III, also known as β-1,4-mannosyl-glycoprotein 4-beta-N-acetylglucosaminyl-transferase (EC 2.4.1.144), according to the Nomenclature Committee of the International Union of Biochemistry and Molecular Biology (NC-IUBMB), as measured in a particular biological assay, with or without dose dependency. In the case where dose dependency does exist, it need not be identical to that of GnTIII, but rather substantially similar to the dose-dependency in a given activity as compared to the GnTIII (i.e., the candidate polypeptide will exhibit greater activity or not more than about 25-fold less and, preferably, not more than about ten-fold less activity, and most preferably, not more than about three-fold less activity relative to the GnTIII). In certain embodiments the polypeptide having GnTIII activity is a fusion polypeptide comprising the catalytic domain of GnTIII and the Golgi localization domain of a heterologous Golgi resident polypeptide. Particularly, the Golgi localization domain is the localization domain of mannosidase II or GnTI, most particularly the localization domain of mannosidase II. Alternatively, the Golgi localization domain is selected from the group consisting of: the localization domain of mannosidase I, the localization domain of GnTII, and the localization domain of α1,6 core fucosyltransferase. Methods for generating such fusion polypeptides and using them to produce antibodies with increased effector functions are disclosed in WO2004/065540, U.S. Provisional Pat. Appl. No. 60/495,142 and U.S. Pat. Appl. Publ. No. 2004/0241817, the entire contents of which are expressly incorporated herein by reference.

As used herein, the term "Golgi localization domain" refers to the amino acid sequence of a Golgi resident polypeptide which is responsible for anchoring the polypeptide to a location within the Golgi complex. Generally, localization domains comprise amino terminal "tails" of an enzyme.

As used herein, the term "polypeptide having ManII activity" refers to polypeptides that are able to catalyze the hydrolysis of the terminal 1,3- and 1,6-linked α-D-mannose residues in the branched GlcNAcMan$_5$GlcNAc$_2$ mannose intermediate of N-linked oligosaccharides. This includes polypeptides exhibiting enzymatic activity similar to, but not necessarily identical to, an activity of Golgi α-mannosidase II, also known as mannosyl oligosaccharide 1,3-1,6-α-mannosidase II (EC 3.2.1.114), according to the Nomenclature Committee of the International Union of Biochemistry and Molecular Biology (NC-IUBMB).

Antibody-dependent cell-mediated cytotoxicity (ADCC) is an immune mechanism leading to the lysis of antibody-coated target cells by immune effector cells. The target cells are cells to which antibodies or fragments thereof comprising an Fc region specifically bind, generally via the protein part that is N-terminal to the Fc region. As used herein, the term "increased/reduced ADCC" is defined as either an increase/reduction in the number of target cells that are lysed in a given time, at a given concentration of antibody in the medium surrounding the target cells, by the mechanism of ADCC defined above, and/or a reduction/increase in the concentration of antibody, in the medium surrounding the target cells, required to achieve the lysis of a given number of target cells in a given time, by the mechanism of ADCC. The increase/reduction in ADCC is relative to the ADCC mediated by the same antibody produced by the same type of host cells, using the same standard production, purification, formulation and storage methods (which are known to those skilled in the art), but that has not been engineered. For example the increase in ADCC mediated by an antibody produced by host cells engineered to have an altered pattern of glycosylation (e.g., to express the glycosyltransferase, GnTIII, or other glycosyltransferases) by the methods described herein, is relative to the ADCC mediated by the same antibody produced by the same type of non-engineered host cells.

By "antibody having increased/reduced antibody dependent cell-mediated cytotoxicity (ADCC)" is meant an antibody having increased/reduced ADCC as determined by any suitable method known to those of ordinary skill in the art. One accepted in vitro ADCC assay is as follows:
1) the assay uses target cells that are known to express the target antigen recognized by the antigen-binding region of the antibody;
2) the assay uses human peripheral blood mononuclear cells (PBMCs), isolated from blood of a randomly chosen healthy donor, as effector cells;
3) the assay is carried out according to following protocol:
   i) the PBMCs are isolated using standard density centrifugation procedures and are suspended at $5 \times 10^6$ cells/ml in RPMI cell culture medium;

ii) the target cells are grown by standard tissue culture methods, harvested from the exponential growth phase with a viability higher than 90%, washed in RPMI cell culture medium, labeled with 100 micro-Curies of $^{51}$Cr, washed twice with cell culture medium, and resuspended in cell culture medium at a density of $10^5$ cells/ml;

iii) 100 microliters of the final target cell suspension above are transferred to each well of a 96-well microtiter plate;

iv) the antibody is serially-diluted from 4000 ng/ml to 0.04 ng/ml in cell culture medium and 50 microliters of the resulting antibody solutions are added to the target cells in the 96-well microtiter plate, testing in triplicate various antibody concentrations covering the whole concentration range above;

v) for the maximum release (MR) controls, 3 additional wells in the plate containing the labeled target cells, receive 50 microliters of a 2% (V/V) aqueous solution of non-ionic detergent (Nonidet, Sigma, St. Louis), instead of the antibody solution (point iv above);

vi) for the spontaneous release (SR) controls, 3 additional wells in the plate containing the labeled target cells, receive 50 microliters of RPMI cell culture medium instead of the antibody solution (point iv above);

vii) the 96-well microtiter plate is then centrifuged at 50×g for 1 minute and incubated for 1 hour at 4° C.;

viii) 50 microliters of the PBMC suspension (point i above) are added to each well to yield an effector:target cell ratio of 25:1 and the plates are placed in an incubator under 5% $CO_2$ atmosphere at 37° C. for 4 hours;

ix) the cell-free supernatant from each well is harvested and the experimentally released radioactivity (ER) is quantified using a gamma counter;

x) the percentage of specific lysis is calculated for each antibody concentration according to the formula (ER-MR)/(MR-SR)×100, where ER is the average radioactivity quantified (see point ix above) for that antibody concentration, MR is the average radioactivity quantified (see point ix above) for the MR controls (see point v above), and SR is the average radioactivity quantified (see point ix above) for the SR controls (see point vi above);

4) "increased/reduced ADCC" is defined as either an increase/reduction in the maximum percentage of specific lysis observed within the antibody concentration range tested above, and/or a reduction/increase in the concentration of antibody required to achieve one half of the maximum percentage of specific lysis observed within the antibody concentration range tested above. The increase/reduction in ADCC is relative to the ADCC, measured with the above assay, mediated by the same antibody, produced by the same type of host cells, using the same standard production, purification, formulation and storage methods, which are known to those skilled in the art, but that has not been engineered.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

A "naked antibody" refers to an antibody that is not conjugated to a heterologous moiety (e.g., a cytotoxic moiety) or radiolabel. The naked antibody may be present in a pharmaceutical formulation.

"Native antibodies" refer to naturally occurring immunoglobulin molecules with varying structures. For example, native IgG antibodies are heterotetrameric glycoproteins of about 150,000 Daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

As used herein, the terms "first," "second," "third," etc. with respect to antigen binding moieties or domains, are used for convenience of distinguishing when there is more than one of each type of moiety or domain. Use of these terms is not intended to confer a specific order or orientation unless explicitly so stated.

The terms "multispecific" and "bispecific" mean that the antigen binding molecule is able to specifically bind to at least two distinct antigenic determinants. Typically, a bispecific antigen binding molecule comprises two antigen binding sites, each of which is specific for a different antigenic determinant. In certain embodiments, a bispecific antigen binding molecule is capable of simultaneously binding two antigenic determinants, particularly two antigenic determinants expressed on two distinct cells.

The term "valent" or "valency" as used herein denotes the presence of a specified number of antigen binding sites in an antigen binding molecule. As such, the term "monovalent binding to an antigen" denotes the presence of one (and not more than one) antigen binding site specific for the antigen in the antigen binding molecule.

An "antigen binding site" refers to the site, i.e., one or more amino acid residues, of an antigen binding molecule which provides interaction with the antigen. For example, the antigen binding site of an antibody comprises amino acid residues from the complementarity determining regions (CDRs). A native immunoglobulin molecule typically has two antigen binding sites, a Fab molecule typically has a single antigen binding site.

An "activating T cell antigen" as used herein refers to an antigenic determinant expressed by a T lymphocyte, particularly a cytotoxic T lymphocyte, which is capable of inducing or enhancing T cell activation upon interaction with an antigen binding molecule. Specifically, interaction of an antigen binding molecule with an activating T cell antigen may induce T cell activation by triggering the signaling cascade of the T cell receptor complex. An exemplary activating T cell antigen is CD3. In a particular embodiment the activating T cell antigen is CD3, particularly the epsilon subunit of CD3 (see UniProt no. P07766 (version 130), NCBI RefSeq no. NP_000724.1, for the human sequence; or UniProt no. Q95L15 (version 49), NCBI GenBank no. BAB71849.1, for the cynomolgus [*Macaca fascicularis*] sequence).

"T cell activation" as used herein refers to one or more cellular response of a T lymphocyte, particularly a cytotoxic T lymphocyte, selected from: proliferation, differentiation, cytokine secretion, cytotoxic effector molecule release, cytotoxic activity, and expression of activation markers. The T cell activating therapeutic agents used in the present invention are capable of inducing T cell activation. Suitable assays to measure T cell activation are known in the art described herein.

A "target cell antigen" as used herein refers to an antigenic determinant presented on the surface of a target cell, for example a cell in a tumor such as a cancer cell or a cell of the tumor stroma. In a particular embodiment, the target cell antigen is CD20, particularly human CD20 (see UniProt no. P11836).

A "B-cell antigen" as used herein refers to an antigenic determinant presented on the surface of a B lymphocyte, particularly a malignant B lymphocyte (in that case the antigen also being referred to as "malignant B-cell antigen").

A "T-cell antigen" as used herein refers to an antigenic determinant presented on the surface of a T lymphocyte, particularly a cytotoxic T lymphocyte.

A "Fab molecule" refers to a protein consisting of the VH and CH1 domain of the heavy chain (the "Fab heavy chain") and the VL and CL domain of the light chain (the "Fab light chain") of an immunoglobulin.

By "chimeric antigen receptor" or "CAR" is meant a genetically engineered receptor protein comprising an antigen binding moiety, e.g., a single-chain variable fragment (scFv) of a targeting antibody, a transmembrane domain, an intracellular T-cell activating signaling domain (e.g., the CD3 zeta chain of the T-cell receptor) and optionally one or more intracellular co-stimulatory domains (e.g., of CD28, CD27, CD137 (4-1 BB), Ox40). CARs mediate antigen recognition, T cell activation, and—in the case of second-generation CARs—costimulation to augment T cell functionality and persistence. For a review see e.g., Jackson et al., *Nat Rev Clin Oncol*. (2016) 13, 370-383.

By "fused" is meant that the components (e.g., a Fab molecule and an Fc domain subunit) are linked by peptide bonds, either directly or via one or more peptide linkers.

An "effective amount" of an agent refers to the amount that is necessary to result in a physiological change in the cell or tissue to which it is administered.

A "therapeutically effective amount" of an agent, e.g., a pharmaceutical composition, refers to an amount effective, at dosages and for periods of time necessary, to achieve the desired therapeutic or prophylactic result. A therapeutically effective amount of an agent for example eliminates, decreases, delays, minimizes or prevents adverse effects of a disease.

By "therapeutic agent" is meant an active ingredient, e.g., of a pharmaceutical composition, that is administered to a subject in an attempt to alter the natural course of a disease in the subject being treated, and can be performed either for prophylaxis or during the course of clinical pathology. An "immunotherapeutic agent" refers to a therapeutic agent that is administered to a subject in an attempt to restore or enhance the subject's immune response, e.g., to a tumor.

The term "pharmaceutical composition" refers to a preparation which is in such form as to permit the biological activity of an active ingredient contained therein to be effective, and which contains no additional components which are unacceptably toxic to a subject to which the composition would be administered.

A "pharmaceutically acceptable carrier" refers to an ingredient in a pharmaceutical composition, other than an active ingredient, which is nontoxic to a subject. A pharmaceutically acceptable carrier includes, but is not limited to, a buffer, excipient, stabilizer, or preservative.

The term "package insert" or "instructions for use" is used to refer to instructions customarily included in commercial packages of therapeutic products that contain information about the indications, usage, dosage, administration, combination therapy, contraindications and/or warnings concerning the use of such therapeutic products.

The term "combination treatment" noted herein encompasses combined administration (where two or more therapeutic agents are included in the same or separate formulations), and separate administration, in which case, administration of an antibody as reported herein can occur prior to, simultaneously, and/or following, administration of the additional therapeutic agent or agents, preferably an antibody or antibodies.

By a "crossover" Fab molecule (also termed "Crossfab") is meant a Fab molecule wherein the variable domains or the constant domains of the Fab heavy and light chain are exchanged (i.e., replaced by each other), i.e., the crossover Fab molecule comprises a peptide chain composed of the light chain variable domain VL and the heavy chain constant domain 1 CH1 (VL-CH1, in N- to C-terminal direction), and a peptide chain composed of the heavy chain variable domain VH and the light chain constant domain CL (VH-CL, in N- to C-terminal direction). For clarity, in a crossover Fab molecule wherein the variable domains of the Fab light chain and the Fab heavy chain are exchanged, the peptide chain comprising the heavy chain constant domain 1 CH1 is referred to herein as the "heavy chain" of the (crossover) Fab molecule. Conversely, in a crossover Fab molecule wherein the constant domains of the Fab light chain and the Fab heavy chain are exchanged, the peptide chain comprising the heavy chain variable domain VH is referred to herein as the "heavy chain" of the (crossover) Fab molecule.

In contrast thereto, by a "conventional" Fab molecule is meant a Fab molecule in its natural format, i.e., comprising a heavy chain composed of the heavy chain variable and constant domains (VH-CH1, in N- to C-terminal direction), and a light chain composed of the light chain variable and constant domains (VL-CL, in N- to C-terminal direction).

The term "polynucleotide" refers to an isolated nucleic acid molecule or construct, e.g., messenger RNA (mRNA), virally-derived RNA, or plasmid DNA (pDNA). A polynucleotide may comprise a conventional phosphodiester bond or a non-conventional bond (e.g., an amide bond, such as found in peptide nucleic acids (PNA). The term "nucleic acid molecule" refers to any one or more nucleic acid segments, e.g., DNA or RNA fragments, present in a polynucleotide.

By "isolated" nucleic acid molecule or polynucleotide is intended a nucleic acid molecule, DNA or RNA, which has been removed from its native environment. For example, a recombinant polynucleotide encoding a polypeptide contained in a vector is considered isolated for the purposes of the present invention. Further examples of an isolated polynucleotide include recombinant polynucleotides maintained in heterologous host cells or purified (partially or substantially) polynucleotides in solution. An isolated polynucleotide includes a polynucleotide molecule contained in cells that ordinarily contain the polynucleotide molecule, but the polynucleotide molecule is present extrachromosomally or at a chromosomal location that is different from its natural chromosomal location. Isolated RNA molecules include in vivo or in vitro RNA transcripts of the present invention, as well as positive and negative strand forms, and double-stranded forms. Isolated polynucleotides or nucleic acids according to the present invention further include such molecules produced synthetically. In addition, a polynucleotide or a nucleic acid may be or may include a regulatory element such as a promoter, ribosome binding site, or a transcription terminator.

By a nucleic acid or polynucleotide having a nucleotide sequence at least, for example, 95% "identical" to a reference nucleotide sequence of the present invention, it is intended that the nucleotide sequence of the polynucleotide is identical to the reference sequence except that the polynucleotide sequence may include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These alterations of the reference sequence may occur at the 5' or 3' terminal positions of the reference nucleotide sequence or anywhere between those terminal positions, interspersed either individually among residues in the reference sequence or in one or more contiguous groups within the reference sequence. As a practical matter, whether any particular polynucleotide sequence is at least 80%, 85%, 90%, 95%, 96%, 97%, 98%, or 99% identical to a nucleotide sequence of the present invention can be determined conventionally using known computer programs, such as the ones discussed above for polypeptides (e.g., ALIGN-2).

The term "expression cassette" refers to a polynucleotide generated recombinantly or synthetically, with a series of specified nucleic acid elements that permit transcription of a particular nucleic acid in a target cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid sequence to be transcribed and a promoter. In certain embodiments, the expression cassette of the invention comprises polynucleotide sequences that encode bispecific antigen binding molecules of the invention or fragments thereof.

The term "vector" or "expression vector" is synonymous with "expression construct" and refers to a DNA molecule that is used to introduce and direct the expression of a specific gene to which it is operably associated in a target cell. The term includes the vector as a self-replicating nucleic acid structure as well as the vector incorporated into the genome of a host cell into which it has been introduced. The expression vector of the present invention comprises an expression cassette. Expression vectors allow transcription of large amounts of stable mRNA. Once the expression vector is inside the target cell, the ribonucleic acid molecule or protein that is encoded by the gene is produced by the cellular transcription and/or translation machinery. In one embodiment, the expression vector of the invention comprises an expression cassette that comprises polynucleotide sequences that encode bispecific antigen binding molecules of the invention or fragments thereof.

The term "about" as used herein refers to the usual error range for the respective value readily known to the skilled person in this technical field. Reference to "about" a value or parameter herein includes (and describes) embodiments that are directed to that value or parameter per se.

By "B cell proliferative disorder" is meant a disease wherein the number of B cells in a patient is increased as compared to the number of B cells in a healthy subject, and particularly wherein the increase in the number of B cells is the cause or hallmark of the disease. A "CD20-positive B cell proliferative disorder" is a B cell proliferative disorder wherein B-cells, particularly malignant B-cells (in addition to normal B-cells), express CD20.

Exemplary B cell proliferation disorders include Non-Hodgkin lymphoma (NHL), diffuse large B-cell lymphoma (DLBCL; e.g., relapsed or refractory DLBCL not otherwise specified (NOS), high grade B cell lymphoma (HGBCL; e.g., HGBCL NOS, double-hit HGBCL, and triple-hit HGBCL), primary mediastinal large B-cell lymphoma (PMBCL), and DLBCL arising from FL (transformed FL; trFL)); follicular lymphoma (FL), including Grade 1-3b FL; mantle-cell lymphoma (MCL); and marginal zone lymphoma (MZL), including splenic, nodal or extra-nodal MZL. In one embodiment the CD20-positive B cell proliferative disorder is a relapsed or refractory NHL (e.g., a relapsed or refractory DLBCL, a relapsed or refractory FL, or a relapsed or refractory MCL).

"Refractory disease" is defined as no complete remission to first-line therapy. In one embodiment refractory disease defined as no response to or relapse within 6 months of prior therapy. In one embodiment refractory disease is characterized by one or more of the following: Progressive disease (PD) as best response to first-line therapy, Stable disease (SD) as best response after at least 4 cycles of first line therapy (e.g., 4 cycles of rituximab, cyclophosphamide, doxorubicin hydrochloride (hydroxydaunorubicin), vincristine sulfate (Oncovin), and prednisone, also abbreviated as R-CHOP), or Partial response (PR) as best response after at least 6 cycles, and biopsy-proven residual disease or disease progression after the partial response. "Relapsed disease" is defined as complete remission to first-line therapy. In one embodiment disease relapse is proven by biopsy. In one embodiment, patients have relapsed after or failed to respond to at least two prior systemic treatment regimens (including at least one prior regimen containing anthracycline, and at least one containing an anti CD20-directed therapy).

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). Preferably, the individual or subject is a human. In one instance, each subject in a population of subjects is human. In one instance, each subject in a reference population of subjects is human.

A "transplant ineligible" subject or a subject "ineligible for autologous stem cell transplantation (SCT)" is a subject who does not meet eligibility for, who is not recommended for, who cannot receive, or who refuses autologous SCT. Examples of preferable subject characteristics include age ≤65 years, Karnofsky performance status (KPS; Karnofsky et al. *Cancer.* 1948; 1(4): 634-656) >60, force expiratory volume in 1 second (FEV$_1$) >60% of predicted value, diffusion lung capacity (DLCO) >60% of predicted value, left ventricular ejection fraction >45%, heart rhythm normal, serum bilirubin ≤2 mg/100 ml, alanine aminotransferase (ALT)/aspartate aminotransferase (AST)<2×normal, serum creatinine ≤1.5 mg/100 ml, creatinine clearance >60 ml/min, no second active malignancy, not pregnant, and no uncontrolled infections (including dental) (Hamadani M et al. *Bone Marrow Transplant.* 2010; 45:1259-68).

As used herein, "treatment" (and grammatical variations thereof such as "treat" or "treating") refers to clinical intervention in an attempt to alter the natural course of a disease in the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, methods of the invention are used to delay development of a disease or to slow the progression of a disease.

As used herein, "delaying progression" of a disorder or disease means to defer, hinder, slow, retard, stabilize, and/or postpone development of the disease or disorder (e.g., a CD20-positive B cell proliferative disorder, e.g., NHL, e.g., DLBCL). This delay can be of varying length of time, depending on the history of the disease and/or individual being treated. As is evident to one skilled in the art, a sufficient or significant delay can, in effect, encompass prevention, in that the individual does not develop the disease. For example, in a late stage cancer, development of central nervous system (CNS) metastasis, may be delayed.

By "reduce" or "inhibit" is meant the ability to cause an overall decrease, for example, of 20%, 30%, 40%, 50%, 60%, 70%, 75%, 80%, 85%, 90%, 95%, or greater. For clarity the term includes also reduction to zero (or below the detection limit of the analytical method), i.e., complete abolishment or elimination. In certain embodiments, reduce or inhibit can refer to the reduction or inhibition of undesirable events, such as cytokine-driven toxicities (e.g., cytokine release syndrome (CRS)), infusion-related reactions (IRRs), macrophage activation syndrome (MAS), neurologic toxicities, severe tumor lysis syndrome (TLS), neutropenia, thrombocytopenia, elevated liver enzymes, and/or central nervous system (CNS) toxicities, following treatment with an anti-CD20/anti-CD3 bispecific antibody using the step-up dosing regimen of the invention relative to unchanging, preset dosing with the target dose of the anti-CD20/anti-CD3 bispecific antibody. In other embodiments, reduce or inhibit can refer to effector function of an antibody that is mediated by the antibody Fc region, such effector functions specifically including complement-dependent cytotoxicity (CDC), antibody-dependent cellular cytotoxicity (ADCC), and antibody-dependent cellular phagocytosis (ADCP). In other embodiments reduce or inhibit can refer to the symptoms of the CD20-positive B cell proliferative disorder being treated (e.g., an NHL (e.g., a DLBCL), an FL (e.g., a relapsed and/or refractor FL or a transformed FL), an MCL, a high-grade B cell lymphoma, or a PMLBCL), the presence or size of metastases, or the size of the primary tumor.

As used herein, "administering" is meant a method of giving a dosage of a compound (e.g., an anti-CD20/anti-CD3 bispecific antibody) or a composition (e.g., a pharmaceutical composition, e.g., a pharmaceutical composition including an anti-CD20/anti-CD3 bispecific antibody) to a subject. The compounds and/or compositions utilized in the methods described herein can be administered intravenously (e.g., by intravenous infusion).

A "fixed" or "flat" dose of a therapeutic agent (e.g., a bispecific antibody) herein refers to a dose that is administered to a patient without regard for the weight or body surface area (BSA) of the patient.

The fixed or flat dose is therefore not provided as a mg/kg dose or a mg/m$^2$ dose, but rather as an absolute amount of the therapeutic agent (e.g., mg).

A "target dose" herein refers to the dose of the anti-CD20/anti-CD3 bispecific antibody that achieves therapeutic effect, i.e., achieves the desired clinical efficacy. It was found that for glofitamab a possible target dose is 16 mg or 30 mg.

An "unchanging or preset dosing with target dose" and a "treatment regimen without a step-up dosing regimen" refers to a dosing schedule that uses the same dosage in the first and second cycle (e.g., dosing cycle) and optionally also any subsequent treatment or dosing cycle, as opposed to a step-up dosing regimen, which uses lower dosages in the first few treatment or dosing cycles and only reaches the target dose in the second or in a later treatment or dosing cycle.

The terms "treatment cycle," "dosing cycle," or "cycle" (abbreviated: "C") as used herein mean a course of one or more doses of the anti-CD20/anti-CD3 bispecific antibody that is repeated on a regular schedule, optionally with periods of rest (no treatment) in between. In one aspect of the invention, the first treatment cycle comprises a first and a second dose of the anti-CD20/anti-CD3 bispecific antibody, followed by a period of rest. In one such embodiment, the first treatment cycle comprises a first dose of the anti-CD20/anti-CD3 bispecific antibody on day 1 of the first dosing cycle, and a second dose of the anti-CD20/anti-CD3 bispecific antibody on day 8 of the first dosing cycle, followed by 12 days of rest. In one embodiment the second and any subsequent dosing cycles comprise one dose of the anti-CD20/anti-CD3 bispecific antibody given at day 1 of that dosing cycle, followed by 20 days of rest. In one embodiment, one treatment or dosing cycle comprises 21 days. In another embodiment, one treatment or dosing cycle comprises 14 days. The treatment or dosing cycle comprising one or more doses of the anti-CD20/anti-CD3 bispecific antibody may further comprise one or more dosages of one or more other therapeutic agents, such as e.g., an anti-CD20 antibody, in particular obinutuzumab. The treatment schedule according to the invention may comprise 2 or more treatment or dosing cycles, or 3, 4, 5, 6, 7, 8, 9, 10, 11, in particular 12 treatment or dosing cycles.

"Individual response" or "response" can be assessed using any endpoint indicating a benefit to the subject, including, without limitation, (1) inhibition, to some extent, of disease progression (e.g., progression of a CD20-positive B cell proliferative disorder, e. g., a non-Hodgkin's lymphoma (NHL)); including slowing down and complete arrest; (2) a reduction in tumor size; (3) inhibition (i.e., reduction, slowing down or complete stopping) of cancer cell infiltration into adjacent peripheral organs and/or tissues; (4) inhibition (i.e., reduction, slowing down or complete stopping) of metastasis; (5) relief, to some extent, of one or more symptoms associated with the CD20-positive B cell proliferative disorder, e.g., a B cell proliferative disorder; (6) increase or extend in the length of survival, including overall survival and progression-free survival; and/or (7) decreased mortality at a given point of time following treatment.

As used herein, "complete response" or "CR" refers to disappearance of all target lesions. In one embodiment standard NHL response criteria are assessed for determining CR. (Lugano Classification, Cheson et al. *J Clin Oncol.* 2014 Sep. 20; 32(27): 3059-3067).

As used herein, "partial response" or "PR" refers to at least a 30% decrease in the sum of the longest diameters (SLD) of target lesions, taking as reference the baseline SLD, or at least a 50% decrease in the product of the diameters (SPD) of target lesions, taking as reference the baseline SPD.

"Sustained response" refers to the sustained effect on reducing tumor growth after cessation of a treatment. For example, the tumor size may remain to be the same or smaller as compared to the size at the beginning of the administration phase. In some embodiments, the sustained response has a duration at least the same as the treatment duration, at least 1.5×, 2.0×, 2.5×, or 3.0× length of the treatment duration.

An "effective response" of a subject or a subject's "responsiveness" to treatment with a medicament and similar wording refers to the clinical or therapeutic benefit imparted to a subject as risk for, or suffering from, a disease or disorder, such as cancer. In one embodiment, such benefit includes any one or more of: extending survival (including overall survival and progression free survival); resulting in an objective response (including a complete response or a partial response); or improving signs or symptoms of cancer.

"Duration of complete response" (DOCR) is defined as the time from the initial occurrence of a documented CR until documented disease progression or death due to any cause, whichever occurs first. In one embodiment, DOCR is assessed based on the Lugano Classification (Cheson et al. *J Clin Oncol.* 2014 Sep. 20; 32(27): 3059-3067).

"Duration of objective response" (DOR) is defined as the first occurrence of a documented, objective response until the time of disease progression, relapse or death from any cause. In one embodiment, DOR is assessed based on the Lugano Classification (Cheson et al. *J Clin Oncol.* 2014 Sep. 20; 32(27): 3059-3067).

"Progression-free survival" (PFS) is defined as the time from the first treatment with the anti-CD20/anti-CD3 bispecific antibody to the first occurrence of disease progression or death from any cause, whichever occurs first. In one embodiment, PFS is assessed based on the Lugano Classification (Cheson et al. *J Clin Oncol.* 2014 Sep. 20; 32(27): 3059-3067).

"Overall survival" (OS) is defined as time from the first treatment with the anti-CD20/anti-CD3 bispecific antibody to the date of death from any cause.

"Time to first overall response" (TFOR) is defined as time from treatment start to first documented response. In one embodiment, TFOR is evaluated based on the Lugano Classification (Cheson et al. *J Clin Oncol.* 2014 Sep. 20; 32(27): 3059-3067).

"Time to first complete response" (TFCR) defined as time from treatment start to first documented complete response. In one embodiment, TFCR is evaluated based on the Lugano Classification (Cheson et al. *J Clin Oncol.* 2014 Sep. 20; 32(27): 3059-3067).

As used herein, "objective response rate" or "overall response rate" (ORR) is defined as the sum of partial response (PR) rate and complete response (CR) rate. In one embodiment, ORR is evaluated based on the Lugano Classification (Cheson et al. *J Clin Oncol.* 2014 Sep. 20; 32(27): 3059-3067).

As used herein, "stable disease" or "SD" refers to neither sufficient shrinkage of target lesions to qualify for PR, nor sufficient increase to qualify for PD, taking as reference the smallest SLD since the treatment started.

As used herein, "progressive disease" or "PD" refers to at least a 20% increase in the SLD of target lesions, taking as reference the smallest SLD, or at least a 50% increase in the SPD of target legions, taking as reference the smallest SPD, recorded since the treatment started or the presence of one or more new lesions.

As used herein, an "infusion-related reaction," "IRR," or infusion-related adverse event" is an adverse event that occurs in a patient or subject during or within 24 hours after administration of a drug (e.g., an anti-CD20/anti-CD3 bispecific antibody, e.g., glofitamab; or an anti-CD79b antibody drug conjugate, e.g., polatuzumab vedotin). IRRs may be graded as Grade 1-5 according to, e.g., NCI CTCAE v.4.

The term "PD-1 axis binding antagonist" refers to a molecule that inhibits the interaction of a PD-1 axis binding partner with either one or more of its binding partner, so as to remove T-cell dysfunction resulting from signaling on the PD-1 signaling axis, with a result being to restore or enhance T-cell function (e.g., proliferation, cytokine production, target cell killing). As used herein, a PD-1 axis binding antagonist includes a PD-1 binding antagonist, a PD-L1 binding antagonist, and a PD-L2 binding antagonist.

The term "PD-1 binding antagonist" refers to a molecule that decreases, blocks, inhibits, abrogates or interferes with signal transduction resulting from the interaction of PD-1 with one or more of its binding partners, such as PD-L1, PD-L2. In some embodiments, the PD-1 binding antagonist is a molecule that inhibits the binding of PD-1 to one or more of its binding partners. In a specific aspect, the PD-1 binding antagonist inhibits the binding of PD-1 to PD-L1 and/or PD-L2. For example, PD-1 binding antagonists include anti-PD-1 antibodies, antigen binding fragments thereof, immunoadhesins, fusion proteins, oligopeptides and other molecules that decrease, block, inhibit, abrogate or interfere with signal transduction resulting from the interaction of PD-1 with PD-L1 and/or PD-L2. In one embodiment, a PD-1 binding antagonist reduces the negative co-stimulatory signal mediated by or through cell surface proteins expressed on T lymphocytes mediated signaling through PD-1 so as render a dysfunctional T-cell less dysfunctional (e.g., enhancing effector responses to antigen recognition). In some embodiments, the PD-1 binding antagonist is an anti-PD-1 antibody. In a specific aspect, a PD-1 binding antagonist is MDX-1106 (nivolumab). In another specific aspect, a PD-1 binding antagonist is pembrolizumab (formerly lambrolizumab (MK-3475)). In another specific aspect, a PD-1 binding antagonist is AMP-224. In some embodiments, the PD-1 binding antagonist is MDX-1106 (nivolumab). In some embodiments, the PD-1 binding antagonist is MK-3475 (pembrolizumab). In some embodiments, the PD-1 binding antagonist is MED1-0680. In some instances, the PD-1 binding antagonist is PDR001 (spartalizumab). In some instances, the PD-1 binding antagonist is REGN2810 (cemiplimab). In some instances, the PD-1 binding antagonist is BGB-108. In other instances, the PD-1 binding antagonist is prolgolimab, camrelizumab, sintilimab, tislelizumab, or toripalimab.

Further examples of PD-1 axis binding antagonists include cemiplimab, prolgolimab, camrelizumab, sintilimab, tislelizumab, toripalimab, dostarlimab, retifanlimab, spartalizumab, sasanlimab, penpulimab, CS1003, HLX10, SCT-I10A, SHR-1316, CS1001, envafolimab, TQB2450, ZKAB001, LP-002, zimberelimab, balstilimab, genolimzumab, BI 754091, cetrelimab, YBL-006, BAT1306, HX008, CX-072, IMC-001, KL-A167, budigalimab, AMG 404, CX-188, JTX-4014, 609A, Sym021, LZM009, F520, SG001, APL-502, cosibelimab, lodapolimab, GS-4224, INCB086550, FAZ053, TG-1501, BGB-A333, BCD-135, AK-106, LDP, GR1405, HLX20, MSB2311, MAX-10181, RC98, BION-004, AM0001, CB201, ENUM 244C8, ENUM 388D4, AUNP-012, STI-1110, ADG104, AK-103, LBL-006, hAb21, AVA-004, PDL-GEX, INCB090244, KD036, KY1003, LYN192, MT-6035, VXM10, YBL-007, ABSK041, GB7003, JS-003, and HS-636.

The term "PD-L1 binding antagonist" refers to a molecule that decreases, blocks, inhibits, abrogates, or interferes with signal transduction resulting from the interaction of PD-L1 with either one or more of its binding partners, such as PD-1 or B7-1. In some embodiments, a PD-L1 binding antagonist is a molecule that inhibits the binding of PD-L1 to its binding partners. In a specific aspect, the PD-L1 binding antagonist inhibits binding of PD-L1 to PD-1 and/or B7-1. In some embodiments, the PD-L1 binding antagonists include anti-PD-L1 antibodies, antigen-binding fragments thereof, immunoadhesins, fusion proteins, oligopeptides, and other molecules that decrease, block, inhibit, abrogate, or interfere with signal transduction resulting from the interaction of PD-L1 with one or more of its binding partners, such as PD-1 or B7-1. In one embodiment, a PD-L1 binding antagonist reduces the negative co-stimulatory signal mediated by or through cell surface proteins expressed on T lymphocytes mediated signaling through PD-L1 so as to render a dysfunctional T-cell less dysfunctional (e.g., enhancing effector responses to antigen recognition). In some embodiments, a PD-L1 binding antagonist is an anti-PD-L1 antibody. In a specific embodiment, the anti-PD-L1 antibody is atezolizumab (CAS Registry Number: 1422185-06-5), also known as MPDL3280A, and described herein. In another specific embodiment, the anti-PD-L1 antibody is MDX-1105, described herein. In still another specific aspect, the anti-PD-L1 antibody is MEDI4736, described herein.

As used herein, the term "atezolizumab" refers to an anti-PD-L1 antagonist antibody having the International Nonproprietary Names for Pharmaceutical Substances (INN) List 112 (WHO Drug Information, Vol. 28, No. 4, 2014, p. 488), or the CAS Registry Number 1380723-44-3.

The term "PD-L2 binding antagonist" refers to a molecule that decreases, blocks, inhibits, abrogates, or interferes with signal transduction resulting from the interaction of PD-L2 with either one or more of its binding partners, such as PD-1. In some embodiments, a PD-L2 binding antagonist is a molecule that inhibits the binding of PD-L2 to one or more of its binding partners. In a specific aspect, the PD-L2 binding antagonist inhibits binding of PD-L2 to PD-1. In some embodiments, the PD-L2 antagonists include anti-PD-L2 antibodies, antigen-binding fragments thereof, immunoadhesins, fusion proteins, oligopeptides, and other molecules that decrease, block, inhibit, abrogate, or interfere with signal transduction resulting from the interaction of PD-L2 with either one or more of its binding partners, such as PD-1. In one embodiment, a PD-L2 binding antagonist reduces the negative co-stimulatory signal mediated by or through cell surface proteins expressed on T lymphocytes mediated signaling through PD-L2 so as render a dysfunctional T-cell less dysfunctional (e.g., enhancing effector responses to antigen recognition). In some embodiments, a PD-L2 binding antagonist is an immunoadhesin.

As used herein, the term "chemotherapeutic agent" refers to a compound useful in the treatment of cancer, such as a CD20-positive cell proliferative disorder (e.g., a B cell proliferative disorder (e.g., a relapsed or refractory B cell proliferative disorder), e.g., a non-Hodgkin's lymphoma (NHL; e.g., a diffuse large B cell lymphoma (DLBCL), a follicular lymphoma (FL; e.g., a Grade 1 FL, a Grade 2 FL, a Grade 3 FL (e.g., a Grade 3a FL, Grade 3b FL), or a transformed FL), a mantle cell lymphoma (MCL), or a marginal zone lymphoma (MZL)), e.g., a relapsed or refractory NHL (e.g., a relapsed or refractory DLBCL, a relapsed or refractory FL, a relapsed or refractory MCL, or a marginal zone lymphoma (MZL))). Examples of chemotherapeutic agents include EGFR inhibitors (including small molecule inhibitors (e.g., erlotinib (TARCEVA®, Genentech/OSI Pharm.); PD 183805 (CI 1033, 2-propenamide, N-[4-[(3-chloro-4-fluorophenyl)amino]-7-[3-(4-morpholinyl) propoxy]-6-quinazolinyl]-, dihydrochloride, Pfizer Inc.); ZD1839, gefitinib (IRESSA®) 4-(3'-Chloro-4'-fluoroanilino)-7-methoxy-6-(3-morpholinopropoxy)quinazoline, AstraZeneca); ZM 105180 ((6-amino-4-(3-methylphenyl-amino)-quinazoline, Zeneca); BIBX-1382 (N8-(3-chloro-4-fluoro-phenyl)-N2-(1-methyl-piperidin-4-yl)-pyrimido[5,4-d]pyrimidine-2,8-diamine, Boehringer Ingelheim); PKI-166 ((R)-4-[4-[(1-phenylethyl)amino]-1H-pyrrolo[2,3-d]pyrimidin-6-yl]-phenol); (R)-6-(4-hydroxyphenyl)-4-[(1-phenylethyl)amino]-7H-pyrrolo[2,3-d]pyrimidine); CL-387785 (N-[4-[(3-bromophenyl)amino]-6-quinazolinyl]-2-butynamide); EKB-569 (N-[4-[(3-chloro-4-fluorophenyl)amino]-3-cyano-7-ethoxy-6-quinolinyl]-4-(dimethylamino)-2-butenamide) (Wyeth); AG1478 (Pfizer); AG1571 (SU 5271; Pfizer); and dual EGFR/HER2 tyrosine kinase inhibitors such as lapatinib (TYKERB®, GSK572016 or N-[3-chloro-4-[(3 fluorophenyl)methoxy]phenyl]-6-[5-[[[2methylsulfonyl)ethyl]amino]methyl]-2-furanyl]-4-quinazolinamine)); a tyrosine kinase inhibitor (e.g., an EGFR inhibitor; a small molecule HER2 tyrosine kinase inhibitor such as TAK165 (Takeda); CP-724,714, an oral selective inhibitor of the ErbB2 receptor tyrosine kinase (Pfizer and OSI); dual-HER inhibitors such as EKB-569 (available from Wyeth) which preferentially binds EGFR but inhibits both HER2 and EGFR-overexpressing cells; PKI-166 (Novartis); pan-HER inhibitors such as canertinib (CI-1033; Pharmacia); Raf-1 inhibitors such as antisense agent ISIS-5132 (ISIS Pharmaceuticals) which inhibit Raf-1 signaling; non-HER-targeted tyrosine kinase inhibitors such as imatinib mesylate (GLEEVEC®, Glaxo SmithKline); multi-targeted tyrosine kinase inhibitors such as sunitinib (SUTENT®, Pfizer); VEGF receptor tyrosine kinase inhibitors such as vatalanib (PTK787/ZK222584, Novartis/Schering AG); MAPK extracellular regulated kinase I inhibitor CI-1040 (Pharmacia); quinazolines, such as PD 153035,4-(3-chloroanilino) quinazoline; pyridopyrimidines; pyrimidopyrimidines; pyrrolopyrimidines, such as CGP 59326, CGP 60261 and CGP 62706; pyrazolopyrimidines, 4-(phenylamino)-7H-pyrrolo [2,3-d] pyrimidines; curcumin (diferuloyl methane, 4,5-bis (4-fluoroanilino)phthalimide); tyrphostines containing nitrothiophene moieties; PD-0183805 (Warner-Lamber); antisense molecules (e.g., those that bind to HER-encoding nucleic acid); quinoxalines (U.S. Pat. No. 5,804,396); tryphostins (U.S. Pat. No. 5,804,396); ZD6474 (Astra Zeneca); PTK-787 (Novartis/Schering AG); pan-HER inhibitors such as CI-1033 (Pfizer); Affinitac (ISIS 3521; Isis/Lilly); PKI 166 (Novartis); GW2016 (Glaxo SmithKline); CI-1033 (Pfizer); EKB-569 (Wyeth); Semaxinib (Pfizer); ZD6474 (AstraZeneca); PTK-787 (Novartis/Schering AG); INC-1C11 (Imclone); and rapamycin (sirolimus, RAPAMUNE®)); proteasome inhibitors such as bortezomib (VELCADE®, Millennium Pharm.); disulfiram; epigallocatechin gallate; salinosporamide A; carfilzomib; 17-AAG (geldanamycin); radicicol; lactate dehydrogenase A (LDH-A); fulvestrant (FASLODEX®, AstraZeneca); letrozole (FEMARA®, Novartis), finasunate (VATALANIB®, Novartis); oxaliplatin (ELOXATIN®, Sanofi); 5-FU (5-fluorouracil); leucovorin; lonafamib (SCH 66336); sorafenib (NEXAVAR®, Bayer Labs); AG1478, alkylating agents such as thiotepa and CYTOXAN® cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including topotecan and irinotecan); bryostatin; callystatin; CC-1065 (including its adozelesin, carzelesin and bizelesin synthetic analogs); cryptophycins (particularly cryptophycin 1 and cryptophycin 8); adrenocorticosteroids (including prednisone and prednisolone); cyproterone acetate; 5α-reductases including finasteride and dutasteride); vorinostat, romidepsin, panobinostat, valproic acid, mocetinostat dolastatin; aldesleukin, talc duocarmycin (including the synthetic analogs, KW-2189 and CB1-TM1); eleutherobin; pancratistatin; a sarcodictyin; spongistatin; nitrogen mustards such as chlorambucil, chlomaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimustine; antibiotics such as the enediyne antibiotics (e.g., calicheamicin, especially calicheamicin γ1 and calicheamicin ω1); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, cactinomycin, carabicin, caminomycin, carzinophilin, chromomycinis, dactinomycin, detorubicin, 6-diazo-5-oxo-L-norleucine, morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfomithine; elliptinium acetate; an epothilone; etoglucid; gallium nitrate; hydroxyurea; lentinan; lonidainine; maytansinoids such as maytansine and ansamitocins; mitoguazone; mitoxantrone; mopidamnol; nitraerine; pentostatin; phenamet; pirarubicin; losoxantrone; podophyllinic acid; 2-ethylhydrazide; procarbazine; PSK® polysaccharide complex (JHS Natural Products); razoxane; rhizoxin; sizofuran; spirogermanium; tenuazonic acid; triaziquone; 2,2',2''-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); thiotepa; chloranmbucil; GEMZAR® (gemcitabine); 6-thioguanine; mercaptopurine; methotrexate; etoposide (VP-16); ifosfamide; mitoxantrone; novantrone; teniposide; edatrexate; daunomycin; aminopterin; capecitabine (XELODA®); ibandronate; CPT-11; topoisomerase inhibitor RFS 2000; difluoromethylornithine (DMFO); retinoids such as retinoic acid; and pharmaceutically acceptable salts, acids, prodrugs, and derivatives of any of the above.

Chemotherapeutic agents also include (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, iodoxyfene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide and goserelin; buserelin, tripterelin, medroxyprogesterone acetate, diethylstilbestrol, premarin, fluoxymesterone, all transretionic acid, fenretinide, as well as troxacitabine (a 1,3-dioxolane nucleoside cytosine analog); (iv) protein kinase inhibitors; (v) lipid kinase inhibitors; (vi) antisense oligonucleotides, particularly those which inhibit expression of genes in signaling pathways implicated in aberrant cell proliferation, such as, for example, PKC-alpha, Ralf and H-Ras; (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; (ix) growth inhibitory agents including vincas (e.g., vincristine and vinblastine), NAVELBINE® (vinorelbine), taxanes (e.g., paclitaxel, nab-paclitaxel, and docetaxel), topoisomerase II inhibitors (e.g., doxorubicin, epirubicin, daunorubicin, etoposide, and bleomycin), and DNA alkylating agents (e.g., tamoxigen, dacarbazine, mechlorethamine, cisplatin, methotrexate, 5-fluorouracil, and ara-C); and (x) pharmaceutically acceptable salts, acids, prodrugs, and derivatives of any of the above.

The term "cytotoxic agent" as used herein refers to a substance that inhibits or prevents a cellular function and/or causes cell death or destruction. Cytotoxic agents include, but are not limited to, radioactive isotopes (e.g., $^{211}$At, $^{131}$I, $^{125}$I, $^{90}$Y, $^{186}$Re, $^{188}$Re, $^{153}$Sm, $^{212}$Bi, $^{32}$P, $^{212}$Pb and radioactive isotopes of Lu); chemotherapeutic agents or drugs (e.g., methotrexate, adriamicin, or vinca alkaloids (vincristine, vinblastine, or etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anticancer agents disclosed below.

III. Therapeutic Agents for Use in the Methods of the Invention

A. Anti-CD20/Anti-CD3 Bispecific Antibodies

The present invention provides new dosages for anti-CD20/anti-CD3 bispecific antibodies. In one embodiment, the anti-CD20/anti-CD3 bispecific antibody is a monoclonal antibody. In one embodiment, the anti-CD20/anti-CD3 bispecific antibody is a polyclonal antibody. In one embodiment the anti-CD20/anti-CD3 bispecific antibody is a human antibody. In one embodiment, the anti-CD20/anti-CD3 bispecific antibody is humanized antibody. In one embodiment the anti-CD20/anti-CD3 bispecific antibody is a chimeric antibody. In one embodiment the anti-CD20/anti-CD3 bispecific antibody is full-length antibody. In one embodiment the anti-CD20/anti-CD3 bispecific antibody is an IgG-class antibody, particularly an IgG1 subclass antibody. In one embodiment, the anti-CD20/anti-CD3 bispecific antibody is a recombinant antibody.

In certain embodiments, the anti-CD20/anti-CD3 bispecific antibody comprises an antibody fragment. Antibody fragments include, but are not limited to, Fab, Fab', Fab'-SH, F(ab')$_2$, Fv, and scFv fragments, and other fragments described below. For a review of certain antibody fragments, see Hudson et al. *Nat. Med.* 9:129-134 (2003). For a review of scFv fragments, see, e.g., Plückthun, in *The Pharmacology of Monoclonal Antibodies*, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and F(ab')$_2$ fragments comprising salvage receptor binding epitope residues and having increased in vivo half-life, see U.S. Pat. No. 5,869,046. In one embodiment, the antibody fragment is a Fab fragment or a scFv fragment.

Diabodies are antibody fragments with two antigen-binding sites that may be bivalent or bispecific. See, for example, EP 404,097; WO 1993/01161; Hudson et al., *Nat. Med.* 9:129-134 (2003); and Hollinger et al., *Proc. Natl. Acad. Sci. USA* 90: 6444-6448 (1993). Triabodies and tetrabodies are also described in Hudson et al., *Nat. Med.* 9:129-134 (2003).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, MA; see, e.g., U.S. Pat. No. 6,248,516 B1).

Antibody fragments can be made by various techniques, including but not limited to proteolytic digestion of an intact antibody as well as production by recombinant host cells (e.g., *E. coli* or phage), as described herein.

In certain embodiments, the anti-CD20/anti-CD3 bispecific antibody is a chimeric antibody. Certain chimeric antibodies are described, e.g., in U.S. Pat. No. 4,816,567; and Morrison et al., *Proc. Nat. Acad. Sci. USA,* 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, the anti-CD20/anti-CD3 bispecific antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, *Front. Biosci.* 13:1619-1633 (2008), and are further described, e.g., in Riechmann et al., *Nature* 332:323-329 (1988); Queen et al., *Proc. Nat'l Acad. Sci. USA* 86:10029-10033 (1989); U.S. Pat. Nos. 5,821,337, 7,527,791, 6,982,321, and 7,087,409; Kashmiri et al., *Methods* 36:25-34 (2005) (describing specificity determining region (SDR) grafting); Padlan, *Mol. Immunol.* 28:489-498 (1991) (describing "resurfacing"); Dall'Acqua et al., *Methods* 36:43-60 (2005) (describing "FR shuffling"); and Osbourn et al., *Methods* 36:61-68 (2005) and Klimka et al., *Br. J. Cancer,* 83:252-260 (2000) (describing the "guided selection" approach to FR shuffling).

Human framework regions that may be used for humanization include but are not limited to: framework regions selected using the "best-fit" method (see, e.g., Sims et al. *J. Immunol.* 151:2296 (1993)); framework regions derived from the consensus sequence of human antibodies of a particular subgroup of light or heavy chain variable regions (see, e.g., Carter et al. *Proc. Natl. Acad. Sci. USA,* 89:4285 (1992); and Presta et al. *J. Immunol.,* 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et al., *J. Biol. Chem.* 272:10678-10684 (1997) and Rosok et al., *J. Biol. Chem.* 271:22611-22618 (1996)).

In certain embodiments, the anti-CD20/anti-CD3 bispecific antibody is a human antibody. Human antibodies can be produced using various techniques known in the art. Human antibodies are described generally in van Dijk and van de Winkel, *Curr. Opin. Pharmacol.* 5: 368-74 (2001) and Lonberg, *Curr. Opin. Immunol.* 20:450-459 (2008).

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, *Nat. Biotech.* 23:1117-1125 (2005). See also, e.g., U.S. Pat. Nos. 6,075,181 and 6,150,584 describing XENO-MOUSE™ technology; U.S. Pat. No. 5,770,429 describing HuMab® technology; U.S. Pat. No. 7,041,870 describing K-M MOUSE® technology, and U.S. Patent Application Publication No. US 2007/0061900, describing VelociMouse® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor *J. Immunol.,* 133: 3001 (1984); Brodeur et al., *Monoclonal Antibody Production Techniques and Applications,* pp. 51-63 (Marcel Dekker, Inc., New York, 1987); and Boerner et al., *J. Immunol.,* 147: 86 (1991).) Human antibodies generated via human B-cell hybridoma technology are also described in Li et al, *Proc. Natl. Acad. Sci. USA,* 103:3557-3562 (2006). Additional methods include those described, for example, in U.S. Pat. No. 7,189,826 (describing production of monoclonal human IgM antibodies from hybridoma cell lines) and Ni, Xiandai Mianyixue, 26(4):265-268 (2006) (describing human-human hybridomas). Human hybridoma technology (Trioma technology) is also described in Vollmers and Brandlein, Histology and Histopathology, 20(3):927-937 (2005) and Vollmers and Brandlein, *Methods and Findings in Experimental and Clinical Pharmacology,* 27(3):185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

Binding domains comprised in the anti-CD20/anti-CD3 bispecific antibody may be isolated by screening combinatorial libraries for binding moieties with the desired activity or activities. For example, a variety of methods are known in the art for generating phage display libraries and screening such libraries for antibodies possessing the desired binding characteristics. Such methods are reviewed, e.g., in Hoogenboom et al. in *Methods in Molecular Biology* 178: 1-37 (O'Brien et al., ed., Human Press, Totowa, NJ, 2001) and further described, e.g., in the McCafferty et al., *Nature* 348:552-554; Clackson et al., *Nature* 352: 624-628 (1991); Marks et al., *J. Mol. Biol.* 222: 581-597 (1992); Marks and Bradbury, in *Methods in Molecular Biology* 248:161-175 (Lo, ed., Human Press, Totowa, NJ, 2003); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132(2004).

In certain phage display methods, repertoires of VH and VL genes are separately cloned by polymerase chain reaction (PCR) and recombined randomly in phage libraries, which can then be screened for antigen-binding phage as described in Winter et al., *Ann. Rev. Immunol.,* 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self-antigens without any immunization as described by Griffiths et al., *EMBO J,* 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J. Mol. Biol.,* 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

Techniques for making bispecific antibodies include, but are not limited to, recombinant co-expression of two immunoglobulin heavy chain-light chain pairs having different specificities (see Milstein and Cuello, *Nature* 305: 537 (1983)), WO 93/08829, and Traunecker et al., EMBO J. 10: 3655 (1991)), and "knob-in-hole" engineering (see, e.g., U.S. Pat. No. 5,731,168). Multi-specific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., *Science,* 229: 81 (1985)); using leucine zippers to produce bi-specific antibodies (see, e.g., Kostelny et al., *J. Immunol.,* 148(5):1547-1553 (1992)); using "diabody" technology for making bispecific antibody fragments (see, e.g., Hollinger et al., *Proc. Natl. Acad. Sci. USA,* 90:6444-6448 (1993)); and using single-chain Fv (scFv) dimers (see, e.g., Gruber et al., *J. Immunol.,* 152:5368 (1994)); and preparing trispecific antibodies as described, e.g., in Tutt et al. *J. Immunol.* 147: 60 (1991).

Engineered antibodies with three or more functional antigen binding sites, including "Octopus antibodies," are also included herein (see, e.g., US 2006/0025576A1).

The anti-CD20/anti-CD3 bispecific antibody herein also includes a "Dual Acting FAb" or "DAF" comprising an antigen binding site that binds to two different antigens (see, US 2008/0069820, for example).

"Crossmab" antibodies are also included herein (see e.g., WO2009080251, WO2009080252, WO2009080253, WO2009080254).

Another technique for making bispecific antibody fragments is the "bispecific T cell engager" or BiTE® approach (see, e.g., WO2004/106381 WO2005/061547, WO2007/042261, and WO2008/1119567). This approach utilizes two antibody variable domains arranged on a single polypeptide. For example, a single polypeptide chain includes two single chain Fv (scFv) fragments, each having a variable heavy chain (VH) and a variable light chain (VL) domain separated by a polypeptide linker of a length sufficient to allow intramolecular association between the two domains. This single polypeptide further includes a polypeptide spacer sequence between the two scFv fragments. Each scFv recognizes a different epitope, and these epitopes may be specific for different cell types, such that cells of two different cell types are brought into proximity or tethered when each scFv is engaged with its cognate epitope. One particular embodiment of this approach includes a scFv recognizing a cell-surface antigen expressed by an immune cell, e.g., a CD3 polypeptide on a T cell, linked to another scFv that recognizes a cell-surface antigen expressed by a target cell, such as a malignant or tumor cell.

As it is a single polypeptide, the bispecific T cell engager may be expressed using any prokaryotic or eukaryotic cell expression system known in the art, e.g., a CHO cell line. However, specific purification techniques (see, e.g., EP1691833) may be necessary to separate monomeric bispecific T cell engagers from other multimeric species, which may have biological activities other than the intended activity of the monomer. In one exemplary purification scheme, a solution containing secreted polypeptides is first subjected to a metal affinity chromatography, and polypeptides are eluted with a gradient of imidazole concentrations. This eluate is further purified using anion exchange chromatography, and polypeptides are eluted using with a gradient of sodium chloride concentrations. Finally, this eluate is subjected to size exclusion chromatography to separate monomers from multimeric species.

In certain embodiments, the anti-CD20/anti-CD3 bispecific antibody may be further modified to contain additional nonproteinaceous moieties that are known in the art and readily available. The moieties suitable for derivatization of the anti-CD20/anti-CD3 bispecific antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, polypropylene glycol homopolymers, polypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight and may be branched or unbranched. The number of polymers attached to the antibody may vary, and if more than one polymer is attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

The anti-CD20/anti-CD3 bispecific antibody may also be conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

In one embodiment, the anti-CD20/anti-CD3 bispecific antibody comprises an antibody-drug conjugate (ADC) in which an antibody is conjugated to one or more drugs, including but not limited to a maytansinoid (see U.S. Pat. Nos. 5,208,020, 5,416,064 and European Patent EP 0 425 235 B1); an auristatin such as monomethylauristatin drug moieties DE and DF (MMAE and MMAF) (see U.S. Pat. Nos. 5,635,483 and 5,780,588, and 7,498,298); a dolastatin; a calicheamicin or derivative thereof (see U.S. Pat. Nos. 5,712,374, 5,714,586, 5,739,116, 5,767,285, 5,770,701, 5,770,710, 5,773,001, and 5,877,296; Hinman et al., *Cancer Res.* 53:3336-3342 (1993); and Lode et al., *Cancer Res.* 58:2925-2928 (1998)); an anthracycline such as daunomycin or doxorubicin (see Kratz et al., *Current Med. Chem.* 13:477-523 (2006); Jeffrey et al., *Bioorganic & Med. Chem. Letters* 16:358-362 (2006); Torgov et al., *Bioconj. Chem.* 16:717-721 (2005); Nagy et al., *Proc. Natl. Acad. Sci. USA* 97:829-834 (2000); Dubowchik et al., *Bioorg. & Med. Chem. Letters* 12:1529-1532 (2002); King et al., *J. Med. Chem.* 45:4336-4343 (2002); and U.S. Pat. No. 6,630,579); methotrexate; vindesine; a taxane such as docetaxel, paclitaxel, larotaxel, tesetaxel, and ortataxel; a trichothecene; and CC1065.

In another embodiment, the anti-CD20/anti-CD3 bispecific antibody is conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Saponaria officinalis* inhibitor, gelonin, mitogellin, restrictocin, phenomycin, enomycin, and the tricothecenes.

In another embodiment, the anti-CD20/anti-CD3 bispecific antibody is conjugated to a radioactive atom to form a radioconjugate. A variety of radioactive isotopes are available for the production of radioconjugates. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the radioconjugate is used for detection, it may comprise a radioactive atom for scintigraphic studies, for example $Tc^{99m}$ or $I^{123}$, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

Conjugates of the anti-CD20/anti-CD3 bispecific antibody and a cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., *Science* 238:1098 (1987). Carbon-14-labeled 1-isothiocyanatobenzyl-3-methyldiethylene triaminepentaacetic acid (MX-DTPA) is an exemplary chelating agent for conjugation of a radionucleotide to an antibody. See WO94/11026. The linker may be a "cleavable linker" facilitating release of a cytotoxic drug in the cell. For example, an acid-labile linker, peptidase-sensitive linker, photolabile linker, dimethyl linker or disulfide-containing linker (Chari et al., *Cancer Res.* 52:127-131 (1992); U.S. Pat. No. 5,208,020) may be used.

In one embodiment, the anti-CD20/anti-CD3 bispecific antibody is indicated for the treatment of cancer. In one embodiment, cancer is a B-cell proliferative disorder. In one embodiment, the cancer is a CD20-positive B-cell proliferative disorder. In one embodiment, the cancer is a non-Hodgkin's lymphoma (NHL). In one embodiment the NHL is a diffuse large B cell lymphoma (DLBCL), a high grade B cell lymphoma (HGBCL), a DLBCL arising from FL [transformed FL; trFL], a primary mediastinal large B-cell lymphoma (PMBCL), or marginal zone lymphoma (MZL). MZL can be categorized as splenic, nodal and extra-nodal MZL. In on embodiment the NHL is a mantle cell lymphoma (MCL). In one embodiment, the NHL is a Grade 1-3a Follicular Lymphoma (FL). In one embodiment, the CD20-positive B cell proliferative disorder is a relapsed or refractory B cell proliferative disorder. In one embodiment, the relapsed or refractory B cell proliferative disorder is relapsed or refractory NHL (e.g., a relapsed or refractory DLBCL, a relapsed or refractory FL, or a relapsed or refractory MCL).

In one embodiment, the anti-CD20/anti-CD3 bispecific antibody specifically binds to CD3s.

In one embodiment, the anti-CD20/anti-CD3 bispecific antibody can compete for binding with antibody H2C (PCT publication no. WO2008/119567), antibody V9 (Rodrigues et al., *Int J Cancer Suppl.* 7, 45-50 (1992) and U.S. Pat. No.

6,054,297), antibody FN18 (Nooij et al., *Eur J Immunol.* 19, 981-984 (1986)), antibody SP34 (Pessano et al., *EMBO J.* 4, 337-340 (1985)), antibody OKT3 (Kung et al., Science 206, 347-349 (1979)), antibody WT31 (Spits et al., *J Immunol.* 135, 1922 (1985)), antibody UCHT1 (Burns et al., *J Immunol.* 129, 1451-1457 (1982)), antibody 7D6 (Coulie et al., *Eur J Immunol.* 21, 1703-1709 (1991)) or antibody Leu-4. In some embodiments, the anti-CD20/anti-CD3 bispecific antibody may also comprise an antigen binding moiety that specifically binds to CD3 as described in WO 2005/040220, WO 2005/118635, WO 2007/042261, WO 2008/119567, WO 2008/119565, WO 2012/162067, WO 2013/158856, WO 2013/188693, WO 2013/186613, WO 2014/110601, WO 2014/145806, WO 2014/191113, WO 2014/047231, WO 2015/095392, WO 2015/181098, WO 2015/001085, WO 2015/104346, WO 2015/172800, WO 2016/020444, or WO 2016/014974.

In some embodiments, the anti-CD20/anti-CD3 bispecific antibody may comprise an antibody or an antigen binding moiety from rituximab, obinutuzumab ocrelizumab, ofatumumab, ocaratuzumab, veltuzumab, and ublituximab.

In one embodiment, the anti-CD20/anti-CD3 bispecific antibody is XmAb®13676. In one embodiment, the anti-CD20/anti-CD3 bispecific antibody is REGN1979. In one embodiment, the anti-CD20/anti-CD3 bispecific antibody is FBTA05 (Lymphomun). In a preferred embodiment, the anti-CD20/anti-CD3 bispecific antibody is glofitamab.

In some embodiments, the anti-CD20/anti-CD3 bispecific antibody may comprise a generic, biosimilar or non-comparable biologic version of an antibody, named herein.

In one embodiment, the anti-CD20/anti-CD3 bispecific antibody comprises at least one antigen binding domain that specifically binds to CD20, comprising a heavy chain variable region comprising
  (i) an HVR-H1 comprising the amino acid sequence of SEQ ID NO: 1;
  (ii) an HVR-H2 comprising the amino acid sequence of SEQ ID NO: 2;
  (iii) an HVR-H3 comprising the amino acid sequence of SEQ ID NO:3;
and a light chain variable region comprising
  (i) an HVR-L1 comprising the amino acid sequence of SEQ ID NO: 4;
  (ii) an HVR-L2 comprising the amino acid sequence of SEQ ID NO: 5; and
  (iii) an HVR-L3 comprising the amino acid sequence of SEQ ID NO: 6.

In one embodiment, anti-CD20/anti-CD3 bispecific antibody comprises at least one antigen binding domain that specifically binds to CD20, comprising a heavy chain variable region sequence that is at least 80%, 85%, 90%, 95%, 96%, 97%, 98%, or 99% identical to of SEQ ID NO: 7 and a light chain variable region sequence that is at least 80%, 85%, 90%, 95%, 96%, 97%, 98%, or 99% identical to the sequence of SEQ ID NO: 8. In a further embodiment, the anti-CD20/anti-CD3 bispecific antibody comprises at least one antigen binding domain that specifically binds to CD20 comprising the heavy chain variable region sequence of SEQ ID NO: 7 and the light chain variable region sequence of SEQ ID NO: 8.

In one embodiment, the anti-CD20/anti-CD3 bispecific antibody comprises at least one antigen binding domain that specifically binds to CD3 comprising a heavy chain variable region comprising:
  (i) an HVR-H1 comprising the amino acid sequence of SEQ ID NO: 9;
  (ii) an HVR-H2 comprising the amino acid sequence of SEQ ID NO: 10;
  (iii) an HVR-H3 comprising the amino acid sequence of SEQ ID NO:11; and and a light chain variable region comprising
  (i) an HVR-L1 comprising the amino acid sequence of SEQ ID NO: 12;
  (ii) an HVR-L2 comprising the amino acid sequence of SEQ ID NO: 13; and
  (iii) an HVR-L3 comprising the amino acid sequence of SEQ ID NO: 14.

In one embodiment, anti-CD20/anti-CD3 bispecific antibody comprises at least one antigen binding domain that specifically binds to CD3, comprising a heavy chain variable region sequence that is at least 80%, 85%, 90%, 95%, 96%, 97%, 98%, or 99% identical to of SEQ ID NO: 15 and a light chain variable region sequence that is at least 80%, 85%, 90%, 95%, 96%, 97%, 98%, or 99% identical to the sequence of SEQ ID NO: 16. In a further embodiment, the anti-CD20/anti-CD3 bispecific antibody comprises at least one antigen binding domain that specifically binds to CD3 comprising the heavy chain variable region sequence of SEQ ID NO: 15 and the light chain variable region sequence of SEQ ID NO: 16.

In one embodiment, the anti-CD20/anti-CD3 bispecific antibody comprises
  a) at least one antigen binding domain that specifically binds to CD20 comprising a heavy chain variable region comprising:
    (i) an HVR-H1 comprising the amino acid sequence of SEQ ID NO: 1;
    (ii) an HVR-H2 comprising the amino acid sequence of SEQ ID NO: 2;
    (iii) an HVR-H3 comprising the amino acid sequence of SEQ ID NO:3;
  and a light chain variable region comprising:
    (i) an HVR-L1 comprising the amino acid sequence of SEQ ID NO: 4;
    (ii) an HVR-L2 comprising the amino acid sequence of SEQ ID NO: 5;
    (iii) an HVR-L3 comprising the amino acid sequence of SEQ ID NO: 6; and
  b) at least one antigen binding domain that specifically binds to CD3 comprising a heavy chain variable region comprising:
    (i) an HVR-H1 comprising the amino acid sequence of SEQ ID NO: 9;
    (ii) an HVR-H2 comprising the amino acid sequence of SEQ ID NO: 10;
    (iii) an HVR-H3 comprising the amino acid sequence of SEQ ID NO:11; and
  a light chain variable region comprising:
    (i) an HVR-L1 comprising the amino acid sequence of SEQ ID NO: 12;
    (ii) an HVR-L2 comprising the amino acid sequence of SEQ ID NO: 13; and
    (iii) an HVR-L3 comprising the amino acid sequence of SEQ ID NO: 14.

In one embodiment, the anti-CD20/anti-CD3 bispecific antibody comprises
  (i) at least one antigen binding domain that specifically binds to CD20 comprising the heavy chain variable region sequence of SEQ ID NO: 7 and the light chain variable region sequence of SEQ ID NO: 8, and
  (ii) at least one antigen binding domain that specifically binds to CD3 comprising the heavy chain variable region sequence of SEQ ID NO: 15 and the light chain variable region sequence of SEQ ID NO: 16.

In one embodiment, the antigen binding domain that specifically binds to CD3 of the anti-CD20/anti-CD3 bispecific antibody is an antibody fragment, particularly a Fab molecule or a scFv molecule, more particularly a Fab molecule. In a particular embodiment, the antigen binding domain that specifically binds to CD3 of the anti-CD20/anti-CD3 bispecific antibody is a crossover Fab molecule wherein the variable domains or the constant domains of the Fab heavy and light chain are exchanged (i.e., replaced by each other).

In one embodiment, the anti-CD20/anti-CD3 bispecific antibody comprises at least one antigen binding domain that specifically binds to CD20, and one antigen binding domain that specifically binds to CD3. In one embodiment, the anti-CD20/anti-CD3 bispecific antibody comprises a first antigen binding domain that specifically binds to CD3, and a second and a third antigen binding domain that specifically bind to CD20. In one embodiment, the first antigen binding domain is a crossover Fab molecule, and the second and the third antigen binding domain are each a conventional Fab molecule. In one embodiment, the anti-CD20/anti-CD3 bispecific antibody further comprises an Fc domain. The anti-CD20/anti-CD3 bispecific antibody may comprise modifications in the Fc region and/or the antigen binding domains as described herein. In one embodiment, the anti-CD20/anti-CD3 bispecific antibody comprises an IgG1 Fc domain comprising one or more amino acid substitutions that reduce binding to an Fc receptor and/or effector function. In one embodiment the anti-CD20/anti-CD3 bispecific antibody comprises an IgG1 Fc domain comprising the amino acid substitutions L234A, L235A and P329G (EU numbering).

In one embodiment the anti-CD20/anti-CD3 bispecific antibody comprises
  (i) an antigen binding domain that specifically binds to CD3 which is fused at the C-terminus of the Fab heavy chain to the N-terminus of the first subunit of the Fc domain;
  (ii) a first antigen binding domain that specifically binds to CD20 which is fused at the C-terminus of the Fab heavy chain to the N-terminus of the Fab heavy chain of the antigen binding domain that specifically binds to CD3; and
  (iii) a second antigen binding domain that specifically binds to CD20 which is fused at the C-terminus of the Fab heavy chain to the N-terminus of the second subunit of the Fc domain.

In a particular embodiment, the anti-CD20/anti-CD3 bispecific antibody comprises
  a) a first Fab molecule which specifically binds to CD3, particularly CD3 epsilon; and wherein the variable domains VL and VH of the Fab light chain and the Fab heavy chain are replaced by each other;
  b) a second Fab and a third Fab molecule which specifically bind to CD20, wherein in the constant domain CL of the second Fab and third Fab molecule the amino acid at position 124 is substituted by lysine (K) (numbering according to Kabat) and the amino acid at position 123 is substituted by lysine (K) or arginine (R), particularly by arginine (R) (numbering according to Kabat), and wherein in the constant domain CH1 o of the second Fab and third Fab molecule the amino acid at position 147 is substituted by glutamic acid (E) (EU numbering) and the amino acid at position 213 is substituted by glutamic acid (E) (EU numbering); and
  c) a Fc domain composed of a first and a second subunit capable of stable association.

In one embodiment, the anti-CD20/anti-CD3 bispecific antibody comprises two antigen binding domains that specifically bind to CD20 and one antigen binding domain that specifically binds to CD3. In one embodiment, the anti-CD20/anti-CD3 bispecific antibody is bivalent for CD20 and monovalent for CD3.

In one embodiment the first Fab molecule under a) is fused at the C-terminus of the Fab heavy chain to the N-terminus of one of the subunits of the Fc domain under c), the second Fab molecule under b) is fused at the C-terminus of the Fab heavy chain to the N-terminus of the heavy chain of the first Fab molecule under a), and the third Fab molecule under b) is fused at the C-terminus of the Fab heavy chain to the N-terminus of the other subunit of the Fc domain under c). In one embodiment, the first Fab molecule under a) comprises a heavy chain variable region that is at least 95%, 96%, 97%, 98%, or 99% identical to the sequence of SEQ ID NO: 15, and a light chain variable region that is at least 95%, 96%, 97%, 98%, or 99% identical to the sequence of SEQ ID NO: 16.

In still a further embodiment, the first Fab molecule under a) comprises the heavy chain variable region sequence of SEQ ID NO: 15, and the light chain variable region sequence of SEQ ID NO: 16.

In one embodiment, the second Fab molecule and the third Fab molecule under b) each comprise a heavy chain variable region that is at least 95%, 96%, 97%, 98%, or 99% identical to the sequence of SEQ ID NO: 7, and a light chain variable region that is at least 95%, 96%, 97%, 98%, or 99% identical to the sequence of SEQ ID NO: 8.

In one embodiment, the second Fab molecule under and the third Fab molecule under b) each comprise the heavy chain variable region sequence of SEQ ID NO: 7, and the light chain variable region sequence of SEQ ID NO: 8.

In a particular embodiment, the anti-CD20/anti-CD3 bispecific antibody comprises a polypeptide that is at least 95%, 96%, 97%, 98%, or 99% identical to the sequence of SEQ ID NO: 17, a polypeptide that is at least 95%, 96%, 97%, 98%, or 99% identical to the sequence of SEQ ID NO: 18, a polypeptide that is at least 95%, 96%, 97%, 98%, or 99% identical to the sequence of SEQ ID NO: 19, and a polypeptide that is at least 95%, 96%, 97%, 98%, or 99% identical to the sequence of SEQ ID NO: 20. In a further particular embodiment, the anti-CD20/anti-CD3 bispecific antibody comprises a polypeptide sequence of SEQ ID NO: 17, a polypeptide sequence of SEQ ID NO: 18, a polypeptide sequence of SEQ ID NO: 19 and a polypeptide sequence of SEQ ID NO: 20. In a further particular embodiment, the anti-CD20/anti-CD3 bispecific antibody comprises one polypeptide chain comprising SEQ ID NO: 17, one polypeptide chain comprising SEQ ID NO: 18, one polypeptide chain comprising SEQ ID NO: 19, and two polypeptide chains comprising SEQ ID NO: 20.

Particular anti-CD20/anti-CD3 bispecific antibodies are described in PCT Publication No. WO 2016/020309 and European Patent Application Nos. EP15188093 and EP16169160, each incorporated herein by reference in its entirety.

Glofitamab

In one embodiment the anti-CD20/anti-CD3 bispecific antibody useful in the methods provided herein is glofitamab. Glofitamab (WHO Drug Information (International Nonproprietary Names for Pharmaceutical Substances), Recommended INN: List 83, 2020, vol. 34, no. 1, p. 39; also known as CD20-TCB, RO7082859, or RG6026; CAS #:

2229047-91-8) is a novel T-cell-engaging bispecific (TCB) full-length antibody with a 2:1 molecular configuration for bivalent binding to CD20 on B cells and monovalent binding to CD3, particularly on the CD3 epsilon chain (CD3ε), on T cells. Its CD3-binding region is fused to one of the CD20-binding regions in a head-to-tail fashion via a flexible linker. This structure endows glofitamab with superior in vitro potency versus other CD20-CD3 bispecific antibodies with a 1:1 configuration and leads to profound antitumor efficacy in preclinical DLBCL models. CD20 bivalency preserves this potency in the presence of competing anti-CD20 antibodies, providing the opportunity for pre- or co-treatment with these agents. Glofitamab comprises an engineered, heterodimeric Fc region with completely abolished binding to FcγRs and C1q. By simultaneously binding to human CD20-expressing tumor cells and to the CD3ε of the T-cell receptor (TCR) complex on T-cells, it induces tumor cell lysis, in addition to T-cell activation, proliferation and cytokine release. Lysis of B-cells mediated by glofitamab is CD20-specific and does not occur in the absence of CD20 expression or in the absence of simultaneous binding (cross-linking) of T-cells to CD20-expressing cells. In addition to killing, T-cells undergo activation due to CD3 cross-linking, as detected by an increase in T-cell activation markers (CD25 and CD69), cytokine release (IFNγ, TNFα, IL-2, IL-6, IL-10), cytotoxic granule release (Granzyme B) and T-cell proliferation. A schematic of the molecule structure of glofitamab is depicted in FIG. 2. The sequences of glofitamab are summarized in Table 2.

TABLE 2

Sequence IDs for glofitamab
Sequence IDs for glofitamab

| SEQ ID NO: | Description | SEQ ID NO: | Description |
| --- | --- | --- | --- |
| CD3 Heavy Chain | | CD3 Light Chain | |
| 9 | HVR-H1 (Kabat) | 12 | HVR-L1 (Kabat) |
| 10 | HVR-H2 (Kabat) | 13 | HVR-L2 (Kabat) |
| 11 | HVR-H3 (Kabat) | 14 | HVR-L3 (Kabat) |
| 15 | VH | 16 | VL |
| CD20 Heavy Chain | | CD20 Light Chain | |
| 1 | HVR-H1 (Kabat) | 4 | HVR-L1 (Kabat) |
| 2 | HVR-H2 (Kabat) | 5 | HVR-L2 (Kabat) |
| 3 | HVR-H3 (Kabat) | 6 | HVR-L3 (Kabat) |
| 7 | VH | 8 | VH |
| Full-length antibody | | | |
| 17 | HC-knob | 18 | HC-hole |
| 19 | LC-CD3 | 20 | LC-CD20 |

B. Anti-CD79b Antibody Drug Conjugates

Anti-CD79b antibody drug conjugates useful in the methods described herein (e.g., for treating a CD20-positive cell proliferative disorder, e.g., a B cell proliferative disorder (e.g., an NHL (e.g., a relapsed and/or refractory NHL, a DLBCL (e.g., a relapsed and/or refractory DLBCL), a FL (e.g., a relapsed and/or refractory FL or a transformed FL), or an MCL (e.g., a relapsed or refractory MCL)), or a CNSL) include any of the anti-CD79b antibody drug conjugates described in U.S. Pat. No. 8,088,378, which is incorporated herein by reference in its entirety. In some instances, the anti-CD79b antibody drug conjugate includes an anti-CD79b binding domain comprising at least one, two, three, four, five, or six hypervariable regions (HVRs) selected from (a) an HVR-H1 comprising the amino acid sequence of SEQ ID NO: 21; (b) an HVR-H2 comprising the amino acid sequence of SEQ ID NO: 22; (c) an HVR-H3 comprising the amino acid sequence of SEQ ID NO: 23; (d) an HVR-L1 comprising the amino acid sequence of SEQ ID NO: 24; (e) an HVR-L2 comprising the amino acid sequence of SEQ ID NO: 25; and (f) an HVR-L3 comprising the amino acid sequence of SEQ ID NO: 26. In some instances, the anti-CD79b antibody drug conjugate includes an anti-CD79b binding domain comprising all six of the following HVRs: (a) an HVR-H1 comprising the amino acid sequence of GYTFSSYWIE (SEQ ID NO: 21); (b) an HVR-H2 comprising the amino acid sequence of GEILPGGGDTNYNE-IFKG (SEQ ID NO: 22); (c) an HVR-H3 comprising the amino acid sequence of TRRVPIRLDY (SEQ ID NO: 23); (d) an HVR-L1 comprising the amino acid sequence of KASQSVDYEGDSFLN (SEQ ID NO: 24); (e) an HVR-L2 comprising the amino acid sequence of AASNLES (SEQ ID NO: 25); and (f) an HVR-L3 comprising the amino acid sequence of QQSNEDPLT (SEQ ID NO: 26). In some instances, the anti-CD79b antibody drug conjugate comprises at least one (e.g., 1, 2, 3, or 4) of heavy chain framework regions FR-H1, FR-H2, FR-H3, and FR-H4 comprising the sequences of SEQ ID NOs: 29-32, respectively, and/or at least one (e.g., 1, 2, 3, or 4) of the light chain framework regions FR-L1, FR-L2, FR-L3, and FR-L4 comprising the sequences of SEQ ID NOs: 33-36, respectively. In some instances, the anti-CD79b antibody drug conjugate comprises (a) a heavy chain variable (VH) domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 27; (b) a light chain variable (VL) domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 28; or (c) a VH domain as in (a) and a VL domain as in (b). Accordingly, in some instances, the first binding domain comprises a VH domain comprising an amino acid sequence of SEQ ID NO: 27 and a VL domain comprising an amino acid sequence of SEQ ID NO: 28.

In some instances, the anti-CD79b antibody drug conjugate comprises (a) a heavy chain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 37; (b) a light chain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 38; or (c) a VH domain as in (a) and a VL domain as in (b). Accordingly, in some instances, the first binding domain comprises a VH domain comprising an amino acid sequence of SEQ ID NO: 37 and a VL domain comprising an amino acid sequence of SEQ ID NO: 38.

The sequences of the anti-CD79b antibody of polatuzumab vedotin are summarized in Table 3 below.

TABLE 3

Sequence IDs for anti-CD79b antibody of polatuzumab vedotin

| Heavy Chain | | Light Chain | |
| --- | --- | --- | --- |
| SEQ ID NO: | Description | SEQ ID NO: | Description |
| 21 | HVR-H1 | 24 | HVR-L1 |
| 22 | HVR-H2 | 25 | HVR-L2 |
| 23 | HVR-H3 | 26 | HVR-L3 |
| 27 | VH | 28 | VL |
| 37 | Heavy Chain | 38 | Light Chain |

In some instances, the anti-CD79b antibody is linked to a toxin such as monomethyl auristatin E (MMAE, i.e., vedotin). In some instances, the anti-CD79b antibody drug conjugate is polatuzumab vedotin (immunoglobulin G1-kappa auristatin E conjugate, anti-[*Homo sapiens* CD79b (immunoglobulin-associated CD79 beta)], humanized monoclonal antibody conjugated to auristatin E; gamma1 heavy chain (1-447) [humanized VH (*Homo sapiens* IGHV3-23*04 (76.50%)-(IGHD)-IGHJ4*01) [8.8.10] (1-117)-*Homo sapiens* IGHG1*03 (CH1 R120>K (214)(118-215), hinge (216-230), CH2 (231-340), CH3 (341-445), CHS (446-447)) (118-447)], (220-218')-disulfide with kappa light chain (1'-218') [humanized V-KAPPA (*Homo sapiens* IGKV1-39*01 (85.90%)—IGKJ1*01) [10.3.9] (1'-111')—*Homo sapiens* IGKC*01 (112'-218')]; dimer (226-226":229-229")-bisdisulfide; conjugated, on an average of 3 to 4 cysteinyl, to monomethylauristatin E (MMAE), via a cleavable maleimidocaproyl-valyl-citrullinyl-p-aminobenzyloxycarbonyl (mc-val-cit-PABC) type linker; also known as RG-7596, or RO5541077-000)), as defined by International Nonproprietary Names for Pharmaceutical Substances (INN) List 110 (WHO Drug Information, Vol. 27, No. 4, 2016, p. 443). Polatuzumab vedotin is also referred to as IUPHAR/BPS Number 8404, the KEGG Number D10761, or the CAS Registry Number 1313206-42-6. Polatuzumab vedotin-piiq is also interchangeably referred to as "polatuzumab vedotin-piiq", "huMA79bv28-MC-vc-PAB-MMAE", or "DCDS4501A." In some embodiments, the anti-CD79b antibody (e.g., the anti-CD79b ADC) comprises a heavy chain sequence of SEQ ID NO: 37 and a light chain sequence of SEQ ID NO: 38.

In some instances, the anti-CD79b antibody drug conjugate comprises the formula:

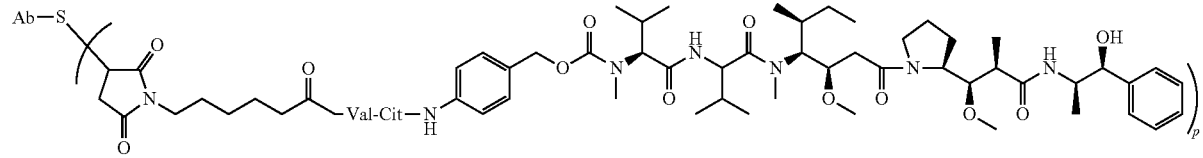

wherein Ab is an anti-CD79b antibody comprising (i) a hypervariable region-H1 (HVR-H1) that comprises the amino acid sequence of SEQ ID NO: 21; (ii) an HVR-H2 comprising the amino acid sequence of SEQ ID NO: 22; (iii) an HVR-H3 comprising the amino acid sequence of SEQ ID NO: 23; (iv) an HVR-L1 comprising the amino acid sequence of SEQ ID NO: 24; (v) an HVR-L2 comprising the amino acid sequence of SEQ ID NO: 25; and (vi) an HVR-L3 comprising the amino acid sequence of SEQ ID NO: 26, and wherein p is between 1 and 8.

In some embodiments, the antibody drug conjugate comprises an anti-CD79b antibody comprising (a) a VH domain comprising at least one, at least two, or all three VH HVR sequences selected from (i) HVR-H1 comprising the amino acid sequence of SEQ ID NO: 21, (ii) HVR-H2 comprising the amino acid sequence of SEQ ID NO: 22, and (iii) HVR-H3 comprising an amino acid sequence selected from SEQ ID NO: 23; and (b) a VL domain comprising at least one, at least two, or all three VL HVR sequences selected from (i) HVR-L1 comprising an amino acid sequence of SEQ ID NO: 24, (ii) HVR-L2 comprising the amino acid sequence of SEQ ID NO: 25, and (iii) HVR-L3 comprising the amino acid sequence of SEQ ID NO: 26. In some embodiments, the antibody drug conjugate comprises an anti-CD79b antibody that comprises at least one of: (i) HVR-H3 comprising the amino acid sequence of SEQ ID NO: 23, and/or (ii) HVR-L1 comprising the amino acid sequence of SEQ ID NO: 24. In some embodiments, the antibody drug conjugate comprises an anti-CD79b antibody that comprises (a) HVR-H1 comprising the amino acid sequence of SEQ ID NO: 21; (b) HVR-H2 comprising the amino acid sequence of SEQ ID NO: 22; (c) HVR-H3 comprising the amino acid sequence of SEQ ID NO: 23; (d) HVR-L1 comprising an amino acid sequence of SEQ ID NO: 24; (e) HVR-L2 comprising the amino acid sequence of SEQ ID NO: 25; and (f) HVR-L3 comprising the amino acid sequence of SEQ ID NO: 26.

In some embodiments, the antibody drug conjugate comprises at least one of: HVR-H3 comprising the amino acid sequence of SEQ ID NO: 23 and/or HVR-L1 comprising an amino acid sequence of SEQ ID NO: 24. In some embodiments, the antibody drug conjugate comprises an anti-CD79b antibody that comprises (a) HVR-H1 comprising the amino acid sequence of SEQ ID NO: 21; (b) HVR-H2 comprising the amino acid sequence of SEQ ID NO: 22; (c) HVR-H3 comprising the amino acid sequence of SEQ ID NO: 23; (d) HVR-L1 comprising the amino acid sequence of SEQ ID NO: 24; (e) HVR-L2 comprising the amino acid sequence of SEQ ID NO: 25; and (f) HVR-L3 comprising the amino acid sequence of SEQ ID NO: 26.

In some embodiments, the anti-CD79b antibody drug conjugate comprises a humanized anti-CD79b antibody. In some embodiments, an anti-CD79b antibody comprises HVRs as in any of the embodiments provided herein, and further comprises a human acceptor framework, e.g., a human immunoglobulin framework or a human consensus framework. In some embodiments, the human acceptor framework is the human VL kappa 1 (VLK1) framework and/or the VH framework VHIII. In some embodiments, a humanized anti-CD79b antibody comprises (a) HVR-H1 comprising the amino acid sequence of SEQ ID NO: 21; (b) HVR-H2 comprising the amino acid sequence of SEQ ID NO: 22; (c) HVR-H3 comprising the amino acid sequence of SEQ ID NO: 23; (d) HVR-L1 comprising an amino acid sequence of SEQ ID NO: 24; (e) HVR-L2 comprising the amino acid sequence of SEQ ID NO: 25; and (f) HVR-L3 comprising the amino acid sequence of SEQ ID NO: 26. In some embodiments, a humanized anti-CD79b antibody comprises (a) HVR-H1 comprising the amino acid sequence of SEQ ID NO: 21; (b) HVR-H2 comprising the amino acid sequence of SEQ ID NO: 22; (c) HVR-H3 comprising the amino acid sequence of SEQ ID NO: 23; (d) HVR-L1 comprising the amino acid sequence of SEQ ID NO: 24; (e) HVR-L2 comprising the amino acid sequence of SEQ ID NO: 25; and (f) HVR-L3 comprising the amino acid sequence of SEQ ID NO: 26.

In some embodiments, the antibody drug conjugate (e.g., the anti-CD79b antibody drug conjugate) comprises an anti-CD79 antibody comprising a heavy chain variable domain (VH) sequence having at least 90%, 91%, 92%, 93%, 94%, 95%, 96%, 97%, 98%, 99%, or 100% sequence identity to the amino acid sequence of SEQ ID NO: 27. In some embodiments, a VH sequence having at least 90%, 91%, 92%, 93%, 94%, 95%, 96%, 97%, 98%, or 99% identity to the amino acid sequence of SEQ ID NO: 27 contains substitutions (e.g., conservative substitutions), insertions, or deletions relative to the reference sequence, but an anti-CD79b antibody drug conjugate comprising that sequence retains the ability to bind to CD79b. In some embodiments, a total of 1 to 10 amino acids have been substituted, inserted and/or deleted in SEQ ID NO: 27. In some embodiments, a total of 1 to 5 amino acids have been substituted, inserted and/or deleted in SEQ ID NO: 27. In some embodiments, substitutions, insertions, or deletions occur in regions outside the HVRs (i.e., in the FRs, e.g., SEQ ID NOs: 29-32). In some embodiments, the antibody drug conjugate (e.g., the anti-CD79b antibody drug conjugate) comprises the VH sequence of SEQ ID NO: 27, including posttranslational modifications of that sequence. In some embodiments, the VH comprises one, two, or three HVRs selected from: (a) HVR-H1 comprising the amino acid sequence of SEQ ID NO: 21, (b) HVR-H2 comprising the amino acid sequence of SEQ ID NO: 22, and (c) HVR-H3 comprising the amino acid sequence of SEQ ID NO: 23.

In some embodiments, the antibody drug conjugate (e.g., the anti-CD79b antibody drug conjugate) comprises an anti-CD79b antibody that comprises a light chain variable domain (VL) having at least 90%, 91%, 92%, 93%, 94%, 95%, 96%, 97%, 98%, 99%, or 100% sequence identity to the amino acid sequence of SEQ ID NO: 28. In certain embodiments, a VL sequence having at least 90%, 91%, 92%, 93%, 94%, 95%, 96%, 97%, 98%, or 99% identity to the amino acid sequence of SEQ ID NO: 28 contains substitutions (e.g., conservative substitutions), insertions, or deletions relative to the reference sequence, but an anti-CD79b antibody drug conjugate comprising that sequence retains the ability to bind to CD79b. In certain embodiments, a total of 1 to 10 amino acids have been substituted, inserted and/or deleted in SEQ ID NO: 28. In certain embodiments, a total of 1 to 5 amino acids have been substituted, inserted and/or deleted in SEQ ID NO: 28. In certain embodiments, the substitutions, insertions, or deletions occur in regions outside the HVRs (i.e., in the FRs, e.g., SEQ ID NOs: 33-36). In some embodiments, the anti-CD79b antibody drug conjugate comprises an anti-CD79b antibody that comprises the VL sequence of SEQ ID NO: 28, including post-translational modifications of that sequence. In some embodiments, the VL comprises one, two, or three HVRs selected from (a) HVR-L1 comprising an amino acid sequence of SEQ ID NO: 24; (b) HVR-L2 comprising the amino acid sequence of SEQ ID NO: 25; and (c) HVR-L3 comprising the amino acid sequence of SEQ ID NO: 26. In some embodiments, the VL comprises one, two or three HVRs selected from (a) HVR-L1 comprising the amino acid sequence of SEQ ID NO: 24; (b) HVR-L2 comprising the amino acid sequence of SEQ ID NO: 25; and (c) HVR-L3 comprising the amino acid sequence of SEQ ID NO: 26.

In some embodiments, the antibody drug conjugate (e.g., the anti-CD79b antibody drug conjugate) comprises an anti-CD79b antibody that comprises VH as in any of the embodiments provided herein, and a VL as in any of the embodiments provided herein. In some embodiments, the antibody drug conjugate comprises an anti-CD79b antibody that comprises the VH and VL sequences in SEQ ID NO: 27 and SEQ ID NO: 28, respectively, including post-translational modifications of those sequences.

In some embodiments, the antibody drug conjugate (e.g., anti-CD79b antibody drug conjugate) comprises an anti-CD79b antibody that binds to the same epitope as an anti-CD79b antibody described herein. For example, in some embodiments, the antibody drug conjugate (e.g., anti-CD79b antibody drug conjugate) comprises an anti-CD79b antibody that binds to the same epitope as an anti-CD79b antibody comprising a VH sequence of SEQ ID NO: 27 and a VL sequence of SEQ ID NO: 28.

In some embodiments, the antibody drug conjugate comprises an anti-CD79b antibody that is a monoclonal antibody, a chimeric antibody, humanized antibody, or human antibody. In some embodiments, antibody drug conjugate comprises an antigen-binding fragment of an anti-CD79b antibody described herein, e.g., a Fv, Fab, Fab', scFv, diabody, or F(ab')₂ fragment. In some embodiments, the antibody drug conjugate comprises a substantially full-length anti-CD79b antibody, e.g., an IgG1 antibody or other antibody class or isotype as described elsewhere herein. Anti-CD79b antibody drug conjugates may be produced using recombinant methods and compositions, for example, as described in U.S. Pat. No. 4,816,567.

In some instances, the anti-CD79b antibody drug conjugates according to any of the embodiments described above may incorporate any of the features, singly or in combination, as described below.

C. Antibody Formats

1. Anti-CD20/Anti-CD3 Bispecific Antibody

The components of the anti-CD20/anti-CD3 bispecific antibody can be fused to each other in a variety of configurations. Exemplary configurations are depicted in FIG. 1.

In particular embodiments, the antigen binding moieties comprised in the anti-CD20/anti-CD3 bispecific antibody are Fab molecules. In such embodiments, the first, second, third, etc. antigen binding moiety may be referred to herein as first, second, third, etc. Fab molecule, respectively. Furthermore, in particular embodiments, the anti-CD20/anti-CD3 bispecific antibody comprises an Fc domain composed of a first and a second subunit capable of stable association.

In some embodiments, the first Fab molecule is fused at the C-terminus of the Fab heavy chain to the N-terminus of the first or the second subunit of the Fc domain.

In one such embodiment, the second Fab molecule is fused at the C-terminus of the Fab heavy chain to the N-terminus of the Fab heavy chain of the first Fab molecule. In a specific such embodiment, the anti-CD20/anti-CD3 bispecific antibody essentially consists of the first and the second Fab molecule, the Fc domain composed of a first and a second subunit, and optionally one or more peptide linkers, wherein the first Fab molecule is fused at the C-terminus of the Fab heavy chain to the N-terminus of the first or the second subunit of the Fc domain and the second Fab molecule is fused at the C-terminus of the Fab heavy chain to the N-terminus of the Fab heavy chain of the first Fab molecule. Such a configuration is schematically depicted in FIG. 1G and FIG. 1K. Optionally, the Fab light chain of the first Fab molecule and the Fab light chain of the second Fab molecule may additionally be fused to each other.

In another embodiment, the second Fab molecule is fused at the C-terminus of the Fab heavy chain to the N-terminus of the first or second subunit of the Fc domain. In a specific such embodiment, the antibody essentially consists of the first and the second Fab molecule, the Fc domain composed of a first and a second subunit, and optionally one or more peptide linkers, wherein the first and the second Fab molecule are each fused at the C-terminus of the Fab heavy chain to the N-terminus of one of the subunits of the Fc domain. Such a configuration is schematically depicted in FIG. 1A and FIG. 1D. The first and the second Fab molecule may be fused to the Fc domain directly or through a peptide linker. In a particular embodiment the first and the second Fab molecule are each fused to the Fc domain through an immunoglobulin hinge region. In a specific embodiment, the immunoglobulin hinge region is a human IgG$_1$ hinge region, particularly where the Fc domain is an IgG$_1$ Fc domain.

In other embodiments, the second Fab molecule is fused at the C-terminus of the Fab heavy chain to the N-terminus of the first or second subunit of the Fc domain. In one such embodiment, the first Fab molecule is fused at the C-terminus of the Fab heavy chain to the N-terminus of the Fab heavy chain of the second Fab molecule. In a specific such embodiment, the antibody essentially consists of the first and the second Fab molecule, the Fc domain composed of a first and a second subunit, and optionally one or more peptide linkers, wherein the first Fab molecule is fused at the C-terminus of the Fab heavy chain to the N-terminus of the Fab heavy chain of the second Fab molecule, and the second Fab molecule is fused at the C-terminus of the Fab heavy chain to the N-terminus of the first or the second subunit of the Fc domain. Such a configuration is schematically depicted in FIG. 1H and FIG. 1L. Optionally, the Fab light chain of the first Fab molecule and the Fab light chain of the second Fab molecule may additionally be fused to each other.

The Fab molecules may be fused to the Fc domain or to each other directly or through a peptide linker, comprising one or more amino acids, typically about 2-20 amino acids. Peptide linkers are known in the art and are described herein. Suitable, non-immunogenic peptide linkers include, for example, (G$_4$S)$_n$ (SEQ ID NO: 39), (SG$_4$)$_n$ (SEQ ID NO: 40), or G$_4$(SG$_4$)$_n$ (SEQ ID NO: 41) peptide linkers. "n" is generally an integer from 1 to 10, typically from 2 to 4. In one embodiment said peptide linker has a length of at least 5 amino acids, in one embodiment a length of 5 to 100, in a further embodiment of 10 to 50 amino acids. In one embodiment said peptide linker is (GxS)$_n$ or (GxS)$_n$Gm with G=glycine, S=serine, and (x=3, n=3, 4, 5 or 6, and m=0, 1, 2 or 3) or (x=4, n=2, 3, 4 or 5 and m=0, 1, 2 or 3) (SEQ ID NOs: 45-76), in one embodiment x=4 and n=2 or 3, in a further embodiment x=4 and n=2. In one embodiment said peptide linker is (G$_4$S)$_2$ (SEQ ID NO: 42). A particularly suitable peptide linker for fusing the Fab light chains of the first and the second Fab molecule to each other is (G$_4$S)$_2$ (SEQ ID NO: 42). An exemplary peptide linker suitable for connecting the Fab heavy chains of the first and the second Fab fragments comprises the sequence (D)-(G$_4$S)$_2$ (SEQ ID NO: 43). Another suitable such linker comprises the sequence (G$_4$S)$_4$ (SEQ ID NO: 44). Additionally, linkers may comprise (a portion of) an immunoglobulin hinge region. Particularly where a Fab molecule is fused to the N-terminus of an Fc domain subunit, it may be fused via an immunoglobulin hinge region or a portion thereof, with or without an additional peptide linker.

An antibody with a single antigen binding moiety (such as a Fab molecule) capable of specific binding to a target cell antigen (for example as shown in FIG. 1A, FIG. 1D, FIG. 1G, FIG. 1H, FIG. 1K, or FIG. 1L) is useful, particularly in cases where internalization of the target cell antigen is to be expected following binding of a high affinity antigen binding moiety. In such cases, the presence of more than one antigen binding moiety specific for the target cell antigen may enhance internalization of the target cell antigen, thereby reducing its availability.

In many other cases, however, it will be advantageous to have an antibody comprising two or more antigen binding moieties (such as Fab molecules) specific for a target cell antigen (see examples shown in FIG. 1B, FIG. 1C, FIG. 1E, FIG. 1F, FIG. 1I, FIG. 1J, FIG. 1M, or FIG. 1N), for example to optimize targeting to the target site or to allow crosslinking of target cell antigens.

Accordingly, in particular embodiments, the anti-CD20/anti-CD3 bispecific antibody comprises two anti-CD20 binding moieties, e.g., two Fab molecules targeting CD20. In one embodiment the two Fab molecules targeting CD20 are conventional Fab molecules. In one embodiment, the two Fab molecules targeting CD20 comprise the same heavy and light chain amino acid sequences and have the same arrangement of domains (i.e., conventional or crossover).

In alternative embodiments, the anti-CD20/anti-CD3 bispecific antibody comprises two anti-CD3 binding moieties, e.g., two Fab molecules targeting CD3. In one such embodiment, the two Fab molecules targeting CD3 are both crossover Fab molecules (a Fab molecule wherein the variable domains VH and VL or the constant domains CL and CH1 of the Fab heavy and light chains are exchanged/replaced by each other). In one such embodiment, the two Fab molecules targeting CD3 comprise the same heavy and light chain amino acid sequences and have the same arrangement of domains (i.e., conventional or crossover).

In one embodiment, the third Fab molecule is fused at the C-terminus of the Fab heavy chain to the N-terminus of the first or second subunit of the Fc domain.

In a particular embodiment, the second and the third Fab molecule are each fused at the C-terminus of the Fab heavy chain to the N-terminus of one of the subunits of the Fc domain, and the first Fab molecule is fused at the C-terminus of the Fab heavy chain to the N-terminus of the Fab heavy chain of the second Fab molecule. In a specific such embodiment, the antibody essentially consists of the first, the second and the third Fab molecule, the Fc domain composed of a first and a second subunit, and optionally one or more peptide linkers, wherein the first Fab molecule is fused at the C-terminus of the Fab heavy chain to the N-terminus of the Fab heavy chain of the second Fab molecule, and the second Fab molecule is fused at the C-terminus of the Fab heavy chain to the N-terminus of the first subunit of the Fc domain, and wherein the third Fab molecule is fused at the C-terminus of the Fab heavy chain to the N-terminus of the second subunit of the Fc domain. Such a configuration is schematically depicted in FIG. 1B and FIG. 1E (embodiments, wherein the third Fab molecule is a conventional Fab molecule and identical to the second Fab molecule), and FIG. 1I and FIG. 1M (embodiments, wherein the third Fab molecule is a crossover Fab molecule and preferably identical to the first Fab molecule). The second and the third Fab molecule may be fused to the Fc domain directly or through a peptide linker. In a particular embodiment the second and the third Fab molecule are each fused to the Fc domain through an immunoglobulin hinge region. In a specific embodiment, the immunoglobulin hinge region is a human IgG$_1$ hinge region, particularly where the Fc domain is an IgG$_1$ Fc domain. Optionally, the Fab light chain of the first Fab molecule and the Fab light chain of the second Fab molecule may additionally be fused to each other.

In another embodiment, the second and the third Fab molecule are each fused at the C-terminus of the Fab heavy chain to the N-terminus of one of the subunits of the Fc domain, and the first Fab molecule is fused at the C-terminus of the Fab heavy chain to the N-terminus of the Fab heavy chain of the second Fab molecule. In a specific such embodiment, the antibody essentially consists of the first, the second and the third Fab molecule, the Fc domain composed of a first and a second subunit, and optionally one or more peptide linkers, wherein the first Fab molecule is fused at the C-terminus of the Fab heavy chain to the N-terminus of the Fab heavy chain of the second Fab molecule, and the second Fab molecule is fused at the C-terminus of the Fab heavy chain to the N-terminus of the first subunit of the Fc domain, and wherein the third Fab molecule is fused at the C-terminus of the Fab heavy chain to the N-terminus of the second subunit of the Fc domain. Such a configuration is schematically depicted in FIG. 1C and FIG. 1F (embodiments, wherein the third Fab molecule is a conventional Fab molecule and identical to the second Fab molecule) and in FIG. 1J and FIG. 1N (embodiments, wherein the third Fab molecule is a crossover Fab molecule and identical to the first Fab molecule). The first and the third Fab molecule may be fused to the Fc domain directly or through a peptide linker. In a particular embodiment the second and the third Fab molecule are each fused to the Fc domain through an immunoglobulin hinge region. In a specific embodiment, the immunoglobulin hinge region is a human $IgG_1$ hinge region, particularly where the Fc domain is an $IgG_1$ Fc domain. Optionally, the Fab light chain of the first Fab molecule and the Fab light chain of the second Fab molecule may additionally be fused to each other.

In configurations of the antibody wherein a Fab molecule is fused at the C-terminus of the Fab heavy chain to the N-terminus of each of the subunits of the Fc domain through an immunoglobulin hinge regions, the two Fab molecules, the hinge regions and the Fc domain essentially form an immunoglobulin molecule. In a particular embodiment, the immunoglobulin molecule is an IgG class immunoglobulin. In an even more particular embodiment, the immunoglobulin is an $IgG_1$ subclass immunoglobulin. In another embodiment, the immunoglobulin is an $IgG_4$ subclass immunoglobulin. In a further particular embodiment, the immunoglobulin is a human immunoglobulin. In other embodiments, the immunoglobulin is a chimeric immunoglobulin or a humanized immunoglobulin.

In some of the antibodies, the Fab light chain of the first Fab molecule and the Fab light chain of the second Fab molecule are fused to each other, optionally via a peptide linker. Depending on the configuration of the first and the second Fab molecule, the Fab light chain of the first Fab molecule may be fused at its C-terminus to the N-terminus of the Fab light chain of the second Fab molecule, or the Fab light chain of the second Fab molecule may be fused at its C-terminus to the N-terminus of the Fab light chain of the first Fab molecule. Fusion of the Fab light chains of the first and the second Fab molecule further reduces mispairing of unmatched Fab heavy and light chains, and also reduces the number of plasmids needed for expression of some of the antibodies.

In certain embodiments, the antibody comprises a polypeptide wherein the Fab light chain variable region of the first Fab molecule shares a carboxy-terminal peptide bond with the Fab heavy chain constant region of the first Fab molecule (i.e., the first Fab molecule comprises a crossover Fab heavy chain, wherein the heavy chain variable region is replaced by a light chain variable region), which in turn shares a carboxy-terminal peptide bond with an Fc domain subunit ($VL_{(1)}$-$CH1_{(1)}$-CH2-CH3(-CH4)), and a polypeptide wherein the Fab heavy chain of the second Fab molecule shares a carboxy-terminal peptide bond with an Fc domain subunit ($VH_{(2)}$-$CH1_{(2)}$-CH2-CH3(-CH4)). In some embodiments, the antibody further comprises a polypeptide wherein the Fab heavy chain variable region of the first Fab molecule shares a carboxy-terminal peptide bond with the Fab light chain constant region of the first Fab molecule ($VH_{(1)}$-$CL_{(1)}$) and the Fab light chain polypeptide of the second Fab molecule ($VL_{(2)}$-$CL_{(2)}$). In certain embodiments, the polypeptides are covalently linked, e.g., by a disulfide bond.

In certain embodiments, the antibody comprises a polypeptide wherein the Fab heavy chain variable region of the first Fab molecule shares a carboxy-terminal peptide bond with the Fab light chain constant region of the first Fab molecule (i.e., the first Fab molecule comprises a crossover Fab heavy chain, wherein the heavy chain constant region is replaced by a light chain constant region), which in turn shares a carboxy-terminal peptide bond with an Fc domain subunit ($VH_{(1)}$-$CL_{(1)}$-CH2-CH3(-CH4)), and a polypeptide wherein the Fab heavy chain of the second Fab molecule shares a carboxy-terminal peptide bond with an Fc domain subunit ($VH_{(2)}$—$CH1_{(2)}$-CH2-CH3(-CH4)). In some embodiments, the antibody further comprises a polypeptide wherein the Fab light chain variable region of the first Fab molecule shares a carboxy-terminal peptide bond with the Fab heavy chain constant region of the first Fab molecule ($VL_{(1)}$-$CH1_{(1)}$) and the Fab light chain polypeptide of the second Fab molecule ($VL_{(2)}$-$CL_{(2)}$). In certain embodiments the polypeptides are covalently linked, e.g., by a disulfide bond.

In some embodiments, the antibody comprises a polypeptide wherein the Fab light chain variable region of the first Fab molecule shares a carboxy-terminal peptide bond with the Fab heavy chain constant region of the first Fab molecule (i.e., the first Fab molecule comprises a crossover Fab heavy chain, wherein the heavy chain variable region is replaced by a light chain variable region), which in turn shares a carboxy-terminal peptide bond with the Fab heavy chain of the second Fab molecule, which in turn shares a carboxy-terminal peptide bond with an Fc domain subunit ($VL_{(1)}$-$CH1_{(1)}$-$VH_{(2)}$—$CH1_{(2)}$-CH2-CH3(-CH4)). In other embodiments, the antibody comprises a polypeptide wherein the Fab heavy chain of the second Fab molecule shares a carboxy-terminal peptide bond with the Fab light chain variable region of the first Fab molecule which in turn shares a carboxy-terminal peptide bond with the Fab heavy chain constant region of the first Fab molecule (i.e., the first Fab molecule comprises a crossover Fab heavy chain, wherein the heavy chain variable region is replaced by a light chain variable region), which in turn shares a carboxy-terminal peptide bond with an Fc domain subunit ($VH_{(2)}$—$CH1_{(2)}$-$VL_{(1)}$-$CH1_{(1)}$-CH2-CH3(-CH4)).

In some of these embodiments, the antibody further comprises a crossover Fab light chain polypeptide of the first Fab molecule, wherein the Fab heavy chain variable region of the first Fab molecule shares a carboxy-terminal peptide bond with the Fab light chain constant region of the first Fab molecule ($VH_{(1)}$-$CL_{(1)}$), and the Fab light chain polypeptide of the second Fab molecule ($VL_{(2)}$-$CL_{(2)}$). In others of these embodiments, the antibody further comprises a polypeptide wherein the Fab heavy chain variable region of the first Fab molecule shares a carboxy-terminal peptide bond with the Fab light chain constant region of the first Fab molecule which in turn shares a carboxy-terminal peptide bond with the Fab light chain polypeptide of the second Fab molecule ($VH_{(1)}$-$CL_{(1)}$-$VL_{(2)}$-$CL_{(2)}$), or a polypeptide wherein the Fab light chain polypeptide of the second Fab molecule shares a carboxy-terminal peptide bond with the Fab heavy chain variable region of the first Fab molecule which in turn shares a carboxy-terminal peptide bond with the Fab light chain constant region of the first Fab molecule ($VL_{(2)}$-$CL_{(2)}$-$VH_{(1)}$-$CL_{(1)}$), as appropriate.

The antibody according to these embodiments may further comprise (i) an Fc domain subunit polypeptide (CH2-

CH3(-CH4)), or (ii) a polypeptide wherein the Fab heavy chain of a third Fab molecule shares a carboxy-terminal peptide bond with an Fc domain subunit (VH$_{(3)}$—CH1$_{(3)}$-CH2-CH3(-CH4)) and the Fab light chain polypeptide of a third Fab molecule (VL$_{(3)}$-CL$_{(3)}$). In certain embodiments the polypeptides are covalently linked, e.g., by a disulfide bond.

In some embodiments, the antibody comprises a polypeptide wherein the Fab heavy chain variable region of the second Fab molecule shares a carboxy-terminal peptide bond with the Fab light chain constant region of the first Fab molecule (i.e., the first Fab molecule comprises a crossover Fab heavy chain, wherein the heavy chain constant region is replaced by a light chain constant region), which in turn shares a carboxy-terminal peptide bond with the Fab heavy chain of the second Fab molecule, which in turn shares a carboxy-terminal peptide bond with an Fc domain subunit (VH$_{(1)}$-CL$_{(1)}$-VH$_{(2)}$—CH1$_{(2)}$-CH2-CH3(-CH4)). In other embodiments, the antibody comprises a polypeptide wherein the Fab heavy chain of the second Fab molecule shares a carboxy-terminal peptide bond with the Fab heavy chain variable region of the first Fab molecule which in turn shares a carboxy-terminal peptide bond with the Fab light chain constant region of the first Fab molecule (i.e., the first Fab molecule comprises a crossover Fab heavy chain, wherein the heavy chain constant region is replaced by a light chain constant region), which in turn shares a carboxy-terminal peptide bond with an Fc domain subunit (VH$_{(2)}$—CH1$_{(2)}$-VH$_{(1)}$-CL$_{(1)}$-CH2-CH3(-CH4)).

In some of these embodiments, the antibody further comprises a crossover Fab light chain polypeptide of the first Fab molecule, wherein the Fab light chain variable region of the first Fab molecule shares a carboxy-terminal peptide bond with the Fab heavy chain constant region of the first Fab molecule (VL$_{(1)}$-CH1$_{(1)}$), and the Fab light chain polypeptide of the second Fab molecule (VL$_{(2)}$-CL$_{(2)}$). In others of these embodiments, the antibody further comprises a polypeptide wherein the Fab light chain variable region of the first Fab molecule shares a carboxy-terminal peptide bond with the Fab heavy chain constant region of the first Fab molecule which in turn shares a carboxy-terminal peptide bond with the Fab light chain polypeptide of the second Fab molecule (VL$_{(1)}$-CH1$_{(1)}$-VL$_{(2)}$-CL$_{(2)}$), or a polypeptide wherein the Fab light chain polypeptide of the second Fab molecule shares a carboxy-terminal peptide bond with the Fab heavy chain variable region of the first Fab molecule which in turn shares a carboxy-terminal peptide bond with the Fab light chain constant region of the first Fab molecule (VL$_{(2)}$-CL$_{(2)}$-VH$_{(1)}$-CL$_{(1)}$), as appropriate.

The antibody according to these embodiments may further comprise (i) an Fc domain subunit polypeptide (CH2-CH3(-CH4)), or (ii) a polypeptide wherein the Fab heavy chain of a third Fab molecule shares a carboxy-terminal peptide bond with an Fc domain subunit (VH$_{(3)}$—CH1$_{(3)}$-CH2-CH3(-CH4)) and the Fab light chain polypeptide of a third Fab molecule (VL$_{(3)}$-CL$_{(3)}$). In certain embodiments, the polypeptides are covalently linked, e.g., by a disulfide bond.

In certain embodiments, the antibody comprises a polypeptide wherein the Fab heavy chain of the first Fab molecule shares a carboxy-terminal peptide bond with the Fab light chain variable region of the second Fab molecule, which in turn shares a carboxy-terminal peptide bond with the Fab heavy chain constant region of the second Fab molecule (i.e., the second Fab molecule comprises a crossover Fab heavy chain, wherein the heavy chain variable region is replaced by a light chain variable region) (VH$_{(1)}$-CH1$_{(1)}$-VL$_{(2)}$-CH1$_{(2)}$). In some embodiments, the antibody further comprises a polypeptide wherein the Fab heavy chain variable region of the second Fab molecule shares a carboxy-terminal peptide bond with the Fab light chain constant region of the second Fab molecule (VH$_{(2)}$-CL$_{(2)}$) and the Fab light chain polypeptide of the first Fab molecule (VL$_{(1)}$-CL$_{(1)}$).

In certain embodiments, the antibody comprises a polypeptide wherein the Fab light chain variable region of the second Fab molecule shares a carboxy-terminal peptide bond with the Fab heavy chain constant region of the second Fab molecule (i.e., the second Fab molecule comprises a crossover Fab heavy chain, wherein the heavy chain variable region is replaced by a light chain variable region), which in turn shares a carboxy-terminal peptide bond with the Fab heavy chain of the first Fab molecule (VL$_{(2)}$-CH1$_{(2)}$-VH$_{(1)}$-CH1$_{(1)}$). In some embodiments, the antibody further comprises a polypeptide wherein the Fab heavy chain variable region of the second Fab molecule shares a carboxy-terminal peptide bond with the Fab light chain constant region of the second Fab molecule (VH$_{(2)}$-CL$_{(2)}$) and the Fab light chain polypeptide of the first Fab molecule (VL$_{(1)}$-CL$_{(1)}$).

In certain embodiments, the antibody comprises a polypeptide wherein the Fab heavy chain variable region of the second Fab molecule shares a carboxy-terminal peptide bond with the Fab light chain constant region of the second Fab molecule (i.e., the second Fab molecule comprises a crossover Fab heavy chain, wherein the heavy chain constant region is replaced by a light chain constant region), which in turn shares a carboxy-terminal peptide bond with the Fab heavy chain of the first Fab molecule (VH$_{(2)}$-CL$_{(2)}$-VH$_{(1)}$-CH1$_{(1)}$). In some embodiments, the antibody further comprises a polypeptide wherein the Fab light chain variable region of the second Fab molecule shares a carboxy-terminal peptide bond with the Fab heavy chain constant region of the second Fab molecule (VL$_{(2)}$-CH1$_{(2)}$) and the Fab light chain polypeptide of the first Fab molecule (VL$_{(1)}$-CL$_{(1)}$).

In certain embodiments, the antibody comprises a polypeptide wherein the Fab heavy chain of a third Fab molecule shares a carboxy-terminal peptide bond with the Fab heavy chain of the first Fab molecule, which in turn shares a carboxy-terminal peptide bond with the Fab light chain variable region of the second Fab molecule, which in turn shares a carboxy-terminal peptide bond with the Fab heavy chain constant region of the second Fab molecule (i.e., the second Fab molecule comprises a crossover Fab heavy chain, wherein the heavy chain variable region is replaced by a light chain variable region) (VH$_{(3)}$—CH1$_{(3)}$-VH$_{(1)}$—CH1$_{(1)}$-VL$_{(2)}$-CH1$_{(2)}$). In some embodiments, the antibody further comprises a polypeptide wherein the Fab heavy chain variable region of the second Fab molecule shares a carboxy-terminal peptide bond with the Fab light chain constant region of the second Fab molecule (VH$_{(2)}$-CL$_{(2)}$) and the Fab light chain polypeptide of the first Fab molecule (VL$_{(1)}$-CL$_{(1)}$). In some embodiments, the antibody further comprises the Fab light chain polypeptide of a third Fab molecule (VL$_{(3)}$-CL$_{(3)}$).

In certain embodiments, the antibody comprises a polypeptide wherein the Fab heavy chain of a third Fab molecule shares a carboxy-terminal peptide bond with the Fab heavy chain of the first Fab molecule, which in turn shares a carboxy-terminal peptide bond with the Fab heavy chain variable region of the second Fab molecule, which in turn shares a carboxy-terminal peptide bond with the Fab light chain constant region of the second Fab molecule (i.e., the second Fab molecule comprises a crossover Fab heavy chain, wherein the heavy chain constant region is replaced by a light chain constant region) (VH$_{(3)}$—CH1$_{(3)}$-VH$_{(1)}$-CH1$_{(1)}$-VH$_{(2)}$-CL$_{(2)}$). In some embodiments, the antibody further comprises a polypeptide wherein the Fab light chain variable region of the second Fab molecule shares a carboxy-terminal peptide bond with the Fab heavy chain constant region of the second Fab molecule (VL$_{(2)}$-CH1$_{(2)}$) and the Fab light chain polypeptide of the first Fab molecule (VL$_{(1)}$-CL$_{(1)}$). In some embodiments, the antibody further comprises the Fab light chain polypeptide of a third Fab molecule (VL$_{(3)}$-CL$_{(3)}$).

In certain embodiments, the antibody comprises a polypeptide wherein the Fab light chain variable region of the second Fab molecule shares a carboxy-terminal peptide bond with the Fab heavy chain constant region of the second Fab molecule (i.e., the second Fab molecule comprises a crossover Fab heavy chain, wherein the heavy chain variable region is replaced by a light chain variable region), which in turn shares a carboxy-terminal peptide bond with the Fab heavy chain of the first Fab molecule, which in turn shares a carboxy-terminal peptide bond with the Fab heavy chain of a third Fab molecule (VL$_{(2)}$-CH1$_{(2)}$-VH$_{(1)}$-CH1$_{(1)}$-VH$_{(3)}$—CH1$_{(3)}$). In some embodiments, the antibody further comprises a polypeptide wherein the Fab heavy chain variable region of the second Fab molecule shares a carboxy-terminal peptide bond with the Fab light chain constant region of the second Fab molecule (VH$_{(2)}$-CL$_{(2)}$) and the Fab light chain polypeptide of the first Fab molecule (VL$_{(1)}$-CL$_{(1)}$). In some embodiments, the antibody further comprises the Fab light chain polypeptide of a third Fab molecule (VL$_{(3)}$-CL$_{(3)}$).

In certain embodiments, the antibody comprises a polypeptide wherein the Fab heavy chain variable region of the second Fab molecule shares a carboxy-terminal peptide bond with the Fab light chain constant region of the second Fab molecule (i.e., the second Fab molecule comprises a crossover Fab heavy chain, wherein the heavy chain constant region is replaced by a light chain constant region), which in turn shares a carboxy-terminal peptide bond with the Fab heavy chain of the first Fab molecule, which in turn shares a carboxy-terminal peptide bond with the Fab heavy chain of a third Fab molecule (VH$_{(2)}$-CL$_{(2)}$-VH$_{(1)}$-CH1$_{(1)}$-VH$_{(3)}$—CH1$_{(3)}$). In some embodiments, the antibody further comprises a polypeptide wherein the Fab light chain variable region of the second Fab molecule shares a carboxy-terminal peptide bond with the Fab heavy chain constant region of the second Fab molecule (VL$_{(2)}$-CH1$_{(2)}$) and the Fab light chain polypeptide of the first Fab molecule (VL$_{(1)}$-CL$_{(1)}$). In some embodiments, the antibody further comprises the Fab light chain polypeptide of a third Fab molecule (VL$_{(3)}$-CL$_{(3)}$).

In certain embodiments, the antibody comprises a polypeptide wherein the Fab heavy chain of the first Fab molecule shares a carboxy-terminal peptide bond with the Fab light chain variable region of the second Fab molecule, which in turn shares a carboxy-terminal peptide bond with the Fab heavy chain constant region of the second Fab molecule (i.e., the second Fab molecule comprises a crossover Fab heavy chain, wherein the heavy chain variable region is replaced by a light chain variable region), which in turn shares a carboxy-terminal peptide bond with the Fab light chain variable region of a third Fab molecule, which in turn shares a carboxy-terminal peptide bond with the Fab heavy chain constant region of a third Fab molecule (i.e., the third Fab molecule comprises a crossover Fab heavy chain, wherein the heavy chain variable region is replaced by a light chain variable region) (VH$_{(1)}$-CH1$_{(1)}$-VL$_{(2)}$-CH1$_{(2)}$-VL$_{(3)}$-CH1$_{(3)}$). In some embodiments, the antibody further comprises a polypeptide wherein the Fab heavy chain variable region of the second Fab molecule shares a carboxy-terminal peptide bond with the Fab light chain constant region of the second Fab molecule (VH$_{(2)}$-CL$_{(2)}$) and the Fab light chain polypeptide of the first Fab molecule (VL$_{(1)}$-CL$_{(1)}$). In some embodiments, the antibody further comprises a polypeptide wherein the Fab heavy chain variable region of a third Fab molecule shares a carboxy-terminal peptide bond with the Fab light chain constant region of a third Fab molecule (VH$_{(3)}$-CL$_{(3)}$).

In certain embodiments, the antibody comprises a polypeptide wherein the Fab heavy chain of the first Fab molecule shares a carboxy-terminal peptide bond with the Fab heavy chain variable region of the second Fab molecule, which in turn shares a carboxy-terminal peptide bond with the Fab light chain constant region of the second Fab molecule (i.e., the second Fab molecule comprises a crossover Fab heavy chain, wherein the heavy chain constant region is replaced by a light chain constant region), which in turn shares a carboxy-terminal peptide bond with the Fab heavy chain variable region of a third Fab molecule, which in turn shares a carboxy-terminal peptide bond with the Fab light chain constant region of a third Fab molecule (i.e., the third Fab molecule comprises a crossover Fab heavy chain, wherein the heavy chain constant region is replaced by a light chain constant region) (VH$_{(1)}$-CH1$_{(1)}$-VH$_{(2)}$-CL$_{(2)}$-VH$_{(3)}$-CL$_{(3)}$). In some embodiments, the antibody further comprises a polypeptide wherein the Fab light chain variable region of the second Fab molecule shares a carboxy-terminal peptide bond with the Fab heavy chain constant region of the second Fab molecule (VL$_{(2)}$-CH1$_{(2)}$) and the Fab light chain polypeptide of the first Fab molecule (VL$_{(1)}$-CL$_{(1)}$). In some embodiments, the antibody further comprises a polypeptide wherein the Fab light chain variable region of a third Fab molecule shares a carboxy-terminal peptide bond with the Fab heavy chain constant region of a third Fab molecule (VL$_{(3)}$-CH1$_{(3)}$).

In certain embodiments, the antibody comprises a polypeptide wherein the Fab light chain variable region of a third Fab molecule shares a carboxy-terminal peptide bond with the Fab heavy chain constant region of a third Fab molecule (i.e., the third Fab molecule comprises a crossover Fab heavy chain, wherein the heavy chain variable region is replaced by a light chain variable region), which in turn shares a carboxy-terminal peptide bond with the Fab light chain variable region of the second Fab molecule, which in turn shares a carboxy-terminal peptide bond with the Fab heavy chain constant region of the second Fab molecule (i.e., the second Fab molecule comprises a crossover Fab heavy chain, wherein the heavy chain variable region is replaced by a light chain variable region), which in turn shares a carboxy-terminal peptide bond with the Fab heavy chain of the first Fab molecule (VL$_{(3)}$-CH1$_{(3)}$-VL$_{(2)}$-CH1$_{(2)}$-VH$_{(1)}$-CH1$_{(1)}$). In some embodiments, the antibody further comprises a polypeptide wherein the Fab heavy chain variable region of the second Fab molecule shares a carboxy-terminal peptide bond with the Fab light chain constant region of the second Fab molecule (VH$_{(2)}$-CL$_{(2)}$) and the Fab light chain polypeptide of the first Fab molecule (VL$_{(1)}$-CL$_{(1)}$). In some embodiments, the antibody further comprises a polypeptide wherein the Fab heavy chain variable region of a third Fab molecule shares a carboxy-terminal peptide bond with the Fab light chain constant region of a third Fab molecule (VH$_{(3)}$-CL$_{(3)}$).

In certain embodiments, the antibody comprises a polypeptide wherein the Fab heavy chain variable region of a third Fab molecule shares a carboxy-terminal peptide bond with the Fab light chain constant region of a third Fab molecule (i.e., the third Fab molecule comprises a crossover Fab heavy chain, wherein the heavy chain constant region is replaced by a light chain constant region), which in turn shares a carboxy-terminal peptide bond with the Fab heavy chain variable region of the second Fab molecule, which in turn shares a carboxy-terminal peptide bond with the Fab light chain constant region of the second Fab molecule (i.e., the second Fab molecule comprises a crossover Fab heavy chain, wherein the heavy chain constant region is replaced by a light chain constant region), which in turn shares a carboxy-terminal peptide bond with the Fab heavy chain of the first Fab molecule ($VH_{(3)}$-$CL_{(3)}$-$VH_{(2)}$-$CL_{(2)}$-$VH_{(1)}$-$CH1_{(1)}$). In some embodiments, the antibody further comprises a polypeptide wherein the Fab light chain variable region of the second Fab molecule shares a carboxy-terminal peptide bond with the Fab heavy chain constant region of the second Fab molecule ($VL_{(2)}$-$CH1_{(2)}$) and the Fab light chain polypeptide of the first Fab molecule ($VL_{(1)}$-$CL_{(1)}$). In some embodiments, the antibody further comprises a polypeptide wherein the Fab light chain variable region of a third Fab molecule shares a carboxy-terminal peptide bond with the Fab heavy chain constant region of a third Fab molecule ($VL_{(3)}$-$CH1_{(3)}$).

According to any of the above embodiments, components of the antibody (e.g., Fab molecules, Fc domain) may be fused directly or through various linkers, particularly peptide linkers comprising one or more amino acids, typically about 2-20 amino acids, that are described herein or are known in the art. Suitable, non-immunogenic peptide linkers include, for example, $(G_4S)_n$ (SEQ ID NO:39), $(SG_4)_n$ (SEQ ID NO:40), or $G_4(SG_4)_n$ (SEQ ID NO: 41) peptide linkers, wherein n is generally an integer from 1 to 10, typically from 2 to 4.

2. Fc Domain

The anti-CD20/anti-CD3 bispecific antibody and/or the anti-CD79b antibody drug conjugate may comprise an Fc domain which consists of a pair of polypeptide chains comprising heavy chain domains of an antibody molecule. For example, the Fc domain of an immunoglobulin G (IgG) molecule is a dimer, each subunit of which comprises the CH2 and CH3 IgG heavy chain constant domains. The two subunits of the Fc domain are capable of stable association with each other.

In one embodiment, the Fc domain is an IgG Fc domain. In a particular embodiment, the Fc domain is an $IgG_1$ Fc domain. In another embodiment the Fc domain is an $IgG_4$ Fc domain. In a more specific embodiment, the Fc domain is an $IgG_4$ Fc domain comprising an amino acid substitution at position S228 (Kabat numbering), particularly the amino acid substitution S228P. This amino acid substitution reduces in vivo Fab arm exchange of $IgG_4$ antibodies (see Stubenrauch et al., *Drug Metabolism and Disposition* 38, 84-91 (2010)). In a further particular embodiment, the Fc domain is human.

(i) Fc Domain Modifications Promoting Heterodimerization

The anti-CD20/anti-CD3 bispecific antibody and/or the anti-CD79b antibody drug conjugate may comprise different components (e.g., antigen binding domains) fused to one or the other of the two subunits of the Fc domain, thus the two subunits of the Fc domain are typically comprised in two non-identical polypeptide chains. Recombinant co-expression of these polypeptides and subsequent dimerization leads to several possible combinations of the two polypeptides. To improve the yield and purity of such antibodies in recombinant production, it will thus be advantageous to introduce in the Fc domain of the antibody a modification promoting the association of the desired polypeptides.

Accordingly, in particular embodiments the Fc domain comprises a modification promoting the association of the first and the second subunit of the Fc domain. The site of most extensive protein-protein interaction between the two subunits of a human IgG Fc domain is in the CH3 domain of the Fc domain. Thus, in one embodiment said modification is in the CH3 domain of the Fc domain.

Several approaches for modifications in the CH3 domain of the Fc domain in order to enforce heterodimerization are well described, e.g., in WO 96/27011, WO 98/050431, EP 1870459, WO 2007/110205, WO 2007/147901, WO 2009/089004, WO 2010/129304, WO 2011/90754, WO 2011/143545, WO 2012058768, WO 2013157954, WO 2013096291. Typically, in all such approaches the CH3 domain of the first subunit of the Fc domain and the CH3 domain of the second subunit of the Fc domain are both engineered in a complementary manner so that each CH3 domain (or the heavy chain comprising it) can no longer homodimerize with itself but is forced to heterodimerize with the complementarily engineered other CH3 domain (so that the first and second CH3 domain heterodimerize and no homodimers between the two first or the two second CH3 domains are formed). These different approaches for improved heavy chain heterodimerization are contemplated as different alternatives in combination with heavy-light chain modifications (e.g., variable or constant region exchange/replacement in Fab arms, or introduction of substitutions of charged amino acids with opposite charges in the CH1/CL interface) which reduce light chain mispairing and Bence Jones-type side products.

In a specific embodiment said modification promoting the association of the first and the second subunit of the Fc domain is a so-called "knob-into-hole" modification, comprising a "knob" modification in one of the two subunits of the Fc domain and a "hole" modification in the other one of the two subunits of the Fc domain.

The knob-into-hole technology is described e.g., in U.S. Pat. Nos. 5,731,168; 7,695,936; Ridgway et al., *Prot Eng.* 9, 617-621 (1996) and Carter, *J Immunol Meth.* 248, 7-15 (2001). Generally, the method involves introducing a protuberance ("knob") at the interface of a first polypeptide and a corresponding cavity ("hole") in the interface of a second polypeptide, such that the protuberance can be positioned in the cavity so as to promote heterodimer formation and hinder homodimer formation. Protuberances are constructed by replacing small amino acid side chains from the interface of the first polypeptide with larger side chains (e.g., tyrosine or tryptophan). Compensatory cavities of identical or similar size to the protuberances are created in the interface of the second polypeptide by replacing large amino acid side chains with smaller ones (e.g., alanine or threonine).

Accordingly, in a particular embodiment, in the CH3 domain of the first subunit of the Fc domain an amino acid residue is replaced with an amino acid residue having a larger side chain volume, thereby generating a protuberance within the CH3 domain of the first subunit which is positionable in a cavity within the CH3 domain of the second subunit, and in the CH3 domain of the second subunit of the Fc domain an amino acid residue is replaced with an amino acid residue having a smaller side chain volume, thereby generating a cavity within the CH3 domain of the second subunit within which the protuberance within the CH3 domain of the first subunit is positionable.

Preferably said amino acid residue having a larger side chain volume is selected from the group consisting of arginine (R), phenylalanine (F), tyrosine (Y), and tryptophan (W).

Preferably said amino acid residue having a smaller side chain volume is selected from the group consisting of alanine (A), serine (S), threonine (T), and valine (V).

The protuberance and cavity can be made by altering the nucleic acid encoding the polypeptides, e.g., by site-specific mutagenesis, or by peptide synthesis.

In a specific embodiment, in the CH3 domain of the first subunit of the Fc domain (the "knob" subunit) the threonine residue at position 366 is replaced with a tryptophan residue (T366W), and in the CH3 domain of the second subunit of the Fc domain (the "hole" subunit) the tyrosine residue at position 407 is replaced with a valine residue (Y407V). In one embodiment, in the second subunit of the Fc domain additionally the threonine residue at position 366 is replaced with a serine residue (T366S) and the leucine residue at position 368 is replaced with an alanine residue (L368A) (EU numbering).

In yet a further embodiment, in the first subunit of the Fc domain additionally the serine residue at position 354 is replaced with a cysteine residue (S354C) or the glutamic acid residue at position 356 is replaced with a cysteine residue (E356C), and in the second subunit of the Fc domain additionally the tyrosine residue at position 349 is replaced by a cysteine residue (Y349C) (EU numbering). Introduction of these two cysteine residues results in formation of a disulfide bridge between the two subunits of the Fc domain, further stabilizing the dimer (Carter, J Immunol Methods 248, 7-15 (2001)).

In a particular embodiment, the first subunit of the Fc domain comprises amino acid substitutions S354C and T366W, and the second subunit of the Fc domain comprises amino acid substitutions Y349C, T366S, L368A and Y407V (EU numbering).

In a particular embodiment, the CD3 antigen binding moiety described herein is fused to the first subunit of the Fc domain (comprising the "knob" modification). Without wishing to be bound by theory, fusion of the CD3 antigen binding moiety to the knob-containing subunit of the Fc domain will (further) minimize the generation of bispecific antibodies (e.g., anti-CD20/anti-CD3 bispecific antibodies) comprising two CD3 antigen binding moieties (steric clash of two knob-containing polypeptides).

Other techniques of CH3-modification for enforcing the heterodimerization are contemplated as alternatives according to the invention and are described, e.g., in WO 96/27011, WO 98/050431, EP 1870459, WO 2007/110205, WO 2007/147901, WO 2009/089004, WO 2010/129304, WO 2011/90754, WO 2011/143545, WO 2012/058768, WO 2013/157954, WO 2013/096291.

In one embodiment, the heterodimerization approach described in EP 1870459 A1, is used alternatively. This approach is based on the introduction of charged amino acids with opposite charges at specific amino acid positions in the CH3/CH3 domain interface between the two subunits of the Fc domain. One preferred embodiment are amino acid mutations R409D and K370E in one of the two CH3 domains (of the Fc domain) and amino acid mutations D399K and E357K in the other one of the CH3 domains of the Fc domain (EU numbering).

In another embodiment, the anti-CD20/anti-CD3 bispecific antibody and/or the anti-CD79b antibody drug conjugate may comprise amino acid mutation T366W in the CH3 domain of the first subunit of the Fc domain and amino acid mutations T366S, L368A, and Y407V in the CH3 domain of the second subunit of the Fc domain, and additionally amino acid mutations R409D and K370E in the CH3 domain of the first subunit of the Fc domain and amino acid mutations D399K and E357K in the CH3 domain of the second subunit of the Fc domain (EU numbering).

In another embodiment, the anti-CD20/anti-CD3 bispecific antibody and/or the anti-CD79b antibody drug conjugate may comprise amino acid mutations S354C and T366W in the CH3 domain of the first subunit of the Fc domain and amino acid mutations Y349C, T366S, L368A, and Y407V in the CH3 domain of the second subunit of the Fc domain, or the antibody comprises amino acid mutations Y349C and T366W in the CH3 domain of the first subunit of the Fc domain and amino acid mutations S354C, T366S, L368A, and Y407V in the CH3 domains of the second subunit of the Fc domain and additionally amino acid mutations R409D and K370E in the CH3 domain of the first subunit of the Fc domain and amino acid mutations D399K and E357K in the CH3 domain of the second subunit of the Fc domain (all EU numbering).

In one embodiment, the heterodimerization approach described in WO 2013/157953 is used alternatively. In one embodiment a first CH3 domain comprises amino acid mutation T366K and a second CH3 domain comprises amino acid mutation L351D (EU numbering). In a further embodiment, the first CH3 domain comprises further amino acid mutation L351K. In a further embodiment, the second CH3 domain comprises further an amino acid mutation selected from Y349E, Y349D, and L368E (preferably L368E) (EU numbering).

In one embodiment, the heterodimerization approach described in WO 2012/058768 is used alternatively. In one embodiment, a first CH3 domain comprises amino acid mutations L351Y, Y407A, and a second CH3 domain comprises amino acid mutations T366A and K409F. In a further embodiment, the second CH3 domain comprises a further amino acid mutation at position T411, D399, S400, F405, N390, or K392, e.g., selected from a) T411 N, T411R, T411Q, T411K, T411 D, T411E, or T411W; b) D399R, D399W, D399Y, or D399K; c) S400E, S400D, S400R, or S400K; d) F4051, F405M, F405T, F405S, F405V, or F405W; e) N390R, N390K, or N390D; or f) K392V, K392M, K392R, K392L, K392F, or K392E (EU numbering). In a further embodiment, a first CH3 domain comprises amino acid mutations L351Y and Y407A and a second CH3 domain comprises amino acid mutations T366V and K409F. In a further embodiment, a first CH3 domain comprises amino acid mutation Y407A and a second CH3 domain comprises amino acid mutations T366A and K409F. In a further embodiment, the second CH3 domain further comprises amino acid mutations K392E, T411E, D399R, and S400R (EU numbering).

In one embodiment, the heterodimerization approach described in WO 2011/143545 is used alternatively, e.g., with the amino acid modification at a position selected from the group consisting of 368 and 409 (EU numbering).

In one embodiment, the heterodimerization approach described in WO 2011/090762, which also uses the knobs-into-holes technology described above, is used alternatively. In one embodiment, a first CH3 domain comprises amino acid mutation T366W and a second CH3 domain comprises amino acid mutation Y407A. In one embodiment, a first CH3 domain comprises amino acid mutation T366Y and a second CH3 domain comprises amino acid mutation Y407T (EU numbering).

In one embodiment, the anti-CD20/anti-CD3 bispecific antibody and/or the anti-CD79b antibody drug conjugate or the Fc domain of the anti-CD20/anti-CD3 bispecific antibody and/or the anti-CD79b antibody drug conjugate is of IgG$_2$ subclass and the heterodimerization approach described in WO 2010/129304 is used.

In an alternative embodiment, a modification promoting association of the first and the second subunit of the Fc domain comprises a modification mediating electrostatic steering effects, e.g., as described in PCT publication WO 2009/089004. Generally, this method involves replacement of one or more amino acid residues at the interface of the two Fc domain subunits by charged amino acid residues so that homodimer formation becomes electrostatically unfavorable but heterodimerization electrostatically favorable. In one such embodiment, a first CH3 domain comprises amino acid substitution of K392 or N392 with a negatively charged amino acid (e.g., glutamic acid (E), or aspartic acid (D), preferably K392D or N392D) and a second CH3 domain comprises amino acid substitution of D399, E356, D356, or E357 with a positively charged amino acid (e.g., lysine (K) or arginine (R), preferably D399K, E356K, D356K, or E357K, and more preferably D399K and E356K). In a further embodiment the first CH3 domain further comprises amino acid substitution of K409 or R409 with a negatively charged amino acid (e.g., glutamic acid (E), or aspartic acid (D), preferably K409D or R409D). In a further embodiment the first CH3 domain further or alternatively comprises amino acid substitution of K439 and/or K370 with a negatively charged amino acid (e.g., glutamic acid (E), or aspartic acid (D)) (EU numbering).

In yet a further embodiment, the heterodimerization approach described in WO 2007/147901 is used alternatively. In one embodiment, a first CH3 domain comprises amino acid mutations K253E, D282K, and K322D and a second CH3 domain comprises amino acid mutations D239K, E240K, and K292D (EU numbering).

In still another embodiment, the heterodimerization approach described in WO 2007/110205 can be used.

In one embodiment, the first subunit of the Fc domain comprises amino acid substitutions K392D and K409D, and the second subunit of the Fc domain comprises amino acid substitutions D356K and D399K (EU numbering).

(ii) Fc Domain Modifications Reducing Fc Receptor Binding and/or Effector Function The Fc domain confers to an antibody, such as an anti-CD20/anti-CD3 bispecific antibody and/or the antibody of the anti-CD79b antibody drug conjugate, favorable pharmacokinetic properties, including a long serum half-life which contributes to good accumulation in the target tissue and a favorable tissue-blood distribution ratio. At the same time it may, however, lead to undesirable targeting of the antibody to cells expressing Fc receptors rather than to the preferred antigen-bearing cells. Moreover, the co-activation of Fc receptor signaling pathways may lead to cytokine release which, in combination with other immunostimulatory properties the antibody may have and the long half-life of the antibody, results in excessive activation of cytokine receptors and severe side effects upon systemic administration.

Accordingly, in particular embodiments, the Fc domain of the anti-CD20/anti-CD3 bispecific antibody and/or the anti-CD79b antibody drug conjugate exhibits reduced binding affinity to an Fc receptor and/or reduced effector function, as compared to a native IgG$_1$ Fc domain. In one such embodiment, the Fc domain (or the molecule, e.g., antibody, comprising said Fc domain) exhibits less than 50%, preferably less than 20%, more preferably less than 10% and most preferably less than 5% of the binding affinity to an Fc receptor, as compared to a native IgG$_1$ Fc domain (or a corresponding molecule comprising a native IgG$_1$ Fc domain), and/or less than 50%, preferably less than 20%, more preferably less than 10% and most preferably less than 5% of the effector function, as compared to a native IgG$_1$ Fc domain (or a corresponding molecule comprising a native IgG$_1$ Fc domain). In one embodiment, the Fc domain (or the molecule, e.g., antibody, comprising said Fc domain) does not substantially bind to an Fc receptor and/or induce effector function. In a particular embodiment, the Fc receptor is an Fcγ receptor. In one embodiment the Fc receptor is a human Fc receptor. In one embodiment, the Fc receptor is an activating Fc receptor. In a specific embodiment the Fc receptor is an activating human Fcγ receptor, more specifically human FcγRIIIa, FcγRI or FcγRIIa, most specifically human FcγRIIIa. In one embodiment, the effector function is one or more selected from the group of CDC, ADCC, ADCP, and cytokine secretion. In a particular embodiment, the effector function is ADCC. In one embodiment the Fc domain exhibits substantially similar binding affinity to neonatal Fc receptor (FcRn), as compared to a native IgG$_1$ Fc domain. Substantially similar binding to FcRn is achieved when the Fc domain (or the molecule, e.g., antibody, comprising said Fc domain) exhibits greater than about 70%, particularly greater than about 80%, more particularly greater than about 90% of the binding affinity of a native IgG$_1$ Fc domain (or the corresponding molecule comprising a native IgG$_1$ Fc domain) to FcRn.

In certain embodiments, the Fc domain is engineered to have reduced binding affinity to an Fc receptor and/or reduced effector function, as compared to a non-engineered Fc domain. In particular embodiments, the Fc domain comprises one or more amino acid mutation that reduces the binding affinity of the Fc domain to an Fc receptor and/or effector function. Typically, the same one or more amino acid mutation is present in each of the two subunits of the Fc domain. In one embodiment, the amino acid mutation reduces the binding affinity of the Fc domain to an Fc receptor. In one embodiment, the amino acid mutation reduces the binding affinity of the Fc domain to an Fc receptor by at least 2-fold, at least 5-fold, or at least 10-fold. In embodiments where there is more than one amino acid mutation that reduces the binding affinity of the Fc domain to the Fc receptor, the combination of these amino acid mutations may reduce the binding affinity of the Fc domain to an Fc receptor by at least 10-fold, at least 20-fold, or even at least 50-fold. In one embodiment, the molecule, e.g., antibody, comprising an engineered Fc domain exhibits less than 20%, particularly less than 10%, more particularly less than 5% of the binding affinity to an Fc receptor as compared to a corresponding molecule comprising a non-engineered Fc domain. In a particular embodiment, the Fc receptor is an Fcγ receptor. In some embodiments, the Fc receptor is a human Fc receptor. In some embodiments, the Fc receptor is an activating Fc receptor. In a specific embodiment, the Fc receptor is an activating human Fcγ receptor, more specifically human FcγRIIIa, FcγRI or FcγRIIa, most specifically human FcγRIIIa. Preferably, binding to each of these receptors is reduced. In some embodiments, binding affinity to a complement component, specifically binding affinity to C1q, is also reduced. In one embodiment, binding affinity to neonatal Fc receptor (FcRn) is not reduced. Substantially similar binding to FcRn, i.e., preservation of the binding affinity of the Fc domain to said receptor, is achieved when the Fc domain (or the molecule, e.g., antibody, comprising said Fc domain) exhibits greater than about 70% of the binding affinity of a non-engineered form of the Fc domain (or a corresponding molecule comprising said non-engineered form of the Fc domain) to FcRn. The Fc domain, or molecule (e.g., antibody) comprising said Fc domain, may exhibit greater than about 80% and even greater than about 90% of such affinity. In certain embodiments, the Fc domain is engineered to have reduced effector function, as compared to a non-engineered Fc domain. The reduced effector function can include, but is not limited to, one or more of the following: reduced complement dependent cytotoxicity (CDC), reduced antibody-dependent cell-mediated cytotoxicity (ADCC), reduced antibody-dependent cellular phagocytosis (ADCP), reduced cytokine secretion, reduced immune complex-mediated antigen uptake by antigen-presenting cells, reduced binding to NK cells, reduced binding to macrophages, reduced binding to monocytes, reduced binding to polymorphonuclear cells, reduced direct signaling inducing apoptosis, reduced crosslinking of target-bound antibodies, reduced dendritic cell maturation, or reduced T cell priming. In one embodiment, the reduced effector function is one or more selected from the group of reduced CDC, reduced ADCC, reduced ADCP, and reduced cytokine secretion. In a particular embodiment the reduced effector function is reduced ADCC. In one embodiment the reduced ADCC is less than 20% of the ADCC induced by a non-engineered Fc domain (or a corresponding molecule comprising a non-engineered Fc domain).

In one embodiment, the amino acid mutation that reduces the binding affinity of the Fc domain to an Fc receptor and/or effector function is an amino acid substitution. In one embodiment the Fc domain comprises an amino acid substitution at a position selected from the group of E233, L234, L235, N297, P331, and P329 (EU numbering). In a more specific embodiment, the Fc domain comprises an amino acid substitution at a position selected from the group of L234, L235, and P329 (EU numbering). In some embodiments, the Fc domain comprises the amino acid substitutions L234A and L235A (EU numbering). In one such embodiment, the Fc domain is an $IgG_1$ Fc domain, particularly a human $IgG_1$ Fc domain. In one embodiment, the Fc domain comprises an amino acid substitution at position P329. In a more specific embodiment, the amino acid substitution is P329A or P329G, particularly P329G (EU numbering). In one embodiment, the Fc domain comprises an amino acid substitution at position P329 and a further amino acid substitution at a position selected from E233, L234, L235, N297, and P331 (EU numbering). In a more specific embodiment, the further amino acid substitution is E233P, L234A, L235A, L235E, N297A, N297D, or P331S. In particular embodiments, the Fc domain comprises amino acid substitutions at positions P329, L234, and L235 (EU numbering). In more particular embodiments, the Fc domain comprises the amino acid mutations L234A, L235A, and P329G ("P329G LALA"). In one such embodiment, the Fc domain is an $IgG_1$ Fc domain, particularly a human $IgG_1$ Fc domain. The "P329G LALA" combination of amino acid substitutions almost completely abolishes Fcγ receptor (as well as complement) binding of a human $IgG_1$ Fc domain, as described in PCT publication no. WO 2012/130831, incorporated herein by reference in its entirety. WO 2012/130831 also describes methods of preparing such mutant Fc domains and methods for determining its properties such as Fc receptor binding or effector functions.

$IgG_4$ antibodies exhibit reduced binding affinity to Fc receptors and reduced effector functions as compared to $IgG_1$ antibodies. Hence, in some embodiments the Fc domain is an $IgG_4$ Fc domain, particularly a human $IgG_4$ Fc domain. In one embodiment, the $IgG_4$ Fc domain comprises amino acid substitutions at position S228, specifically the amino acid substitution S228P (EU numbering). To further reduce its binding affinity to an Fc receptor and/or its effector function, in one embodiment the $IgG_4$ Fc domain comprises an amino acid substitution at position L235, specifically the amino acid substitution L235E (EU numbering). In another embodiment, the $IgG_4$ Fc domain comprises an amino acid substitution at position P329, specifically the amino acid substitution P329G (EU numbering). In a particular embodiment, the $IgG_4$ Fc domain comprises amino acid substitutions at positions S228, L235, and P329, specifically amino acid substitutions S228P, L235E, and P329G (EU numbering). Such $IgG_4$ Fc domain mutants and their Fcγ receptor binding properties are described in PCT publication no. WO 2012/130831, incorporated herein by reference in its entirety.

In a particular embodiment, the Fc domain exhibiting reduced binding affinity to an Fc receptor and/or reduced effector function, as compared to a native $IgG_1$ Fc domain, is a human $IgG_1$ Fc domain comprising the amino acid substitutions L234A, L235A, and optionally P329G, or a human $IgG_4$ Fc domain comprising the amino acid substitutions S228P, L235E, and optionally P329G (EU numbering).

In certain embodiments, N-glycosylation of the Fc domain has been eliminated. In one such embodiment, the Fc domain comprises an amino acid mutation at position N297, particularly an amino acid substitution replacing asparagine by alanine (N297A) or aspartic acid (N297D) or glycine (N297G) (EU numbering).

In addition to the Fc domains described hereinabove and in PCT publication no. WO 2012/130831, Fc domains with reduced Fc receptor binding and/or effector function also include those with substitution of one or more of Fc domain residues 238, 265, 269, 270, 297, 327, and 329 (U.S. Pat. No. 6,737,056) (EU numbering). Such Fc mutants include Fc mutants with substitutions at two or more of amino acid positions 265, 269, 270, 297, and 327, including the so-called "DANA" Fc mutant with substitution of residues 265 and 297 to alanine (U.S. Pat. No. 7,332,581).

Mutant Fc domains can be prepared by amino acid deletion, substitution, insertion or modification using genetic or chemical methods well known in the art. Genetic methods may include site-specific mutagenesis of the encoding DNA sequence, PCR, gene synthesis, and the like. The correct nucleotide changes can be verified for example by sequencing.

Binding to Fc receptors can be easily determined, e.g., by ELISA, or by Surface Plasmon Resonance (SPR) using standard instrumentation such as a BIACORE® instrument (GE Healthcare), and Fc receptors such as may be obtained by recombinant expression. Alternatively, binding affinity of Fc domains or molecules comprising an Fc domain for Fc receptors may be evaluated using cell lines known to express particular Fc receptors, such as human NK cells expressing FcγIIIa receptor.

Effector function of an Fc domain, or a molecule (e.g., an antibody) comprising an Fc domain, can be measured by methods known in the art. A suitable assay for measuring ADCC is described herein. Other examples of in vitro assays to assess ADCC activity of a molecule of interest are described in U.S. Pat. No. 5,500,362; Hellstrom et al. *Proc Natl Acad Sci USA*. 83, 7059-7063 (1986) and Hellstrom et al., *Proc Natl Acad Sci USA*. 82, 1499-1502 (1985); U.S. Pat. No. 5,821,337; Bruggemann et al., *J Exp Med* 166, 1351-1361 (1987). Alternatively, non-radioactive assays methods may be employed (see, for example, ACTI™ non-radioactive cytotoxicity assay for flow cytometry (CellTechnology, Inc. Mountain View, CA); and CYTOTOX 96® non-radioactive cytotoxicity assay (Promega, Madison, WI)). Useful effector cells for such assays include peripheral blood mononuclear cells (PBMC) and Natural Killer (NK) cells. Alternatively, or additionally, ADCC activity of the molecule of interest may be assessed, e.g., in a animal model such as that disclosed in Clynes et al., *Proc Natl Acad Sci USA* 95, 652-656 (1998).

In some embodiments, binding of the Fc domain to a complement component, specifically to C1q, is reduced. Accordingly, in some embodiments wherein the Fc domain is engineered to have reduced effector function, said reduced effector function includes reduced CDC. C1q binding assays may be carried out to determine whether the Fc domain, or molecule (e.g., antibody) comprising the Fc domain, is able to bind C1q and hence has CDC activity. See e.g., C1q and C3c binding ELISA in WO 2006/029879 and WO 2005/100402. To assess complement activation, a CDC assay may be performed (see, for example, Gazzano-Santoro et al., *J Immunol Methods* 202, 163 (1996); Cragg et al., *Blood* 101, 1045-1052 (2003); and Cragg and Glennie, *Blood* 103, 2738-2743 (2004)).

3. Substitution, Insertion, and Deletion

In certain instances, anti-CD79b antibody and/or anti-CD20/anti-CD3 bispecific antibody variants having one or more amino acid substitutions are provided. Sites of interest for substitutional mutagenesis include the HVRs and FRs. Conservative substitutions are shown in Table 4 under the heading of "preferred substitutions." More substantial changes are provided in Table 4 under the heading of "exemplary substitutions," and as further described below in reference to amino acid side chain classes. Amino acid substitutions may be introduced into an antibody of interest and the products screened for a desired activity, for example, retained/improved antigen binding, decreased immunogenicity, or improved ADCC or CDC.

TABLE 4

Exemplary and Preferred Amino Acid Substitutions

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g., a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g., binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, *Methods Mol. Biol.* 207:179-196 (2008)), and/or residues that contact antigen, with the resulting variant VH or VL being tested for binding affinity. Affinity maturation by constructing and reselecting from secondary libraries has been described, e.g., in Hoogenboom et al., in *Methods in Molecular Biology* 178:1-37 (O'Brien et al., ed., Human Press, Totowa, NJ, (2001)). In some instances of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain instances, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may, for example, be outside of antigen contacting residues in the HVRs. In certain instances of the variant VH and VL sequences provided above, each HVR either is unaltered, or includes no more than one, two, or three amino acid substitutions.

A useful method for identification of residues or regions of an antibody that may be targeted for mutagenesis is called "alanine scanning mutagenesis" as described by Cunningham and Wells (1989) *Science,* 244:1081-1085. In this method, a residue or group of target residues (e.g., charged residues such as Arg, Asp, His, Lys, and Glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g., for ADEPT) or a polypeptide which increases the serum half-life of the antibody.

4. Glycosylation

In certain instances, anti-CD79b antibody drug conjugates and/or anti-CD20/anti-CD3 bispecific antibodies of the invention can be altered to increase or decrease the extent to which the antibody is glycosylated. Addition or deletion of glycosylation sites to anti-CD79b antibody drug conjugates and/or anti-CD20/anti-CD3 bispecific antibodies of the invention may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al., *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some instances, modifications of the oligosaccharide in an antibody of the invention are made in order to create antibody variants with certain improved properties.

In one instance, anti-CD79b antibody drug conjugate and/or anti-CD20/anti-CD3 bispecific antibody variants are provided having a carbohydrate structure that lacks fucose attached (directly or indirectly) to an Fc region. For example, the amount of fucose in such antibody may be from 1% to 80%, from 1% to 65%, from 5% to 65%, or from 20% to 40%. The amount of fucose is determined by calculating the average amount of fucose within the sugar chain at Asn297, relative to the sum of all glycostructures attached to Asn297 (e. g. complex, hybrid and high mannose structures) as measured by MALDI-TOF mass spectrometry, as described in WO 2008/077546, for example. Asn297 refers to the asparagine residue located at about position 297 in the Fc region (EU numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., U.S. Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO 2005/053742; WO 2002/031140; Okazaki et al., *J. Mol. Biol.* 336:1239-1249 (2004); Yamane-Ohnuki et al., *Biotech. Bioeng.* 87: 614 (2004). Examples of cell lines capable of producing defucosylated antibodies include Lec13 CHO cells deficient in protein fucosylation (Ripka et al., *Arch.* *Biochem. Biophys.* 249:533-545 (1986); U.S. Patent Application No. US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al., *Biotech. Bioeng.* 87: 614 (2004); Kanda, Y. et al., *Biotechnol. Bioeng.*, 94(4):680-688 (2006); and WO 2003/085107).

In view of the above, in some instances, the methods of the invention involve administering to the subject in the context of a fractionated, dose-escalation dosing regimen an anti-CD79b antibody drug conjugate and/or an anti-CD20/anti-CD3 bispecific antibody variant that comprises an aglycosylation site mutation. In some instances, the aglycosylation site mutation reduces effector function of the antibody. In some instances, the aglycosylation site mutation is a substitution mutation. In some instances, the antibody comprises a substitution mutation in the Fc region that reduces effector function. In some instances, the substitution mutation is at amino acid residue N297, L234, L235, and/or D265 (EU numbering). In some instances, the substitution mutation is selected from the group consisting of N297G, N297A, L234A, L235A, D265A, and P329G. In some instances, the substitution mutation is at amino acid residue N297. In a preferred instance, the substitution mutation is N297A.

Anti-CD79b antibody drug conjugate and/or anti-CD20/anti-CD3 bispecific antibody variants are further provided with bisected oligosaccharides, for example, in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878; U.S. Pat. No. 6,602,684; and U.S. 2005/0123546. Antibody variants with at least one galactose residue in the oligosaccharide attached to the Fc region are also provided. Such antibody variants may have improved CDC function. Such antibody variants are described, e.g., in WO 1997/30087, WO 1998/58964, and WO 1999/22764.

5. Antibody Derivatives

In certain instances, an anti-CD79b antibody drug conjugate and/or an anti-CD20/anti-CD3 bispecific antibody provided herein is further modified to contain additional nonproteinaceous moieties that are known in the art and readily available. The moieties suitable for derivatization of the antibody include, but are not limited to, water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1, 3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, polypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another instance, conjugates of an antibody and non-proteinaceous moiety that may be selectively heated by exposure to radiation are provided. In one instance, the nonproteinaceous moiety is a carbon nanotube (Kam et al., *Proc. Natl. Acad. Sci. USA* 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

6. Recombinant Production Methods

Anti-CD79b antibody drug conjugates and/or anti-CD20/anti-CD3 bispecific antibodies of the invention may be produced using recombinant methods and compositions, for example, as described in U.S. Pat. No. 4,816,567, which is incorporated herein by reference in its entirety.

For recombinant production of an anti-CD79b antibody drug conjugate and/or an anti-CD20/anti-CD3 bispecific antibody, nucleic acid encoding an antibody is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, *Methods in Molecular Biology*, Vol. 248 (B.K.C. Lo, ed., Humana Press, Totowa, NJ, 2003), pp. 245-254, describing expression of antibody fragments in *E. coli.*) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, *Nat. Biotech.* 22:1409-1414 (2004), and Li et al., *Nat. Biotech.* 24:210-215 (2006).

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., *J. Gen Virol.* 36:59 (1977)); baby hamster kidney cells (BHK); mouse sertoli cells (TM4 cells as described, e.g., in Mather, *Biol. Reprod.* 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., *Annals N.Y. Acad. Sci.* 383:44-68 (1982); MRC 5 cells; and FS4 cells. Other useful mammalian host cell lines include Chinese hamster ovary (CHO) cells, including DHFR⁻ CHO cells (Urlaub et al., *Proc. Natl. Acad. Sci. USA* 77:4216 (1980)); and myeloma cell lines such as Y0, NS0 and Sp2/0. For a review of certain mammalian host cell lines suitable for antibody production, see, e.g., Yazaki and Wu, *Methods in Molecular Biology*, Vol. 248 (B.K.C. Lo, ed., Humana Press, Totowa, NJ), pp. 255-268 (2003).

7. Immunoconjugates

The invention also provides immunoconjugates or antibody drug conjugates comprising an anti-CD79b antibody and/or an anti-CD20/anti-CD3 bispecific antibody of the invention conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

In some instances, an immunoconjugate is an antibody-drug conjugate (ADC) in which an antibody is conjugated to one or more drugs, including but not limited to an auristatin such as monomethylauristatin drug moieties DE and DF (MMAE (vedotin) and MMAF) (see U.S. Pat. Nos. 5,635,483, 5,780,588, 7,498,298, and 8,088,378); a maytansinoid (see U.S. Pat. Nos. 5,208,020, 5,416,064, and European Patent EP 0 425 235 B1); a dolastatin; a calicheamicin or derivative thereof (see U.S. Pat. Nos. 5,712,374, 5,714,586, 5,739,116, 5,767,285, 5,770,701, 5,770,710, 5,773,001, and 5,877,296; Hinman et al., *Cancer Res.* 53:3336-3342 (1993); and Lode et al., *Cancer Res.* 58:2925-2928 (1998)); an anthracycline such as daunomycin or doxorubicin (see Kratz et al., *Current Med. Chem.* 13:477-523 (2006); Jeffrey et al., *Bioorganic & Med. Chem. Letters* 16:358-362 (2006); Torgov et al., *Bioconj. Chem.* 16:717-721 (2005); Nagy et al., *Proc. Natl. Acad. Sci. USA* 97:829-834 (2000); Dubowchik et al., *Bioorg. & Med. Chem. Letters* 12:1529-1532 (2002); King et al., *J. Med. Chem.* 45:4336-4343 (2002); and U.S. Pat. No. 6,630,579); methotrexate; vindesine; a taxane such as docetaxel, paclitaxel, larotaxel, tesetaxel, and ortataxel; a trichothecene; and CC1065.

In another instance, an immunoconjugate comprises anti-CD79b antibody or an anti-CD20/anti-CD3 bispecific antibody conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes.

In another instance, an immunoconjugate comprises an anti-CD79b antibody and/or an anti-CD20/anti-CD3 bispecific antibody conjugated to a radioactive atom to form a radioconjugate. A variety of radioactive isotopes are available for the production of radioconjugates. Examples include $^{211}$At, $^{131}$I, $^{125}$I, $^{90}$Y, $^{186}$Re, $^{188}$Re, $^{153}$Re, $^{212}$Bi, $^{32}$P, $^{212}$Pb and radioactive isotopes of Lu. When the radioconjugate is used for detection, it may comprise a radioactive atom for scintigraphic studies, for example tc99m or I123, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

Conjugates of an antibody and cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., Science 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of a cytotoxic drug in the cell. For example, an acid-labile linker, peptidase-sensitive linker, photolabile linker, dimethyl linker, or disulfide-containing linker (Chari et al., Cancer Res. 52:127-131 (1992); U.S. Pat. No. 5,208,020) may be used.

The immunoconjugates or ADCs herein expressly contemplate, but are not limited to, such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, IL., U.S.A).

Alternatively, any of the antibodies described herein (e.g., an anti-CD20/anti-CD3 bispecific antibody) can be a naked antibody.

D. Additional Therapeutic Agents

In some instances, the methods described herein include administering the anti-CD20/anti-CD3 bispecific antibody and the anti-CD79b ADC with an additional therapeutic agent. Examples of additional therapeutic agents include biological modifiers, chemotherapeutic agents, PD-1 axis binding antagonists, and therapeutic antibodies. In some instances, the anti-CD20/anti-CD3 bispecific antibody and the anti-CD79b ADC are co-administered with one or more additional therapeutic agents. Administration of the anti-CD20/anti-CD3 bispecific antibody and anti-CD79b ADC can occur prior to, simultaneously, and/or following, administration of the additional therapeutic agent or agents; all are considered co-administration. In one embodiment, the administration of the anti-CD20/anti-CD3 bispecific antibody and anti-CD79b ADC and co-administration of an additional therapeutic agent or exposure to radiotherapy can occur within about one month, or within about one, two, or three weeks, or within about one, two, three, four, five, or six days, of each other.

In some instances, the anti-CD20/anti-CD3 bispecific antibody and the anti-CD79b ADC are co-administered with one or more biological modifiers.

In some instances, the anti-CD20/anti-CD3 bispecific antibody and the anti-CD79b ADC are co-administered with obinutuzumab. In some instances, the anti-CD20/anti-CD3 bispecific antibody and the anti-CD79b ADC are co-administered with obinutuzumab and one or more biological modifiers.

In some instances, the anti-CD20/anti-CD3 bispecific antibody and the anti-CD79b ADC are co-administered with one or more chemotherapeutic agents.

In some instances, the anti-CD20/anti-CD3 bispecific antibody and the anti-CD79b ADC are co-administered with one or more chemotherapeutic agents and one or more biological modifiers.

In some instances, the anti-CD20/anti-CD3 bispecific antibody and the anti-CD79b ADC are co-administered a combination of with one or more chemotherapeutic agents and one or more therapeutic antibodies. In a particular instance, the anti-CD20/anti-CD3 bispecific antibody and the anti-CD79b ADC are co-administered with rituximab (CAS #: 174722-31-7), cyclophosphamide (CAS #: 50-18-0), doxorubicin (CAS #: 23214-92-8), prednisone (CAS #: 53-03-2) (R-CHP).

In some instances, the one or more additional therapeutic agents may reduce the rate or the severity of cytokine release syndrome (CRS). In some instances, the one or more additional therapeutic agents may prevent symptoms associated with CRS. In particular instances, the additional therapeutic agent used to reduce the rate or severity of CRS or prevent symptoms associated with CRS is a corticosteroid (e.g., dexamethasone (CAS #: 50-02-2), prednisone (CAS #: 53-03-2), or methylprednisolone (CAS #: 83-43-2)) or an IL-6R antagonist (e.g., tocilizumab, sarilumab, vobarilizumab (ALX-0061), satralizumab (SA-237), and variants thereof).

In some instances, other examples of therapeutic agents include antihistamines (e.g., diphenhydramine hydrochloride, CAS #: 147-24-0), antipyretics (e.g., paracetamol; CAS #, 103-90-2), or therapeutic agents for the decreasing the blood level of uric acid (e.g., allopurinol, CAS #: 315-30-0; or rasburicase, CAS #: 134774-45-1).

1. Chemotherapeutic Agents

In some instances, the anti-CD20/anti-CD3 bispecific antibody and the anti-CD79b ADC are co-administered with one or more chemotherapeutic agents. Examples of a chemotherapeutic agent include a compound useful in the treatment of cancer, such as a CD20-positive cell proliferative disorder (e.g., a B cell proliferative disorder (e.g., a relapsed or refractory B cell proliferative disorder), e.g., a non-Hodgkin's lymphoma (NHL; e.g., a diffuse large B cell lymphoma (DLBCL), a follicular lymphoma (FL; e.g., a Grade 1 FL, a Grade 2 FL, a Grade 3 FL (e.g., a Grade 3a FL, Grade 3b FL), or a transformed FL), a mantle cell lymphoma (MCL), or a marginal zone lymphoma (MZL)), e.g., a relapsed or refractory NHL (e.g., a relapsed or refractory DLBCL, a relapsed or refractory FL, a relapsed or refractory MCL, or a marginal zone lymphoma (MZL))).

2. PD-1 Axis Binding Antagonists

In some instances, the anti-CD20/anti-CD3 bispecific antibody and the anti-CD79b ADC are co-administered with a PD-1 axis binding antagonist. In some instances, the PD-1 axis binding antagonist is a PD-1 binding antagonist. In some instances, the PD-1 binding antagonist is an anti-PD-1 antibody. A variety of anti-PD-1 antibodies can be utilized in the methods and uses disclosed herein. In any of the instances herein, the PD-1 antibody can bind to a human PD-1 or a variant thereof. In some instances, the anti-PD-1 antibody is a monoclonal antibody. In some instances, the anti-PD-1 antibody is an antibody fragment selected from the group consisting of Fab, Fab', Fab'-SH, Fv, scFv, and (Fab')$_2$ fragments. In some instances, the anti-PD-1 antibody is a humanized antibody. In other instances, the anti-PD-1 antibody is a human antibody. Exemplary anti-PD-1 antagonist antibodies include nivolumab, pembrolizumab, MEDI-0680, PDR001 (spartalizumab), REGN2810 (cemiplimab), BGB-108, prolgolimab, camrelizumab, sintilimab, tislelizumab, toripalimab, dostarlimab, retifanlimab, sasanlimab, penpulimab, CS1003, HLX10, SCT-I10A, zimberelimab, balstilimab, genolimzumab, BI 754091, cetrelimab, YBL-006, BAT1306, HX008, budigalimab, AMG 404, CX-188, JTX-4014, 609A, Sym021, LZM009, F520, SG001, AM0001, ENUM 244C8, ENUM 388D4, STI-1110, AK-103, and hAb21. In some instances, the anti-PD-1 antibody is nivolumab (CAS Registry Number: 946414-94-4). Nivolumab (Bristol-Myers Squibb/Ono), also known as MDX-1106-04, MDX-1106, ONO-4538, BMS-936558, and OPDIVO®, is an anti-PD-1 antibody described in WO 2006/121168. In some instances, the anti-PD-1 antibody is pembrolizumab (CAS Registry Number: 1374853-91-4). Pembrolizumab (Merck), also known as MK-3475, Merck 3475, lambrolizumab, SCH-900475, and KEYTRUDA®, is an anti-PD-1 antibody described in WO 2009/114335. In some instances, the anti-PD-1 antibody is MEDI-0680 (AMP-514; AstraZeneca). MEDI-0680 is a humanized IgG4 anti-PD-1 antibody. In some instances, the anti-PD-1 antibody is PDR001 (CAS Registry No. 1859072-53-9; Novartis). PDR001 is a humanized IgG4 anti-PD-1 antibody that blocks the binding of PD-L1 and PD-L2 to PD-1. In some instances, the anti-PD-1 antibody is REGN2810 (Regeneron). REGN2810 is a human anti-PD-1 antibody. In some instances, the anti-PD-1 antibody is BGB-108 (BeiGene). In some instances, the anti-PD-1 antibody is BGB-A317 (BeiGene). In some instances, the anti-PD-1 antibody is JS-001 (Shanghai Junshi). JS-001 is a humanized anti-PD-1 antibody. In some instances, the anti-PD-1 antibody is STI-A1110 (Sorrento). STI-A1110 is a human anti-PD-1 antibody. In some instances, the anti-PD-1 antibody is INCSHR-1210 (Incyte). INCSHR-1210 is a human IgG4 anti-PD-1 antibody. In some instances, the anti-PD-1 antibody is PF-06801591 (Pfizer). In some instances, the anti-PD-1 antibody is TSR-042 (also known as ANB011; Tesaro/AnaptysBio). In some instances, the anti-PD-1 antibody is AM0001 (ARMO Biosciences). In some instances, the anti-PD-1 antibody is ENUM 244C8 (Enumeral Biomedical Holdings). ENUM 244C8 is an anti-PD-1 antibody that inhibits PD-1 function without blocking binding of PD-L1 to PD-1. In some instances, the anti-PD-1 antibody is ENUM 388D4 (Enumeral Biomedical Holdings). ENUM 388D4 is an anti-PD-1 antibody that competitively inhibits binding of PD-L1 to PD-1. In some instances, the anti-PD-1 antibody comprises the six HVR sequences (e.g., the three heavy chain HVRs and the three light chain HVRs) and/or the heavy chain variable domain and light chain variable domain from an anti-PD-1 antibody described in WO 2015/112800, WO 2015/112805, WO 2015/112900, US 20150210769, WO2016/089873, WO 2015/035606, WO 2015/085847, WO 2014/206107, WO 2012/145493, U.S. Pat. No. 9,205,148, WO 2015/119930, WO 2015/119923, WO 2016/032927, WO 2014/179664, WO 2016/106160, and WO 2014/194302.

In other instances, the PD-1 binding antagonist is an immunoadhesin (e.g., an immunoadhesin comprising an extracellular or PD-1 binding portion of PD-L1 or PD-L2 fused to a constant region (e.g., an Fc region of an immunoglobulin sequence). In other instances, the PD-1 binding antagonist is AMP-224. AMP-224, also known as B7-DCIg, is a PD-L2-Fc fusion soluble receptor described in PCT Pub. Nos. WO 2010/027827 and WO 2011/066342.

In some instances, the PD-1 axis binding antagonist is a PD-L1 binding antagonist. In some instances, the PD-L1 binding antagonist is an anti-PD-L1 antibody. A variety of anti-PD-L1 antibodies are contemplated and described herein. In any of the instances herein, the isolated anti-PD-L1 antibody can bind to a human PD-L1, for example a human PD-L1 as shown in UniProtKB/Swiss-Prot Accession No. Q9NZQ7-1, or a variant thereof. In some instances, the anti-PD-L1 antibody is capable of inhibiting binding between PD-L1 and PD-1 and/or between PD-L1 and B7-1. In some instances, the anti-PD-L1 antibody is a monoclonal antibody. In some instances, the anti-PD-L1 antibody is an antibody fragment selected from the group consisting of Fab, Fab'-SH, Fv, scFv, and (Fab')$_2$ fragments. In some instances, the anti-PD-L1 antibody is a humanized antibody. In some instances, the anti-PD-L1 antibody is a human antibody. Exemplary anti-PD-L1 antibodies include atezolizumab, MDX-1105, MEDI4736 (durvalumab), MSB0010718C (avelumab), SHR-1316, CS1001, envafolimab, TQB2450, ZKAB001, LP-002, CX-072, IMC-001, KL-A167, APL-502, cosibelimab, lodapolimab, FAZ053, TG-1501, BGB-A333, BCD-135, AK-106, LDP, GR1405, HLX20, MSB2311, RC98, PDL-GEX, KD036, KY1003, YBL-007, HS-636, LY3300054 (Eli Lilly), STI-A1014 (Sorrento), and KN035 (Suzhou Alphamab). In some instances, the anti-PD-L1 antibody comprises a cleavable moiety or linker that, when cleaved (e.g., by a protease in the tumor microenvironment), activates an antibody antigen binding domain to allow it to bind its antigen, e.g., by removing a non-binding steric moiety. In some instances, the anti-PD-L1 antibody is CX-072 (CytomX Therapeutics). In some instances, the anti-PD-L1 antibody comprises the six HVR sequences (e.g., the three heavy chain HVRs and the three light chain HVRs) and/or the heavy chain variable domain and light chain variable domain from an anti-PD-L1 antibody described in US 20160108123, WO 2016/000619, WO 2012/145493, U.S. Pat. No. 9,205,148, WO 2013/181634, or WO 2016/061142. Examples of anti-PD-L1 antibodies useful in the methods of this invention and methods of making them are described in International Patent Application Publication No. WO 2010/077634 and U.S. Pat. No. 8,217,149, each of which is incorporated herein by reference in its entirety.

In some instances, the PD-1 axis binding antagonist is a PD-L2 binding antagonist. In other instances, the PD-L2 binding antagonist is an anti-PD-L2 antibody (e.g., a human, a humanized, or a chimeric anti-PD-L2 antibody). In some instances, the PD-L2 binding antagonist is an immunoadhesin.

3. Therapeutic Antibodies

In some instances, the anti-CD20/anti-CD3 bispecific antibody and the anti-CD79b ADC are co-administered with a therapeutic antibody.

For example, in a particular instance, the anti-CD20/anti-CD3 bispecific antibody and anti-CD79b antibody drug conjugate can be co-administered with obinutuzumab (GAZYVA®) or tocilizumab (ACTEMRA®/ROACTEMRA®), wherein the subject is first administered with obinutuzumab (GAZYVA®) or tocilizumab (ACTEMRA®/ROACTEMRA®) and then separately administered with the anti-CD20/anti-CD3 bispecific antibody (e.g., the subject is pre-treated with obinutuzumab (GAZYVA®) or tocilizumab (ACTEMRA®/ROACTEMRA®)).

In another particular instance, the anti-CD20/anti-CD3 bispecific antibody and the anti-CD79b ADC can be co-administered with tocilizumab (ACTEMRA®/RO- ACTEMRA®), wherein the subject is first administered with tocilizumab (ACTEMRA®/ROACTEMRA®) and then separately administered with the anti-CD20/anti-CD3 bispecific antibody (e.g., the subject is pre-treated with tocilizumab (ACTEMRA®/ROACTEMRA®)).

In some instances, the anti-CD20/anti-CD3 bispecific antibody and the anti-CD79b ADC are co-administered an anti-CD19 antibody drug conjugate, an anti-CD22 antibody drug conjugate, an anti-CD45 antibody drug conjugate, or an anti-CD32 antibody drug conjugate.

IV. Combination Therapies

The invention provides methods for treating a subject having a CD20-positive cell proliferative disorder (e.g., a B cell proliferative disorder (e.g., non-Hodgkin's lymphoma (NHL) (e.g., a relapsed and/or refractory NHL, a diffuse-large B cell lymphoma (DLBCL) (e.g., a relapsed and/or refractory DLBCL), a follicular lymphoma (FL) (e.g., a relapsed and/or refractory FL or a transformed FL), or a mantle cell lymphoma (MCL) (e.g., a relapsed or refractory MCL)), or a central nervous system lymphoma (CNSL))) that includes administering to the subject an anti-CD79b antibody drug conjugate and/or an anti-CD20/anti-CD3 bispecific antibody, e.g., in a fractionated, dose-escalation dosing regimen. In some instances, the present methods are used for treating a subject having relapsed and/or refractory NHL (e.g., an aggressive NHL (e.g., a relapsed and/or refractory DLBCL, a relapsed and/or refractory FL, or a relapsed and/or refractory MCL)). In some instances, the subject has relapsed following one or more (e.g., one, two, three, four, five, or more) prior therapies (e.g., one or more prior systemic therapies, e.g., one or more prior systemic chemotherapies (e.g., one or more prior systemic therapies involving administration of anthracycline), one or more prior stem cell therapies, or one or more prior CAR-T cell therapies) after having a documented history of response (e.g., a complete response or a partial response) of at least 6 months in duration from completion of the therapy. In some instances, the subject is refractory to any prior therapy (e.g., has had no response to the prior therapy, or progression within 6 months of completion of the last dose of therapy). Thus, in some embodiments, the present dosing regimen is a second-line therapy. In some embodiments, the present dosing regimen is a third-line therapy. In some embodiments, the subject has a transformed FL, which is a refractory to standard therapies for transformed FL. In some embodiments, the FL is a Graded FL (e.g., a Grade 1, 2, 3a, or 3b FL).

In one aspect, the invention features a method of treating a subject having a CD20-positive cell proliferative disorder, e.g., a B cell proliferative disorder (e.g., an NHL (e.g., a relapsed and/or refractory NHL, a DLBCL (e.g., a relapsed and/or refractory DLBCL), a FL (e.g., a relapsed and/or refractory FL or a transformed FL), or an MCL (e.g., a relapsed or refractory MCL)), or a CNSL), comprising administering to the subject an anti-CD79b antibody drug conjugate and an anti-CD20/anti-CD3 bispecific antibody in a dosing regimen comprising at least a first dosing cycle and a second dosing cycle, wherein: (a) the first dosing cycle comprises a first dose (C1D1) of the anti-CD20/anti-CD3 bispecific antibody and a second dose (C1D2) of the anti-CD20/anti-CD3 bispecific antibody, wherein the C1D1 of the anti-CD20/anti-CD3 bispecific antibody is about 2.5 mg and the C1D2 of the anti-CD20/anti-CD3 bispecific antibody is about 10 mg; and (b) the second dosing cycle comprises a single dose (C2D1) of the anti-CD20/anti-CD3 bispecific antibody, wherein the C2D1 of the anti-CD20/anti-CD3 bispecific antibody is about 10 mg, about 16 mg, or about 30 mg. In particular embodiments, the C1D1 of the anti-CD20/anti-CD3 bispecific antibody is about 2.5 mg and the C1D2 of the anti-CD20/anti-CD3 bispecific antibody is about 10 mg. In particular embodiments, the C2D1 is about 10 mg. In particular embodiments, the C2D1 of the anti-CD20/anti-CD3 bispecific antibody is about 16 mg. In particular embodiments, the C2D1 of the anti-CD20/anti-CD3 bispecific antibody is about 30 mg.

In some embodiments, the first dosing cycle comprises a single dose C1D1 of the anti-CD79b antibody drug conjugate. In some embodiments, the single dose C1D1 of the anti-CD79b antibody drug conjugate is from about 0.1 mg/kg to about 2.4 mg/kg (e.g., from about 0.1 mg/kg to about 2.2 mg/kg, from about 0.1 mg/kg to about 2.0 mg/kg, from about 0.5 mg/kg to about 2.2 mg/kg, from about 0.8 mg/kg to about 2.2 mg/kg, from about 1 mg/kg to about 2.2 mg/kg, from about 1.2 mg/kg to about 2.2 mg/kg, from about 1.4 mg/kg to about 2.2 mg/kg, from about 1.6 mg/kg to about 2.2 mg/kg, from about 1.8 mg/kg to about 2.0 mg/kg, from about 0.1 mg/kg to about 1.6 mg/kg, from about 0.5 mg/kg to about 1.6 mg/kg, or from about 1 mg/kg to about 1.8 mg/kg; e.g., about 1 mg/kg, about 1.2 mg/kg, about 1.6 mg/kg, or about 1.8 mg/kg). In some embodiments, the single dose C1D1 of the anti-CD79b antibody drug conjugate is about 1.8 mg/kg. In some embodiments, the second dosing cycle comprises a single dose C2D1 of the anti-CD79b antibody drug conjugate. In some embodiments, the single dose C2D1 of the anti-CD79b antibody drug conjugate is from about 0.1 mg/kg to about 2.4 mg/kg (e.g., from about 0.1 mg/kg to about 2.2 mg/kg, from about 0.1 mg/kg to about 2.0 mg/kg, from about 0.5 mg/kg to about 2.2 mg/kg, from about 0.8 mg/kg to about 2.2 mg/kg, from about 1 mg/kg to about 2.2 mg/kg, from about 1.2 mg/kg to about 2.2 mg/kg, from about 1.4 mg/kg to about 2.2 mg/kg, from about 1.6 mg/kg to about 2.2 mg/kg, from about 1.8 mg/kg to about 2.0 mg/kg, from about 0.1 mg/kg to about 1.6 mg/kg, from about 0.5 mg/kg to about 1.6 mg/kg, or from about 1 mg/kg to about 1.8 mg/kg; e.g., about 1 mg/kg, about 1.2 mg/kg, about 1.6 mg/kg, or about 1.8 mg/kg). In particular embodiments, the single dose C2D1 of the anti-CD79b antibody drug conjugate is about 1.8 mg/kg.

In some embodiments, the C1D1 of the anti-CD20/anti-CD3 bispecific antibody and the C1D2 of the anti-CD20/anti-CD3 bispecific antibody are administered to the subject on or about Days 8 (±1 day) and 15 (±1 day), respectively, of the first dosing cycle. In some embodiments, the C2D1 of the anti-CD20/anti-CD3 bispecific antibody is administered to the subject on or about Day 1 (±1 day) of the second dosing cycle. In some embodiments, the C1D1 of the anti-CD79b antibody drug conjugate is administered to the subject on or about Day 2 (±1 day) of the first dosing cycle and the C2D1 of the anti-CD79b antibody drug conjugate is administered to the subject on or about Day 1 (±1 day) of the second dosing cycle. In some embodiments, the first and second dosing cycles are 14-day (e.g., 14±3 days) dosing cycles. In some embodiments, the first and second dosing cycles are 21-day (e.g., 21±3 days) dosing cycles.

In some embodiments, the dosing regimen comprises one or more additional dosing cycles. In some embodiments, the dosing regimen comprises six to ten additional dosing cycles (e.g., six additional cycles, seven additional cycles, eight additional cycles, nine additional cycles, or ten additional cycles). In particular embodiments, the dosing regimen comprises ten additional dosing cycles. In some embodiments, the additional dosing cycles are 14-day (e.g., 14±3 days) dosing cycles. In some embodiments, the additional dosing cycles are 21-day (e.g., 21±3 days) dosing cycles.

In some embodiments, one or more of the additional dosing cycles comprise an additional single dose of the anti-CD20/anti-CD3 bispecific antibody and an additional single dose of the anti-CD79b antibody drug conjugate. In some embodiments, the additional single dose of the anti-CD79b antibody drug conjugate is about equivalent in amount to the C2D1 of the anti-CD79b antibody drug conjugate. In some embodiments, the additional single dose of the anti-CD79b antibody drug conjugate is between about 0.1 mg/kg and about 2.4 mg/kg (e.g., from about 0.1 mg/kg to about 2.2 mg/kg, from about 0.1 mg/kg to about 2.0 mg/kg, from about 0.5 mg/kg to about 2.2 mg/kg, from about 0.8 mg/kg to about 2.2 mg/kg, from about 1 mg/kg to about 2.2 mg/kg, from about 1.2 mg/kg to about 2.2 mg/kg, from about 1.4 mg/kg to about 2.2 mg/kg, from about 1.6 mg/kg to about 2.2 mg/kg, from about 1.8 mg/kg to about 2.0 mg/kg, from about 0.1 mg/kg to about 1.6 mg/kg, from about 0.5 mg/kg to about 1.6 mg/kg, or from about 1 mg/kg to about 1.8 mg/kg; e.g., about 1 mg/kg, about 1.2 mg/kg, about 1.6 mg/kg, or about 1.8 mg/kg). In particular embodiments, the additional single dose of the anti-CD79b antibody drug conjugate is about 1.8 mg/kg. In some embodiments, the additional single dose of the anti-CD79b antibody drug conjugate is administered to the subject on or about Day 1 (±1 day) of each additional dosing cycle comprising an additional dose of the anti-CD79b antibody drug conjugate. In some embodiments, the dosing regimen comprises at least four additional dosing cycles comprising an additional single dose of the anti-CD79b antibody drug conjugate. In some embodiments, the dosing regimen comprises between four to ten additional dosing cycles (e.g., four additional cycles, five additional cycles, six additional cycles, seven additional cycles, eight additional cycles, nine additional cycles, or ten additional cycles) comprising an additional single dose of the anti-CD79b antibody drug conjugate. In some embodiments, one or more of the additional dosing cycles comprise an additional single dose of the anti-CD20/ anti-CD3 bispecific antibody and do not comprise administration of the anti-CD79b antibody drug conjugate.

In some embodiments, the dosing regimen comprises at least two additional dosing cycles comprising an additional single dose of the anti-CD20/anti-CD3 bispecific antibody and not comprising administration of the anti-CD79b antibody drug conjugate. In some embodiments, the dosing regimen comprises between two and ten additional dosing cycles (e.g., two additional cycles, three additional cycles, four additional cycles, five additional cycles, six additional cycles, seven additional cycles, eight additional cycles, nine additional cycles, or ten additional cycles) comprising an additional single dose of the anti-CD20/anti-CD3 bispecific antibody and not comprising administration of the anti-CD79b antibody drug conjugate. In some embodiments, the additional single dose of the anti-CD20/anti-CD3 bispecific antibody is about equivalent in amount to the C2D1 of the anti-CD20/anti-CD3 bispecific antibody. In some embodiments, the additional single dose of the anti-CD20/anti-CD3 bispecific antibody is about 10 mg, about 16 mg, or about 30 mg. In particular embodiments, the additional single dose of the anti-CD20/anti-CD3 bispecific antibody is about 30 mg. In some embodiments, the additional single dose of the anti-CD20/anti-CD3 bispecific antibody is administered to the subject on or about Day 1 (±1 day) of each additional dosing cycle comprising an additional dose of the anti-CD20/anti-CD3 bispecific antibody.

In some embodiments, the dosing regimen comprises six or more additional dosing cycles (e.g., six additional cycles, seven additional cycles, eight additional cycles, nine additional cycles, ten additional cycles, or more), wherein each of the six or more additional dosing cycles comprises a single dose of the anti-CD20/anti-CD3 bispecific antibody, and wherein no more than four of the six or more additional dosing cycles (e.g., one additional cycle, two additional cycles, three additional cycles, or four additional cycles) comprise administration of the anti-CD79b antibody drug conjugate. In some embodiments, the dosing regimen comprises six additional dosing cycles, wherein each of the six or more additional dosing cycles comprises a single dose of the anti-CD20/anti-CD3 bispecific antibody, and wherein no more than four of the six additional dosing cycles (e.g., one additional cycle, two additional cycles, three additional cycles, or four additional cycles) comprise administration of the anti-CD79b antibody drug conjugate. In particular embodiments, the dosing regimen comprises ten additional dosing cycles, wherein each of the six or more additional dosing cycles comprises a single dose of the anti-CD20/ anti-CD3 bispecific antibody, and wherein no more than four of the ten additional dosing cycles (e.g., one additional cycle, two additional cycles, three additional cycles, or four additional cycles) comprise administration of the anti-CD79b antibody drug conjugate. In particular embodiments, the dosing regimen comprises ten additional dosing cycles, wherein each of the ten additional dosing cycles comprises a single dose of the anti-CD20/anti-CD3 bispecific antibody, and wherein no more than ten additional dosing cycles (e.g., one additional cycle, two additional cycles, three additional cycles, or four additional cycles, five additional cycles six additional cycles, seven additional cycles, eight additional cycles, nine additional cycles, or ten additional cycles) comprise administration of the anti-CD79b antibody drug conjugate.

In another aspect, the invention features a method of treating a subject having a CD20-positive cell proliferative disorder, e.g., a B cell proliferative disorder (e.g., an NHL (e.g., a relapsed and/or refractory NHL, a DLBCL (e.g., a relapsed and/or refractory DLBCL), a FL (e.g., a relapsed and/or refractory FL or a transformed FL), or an MCL (e.g., a relapsed or refractory MCL)), or a CNSL), comprising administering to the subject an anti-CD79b antibody drug conjugate and an anti-CD20/anti-CD3 bispecific antibody in a dosing regimen comprising at least a first dosing cycle and a second dosing cycle, wherein: (a) the first dosing cycle comprises: (i) a single dose (C1D1) of the anti-CD79b antibody drug conjugate; and (ii) a first dose (C1D1) of the anti-CD20/anti-CD3 bispecific antibody and a second dose (C1D2) of the anti-CD20/anti-CD3 bispecific antibody, wherein the C1D1 and the C1D2 of the anti-CD20/anti-CD3 bispecific antibody are each administered to the subject after the C1D1 of the anti-CD79b antibody drug conjugate, wherein the C1D1 of the anti-CD20/anti-CD3 bispecific antibody is about 2.5 mg, and the C1D2 of the anti-CD20/ anti-CD3 bispecific antibody is about 10 mg; and (b) the second dosing cycle comprises: (i) a single dose (C2D1) of the anti-CD79b antibody drug conjugate; and (ii) a single dose (C2D1) of the anti-CD20/anti-CD3 bispecific antibody, wherein the C2D1 of the anti-CD20/anti-CD3 bispecific antibody is about 10 mg, about 16 mg, or about 30 mg. In particular embodiments, the C1D1 of the anti-CD20/anti-CD3 bispecific antibody is about 2.5 mg and the C1D2 of the anti-CD20/anti-CD3 bispecific antibody is about 10 mg. In some embodiments, the C2D1 of the anti-CD20/anti-CD3 bispecific antibody is about 10 mg, about 16 mg, or about 30 mg. In particular embodiments, the C2D1 of the anti-CD20/ anti-CD3 bispecific antibody is about 10 mg. In particular embodiments, the C2D1 of the anti-CD20/anti-CD3 bispecific antibody is about 16 mg. In particular embodiments, the C2D1 of the anti-CD20/anti-CD3 bispecific antibody is about 30 mg.

In some embodiments, the first dosing cycle comprises a single dose C1D1 of the anti-CD79b antibody drug conjugate. In some embodiments, the single dose C1D1 of the anti-CD79b antibody drug conjugate is from about 0.1 mg/kg to about 2.4 mg/kg (e.g., from about 0.1 mg/kg to about 2.2 mg/kg, from about 0.1 mg/kg to about 2.0 mg/kg, from about 0.5 mg/kg to about 2.2 mg/kg, from about 0.8 mg/kg to about 2.2 mg/kg, from about 1 mg/kg to about 2.2 mg/kg, from about 1.2 mg/kg to about 2.2 mg/kg, from about 1.4 mg/kg to about 2.2 mg/kg, from about 1.6 mg/kg to about 2.2 mg/kg, from about 1.8 mg/kg to about 2.0 mg/kg, from about 0.1 mg/kg to about 1.6 mg/kg, from about 0.5 mg/kg to about 1.6 mg/kg, or from about 1 mg/kg to about 1.8 mg/kg; e.g., about 1 mg/kg, about 1.2 mg/kg, about 1.6 mg/kg, or about 1.8 mg/kg). In particular embodiments, the single dose C1D1 of the anti-CD79b antibody drug conjugate is about 1.8 mg/kg. In some embodiments, the second dosing cycle comprises a single dose C2D1 of the anti-CD79b antibody drug conjugate. In some embodiments, the single dose C2D1 of the anti-CD79b antibody drug conjugate is from about 0.1 mg/kg to about 2.4 mg/kg (e.g., from about 0.1 mg/kg to about 2.2 mg/kg, from about 0.1 mg/kg to about 2.0 mg/kg, from about 0.5 mg/kg to about 2.2 mg/kg, from about 0.8 mg/kg to about 2.2 mg/kg, from about 1 mg/kg to about 2.2 mg/kg, from about 1.2 mg/kg to about 2.2 mg/kg, from about 1.4 mg/kg to about 2.2 mg/kg, from about 1.6 mg/kg to about 2.2 mg/kg, from about 1.8 mg/kg to about 2.0 mg/kg, from about 0.1 mg/kg to about 1.6 mg/kg, from about 0.5 mg/kg to about 1.6 mg/kg, or from about 1 mg/kg to about 1.8 mg/kg; e.g., about 1 mg/kg, about 1.2 mg/kg, about 1.6 mg/kg, or about 1.8 mg/kg). In particular embodiments, the single dose C2D1 of the anti-CD79b antibody drug conjugate is about 1.8 mg/kg.

In some embodiments, the C1D1 of the anti-CD20/anti-CD3 bispecific antibody and the C1D2 of the anti-CD20/anti-CD3 bispecific antibody are administered to the subject on or about Days 8 (±1 day) and 15 (±1 day), respectively, of the first dosing cycle. In some embodiments, the C2D1 of the anti-CD20/anti-CD3 bispecific antibody is administered to the subject on or about Day 1 (±1 day) of the second dosing cycle. In some embodiments, the C1D1 of the anti-CD79b antibody drug conjugate is administered to the subject on or about Day 2 (±1 day) of the first dosing cycle and the C2D1 of the anti-CD79b antibody drug conjugate is administered to the subject on or about Day 1 (±1 day) of the second dosing cycle. In particular embodiments, the first and second dosing cycles are 14-day (e.g., 14±3 days) dosing cycles. In particular embodiments, the first and second dosing cycles are 21-day (e.g., 21±3 days) dosing cycles.

In some embodiments, the dosing regimen comprises one or more additional dosing cycles. In some embodiments, the dosing regimen comprises six to ten additional dosing cycles (e.g., six additional cycles, seven additional cycles, eight additional cycles, nine additional cycles, or ten additional cycles). In particular embodiments, the dosing regimen comprises ten additional dosing cycles. In some embodiments, the additional dosing cycles are 14-day (e.g., 14±3 days) dosing cycles. In some embodiments, the additional dosing cycles are 21-day (e.g., 21±3 days) dosing cycles.

In some embodiments, one or more of the additional dosing cycles comprise an additional single dose of the anti-CD20/anti-CD3 bispecific antibody and an additional single dose of the anti-CD79b antibody drug conjugate. In some embodiments, the additional single dose of the anti-CD79b antibody drug conjugate is about equivalent in amount to the C2D1 of the anti-CD79b antibody drug conjugate. In some embodiments, the additional single dose of the anti-CD79b antibody drug conjugate is between about 0.1 mg/kg and about 2.4 mg/kg (e.g., from about 0.1 mg/kg to about 2.2 mg/kg, from about 0.1 mg/kg to about 2.0 mg/kg, from about 0.5 mg/kg to about 2.2 mg/kg, from about 0.8 mg/kg to about 2.2 mg/kg, from about 1 mg/kg to about 2.2 mg/kg, from about 1.2 mg/kg to about 2.2 mg/kg, from about 1.4 mg/kg to about 2.2 mg/kg, from about 1.6 mg/kg to about 2.2 mg/kg, from about 1.8 mg/kg to about 2.0 mg/kg, from about 0.1 mg/kg to about 1.6 mg/kg, from about 0.5 mg/kg to about 1.6 mg/kg, or from about 1 mg/kg to about 1.8 mg/kg; e.g., about 1 mg/kg, about 1.2 mg/kg, about 1.6 mg/kg, or about 1.8 mg/kg). In particular embodiments, the additional single dose of the anti-CD79b antibody drug conjugate is about 1.8 mg/kg. In some embodiments, the additional single dose of the anti-CD79b antibody drug conjugate is administered to the subject on or about Day 1 (±1 day) of each additional dosing cycle comprising an additional dose of the anti-CD79b antibody drug conjugate. In some embodiments, the dosing regimen comprises at least four additional dosing cycles comprising an additional single dose of the anti-CD20/anti-CD3 bispecific antibody and an additional single dose of the anti-CD79b antibody drug conjugate. In some embodiments, the dosing regimen comprises between four to ten additional dosing cycles (e.g., four additional cycles, five additional cycles, six additional cycles, seven additional cycles, eight additional cycles, nine additional cycles, or ten additional cycles) comprising an additional single dose of the anti-CD20/anti-CD3 bispecific antibody and an additional single dose of the anti-CD79b antibody drug conjugate.

In some embodiments, one or more of the additional dosing cycles comprise an additional single dose of the anti-CD20/anti-CD3 bispecific antibody and do not comprise administration of the anti-CD79b antibody drug conjugate. In some embodiments, the dosing regimen comprises at least two additional dosing cycles comprising an additional single dose of the anti-CD20/anti-CD3 bispecific antibody and not comprising administration of the anti-CD79b antibody drug conjugate. In some embodiments, the dosing regimen comprises between two and ten additional dosing cycles (e.g., two additional cycles, three additional cycles, four additional cycles, five additional cycles, six additional cycles, seven additional cycles, eight additional cycles, nine additional cycles, or ten additional cycles) comprising an additional single dose of the anti-CD20/anti-CD3 bispecific antibody and not comprising administration of the anti-CD79b antibody drug conjugate. In particular embodiments, the additional single dose of the anti-CD20/anti-CD3 bispecific antibody is about equivalent in amount to the C2D1 of the anti-CD20/anti-CD3 bispecific antibody. In some embodiments, the additional single dose of the anti-CD20/anti-CD3 bispecific antibody is about 10 mg, about 16 mg, or about 30 mg. In particular embodiments, the additional single dose of the anti-CD20/anti-CD3 bispecific antibody is about 30 mg. In some embodiments, the additional single dose of the anti-CD20/anti-CD3 bispecific antibody is administered to the subject on or about Day 1 (±1 day) of each additional dosing cycle comprising an additional dose of the anti-CD20/anti-CD3 bispecific antibody.

In some embodiments, the dosing regimen comprises six to ten additional dosing cycles (e.g., six additional dosing cycles, seven additional dosing cycles, eight additional dosing cycles, nine additional dosing cycles, or ten additional dosing cycles), wherein each of the six to ten additional dosing cycles comprises a single dose of the anti-CD20/anti-CD3 bispecific antibody, and wherein no more than four of the six or more additional dosing cycles comprise administration of the anti-CD79b antibody drug conjugate. In some embodiments, the dosing regimen comprises six additional dosing cycles, wherein each of the six or more additional dosing cycles comprises a single dose of the anti-CD20/anti-CD3 bispecific antibody, and wherein no more than four of the six additional dosing cycles (e.g., one additional cycle, two additional cycles, three additional cycles, or four additional cycles) comprise administration of the anti-CD79b antibody drug conjugate. In some embodiments, the dosing regimen comprises ten additional dosing cycles, wherein each of the ten additional dosing cycles comprises a single dose of the anti-CD20/anti-CD3 bispecific antibody, and wherein no more than four of the ten additional dosing cycles (e.g., one additional cycle, two additional cycles, three additional cycles, or four additional cycles) comprise administration of the anti-CD79b antibody drug conjugate.

In another aspect, the invention features a method of treating a subject having a CD20-positive cell proliferative disorder, e.g., a B cell proliferative disorder (e.g., an NHL (e.g., a relapsed and/or refractory NHL, a DLBCL (e.g., a relapsed and/or refractory DLBCL), a FL (e.g., a relapsed and/or refractory FL or a transformed FL), or an MCL (e.g., a relapsed or refractory MCL)), or a CNSL), comprising administering to the subject an anti-CD79b antibody drug conjugate and an anti-CD20/anti-CD3 bispecific antibody in a dosing regimen comprising eight or more dosing cycles, wherein: (a) the first dosing cycle comprises: (i) a first dose (C1D1) of the anti-CD20/anti-CD3 bispecific antibody and a second dose (C1D2) of the anti-CD20/anti-CD3 bispecific antibody, wherein the C1D1 of the anti-CD20/anti-CD3 bispecific antibody is about 2.5 mg and the C1D2 of the anti-CD20/anti-CD3 bispecific antibody is about 10 mg; and (ii) a single dose (C1D1) of the anti-CD79b antibody drug conjugate; (b) the second to sixth dosing cycles each comprises a single dose (C2D1-C6D1) of the anti-CD20/anti-CD3 bispecific antibody and a single dose (C2D1-C6D1) of the anti-CD79b antibody drug conjugate; and (c) the seventh to 12$^{th}$ dosing cycles each comprises a single dose (C7D1-C12D1) of the anti-CD20/anti-CD3 bispecific antibody and does not comprise administration of the anti-CD79b antibody drug conjugate, and wherein each single dose C2D1-C12D1 of the anti-CD20/anti-CD3 bispecific antibody is about 10 mg, about 16 mg, or about 30 mg. In a particular embodiment, the C1D1 of the anti-CD20/anti-CD3 bispecific antibody is about 2.5 mg and the C1D2 of the anti-CD20/anti-CD3 bispecific antibody is about 10 mg. In some embodiments, the C2D1-C12D1 of the anti-CD20/anti-CD3 bispecific antibody are about equivalent in amount. In particular embodiments, the C2D1 is about 10 mg, about 16 mg, or about 30 mg. In particular embodiments, the C2D1 is about 10 mg. In particular embodiments, the C2D1 is about 16 mg. In particular embodiments, the C2D1 is about 30 mg.

In some embodiments, the C1D1-C6D1 of the anti-CD79b antibody drug conjugate are about equivalent in amount. In some embodiments, each of the C1D1-C6D1 of the anti-CD79b antibody drug conjugate is from about 0.1 mg/kg to about 2.4 mg/kg (e.g., from about 0.1 mg/kg to about 2.2 mg/kg, from about 0.1 mg/kg to about 2.0 mg/kg, from about 0.5 mg/kg to about 2.2 mg/kg, from about 0.8 mg/kg to about 2.2 mg/kg, from about 1 mg/kg to about 2.2 mg/kg, from about 1.2 mg/kg to about 2.2 mg/kg, from about 1.4 mg/kg to about 2.2 mg/kg, from about 1.6 mg/kg to about 2.2 mg/kg, from about 1.8 mg/kg to about 2.0 mg/kg, from about 0.1 mg/kg to about 1.6 mg/kg, from about 0.5 mg/kg to about 1.6 mg/kg, or from about 1 mg/kg to about 1.8 mg/kg; e.g., about 1 mg/kg, about 1.2 mg/kg, about 1.6 mg/kg, or about 1.8 mg/kg). In particular embodiments, each of the C1D1-C6D1 of the anti-CD79b antibody drug conjugate is about 1.8 mg/kg.

In some embodiments, the C1D1 of the anti-CD20/anti-CD3 bispecific antibody and the C1D2 of the anti-CD20/anti-CD3 bispecific antibody are administered to the subject on or about Days 8 (±1 day) and 15 (±1 day), respectively, of the first dosing cycle. In some embodiments, the C2D1-C12D1 of the anti-CD20/anti-CD3 bispecific antibody is administered to the subject on or about Day 1 (±1 day) of each dosing cycle. In some embodiments, the C1D1 of the anti-CD79b antibody drug conjugate is administered to the subject on or about Day 2 (±1 day) of the first dosing cycle and the C2D1-C6D1 of the anti-CD79b antibody drug conjugate is administered to the subject on or about Day 1 (±1 day) of each dosing cycle comprising administration of the anti-CD79b antibody drug conjugate. In particular embodiments, each dosing cycle is a 14-day (±3 days) dosing cycle. In particular embodiments, each dosing cycle is a 21-day (±3 days) dosing cycle.

In some embodiments, the C1D1 of the anti-CD20/anti-CD3 bispecific antibody is administered after the C1D1 of the anti-CD79b antibody drug conjugate. In some embodiments, the C1D1 of the anti-CD20/anti-CD3 bispecific antibody is administered about six days after the C1D1 of the anti-CD79b antibody drug conjugate is administered. In some embodiments, the C1D1 of the anti-CD20/anti-CD3 bispecific antibody and the C1D2 of the anti-CD20/anti-CD3 bispecific antibody are administered to the subject on or about Days 8 (±1 day) and 15 (±1 day), respectively, of the first dosing cycle. In some embodiments, the C2D1-C12D1 of the anti-CD20/anti-CD3 bispecific antibody are administered to the subject on or about Day 1 (±1 day) of each dosing cycle. In some embodiments, the C1D1 of the anti-CD79b antibody conjugate is administered on or about Day 1 (±1 day) of the first dosing cycle and C2D1-C6D1 of the anti-CD79b antibody drug conjugate are administered to the subject on or about Day 1 (±1 day) of each dosing cycle comprising administration of the anti-CD79b antibody drug conjugate. In particular embodiments, each dosing cycle is a 14-day (±3 days) dosing cycle. In particular embodiments, each dosing cycle is a 21-day (±3 days) dosing cycle.

In some embodiments, the dosing regimen comprises an additional re-treatment regimen after the completion of the 12 dosing cycles of the dosing regimen. In some embodiments, the additional re-treatment regimen comprises 12 additional dosing cycles, wherein: (a) the first additional dosing cycle comprises: (i) a first dose (C13D1) of the anti-CD20/anti-CD3 bispecific antibody and a second dose (C13D2) of the anti-CD20/anti-CD3 bispecific antibody, wherein the C13D1 of the anti-CD20/anti-CD3 bispecific antibody is about 2.5 mg, and the C13D2 of the anti-CD20/anti-CD3 bispecific antibody is about 10 mg; and (ii) a single dose (C13D1) of the anti-CD79b antibody drug conjugate; (b) the second to sixth additional dosing cycles each comprises a single dose (C14D1-C18D1) of the anti-CD20/anti-CD3 bispecific antibody and a single dose (C14D1-C18D1) of the anti-CD79b antibody drug conjugate; and (c) the seventh to 12$^{th}$ additional dosing cycles each comprises a single dose (C19D1-C24D1) of the anti-CD20/anti-CD3 bispecific antibody and does not comprise administration of the anti-CD79b antibody drug conjugate, and wherein each single dose C14D1-C24D1 of the anti-CD20/anti-CD3 bispecific antibody is about 10 mg, about 16 mg, or about 30 mg. In some embodiments, each single dose C13D1-C18D1 of the anti-CD79b antibody conjugate is between about 0.1 mg/kg and about 2.4 mg/kg (e.g., from about 0.1 mg/kg to about 2.2 mg/kg, from about 0.1 mg/kg to about 2.0 mg/kg, from about 0.5 mg/kg to about 2.2 mg/kg, from about 0.8 mg/kg to about 2.2 mg/kg, from about 1 mg/kg to about 2.2 mg/kg, from about 1.2 mg/kg to about 2.2 mg/kg, from about 1.4 mg/kg to about 2.2 mg/kg, from about 1.6 mg/kg to about 2.2 mg/kg, from about 1.8 mg/kg to about 2.0 mg/kg, from about 0.1 mg/kg to about 1.6 mg/kg, from about 0.5 mg/kg to about 1.6 mg/kg, or from about 1 mg/kg to about 1.8 mg/kg; e.g., about 1 mg/kg, about 1.2 mg/kg, about 1.6 mg/kg, or about 1.8 mg/kg).

In some embodiments, the additional re-treatment regimen comprises 12 additional dosing cycles, wherein (a) the first additional dosing cycle comprises: (i) a first dose (C13D1) of the anti-CD20/anti-CD3 bispecific antibody administered on Day 8 (±1 day) of the first additional dosing cycle and a second dose (C13D2) of the anti-CD20/anti-CD3 bispecific antibody administered on Day 15 (±1 day) of the first additional dosing cycle, wherein the C13D1 of the anti-CD20/anti-CD3 bispecific antibody is about 2.5 mg, and the C13D2 of the anti-CD20/anti-CD3 bispecific antibody is about 10 mg; and (ii) a single dose (C13D1) of the anti-CD79b antibody drug conjugate administered on Day 2 (±1 day) of the first additional dosing cycle; (b) the second to sixth additional dosing cycles each comprises a single dose (C14D1-C18D1) of the anti-CD20/anti-CD3 bispecific antibody and a single dose (C14D1-C18D1) of the anti-CD79b antibody drug conjugate; and (c) the seventh to 12$^{th}$ additional dosing cycles each comprises a single dose (C19D1-C24D1) of the anti-CD20/anti-CD3 bispecific antibody and does not comprise administration of the anti-CD79b antibody drug conjugate, and wherein the C14D1-C24D1 of the anti-CD20/anti-CD3 bispecific antibody are administered on Day 1 (±1 day) of each additional dosing cycle and the C14D1-C18D1 of the anti-CD79b antibody drug conjugate are administered on Day 1 (±1 day) of each additional dosing cycle, and wherein each single dose C14D1-C24D1 of the anti-CD20/anti-CD3 bispecific antibody is about 30 mg and each single dose C13D1-C18D1 of the anti-CD79b antibody drug conjugate is about 1.8 mg/kg.

In some embodiments, there is a waiting period between the completion of the 12 dosing cycles of the dosing regimen and the start of the 12 additional dosing cycles of the additional re-treatment regimen. In some embodiments, the waiting period is between about one to about eight weeks (e.g., about one week, about two weeks, about three weeks, about four weeks, about five weeks, about six weeks, about seven weeks, or about eight weeks). In some embodiments, each additional dosing cycle of the additional re-treatment regimen is a 14-day (±3 days) dosing cycle. In some embodiments, each additional dosing cycle of the additional re-treatment regimen is a 21-day (±3 days) dosing cycle.

In some embodiments, the methods featured by the invention further comprises administering to the subject one or more additional therapeutic agents. In some embodiments, the one or more additional therapeutic agents comprise one or more chemotherapeutic agents. In some embodiments, the one or more chemotherapeutic agents comprise cyclophosphamide, doxorubicin, and rituximab. In some embodiments, the one or more additional therapeutic agents is tocilizumab. In some embodiments, the one or more additional therapeutic agents is a corticosteroid. In some embodiments, the corticosteroid comprises prednisone, prednisolone, methylprednisolone and dexamethasone. In some embodiments, one or more additional therapeutic agents is an antihistamine. In some embodiments, the antihistamine is diphenhydramine. In some embodiments, the one or more additional therapeutic agents comprises allopurinol and rasburicase. In some embodiments, the one or more additional therapeutic agents is an antipyretic. In some embodiments, the methods featured by the invention further comprises administering to the subject rituximab, cyclophosphamide, doxorubicin, and prednisone (R-CHP).

In some embodiments, the anti-CD20/anti-CD3 bispecific antibody is administered intravenously. In some embodiments, the anti-CD79b antibody drug conjugate is administered intravenously.

In some embodiments, if the anti-CD20/anti-CD3 bispecific antibody and the anti-CD79b antibody drug conjugate are administered on the same day, then the anti-CD20/anti-CD3 bispecific antibody is administered after the administration of the anti-CD79b antibody drug conjugate has completed. In some embodiments, the anti-CD20/anti-CD3 bispecific antibody is administered between about 60-120 minutes (e.g., between about 60-110 minutes, between about 60-100 minutes, between about 60-90 minutes, between about 60-80 minutes, between about 60-70 minutes, between about 70-100 minutes, between about 80-100 minutes, between about 90-100 minutes, between about 75-105 minutes, or between about 85-95 minutes; e.g., about 60 minutes, about 70 minutes, about 80 minutes, about 85 minutes, about 88 minutes, about 90 minutes, about 92 minutes, about 95 minutes, about 100 minutes, about 110 minutes, or about 120 minutes) after the administration of the anti-CD79b antibody drug conjugate has completed. In particular embodiments, the anti-CD20/anti-CD3 bispecific antibody is administered about 90 minutes after the administration of the anti-CD79b antibody drug conjugate has completed.

In some embodiments, the dose of the anti-CD79b antibody drug conjugate in one or more dosing cycles may be reduced for drug-related toxicities (i.e., observed adverse events). In particular embodiments, the dose of the anti-CD79b antibody drug conjugate may be reduced to about 1.4 mg/kg or about 1.0 mg/kg as a result of drug-related toxicities (i.e., observed adverse events).

In some embodiments, the one or more additional therapeutic agents is obinutuzumab. In some embodiments, obinutuzumab is administered prior to administration of the anti-CD20/anti-CD3 bispecific antibody. In some embodiments, obinutuzumab is administered at least about one hour prior to administration of the anti-CD20/anti-CD3 bispecific antibody (e.g., about one hour, about two hours, about three hours, about four hours, about six hours, about eight hours, about 12 hours, about 16 hours, about 20 hours, or about 24 hours). In some embodiments, obinutuzumab is administered at least about one day prior to administration of the anti-CD20/anti-CD3 bispecific antibody (e.g., about one day, about two days, about three days, about four days, about five days, about six days, or about seven days). In some embodiments, obinutuzumab is administered about seven days prior to administration of the anti-CD20/anti-CD3 bispecific antibody. In some embodiments, obinutuzumab is administered as a single dose. In some embodiments, obinutuzumab is administered as a single dose of about 1000 mg. In some embodiments, obinutuzumab is administered as a one time treatment only. In some embodiments, obinutuzumab is administered at a first dose of about 1000 mg and a second dose of about 1000 mg. In some embodiments, the first and second dose of obinutuzumab are administered on the same day. In some embodiments, the first and second dose of obinutuzumab are administered about 7 days prior to administration of the C1D1 of the anti-CD20/anti-CD3 bispecific antibody. In some embodiments, the first and second dose of obinutuzumab are administered on different days. In some embodiments, the first dose of obinutuzumab is administered about seven days prior to administration of the C1D1 of the anti-CD20/anti-CD3 bispecific antibody, and the second dose of obinutuzumab is administered about one day prior to administration of the C1D1 of the anti-CD20/anti-CD3 bispecific antibody.

In additional embodiments, the anti-CD20/anti-CD3 bispecific antibody (e.g., glofitamab) step-up dosing regimen with the anti-CD79b antibody drug conjugate (ADC; e.g., polatuzumab vedotin) is performed (e.g., administered) according to any of the embodiments described herein. In another embodiment, subjects foreseen for treatment with the methods provided herein are pretreated with an anti-CD20 antibody, as described herein.

In some instances, the methods described above include administering the anti-CD79b ADC and the anti-CD20/anti-CD3 bispecific antibody with a further chemotherapeutic agent and/or an antibody-drug conjugate (ADC). In some instances, the anti-CD79b ADC and the anti-CD20/anti-CD3 bispecific antibody are co-administered with one or more additional chemotherapeutic agents selected from cyclophosphamide and doxorubicin. In some instances, the anti-CD79b ADC and the anti-CD20/anti-CD3 bispecific antibody are co-administered with an ADC. In some instances, the anti-CD79b ADC and the anti-CD20/anti-CD3 bispecific antibody are co-administered with CHOP, wherein vincristine is replaced with an ADC. In particular instances, the anti-CD79b ADC and the anti-CD20/anti-CD3 bispecific antibody are co-administered with R-CHP.

In some instances, the methods described above include administering the anti-CD79b ADC and the anti-CD20/anti-CD3 bispecific antibody with a corticosteroid. In some instances, the corticosteroid is dexamethasone (CAS #: 50-02-2), prednisone (CAS #: 53-03-2), or methylprednisolone (CAS #: 83-43-2).

Any of the methods of the invention described herein may be useful for treating CD20-positive cell proliferative disorders, e.g., B cell proliferative disorders/malignancies. In particular, B cell proliferative disorders amenable to treatment with a anti-CD20/anti-CD3 bispecific antibody in accordance with the methods described herein include, without limitation, non-Hodgkin's lymphoma (NHL), including diffuse large B cell lymphoma (DLBCL), which may be relapsed or refractory DLBCL, as well as other cancers including germinal-center B cell-like (GCB) diffuse large B cell lymphoma (DLBCL), activated B cell-like (ABC) DLBCL, follicular lymphoma (FL), mantle cell lymphoma (MCL), acute myeloid leukemia (AML), marginal zone lymphoma (MZL), small lymphocytic leukemia (SLL), Waldenstrom macroglobulinemia (WM), central nervous system lymphoma (CNSL), B cell prolymphocytic leukemia, splenic marginal zone lymphoma, hairy cell leukemia, splenic lymphoma/leukemia, unclassifiable, splenic diffuse red pulp small B cell lymphoma, hairy cell leukemia variant, heavy chain diseases, α heavy chain disease, γ heavy chain disease, μ heavy chain disease, plasma cell myeloma, solitary plasmacytoma of bone, extraosseous plasmacytoma, extranodal marginal zone lymphoma of mucosa-associated lymphoid tissue (MALT lymphoma), nodal marginal zone lymphoma, pediatric nodal marginal zone lymphoma, pediatric follicular lymphoma, primary cutaneous follicle centre lymphoma, T cell/histiocyte rich large B cell lymphoma, primary DLBCL of the CNS, primary cutaneous DLBCL, leg type, EBV-positive DLBCL of the elderly, DLBCL associated with chronic inflammation, lymphomatoid granulomatosis, primary mediastinal (thymic) large B cell lymphoma (PMLBCL), intravascular large B cell lymphoma, ALK-positive large B cell lymphoma, plasmablastic lymphoma, large B cell lymphoma arising in HHV8-associated multicentric Castleman disease, primary effusion lymphoma: B cell lymphoma, unclassifiable, with features intermediate between DLBCL and classical Hodgkin's lymphoma. Further examples of B cell proliferative disorders include, but are not limited to, multiple myeloma (MM); low grade/follicular NHL; small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; AIDS-related lymphoma; chronic myeloblastic leukemia; and post-transplant lymphoproliferative disorder (PTLD). In particular instances, the B cell proliferative disorder may be an NHL (e.g., a relapsed and/or refractory NHL, a DLBCL (e.g., a relapsed and/or refractory DLBCL), a FL (e.g., a relapsed and/or refractory FL or a transformed FL), or an MCL (e.g., a relapsed or refractory MCL)), or a CNSL).

The methods described herein may not be suitable for pateints having a chronic lymphoid leukemia (CLL), an acute lymphoblastic leukemia (ALL), a Richter's transformation, a Burkitt lymphoma, or a lymphoplasmacytic lymphoma.

The methods described herein may result in an acceptable safety profile for subjects having a CD20-positive cell proliferative disorder, e.g., a B cell proliferative disorder (e.g., an NHL (e.g., a relapsed and/or refractory NHL, a DLBCL (e.g., a relapsed and/or refractory DLBCL), a FL (e.g., a relapsed and/or refractory FL or a transformed FL), or an MCL (e.g., a relapsed or refractory MCL)), or a CNSL) being treated with an anti-CD79b ADC and an anti-CD20/anti-CD3 bispecific antibody. In some instances, treatment using the methods described herein that result in an acceptable rate and/or severity of undesirable events, such as cytokine-driven toxicities (e.g., cytokine release syndrome (CRS)), infusion-related reactions (IRRs), macrophage activation syndrome (MAS), neurologic toxicities, severe tumor lysis syndrome (TLS), neutropenia, thrombocytopenia, elevated liver enzymes, and/or central nervous system (CNS) toxicities, following treatment with an anti-CD79b ADC and an anti-CD20/anti-CD3 bispecific antibody using the fractionated, dose-escalation dosing regimen of the invention relative to treatment with an anti-CD79b ADC and an anti-CD20/anti-CD3 bispecific antibody using an non-fractioned dosing regimen or relative to treatment with an anti-CD20/anti-CD3 bispecific antibody without an anti-CD79b ADC.

In some embodiments, the rate of neurological or CNS adverse events of Grade ≥3 in a population of subjects having R/R NHL (e.g., R/R DLBCL) is less than or equal to about 50% (e.g., less than or equal to about 40%, less than or equal to about 30%, less than or equal to about 20%, less than or equal to about 10%, less than or equal to about 5%, or less than or equal to about 1%; e.g., between about 0% to about 50%, between about 5% to about 40%, between about 5% to about 20%, between about 5% to about 10%, between about 20% to about 50%, between about 30% to about 40%, between about 20% to about 40%, between about 15% to about 35%, between about 15% to about 25%, between about 35% to about 50%, or between about 25% to about 50%; e.g., about 50%, about 45%, about 40%, about 35%, about 30%, about 25%, about 20%, about 15%, about 10%, about 5%, about 1%, or about 0%). In particular embodiments, the rate of neurological or CNS adverse events of Grade ≥3 in a population of subjects having R/R NHL (e.g., R/R DLBCL) is less than or equal to about 20%. In particular embodiments, the rate of neurological or CNS adverse events of Grade ≥3 in a population of subjects having R/R NHL (e.g., R/R DLBCL) is less than or equal to about 10%. In particular embodiments, the rate of neurological or CNS adverse events of Grade ≥3 in a population of subjects having R/R NHL (e.g., R/R DLBCL) less than or equal to about 5%. In particular embodiments, the rate of neurological or CNS adverse events of Grade ≥3 in a population of subjects having R/R NHL (e.g., R/R DLBCL) is less than or equal to about 3%. In particular embodiments, the rate of neurological or CNS adverse events of Grade ≥3 in a population of subjects having R/R NHL (e.g., R/R DLBCL) is less than or equal to about 1%.

In some instances, the invention features a method of treating a population of subjects having a R/R NHL comprising administering to the subjects an anti-CD79b antibody drug conjugate and an anti-CD20/anti-CD3 bispecific antibody in a dosing regimen comprising at least a first dosing cycle and a second dosing cycle, wherein: (a) the first dosing cycle comprises a first dose (C1D1) of the anti-CD20/anti-CD3 bispecific antibody administered on Day 8 (±1 day) of the first dosing cycle, a second dose (C1D2) of the anti-CD20/anti-CD3 bispecific antibody administered on Day 15 (±1 day) of the first dosing cycle, and a single dose (C1D1) of the anti-CD79b antibody drug conjugate administered on Day 2 (±1 day) of the first dosing cycle, wherein the C1D1 of the anti-CD20/anti-CD3 bispecific antibody is about 2.5 mg, and the C1D2 of the anti-CD20/anti-CD3 bispecific antibody is about 10 mg; and (b) the second dosing cycle comprises a single dose (C2D1) of the anti-CD20/anti-CD3 bispecific antibody administered on Day 1 (±1 day) of the second dosing cycle and a single dose (C2D1) of the anti-CD79b antibody drug conjugate administered on Day 1 (±1 day) of the second dosing cycle, wherein the C2D1 of the anti-CD20/anti-CD3 bispecific antibody is about 30 mg, and wherein the C1D1 and the C1D2 of the anti-CD79b antibody drug conjugate are each about 1.8 mg/kg.

In some instances, the invention features a method of treating a population of subjects having a R/R NHL comprising administering to the subjects an anti-CD79b antibody drug conjugate and an anti-CD20/anti-CD3 bispecific antibody in a dosing regimen comprising 12 dosing cycles, wherein: (a) the first dosing cycle comprises: (i) a first dose (C1D1) of the anti-CD20/anti-CD3 bispecific antibody administered on Day 8 (±1 day) of the first dosing cycle and a second dose (C1D2) of the anti-CD20/anti-CD3 bispecific antibody administered on Day 15 (±1 day) of the first dosing cycle, wherein the C1D1 of the anti-CD20/anti-CD3 bispecific antibody is about 2.5 mg, and the C1D2 of the anti-CD20/anti-CD3 bispecific antibody is about 10 mg; and (ii) a single dose (C1D1) of the anti-CD79b antibody drug conjugate administered on Day 2 (±1 day) of the first dosing cycle; (b) the second to sixth dosing cycles each comprises a single dose (C2D1-C6D1) of the anti-CD20/anti-CD3 bispecific antibody and a single dose (C2D1-C6D1) of the anti-CD79b antibody drug conjugate; and (c) the seventh to 12th dosing cycles each comprises a single dose (C7D1-C12D1) of the anti-CD20/anti-CD3 bispecific antibody and does not comprise administration of the anti-CD79b antibody drug conjugate, and wherein each single dose C2D1-C12D1 of the anti-CD20/anti-CD3 bispecific antibody is administered on Day 1 (±1 day) of each dosing cycle, and each single dose C2D1-C6D1 of the anti-CD79b antibody drug conjugate is administered on Day 1 (±1 day) of each dosing cycle, and wherein each single dose C2D1-C12D1 of the anti-CD20/anti-CD3 bispecific antibody is about 30 mg and each single dose C1D1-C6D1 of the anti-CD79b antibody drug conjugate is about 1.8 mg/kg.

In one embodiment, the anti-CD20/anti-CD3 bispecific antibody of the methods described therein comprises at least one Fab molecule which specifically binds to CD3 comprising the following six HVRs:
  (a) an HVR-H1 comprising the amino acid sequence of TYAMN (SEQ ID NO: 9);
  (b) an HVR-H2 comprising the amino acid sequence of RIRSKYNNYATYYADSVKG (SEQ ID NO: 10);
  (c) an HVR-H3 comprising the amino acid sequence of HGNFGNSYVSWFAY (SEQ ID NO: 11);
  (d) an HVR-L1 comprising the amino acid sequence of GSSTGAVTTSNYAN (SEQ ID NO: 12);
  (e) an HVR-L2 comprising the amino acid sequence of GTNKRAP (SEQ ID NO: 13); and
  (f) an HVR-L3 comprising the amino acid sequence of ALWYSNLWV (SEQ ID NO: 14), and the
bispecific antibody comprises at least one Fab molecule which specifically binds to CD20 comprising the following six hypervariable regions (HVRs):
  (a) an HVR-H1 comprising the amino acid sequence of YSWIN (SEQ ID NO: 1);
  (b) an HVR-H2 comprising the amino acid sequence of RIFPGDGDTDYNGKFKG (SEQ ID NO: 2);
  (c) an HVR-H3 comprising the amino acid sequence of NVFDGYWLVY (SEQ ID NO:3);
  (d) an HVR-L1 comprising the amino acid sequence of RSSKSLLHSNGITYLY (SEQ ID NO: 4);
  (e) an HVR-L2 comprising the amino acid sequence of QMSNLVS (SEQ ID NO: 5); and
  (f) an HVR-L3 comprising the amino acid sequence of AQNLELPYT (SEQ ID NO: 6).

In one embodiment, the anti-CD20/anti-CD3 bispecific antibody comprises a Fab molecule which specifically binds to CD3 comprises (a) a VH domain comprising an amino acid sequence of SEQ ID NO: 15 and (b) a VL domain comprising an amino acid sequence of SEQ ID NO: 16 and a Fab molecule which specifically binds to CD20 comprises (a) a VH domain comprising an amino acid sequence of SEQ ID NO: 7 and (b) a VL domain comprising an amino acid sequence of SEQ ID NO: 8.

In one embodiment, the anti-CD79b antibody drug conjugate is polatuzumab vedotin.

In some instances, the invention features a method of treating a population of subjects having a R/R NHL comprising administering to the subjects polatuzumab vedotin and glofitamab in a dosing regimen comprising at least a first dosing cycle and a second dosing cycle, wherein: (a) the first dosing cycle comprises a first dose (C1D1) of glofitamab administered on Day 8 (±1 day) of the first dosing cycle, a second dose (C1D2) of glofitamab administered on Day 15 (±1 day) of the first dosing cycle, and a single dose (C1D1) of polatuzumab vedotin administered on Day 2 (±1 day) of the first dosing cycle, wherein the C1D1 of glofitamab is about 2.5 mg, and the C1D2 of glofitamab is about 10 mg; and (b) the second dosing cycle comprises a single dose (C2D1) of glofitamab administered on Day 1 (±1 day) of the second dosing cycle and a single dose (C2D1) of polatuzumab vedotin administered on Day 1 of (±1 day) the second dosing cycle, wherein the C2D1 of glofitamab is about 30 mg, and wherein the C1D1 and the C2D1 of polatuzumab vedotin are each about 1.8 mg/kg.

In some instances, the invention features a method of treating a population of subjects having a R/R NHL comprising administering to the subjects polatuzumab vedotin and glofitamab in a dosing regimen comprising 12 dosing cycles, wherein: (a) the first dosing cycle comprises: (i) a first dose (C1D1) of glofitamab administered on Day 8 (±1 day) of the first dosing cycle and a second dose (C1D2) of glofitamab administered on Day 15 (±1 day) of the first dosing cycle, wherein the C1D1 of glofitamab is about 2.5 mg, and the C1D2 of glofitamab is about 10 mg; and (ii) a single dose (C1D1) of polatuzumab vedotin administered on Day 2 (±1 day) of the first dosing cycle; (b) the second to sixth dosing cycles each comprises a single dose (C2D1-C6D1) of glofitamab and a single dose (C2D1-C6D1) of polatuzumab vedotin; and (c) the seventh to 12th dosing cycles each comprises a single dose (C7D1) of glofitamab and does not comprise administration of polatuzumab vedotin, and wherein each single dose C2D1-C12D1 of glofitamab is administered on Day 1 (±1 day) of each dosing cycle, and each single dose C2D1-C6D1 of polatuzumab vedotin is administered on Day 1 (±1 day) of each dosing cycle, and wherein each single dose C2D1-C12D1 of glofitamab is about 30 mg and each single dose C1D1-C6D1 of polatuzumab vedotin is about 1.8 mg/kg.

The methods described herein may result in a complete response rate in the population of subjects having a R/R NHL of at least about 20% (e.g., at least 25%, at least 40%, at least 50%, at least 60%, at least 70%, at least 80%, or at least 90%; e.g., between 20-100%, between 40-100%, between 60-100%, between 80-100%, between 20-80%, between 20-60%, between 20-40%, between 40-80%, between 40-60%, between 30-50%, or between 35-45%; e.g., about 20%, about 25%, about 30%, about 35%, about 40%, about 41%, about 42%, about 43%, about 44%, about 45%, about 50%, about 60%, or more). In particular embodiments, the complete response rate in the population of subjects having a R/R NHL is about 42%. The methods described herein may result in an overall response rate in the population of subjects having a R/R NHL of at least about 30% (e.g., at least 35%, at least 40%, at least 50%, at least 60%, at least 70%, at least 80%, or at least 90%; e.g., between 30-100%, between 50-100%, between 70-100%, between 30-90%, between 30-70%, between 30-50%, between 40-80%, between 40-60%, between 45-55%, or between 35-45%; e.g., about 30%, about 35%, about 40%, about 45%, about 48%, about 49%, about 50%, about 51%, about 52%, about 55%, about 60%, about 70%, or more). In particular embodiments, the overall response rate in the population of subjects having a R/R NHL is about 50%.

The methods described herein may result in a complete response rate in the population of subjects having a R/R MCL of at least about 60% (e.g., at least 60%, at least 70%, at least 80%, at least 90%; e.g., between 60-100%, between 70-100%, between 80-100%, between 90-100%, between 60-90%, between 60-80%, between 60-70%, between 70-90%, between 80-90%, between 80-100%, or between 90-100%; e.g., about 60%, about 70%, about 75%, about 80%, about 83%, about 85%, about 87%, about 90%, about 95%, about 97%, about 98%, about 99%, or more). In particular embodiments, the complete response rate in the population of subjects having a R/R NHL is at least about 85%. In particular embodiments, the complete response rate in the population of subjects having a R/R MCL is at least about 85%. In particular embodiments, the complete response rate in the population of subjects having a R/R MCL is about 100%. The methods described herein may result in an overall response rate in the population of subjects having a R/R MCL of at least about 60% (e.g., at least 60%, at least 70%, at least 80%, or at least 90%; e.g., between 60-100%, between 70-100%, between 80-100%, between 90-100%, between 60-90%, between 60-80%, between 60-70%, between 70-90%, between 80-90%, between 80-100%, or between 90-100%; e.g., about 60%, about 70%, about 75%, about 80%, about 83%, about 85%, about 87%, about 90%, about 95%, about 97%, about 98%, about 99%, or more). In particular embodiments, the overall response rate in the population of subjects having a R/R NHL is at least about 85%. In particular embodiments, the overall response rate in the population of subjects having a R/R MCL is at least about 85%. In particular embodiments, the overall response rate in the population of subjects having a R/R MCL is about 100%.

The methods described herein may result in a complete response rate in the population of subjects having a R/R DLBCL of at least about 60% (e.g., at least 60%, at least 70%, at least 80%, or at least 90%; e.g., between 60-100%, between 70-100%, between 80-100%, between 90-100%, between 60-90%, between 60-80%, between 60-70%, between 60-65%, between 65-75%, or between 75-85%; e.g., about 60%, about 61%, about 62%, about 65%, about 68%, about 69%, about 70%, about 71%, about 72%, about 73%, about 74%, about 75%, about 76%, about 77%, about 80%, about 85%, about 90%, or more). In particular embodiments, the complete response rate in the population of subjects having a R/R DLBCL is about 60%. In particular embodiments, the complete response rate in the population of subjects having a R/R DLBCL is about 65%. In particular embodiments, the complete response rate in the population of subjects having a R/R DLBCL is about 70%. In particular embodiments, the complete response rate in the population of subjects having a R/R DLBCL is about 75%.

The methods described herein may result in an overall response rate in the population of subjects having a R/R DLBCL of at least about 60% (e.g., at least 60%, at least 70%, at least 80%, at least 85%, at least at least 86%, at least 87%, at least 88%, at least 89%, at least 90%, at least 91%, at least 92%, at least 93%, at least 94%, at least 95%, at least 96%, at least 97%, at least 98%, or at least 99%; e.g., between 60-100%, between 70-100%, between 85-97%, between 85-95%, between 85-90%, between 85-87%, between 90-95%, between 93-97%, between 80-100%, between 85-100%, between 87-100%, between 90-100%, between 95-100%, between 60-90%, between 60-80%, between 60-70%, between 60-65%, between 65-75%, between 70-90%, or between 75-85%; e.g., about 60%, about 63%, about 64%, about 65%, about 66%, about 67%, about 70%, about 73%, about 74%, about 75%, about 76%, about 77%, about 80%, about 83%, about 84%, about 85%, about 86%, about 87%, about 88%, about 90%, about 91%, about 92%, about 93%, about 94%, about 95%, about 97%, about 98%, about 99%, or more). In particular embodiments, the overall response rate in the population of subjects having a R/R DLBCL is about 65%. In particular embodiments, the overall response rate in the population of subjects having a R/R DLBCL is about 73%. In particular embodiments, the overall response rate in the population of subjects having a R/R DLBCL is about 75%. In particular embodiments, the overall response rate in the population of subjects having a R/R DLBCL is about 85%. In particular embodiments, the overall response rate in the population of subjects having a R/R DLBCL is about 86%.

The methods described herein may result in a complete response rate in the population of subjects having a R/R DLBCL of at least about 35% (e.g., least 40%, at least 50%, at least 60%, at least 70%, at least 80%, or at least 90%; e.g., between 30-100%, between 50-100%, between 50-90%, between 70-100%, between 35-90%, between 35-70%, between 35-50%, between 40-80%, between 40-60%, between 45-55%, or between 35-45%; e.g., about 35%, about 40%, about 45%, about 48%, about 49%, about 50%, about 51%, about 52%, about 55%, about 60%, about 70%, about 75%, about 80%, about 85%, or more). In some embodiments, the complete response rate is at least 45%. In some embodiments, the complete response rate is at least 55%. In some embodiments, the complete response rate is at least 75%. In some embodiments, the complete response rate is at least 85%. In some embodiments, the complete response rate is at least 90%. In particular embodiments, the complete response rate in the population of subjects having a R/R DLBCL is about 46%. In particular embodiments, the complete response rate in the population of subjects having a R/R DLBCL is about 52%. In particular embodiments, the complete response rate in the population of subjects having a R/R DLBCL is about 86%. In some embodiments, the complete response rate is higher than a reference complete response rate in a reference population of subjects treated with a combination therapy comprising an anti-CD20/anti-CD3 bispecific antibody and an anti-PD-L1 antagonist antibody and not comprising an anti-CD79b antibody drug conjugate. In some embodiments, the objective response rate is higher than a reference objective response rate in a reference population of subjects treated with a combination therapy comprising an anti-CD20/anti-CD3 bispecific antibody and an anti-PD-L1 antagonist antibody and not comprising an anti-CD79b antibody drug conjugate. In some embodiments, the complete response rate is higher than a reference complete response rate in a reference population of subjects treated with a combination therapy comprising glofitamab and atezolizumab and not comprising polatuzumab vedotin. In some embodiments, the objective response rate is higher than a reference objective response rate in a reference population of subjects treated with a combination therapy comprising glofitamab and atezolizumab and not comprising polatuzumab vedotin.

In some embodiments, the subject is human. In some embodiments, each subject in a population of subjects is human. In some embodiments, each subject in a reference population of subjects is human. In some embodiments, the subject or population of subjects has received at least two prior systemic therapies (e.g., two, three, four, five, six, or more prior systemic therapies). In some embodiments, the subject or population of subjects is ineligible for autologous stem cell transplant (SCT) (e.g., the subject or each subject in a population of subjects is transplant ineligible).

V. CRS Risk Mitigation Strategies

The present invention relates to new dosing schedules for anti-CD20/anti-CD3 bispecific antibodies and anti-CD79b antibody drug conjugates, particularly for glofitamab and polatuzumab vedotin, that result in acceptable safety and efficacy profiles, in particular with respect to cytokine release syndrome related side effects.

Bispecific antibody therapeutics involving T-cell activation have been associated with cytokine release syndrome (CRS). CRS is a potentially life-threatening symptom complex caused by the excessive release of cytokines by immune effector or target cells during an exaggerated and sustained immune response. CRS can be triggered by a variety of factors, including infection with virulent pathogens, or by medications that activate or enhance the immune response, resulting in a pronounced and sustained immune response.

Regardless of the inciting agent, severe or life-threatening CRS is a medical emergency. If unsuccessfully managed, it can result in significant disability or fatal outcome. Current clinical management focuses on treating the individual signs and symptoms, providing supportive care, and attempting to dampen down the inflammatory response using high-dose corticosteroids. However, this approach is not always successful, especially in the case of late intervention. Moreover, steroids may negatively impact T-cell function, which may diminish the clinical benefit of immune modulating therapies in the treatment of cancer.

A. CRS Symptoms and Grading

CRS is graded according to the Modified Cytokine Release Syndrome Grading System established by Lee et al., Blood, 124: 188-195, 2014 or Lee et al., Biol Blood Marrow Transplant, 25(4): 625-638, 2019, as described in Table 5. In addition to diagnostic criteria, recommendations on management of CRS based on its severity, including early intervention with corticosteroids and/or anti-cytokine therapy, are provided and referenced in Tables 5 and 6.

TABLE 5

Cytokine release syndrome grading systems

| Grade | Modified Cytokine Release Syndrome Grading System | ASTCT Consensus Grading System |
|---|---|---|
| Grade 1 | Symptoms are not life threatening and require symptomatic treatment only (e.g., fever, nausea, fatigue, headache, myalgia, malaise) | Temperature ≥38° C. No hypotension No hypoxia |
| Grade 2 | Symptoms require and respond to moderate intervention Oxygen requirement <40%; or Hypotension responsive to fluids or low dose$^a$ of one vasopressor; or Grade 2 organ toxicity | Temperature ≥38° C.* with hypotension not requiring vasopressors and/ or$^\dagger$ hypoxia requiring low-flow nasal cannula$^\ddagger$ or blow-by |
| Grade 3 | Symptoms require and respond to aggressive intervention Oxygen requirement ≥40%; or Hypotension requiring high dose$^b$ or multiple vasopressors; or Grade 3 organ toxicity or Grade 4 transaminitis | Temperature ≥38° C.* with hypotension requiring a vasopressor with or without vasopressin and/ or$^\dagger$ hypoxia requiring high-flow nasal cannula$^\ddagger$, facemask, nonrebreather mask, or Venturi mask |
| Grade 4 | Life-threatening symptoms Requirement for ventilation support or Grade 4 organ toxicity (excluding transaminitis) | Temperature ≥38° C.* with hypotension requiring multiple vasopressors (excluding vasopressin) and/or$^\dagger$ hypoxia requiring positive pressure (e.g., CPAP, BiPAP, intubation and mechanical ventilation) |
| Grade 5 | Death | Death |

Lee 2014 criteria: Lee et al., Blood, 124: 188-195, 2014.
ASTCT consensus grading: Lee et al., Biol Blood Marrow Transplant, 25(4): 625-638, 2019.
$^a$Low-dose vasopressor: single vasopressor at doses below that shown in Table 5.
$^b$High-dose vasopressor: as defined in Table 5.
*Fever is defined as temperature ≥38° C. not attributable to any other cause. In patients who have CRS then receive antipyretic or anticytokine therapy such as tocilizumab or steroids, fever is no longer required to grade subsequent CRS severity. In this case, CRS grading is driven by hypotension and/or hypoxia.
$^\dagger$CRS grade is determined by the more severe event: hypotension or hypoxia not attributable to any other cause. For example, a patient with temperature of 39.5° C., hypotension requiring 1 vasopressor, and hypoxia requiring low-flow nasal cannula is classified as grade 3 CRS.
$^\ddagger$Low-flow nasal cannula is defined as oxygen delivered at ≤6 L/minute. Low flow also includes blow-by oxygen delivery, sometimes used in pediatrics. High-flow nasal cannula is defined as oxygen delivered at >6 L/minute.

TABLE 6

High-dose vasopressors
High-Dose Vasopressors (duration ≥3 hours)

| Pressor | Dose |
| --- | --- |
| Norepinephrine monotherapy | ≥20 μg/min |
| Dopamine monotherapy | ≥10 μg/kg/min |
| Phenylephrine monotherapy | ≥200 μg/min |
| Epinephrine monotherapy | ≥10 μg/min |
| If on vasopressin | Vasopressin + norepinephrine equivalent of ≥10 μg/min [a] |
| If on combination or vasopressors (not vasopressin) | Norepinephrine equivalent of ≥20 μg/min [a] | min = minute; VASST = Vasopressin and Septic Shock Trial.
[a] VASST vasopressor equivalent equation: norepinephrine equivalent dose = [norepinephrine (μg/min)] + [dopamine (μg/kg/min) ÷ 2] + [epinephrine (μg/min)] + [phenylephrine (μg/min) ÷ 10].

Mild to moderate presentations of CRS and/or infusion-related reaction (IRR) may include symptoms such as fever, headache, and myalgia, and may be treated symptomatically with analgesics, anti-pyretics, and antihistamines as indicated. Severe or life-threatening presentations of CRS and/or IRR, such as hypotension, tachycardia, dyspnea, or chest discomfort should be treated aggressively with supportive and resuscitative measures as indicated, including the use of high-dose corticosteroids, IV fluids, admission to intensive care unit, and other supportive measures. Severe CRS may be associated with other clinical sequelae such as disseminated intravascular coagulation, capillary leak syndrome, or macrophage activation syndrome (MAS). Standard of care for severe or life threatening CRS resulting from immune-based therapy has not been established; case reports and recommendations using anti-cytokine therapy such as tocilizumab have been published (Teachey et al., *Blood*, 121: 5154-5157, 2013; Lee et al., *Blood*, 124:188-195, 2014; Maude et al., *New Engl J Med*, 371: 1507-1517, 2014).

B. Dosing Regimens for CRS Mitigation

The methods and uses described herein provide acceptable safety profiles for cytokine release syndrome in populations of subjects having a CD20-positive cell proliferative disorder, e.g., a B cell proliferative disorder (e.g., an NHL (e.g., a relapsed and/or refractory NHL, a DLBCL (e.g., a relapsed and/or refractory DLBCL), a FL (e.g., a relapsed and/or refractory FL or a transformed FL), or an MCL (e.g., a relapsed and/or refractory MCL)), or a CNSL) who are administered an anti-CD79b ADC and a anti-CD20/anti-CD3 bispecific antibody.

For example, in some embodiments, the population of subjects exhibits a rate of cytokine release syndrome that is less than or equal to about 60% (e.g., less than or equal to about 55%; e.g., between about 0% to about 60%, between about 10% to about 60%, between about 20% to about 60%, between about 30% to about 60%, between about 40% to about 60%, between about 50% to about 60%, between about 55% to about 60%, between about 50% to about 55%, between about 40% to about 55%, between about 30% to about 55%, between about 20% to about 55%, or between about 10% and about 55%; e.g., about 51%, about 52%, about 53%, about 54%, about 55%, about 56%, about 57%, about 58%, about 59%, or about 60%). In some embodiments, the population of subjects exhibits a rate of cytokine release syndrome that is less than or equal to about 50% (e.g., less than or equal to about 40%, less than or equal to about 30%, less than or equal to about 20%, less than or equal to about 10%, less than or equal to about 5%, or less than or equal to about 1%; e.g., between about 0% to about 50%, between about 5% to about 40%, between about 5% to about 20%, between about 5% to about 10%, between about 20% to about 50%, between about 30% to about 40%, between about 20% to about 40%, between about 15% to about 35%, between about 15% to about 25%, between about 35% to about 50%, or between about 25% to about 50%; e.g., about 50%, about 45%, about 40%, about 35%, about 30%, about 25%, about 20%, about 15%, about 10%, about 5%, about 1%, or about 0%). In particular embodiments, the rate of cytokine release syndrome in a population of subjects is less than or equal to about 55%. In particular embodiments, the rate of cytokine release syndrome in a population of subjects is about 55%.

In some embodiments, the rate of cytokine release syndrome of Grade ≥3 in the population of subjects is less than or equal to about 50% (e.g., less than or equal to about 40%, less than or equal to about 30%, less than or equal to about 20%, less than or equal to about 10%, less than or equal to about 5%, or less than or equal to about 1%; e.g., between about 0% to about 50%, between about 5% to about 40%, between about 5% to about 20%, between about 5% to about 10%, between about 20% to about 50%, between about 30% to about 40%, between about 20% to about 40%, between about 15% to about 35%, between about 15% to about 25%, between about 35% to about 50%, or between about 25% to about 50%; e.g., about 50%, about 45%, about 40%, about 35%, about 30%, about 25%, about 20%, about 15%, about 10%, about 5%, about 1%, or about 0%). In some embodiments, the rate of cytokine release syndrome of Grade ≥3 in the population of subjects is less than or equal to about 20%. In particular embodiments, the rate of cytokine release syndrome of Grade ≥3 in the population of subjects is less than or equal to about 10%. In particular embodiments, the rate of cytokine release syndrome of Grade ≥3 in the population of subjects is less than or equal to about 5%.

In some embodiments, the subjects of the population have R/R DLBCL. In some embodiments, the rate of cytokine release syndrome of Grade ≥3 in the population of subjects having R/R DLBCL is less than or equal to about 50% (e.g., less than or equal to about 40%, less than or equal to about 30%, less than or equal to about 20%, less than or equal to about 10%, less than or equal to about 5%, or less than or equal to about 1%; e.g., between about 0% to about 50%, between about 5% to about 40%, between about 5% to about 20%, between about 5% to about 10%, between about 20% to about 50%, between about 30% to about 40%, between about 20% to about 40%, between about 15% to about 35%, between about 15% to about 25%, between about 35% to about 50%, or between about 25% to about 50%; e.g., about 50%, about 45%, about 40%, about 35%, about 30%, about 25%, about 20%, about 15%, about 10%, about 5%, about 1%, or about 0%). In some embodiments, the rate of cytokine release syndrome of Grade ≥3 in the population of subjects having R/R DLBCL is less than or equal to about 20%. In particular embodiments, the rate of cytokine release syndrome of Grade ≥3 in the population of subjects having R/R DLBCL is less than or equal to about 10%. In particular embodiments, the rate of cytokine release syndrome of Grade ≥3 in the population of subjects having R/R DLBCL is less than or equal to about 5%. In particular embodiments, the rate of cytokine release syndrome of Grade ≥3 in the population of subjects having R/R DLBCL is less than or equal to about 3%. In particular embodiments, the rate of cytokine release syndrome of Grade ≥3 in the population of subjects having R/R DLBCL is less than or equal to about 1%.

C. Pretreatment with an Anti-CD20 Antibody

In one aspect, the subjects foreseen for treatment with the methods provided herein are pretreated with an anti-CD20 antibody. In one embodiment the anti-CD20 antibody is rituximab or obinutuzumab. In a particular embodiment, the anti-CD20 antibody is obinutuzumab (recommended INN, WHO Drug Information, Vol. 26, No. 4, 2012, p. 453). As used herein, obinutuzumab is synonymous for GA101. The tradename is GAZYVA® or GAZYVA®. This replaces all previous versions (e.g., Vol. 25, No. 1, 2011, p. 75-76), and is formerly known as afutuzumab (recommended INN, WHO Drug Information, Vol. 23, No. 2, 2009, p. 176; Vol. 22, No. 2, 2008, p. 124). In one embodiment, the anti-CD20 antibody is tositumomab.

Obinutuzumab is a humanized glyco-engineered type II anti-CD20 mAb that binds with high-affinity to the CD20 antigen, inducing antibody-dependent cellular cytotoxicity (ADCC) and antibody-dependent cellular phagocytosis (ADCP), low complement-dependent cytotoxicity (CDC) activity, and high direct cell death induction. Use of GAZYVA® pre-treatment (Gpt) can aid in the rapid depletion of B cells, both in the peripheral blood and in secondary lymphoid organs, such that the risk of highly relevant adverse events (AEs) from strong systemic T cell activation by T-cell activating therapeutic agents (e.g., CRS) is reduced, while supporting exposure levels of T-cell activating therapeutic agents that are high enough from the start of dosing to mediate tumor cell elimination. To date, the safety profile of obinutuzumab (including cytokine release) has been assessed and managed in hundreds of patients in ongoing obinutuzumab clinical trials. Finally, in addition to supporting the safety profile of T-cell activating therapeutic agents such as anti-CD20/anti-CD3 bispecific antibodies, particularly glofitamab, Gpt could also help prevent the formation of anti-drug antibodies (ADAs) to these unique molecules.

In some embodiments, Gpt or pre-treatment with obinutuzumab comprises administering obinutuzumab or rituximab prior to the administration of the anti-CD20/anti-CD3 bispecific antibody. In some embodiments, administration of obinutuzumab or rituximab occurs at least about 1 day before (e.g., at least 2 days before, at least 3 days before, at least 4 days before, at least 5 days before, at least 6 days before, at least 7 days before, at least 1.5 weeks before, at least 2 weeks before, at least 3 weeks before, or at least 4 weeks before; e.g., between 1 day and 3 days before, between 1 day and 5 days before, between 1 day and 7 days before, between 1 day and 14 days before, 1 day and 21 days before, between 3 days and 7 days before, between 5 days and 10 days before, between 7 days and 14 days before, between 7 days and 21 days before, between 14 days and 21 days before, or between 7 days and 28 days before; e.g., about 1 day before, about 2 days before, about 3 days before, about 4 days before, about 5 days before, about 6 days before, about 7 days before, about 14 days before, about 21 days before, or about 28 days before) the administration of the anti-CD20/anti-CD3 bispecific antibody. In a particular embodiment, obinutuzumab or rituximab is administered about 1 day (±1 day) before administration of the anti-CD20/anti-CD3 bispecific antibody. In another particular embodiment, obinutuzumab or rituximab is administered about 7 days (±1 day) before administration of the anti-CD20/anti-CD3 bispecific antibody. In one embodiment, obinutuzumab is administered as a one time treatment. In one embodiment, obinutuzumab is administered once at a dose of about 1000 mg.

D. Pretreatment or Management of CRS Related Symptoms with Tocilizumab

CRS is associated with high IL-6 levels (Panelli et al., *J Transl Med*, 2: 17, 2004; Lee et al., *Blood*, 124:188-195, 2014; Doessegger and Banholzer, *Clin Transl Immunology*, 4: e39, 2015), and IL-6 correlates with the severity of CRS, with patients who experience severe or life-threatening CRS (NCI CTCAE Grade 4 or 5) having much higher IL-6 levels compared with their counterparts who do not experience CRS or experience milder CRS reactions (NCI CTCAE Grade 0-3) (Chen et al., *J Immunol Methods*, 434:1-8, 2016).

Tocilizumab (ACTEMRA®/ROACTEMRA®) is a recombinant, humanized, anti-human monoclonal antibody directed against soluble and membrane-bound IL-6R, which inhibits IL-6 mediated signaling (see, e.g., WO 1992/019579, which is incorporated herein by reference in its entirety). Tocilizumab has been approved by the U.S. Food and Drug Administration for the treatment of severe or life-threatening CAR-T cell-induced CRS in adults and in pediatric patients 2 years of age and older. Initial clinical data (Locke et al., *Blood*, 130: 1547, 2017) suggests that tocilizumab prophylaxis may reduce the severity of CAR-T cell-induced CRS by blocking IL-6 receptors from signaling prior to cytokine release. Consequently, tocilizumab premedication may also reduce the frequency or lower the severity of CRS associated with bispecific antibody therapy. Other anti-IL-6R antibodies that could be used in combination with tocilizumab include sarilumab, vobarilizumab (ALX-0061), SA-237, and variants thereof.

In some aspects, an effective amount of tocilizumab is administered as a premedication, e.g., is administered to the subject prior to the administration of the anti-CD20/anti-CD3 bispecific antibody. Administration of tocilizumab as a premedication may reduce the frequency or severity of CRS. In some aspects, tocilizumab is administered as a premedication in Cycle 1, e.g., is administered prior to a first dose (C1D1), a second dose (C1D2), and/or a third dose (C1D3) of the anti-CD20/anti-CD3 bispecific antibody. In some aspects, tocilizumab is administered intravenously to the subject as a single dose of about 1 mg/kg to about 15 mg/kg, e.g., about 4 mg/kg to about 10 mg/kg, e.g., about 6 mg/kg to about 10 mg/kg, e.g., about 8 mg/kg. In some aspects, tocilizumab is administered intravenously to the subject as a single dose of about 8 mg/kg. Other anti-IL-6R antibodies that could be used in combination with tocilizumab include sarilumab, vobarilizumab (ALX-0061), SA-237, and variants thereof.

For example, in one aspect, the anti-CD20/anti-CD3 bispecific antibody is co-administered with tocilizumab (ACTEMRA®/ROACTEMRA®), wherein the subject is first administered with tocilizumab (ACTEMRA®/ROACTEMRA®) and then separately administered with the anti-CD20/anti-CD3 bispecific antibody (e.g., the subject is pre-treated with tocilizumab (ACTEMRA®/ROACTEMRA®)).

In another aspect, tocilizumab is administered to treat or alleviate symptoms associated with CRS in subjects treated with an anti-CD20/anti-CD3 bispecific antibody. If the subject has a grade 2 or higher CRS event in the presence of extensive comorbidities following administration of the anti-CD20/anti-CD3 bispecific antibody, the method may further include administering to the subject a first dose of an IL-6R antagonist (e.g., an anti-IL-6R antibody, e.g., tocilizumab (ACTEMRA®/ROACTEMRA®)) to manage the grade 2 or higher CRS event while suspending treatment with the anti-CD20/anti-CD3 bispecific antibody.

In some instances, the first dose of tocilizumab is administered intravenously to the subject at a dose of about 8 mg/kg. Other anti-IL-6R antibodies that could be used in combination with tocilizumab include sarilumab, vobarilizumab (ALX-0061), SA-237, and variants thereof. In some instances, if the grade 2 or higher CRS event resolves to a grade ≤1 CRS event within two weeks, the method further includes resuming treatment with the anti-CD20/anti-CD3 bispecific antibody at a reduced dose. In some instances, the reduced dose is 50% of the initial infusion rate of the previous cycle if the event occurred during or within 24 hours of the infusion. If, on the other hand, the grade 2 or higher CRS event does not resolve or worsens to a grade ≥3 CRS event within 24 hours of treating the symptoms of the grade 2 or higher CRS event, the method may further include administering to the subject one or more (e.g., one, two, three, four, or five or more) additional doses of an IL-6R antagonist (e.g., an anti-IL-6R antibody, e.g., tocilizumab) to manage the grade 2 or grade ≥3 CRS event. In some particular instances, the grade 2 or higher CRS event does not resolve or worsens to a grade ≤3 CRS event within 24 hours of treating the symptoms of the grade 2 or higher CRS event, and the method may further include administering to the subject one or more additional doses of tocilizumab to manage the grade 2 or grade ≥3 CRS event. In some instances, the one or more additional doses of tocilizumab is administered intravenously to the subject at a dose of about 1 mg/kg to about 15 mg/kg, e.g., about 4 mg/kg to about 10 mg/kg, e.g., about 6 mg/kg to about 10 mg/kg, e.g., about 8 mg/kg.

E. Other Pretreatments for CRS Risk Mitigation

In one embodiment, the treatment regimen provided herein further comprise administration of premedication prior to the administration of the anti-CD20/anti-CD3 bispecific antibody and/or the anti-CD79b antibody drug conjugate. In one embodiment the premedication comprises a corticosteroid (such as, e.g., prednisolone, dexamethasone, or methylprednisolone), paracetamol/acetaminophen, and/or an anti-histamine (such as, e.g., diphenhydramine). In one embodiment, the premedication is administered at least 60 minutes prior to the administration of the anti-CD20/anti-CD3 bispecific antibody. In one embodiment, the treatment regimen further comprise administration of premedication prior to the administration of glofitamab. In embodiment the premedication comprises a corticosteroid (such as, e.g., prednisolone, dexamethasone, or methylprednisolone), an anti-pyretic (such as, e.g., paracetamol/acetaminophen), and/or an anti-histamine (such as, e.g., diphenhydramine). In one embodiment, the subject receives corticosteroid premedication prior to the anti-CD20/anti-CD3 bispecific antibody. It has been shown that premedication using dexamethasone reduced glofitamab-induced cytokine levels in mice pretreated with dexamethasone relative to methylprednisolone. Therefore, in one embodiment, the corticosteroid is dexamethasone. In one embodiment, the premedication is administered at least 60 minutes prior to the administration of glofitamab. In one embodiment, the premedication is administered at least 60 minutes prior to each administration of glofitamab. In another embodiment, pre-medication with corticosteroids is administered before the first dose (C1D1) and second dose (C1D2) of the first dosing cycle, before the first dose of the second (C2D1) and third (C3D1) cycle and may be optional for subsequent dosing cycles where the target dose has been reached and tolerated for two doses for patients with no CRS in previous cycles.

In one embodiment, the premedication is administered at least 60 minutes prior to the administration of the pretreatment with the anti-CD20 antibody, particularly obinutuzumab.

In one embodiment, corticosteroids are administered to manage any relevant adverse events arising after administration of the anti-CD20/anti-CD3 bispecific antibody, e.g., glofitamab.

VI. Administration of Anti-CD20/Anti-CD3 Bispecific Antibodies and Anti-CD79b Antibody Drug Conjugates The methods may involve administering the anti-CD20/anti-CD3 bispecific antibody and anti-CD79b ADC (and/or any additional therapeutic agent) by any suitable means, including parenteral, intrapulmonary, and intranasal, and, if desired for local treatment, intralesional administration. Parenteral infusions include intravenous, subcutaneous, intramuscular, intraarterial, and intraperitoneal administration routes. In some embodiments, the anti-CD20/anti-CD3 bispecific antibody and anti-CD79b ADC are administered by intravenous infusion.

In one embodiment the infusion time for the anti-CD20/anti-CD3 bispecific antibody, particularly glofitamab, is at least 4 hours (e.g., about 4 hours, about 4.5 hours, about 5 hours, about 5.5 hours, or about 6 hours). In a particular embodiment, the infusion duration for glofitamab is about 4 hours. In one embodiment the infusion time for the anti-CD20/anti-CD3 bispecific antibody may be reduced or extended. In one embodiment (for example, in the absence of infusion-related adverse events), the infusion time of glofitamab in subsequent dosing cycles is reduced to 2 hours±15 minutes. In one embodiment the infusion time is increased to up to 8 hours (e.g., about 4 hours, about 5 hours, about 6 hours, about 7 hours, or about 8 hours) (for example, for subjects with high risk of experiencing CRS). In one embodiment, for example, for patients who may be at an increased risk of CRS, patients who experience IRRs or CRS with their previous dose of glofitamab or who are at increased risk of recurrent IRR/CRS with subsequent doses, the time of infusion of glofitamab is extended to up to 8 hours.

In one embodiment, when both the anti-CD20/anti-CD3 bispecific antibody, particularly glofitamab, and the anti-CD79b antibody drug conjugate, particularly polatuzumab vedotin, are administered on the same day, the anti-CD20/anti-CD3 bispecific antibody is administered at least 90 minutes after completion of the administration of the anti-CD79b antibody drug conjugate, provided that patients have recovered from any acute toxicity mediated by the preceding administration. In some embodiments, if prior polatuzumab vedotin infusion has been well tolerated, the time interval between the end of infusion of polatuzumab vedotin and the start of glofitamab infusion can be reduced but should be at least 1 hour. In one embodiment, in case of acute toxicity preventing from dosing both agents on the same day, the administration of glofitamab may be delayed up to a maximum of 36 hours (e.g., about 1 hour, about 2 hours, about 4 hours, about 6 hours, about 8 hours, about 10 hours, about 12 hours, about 16 hours, about 20 hours, about 24 hours, about 28 hours, about 32 hours, or about 36 hours), starting from end of polatuzumab vedotin infusion. In one embodiment, the anti-CD79b antibody drug conjugate (e.g., polatuzumab vedotin), is administered over 90±10 minutes. In some embodiments, infusion of polatuzumab vedotin may be slowed or interrupted for infusion-related adverse events.

In one embodiment, in the absence of infusion-related adverse events, the infusion time for Cycle 2 and onward can be shortened to 30±10 minutes.

In one embodiment the pretreatment of the anti-CD20 antibody is given with an infusion time of at least 4.75 hours (e.g., about 4.75 hours, about 5 hours, about 5.5 hours, about 6 hours, about 6.5 hours, about 7 hours, about 7.5 hours, about 8 hours).

For all the methods described herein, the anti-CD20/anti-CD3 bispecific antibody and anti-CD79b ADC would be formulated, dosed, and administered in a fashion consistent with good medical practice. Factors for consideration in this context include the particular disorder being treated, the particular mammal being treated, the clinical condition of the individual subject, the cause of the disorder, the site of delivery of the agent, the method of administration, the scheduling of administration, and other factors known to medical practitioners. The anti-CD20/anti-CD3 bispecific antibody and anti-CD79b ADC need not be, but is optionally formulated with, one or more agents currently used to prevent or treat the disorder in question. The effective amount of such other agents depends on the amount of the anti-CD20/anti-CD3 bispecific antibody and anti-CD79b ADC present in the formulation, the type of disorder or treatment, and other factors discussed above. The anti-CD20/anti-CD3 bispecific antibody and anti-CD79b ADC may be suitably administered to the subject over a series of treatments.

A further aspect of the present invention relates to the invention as described hereinbefore.

EMBODIMENTS

Some embodiments of the technology described herein can be defined according to any of the following numbered embodiments:

1. A method of treating a subject having a CD20-positive cell proliferative disorder comprising administering to the subject an anti-CD79b antibody drug conjugate and an anti-CD20/anti-CD3 bispecific antibody in a dosing regimen comprising at least a first dosing cycle and a second dosing cycle, wherein:
    (a) the first dosing cycle comprises a first dose (C1D1) of the anti-CD20/anti-CD3 bispecific antibody and a second dose (C1D2) of the anti-CD20/anti-CD3 bispecific antibody, wherein the C1D1 of the anti-CD20/anti-CD3 bispecific antibody is about 2.5 mg, and the C1D2 of the anti-CD20/anti-CD3 bispecific antibody is about 10 mg; and
    (b) the second dosing cycle comprises a single dose (C2D1) of the anti-CD20/anti-CD3 bispecific antibody, wherein the C2D1 of the anti-CD20/anti-CD3 bispecific antibody is about 10 mg, about 16 mg, or about 30 mg.

2. An anti-CD79b antibody drug conjugate and an anti-CD20/anti-CD3 bispecific antibody for use in a method of treating a subject having a CD20-positive cell proliferative disorder, wherein the anti-CD79b antibody drug conjugate and the anti-CD20/anti-CD3 bispecific antibody are administered in a dosing regimen comprising at least a first dosing cycle and a second dosing cycle, wherein:
    (a) the first dosing cycle comprises a first dose (C1D1) of the anti-CD20/anti-CD3 bispecific antibody and a second dose (C1D2) of the anti-CD20/anti-CD3 bispecific antibody, wherein the C1D1 of the anti-CD20/anti-CD3 bispecific antibody is about 2.5 mg, and the C1D2 of the anti-CD20/anti-CD3 bispecific antibody is about 10 mg; and
    (b) the second dosing cycle comprises a single dose (C2D1) of the anti-CD20/anti-CD3 bispecific antibody, wherein the C2D1 of the anti-CD20/anti-CD3 bispecific antibody is about 10 mg, about 16 mg, or about 30 mg.

3. Use of an anti-CD79b antibody drug conjugate and an anti-CD20/anti-CD3 bispecific antibody in treating a subject having a CD20-positive cell proliferative disorder, wherein the anti-CD79b antibody drug conjugate and the anti-CD20/anti-CD3 bispecific antibody are administered in a dosing regimen comprising at least a first dosing cycle and a second dosing cycle, wherein:
    (a) the first dosing cycle comprises a first dose (C1D1) of the anti-CD20/anti-CD3 bispecific antibody and a second dose (C1D2) of the anti-CD20/anti-CD3 bispecific antibody, wherein the C1D1 of the anti-CD20/anti-CD3 bispecific antibody is about 2.5 mg, and the C1D2 of the anti-CD20/anti-CD3 bispecific antibody is about 10 mg; and
    (b) the second dosing cycle comprises a single dose (C2D1) of the anti-CD20/anti-CD3 bispecific antibody, wherein the C2D1 of the anti-CD20/anti-CD3 bispecific antibody is about 10 mg, about 16 mg, or about 30 mg.

4. Use of an anti-CD79b antibody drug conjugate and an anti-CD20/anti-CD3 bispecific antibody in the manufacture of a medicament for treating a subject having a CD20-positive cell proliferative disorder, wherein the anti-CD79b antibody drug conjugate and the anti-CD20/anti-CD3 bispecific antibody are administered in a dosing regimen comprising at least a first dosing cycle and a second dosing cycle, wherein:
    (a) the first dosing cycle comprises a first dose (C1D1) of the anti-CD20/anti-CD3 bispecific antibody and a second dose (C1D2) of the anti-CD20/anti-CD3 bispecific antibody, wherein the C1D1 of the anti-CD20/anti-CD3 bispecific antibody is about 2.5 mg, and the C1D2 of the anti-CD20/anti-CD3 bispecific antibody is about 10 mg; and
    (b) the second dosing cycle comprises a single dose (C2D1) of the anti-CD20/anti-CD3 bispecific antibody, wherein the C2D1 of the anti-CD20/anti-CD3 bispecific antibody is about 10 mg, about 16 mg, or about 30 mg.

5. The method, anti-CD79b antibody drug conjugate and bispecific antibody for use, or use of any one of embodiments 1-4, wherein the C2D1 of the anti-CD20/anti-CD3 bispecific antibody is about 10 mg.

6. The method, anti-CD79b antibody drug conjugate and bispecific antibody for use, or use of any one of embodiments 1-4, wherein the C2D1 of the anti-CD20/anti-CD3 bispecific antibody is about 16 mg.

7. The method, anti-CD79b antibody drug conjugate and bispecific antibody for use, or use of any one of embodiments 1-4, wherein the C2D1 of the anti-CD20/anti-CD3 bispecific antibody is about 30 mg.

8. The method, anti-CD79b antibody drug conjugate and bispecific antibody for use, or use of any one of embodiments 1-7, wherein the first dosing cycle comprises a single dose C1D1 of the anti-CD79b antibody drug conjugate.

9. The method, anti-CD79b antibody drug conjugate and bispecific antibody for use, or use of embodiment 8, wherein the single dose C1D1 of the anti-CD79b antibody drug conjugate is from about 0.1 mg/kg to about 2.4 mg/kg.

10. The method, anti-CD79b antibody drug conjugate and bispecific antibody for use, or use of embodiment 9, wherein the single dose C1D1 of the anti-CD79b antibody drug conjugate is about 1.8 mg/kg.

11. The method, anti-CD79b antibody drug conjugate and bispecific antibody for use, or use of any one of embodiments 8-10, wherein the C1D1 of the anti-CD79b antibody drug conjugate is administered or is to be administered on or about Day 2 of the dosing cycles.

12. The method, anti-CD79b antibody drug conjugate and bispecific antibody for use, or use of any one of embodiments 1-11, wherein the second dosing cycle comprises a single dose C2D1 of the anti-CD79b antibody drug conjugate.

13. The method, anti-CD79b antibody drug conjugate and bispecific antibody for use, or use of embodiment 12, wherein the single dose C2D1 of the anti-CD79b antibody drug conjugate is from about 0.1 mg/kg to about 2.4 mg/kg.

14. The method, anti-CD79b antibody drug conjugate and bispecific antibody for use, or use of embodiment 13, wherein the single dose C2D1 of the anti-CD79b antibody drug conjugate is about 1.8 mg/kg.

15. The method, anti-CD79b antibody drug conjugate and bispecific antibody for use, or use of any one of embodiments 1-14, wherein the C1D1 of the anti-CD20/anti-CD3 bispecific antibody and the C1D2 of the anti-CD20/anti-CD3 bispecific antibody are administered or are to be administered to the subject on or about Days 8 and 15, respectively, of the first dosing cycle.

16. The method, anti-CD79b antibody drug conjugate and bispecific antibody for use, or use of any one of embodiments 1-15, wherein the C2D1 of the anti-CD20/anti-CD3 bispecific antibody is administered or is to be administered to the subject on or about Day 1 of the second dosing cycle.

17. The method, anti-CD79b antibody drug conjugate and bispecific antibody for use, or use of any one of embodiments 1-16, wherein the C2D1 of the anti-CD20/anti-CD3 bispecific antibody is administered or is to be administered after the administration of the C2D1 of the anti-CD79b antibody drug conjugate has completed.

18. The method, anti-CD79b antibody drug conjugate and bispecific antibody for use, or use of embodiment 17, wherein the C2D1 of the anti-CD20/anti-CD3 bispecific antibody is administered or is to be administered between about 60-120 minutes after the administration of the C2D1 of the anti-CD79b antibody drug conjugate has completed.

19. The method, anti-CD79b antibody drug conjugate and bispecific antibody for use, or use of embodiment 18, wherein the C2D1 of the anti-CD20/anti-CD3 bispecific antibody is administered or is to be administered about 90 minutes after the administration of the C2D1 of the anti-CD79b antibody drug conjugate has completed.

20. The method, anti-CD79b antibody drug conjugate and bispecific antibody for use, or use of any one of embodiments 1-19, wherein the C1D1 of the anti-CD79b antibody drug conjugate is administered or is to be administered to the subject on or about Day 2 of the first dosing cycle and the C2D1 of the anti-CD79b antibody drug conjugate is administered or is to be administered to the subject on or about Day 1 of the second dosing cycle.

21. The method, anti-CD79b antibody drug conjugate and bispecific antibody for use, or use of any one of embodiments 1-20, wherein the first and second dosing cycles are 14-day dosing cycles.

22. The method, anti-CD79b antibody drug conjugate and bispecific antibody for use, or use of any one of embodiments 1-20, wherein the first and second dosing cycles are 21-day dosing cycles.

23. The method, anti-CD79b antibody drug conjugate and bispecific antibody for use, or use of any one of embodiments 1-22, wherein the dosing regimen comprises one or more additional dosing cycles.

24. The method, anti-CD79b antibody drug conjugate and bispecific antibody for use, or use of embodiment 23, wherein the dosing regimen comprises six to ten additional dosing cycles.

25. The method, anti-CD79b antibody drug conjugate and bispecific antibody for use, or use of embodiment 24, wherein the dosing regimen comprises ten additional dosing cycles.

26. The method, anti-CD79b antibody drug conjugate and bispecific antibody for use, or use of any one of embodiments 23-25, wherein the additional dosing cycles are 14-day dosing cycles.

27. The method, anti-CD79b antibody drug conjugate and bispecific antibody for use, or use of any one of embodiments 23-25, wherein the additional dosing cycles are 21-day dosing cycles.

28. The method, anti-CD79b antibody drug conjugate and bispecific antibody for use, or use of any one of embodiments 23-27, wherein one or more of the additional dosing cycles comprise an additional single dose of the anti-CD20/anti-CD3 bispecific antibody and an additional single dose of the anti-CD79b antibody drug conjugate.

29. The method, anti-CD79b antibody drug conjugate and bispecific antibody for use, or use of embodiment 28, wherein the additional single dose of the anti-CD79b antibody drug conjugate is about equivalent in amount to the C2D1 of the anti-CD79b antibody drug conjugate.

30. The method, anti-CD79b antibody drug conjugate and bispecific antibody for use, or use of embodiment 29, wherein the additional single dose of the anti-CD79b antibody drug conjugate is about 1.8 mg/kg.

31. The method, anti-CD79b antibody drug conjugate and bispecific antibody for use, or use of any one of embodiments 28-30, wherein the additional single dose of the anti-CD79b antibody drug conjugate is administered or is to be administered to the subject on or about Day 1 of each additional dosing cycle comprising an additional dose of the anti-CD79b antibody drug conjugate.

32. The method, anti-CD79b antibody drug conjugate and bispecific antibody for use, or use of any one of embodiments 28-31, wherein the additional single dose of the anti-CD20/anti-CD3 bispecific antibody of each additional dosing cycle comprising an additional dose of the anti-CD79b antibody drug conjugate is administered or is to be administered after the administration of the additional single dose of the anti-CD79b antibody drug conjugate has completed.

33. The method, anti-CD79b antibody drug conjugate and bispecific antibody for use, or use of embodiment 32, wherein the additional single dose of the anti-CD20/anti-CD3 bispecific antibody of each additional dosing cycle comprising an additional dose of the anti-CD79b antibody drug conjugate is administered or is to be administered between about 60-120 minutes after the administration of the additional single dose of the anti-CD79b antibody drug conjugate has completed.

34. The method, anti-CD79b antibody drug conjugate and bispecific antibody for use, or use of embodiment 33, wherein the additional single dose of the anti-CD20/anti- CD3 bispecific antibody of each additional dosing cycle comprising an additional dose of the anti-CD79b antibody drug conjugate is administered or is to be administered about 90 minutes after the administration of the additional single dose of the anti-CD79b antibody drug conjugate has completed.

35. The method, anti-CD79b antibody drug conjugate and bispecific antibody for use, or use of any one of embodiments 28-34, wherein the dosing regimen comprises at least four additional dosing cycles comprising an additional single dose of the anti-CD79b antibody drug conjugate.

36. The method, anti-CD79b antibody drug conjugate and bispecific antibody for use, or use of embodiment 35, wherein the dosing regimen comprises between four to ten additional dosing cycles comprising an additional single dose of the anti-CD79b antibody drug conjugate.

37. The method, anti-CD79b antibody drug conjugate and bispecific antibody for use, or use of any one of embodiments 23-27, wherein one or more of the additional dosing cycles comprise an additional single dose of the anti-CD20/anti-CD3 bispecific antibody and do not comprise administration of the anti-CD79b antibody drug conjugate.

38. The method, anti-CD79b antibody drug conjugate and bispecific antibody for use, or use of embodiment 37, wherein the dosing regimen comprises at least two additional dosing cycles comprising an additional single dose of the anti-CD20/anti-CD3 bispecific antibody and not comprising administration of the anti-CD79b antibody drug conjugate.

39. The method, anti-CD79b antibody drug conjugate and bispecific antibody for use, or use of embodiment 39, wherein the dosing regimen comprises between two and ten additional dosing cycles comprising an additional single dose of the anti-CD20/anti-CD3 bispecific antibody and not comprising administration of the anti-CD79b antibody drug conjugate.

40. The method, anti-CD79b antibody drug conjugate and bispecific antibody for use, or use of any one of embodiments 28-39, wherein the additional single dose of the anti-CD20/anti-CD3 bispecific antibody is about equivalent in amount to the C2D1 of the anti-CD20/anti-CD3 bispecific antibody.

41. The method, anti-CD79b antibody drug conjugate and bispecific antibody for use, or use of embodiment 40, wherein the additional single dose of the anti-CD20/anti-CD3 bispecific antibody is about 30 mg.

42. The method, anti-CD79b antibody drug conjugate and bispecific antibody for use, or use of any one of embodiments 28-41, wherein the additional single dose of the anti-CD20/anti-CD3 bispecific antibody is administered or is to be administered to the subject on or about Day 1 of each additional dosing cycle comprising an additional dose of the anti-CD20/anti-CD3 bispecific antibody.

43. The method, anti-CD79b antibody drug conjugate and bispecific antibody for use, or use of any one of embodiments 23-36 and 40-42, wherein the dosing regimen comprises six or more additional dosing cycles, wherein each of the six or more additional dosing cycles comprises a single dose of the anti-CD20/anti-CD3 bispecific antibody, and wherein no more than four of the six or more additional dosing cycles comprise administration of the anti-CD79b antibody drug conjugate.

44. The method, anti-CD79b antibody drug conjugate and bispecific antibody for use, or use of embodiment 43, wherein the dosing regimen comprises six additional dosing cycles, wherein each of the six or more additional dosing cycles comprises a single dose of the anti-CD20/anti-CD3 bispecific antibody, and wherein no more than four of the six additional dosing cycles comprise administration of the anti-CD79b antibody drug conjugate.

45. A method of treating a subject having a CD20-positive cell proliferative disorder comprising administering to the subject an anti-CD79b antibody drug conjugate and an anti-CD20/anti-CD3 bispecific antibody in a dosing regimen comprising at least a first dosing cycle and a second dosing cycle, wherein:
(a) the first dosing cycle comprises:
(i) a single dose (C1D1) of the anti-CD79b antibody drug conjugate; and
(ii) a first dose (C1D1) of the anti-CD20/anti-CD3 bispecific antibody and a second dose (C1D2) of the anti-CD20/anti-CD3 bispecific antibody, wherein the C1D1 and the C1D2 of the anti-CD20/anti-CD3 bispecific antibody are each administered to the subject after the C1D1 of the anti-CD79b antibody drug conjugate, wherein the C1D1 of the anti-CD20/anti-CD3 bispecific antibody is about 2.5 mg, and the C1D2 of the anti-CD20/anti-CD3 bispecific antibody is about 10 mg; and
(b) the second dosing cycle comprises:
(i) a single dose (C2D1) of the anti-CD79b antibody drug conjugate; and
(ii) a single dose (C2D1) of the anti-CD20/anti-CD3 bispecific antibody, wherein the C2D1 of the anti-CD20/anti-CD3 bispecific antibody is about 10 mg, about 16 mg, or about 30 mg.

46. An anti-CD79b antibody drug conjugate and an anti-CD20/anti-CD3 bispecific antibody for use in a method of treating a subject having a CD20-positive cell proliferative disorder comprising, wherein the anti-CD79b antibody drug conjugate and the anti-CD20/anti-CD3 bispecific antibody are administered to the subject in a dosing regimen comprising at least a first dosing cycle and a second dosing cycle, wherein:
(a) the first dosing cycle comprises:
(i) a single dose (C1D1) of the anti-CD79b antibody drug conjugate; and
(ii) a first dose (C1D1) of the anti-CD20/anti-CD3 bispecific antibody and a second dose (C1D2) of the anti-CD20/anti-CD3 bispecific antibody, wherein the C1D1 and the C1D2 of the anti-CD20/anti-CD3 bispecific antibody are each to be administered to the subject after the C1D1 of the anti-CD79b antibody drug conjugate, wherein the C1D1 of the anti-CD20/anti-CD3 bispecific antibody is about 2.5 mg, and the C1D2 of the anti-CD20/anti-CD3 bispecific antibody is about 10 mg; and
(b) the second dosing cycle comprises:
(i) a single dose (C2D1) of the anti-CD79b antibody drug conjugate; and
(ii) a single dose (C2D1) of the anti-CD20/anti-CD3 bispecific antibody, wherein the C2D1 of the anti-CD20/anti-CD3 bispecific antibody is about 10 mg, about 16 mg, or about 30 mg.

47. Use of an anti-CD79b antibody drug conjugate and an anti-CD20/anti-CD3 bispecific antibody for treating a subject having a CD20-positive cell proliferative disorder, wherein the anti-CD79b antibody drug conjugate and the anti-CD20/anti-CD3 bispecific antibody are administered to the subject in a dosing regimen comprising at least a first dosing cycle and a second dosing cycle, wherein:
(a) the first dosing cycle comprises:
(i) a single dose (C1D1) of the anti-CD79b antibody drug conjugate; and (ii) a first dose (C1D1) of the anti-CD20/anti-CD3 bispecific antibody and a second dose (C1D2) of the anti-CD20/anti-CD3 bispecific antibody, wherein the C1D1 and the C1D2 of the anti-CD20/anti-CD3 bispecific antibody are each to be administered to the subject after the C1D1 of the anti-CD79b antibody drug conjugate, wherein the C1D1 of the anti-CD20/anti-CD3 bispecific antibody is about 2.5 mg, and the C1D2 of the anti-CD20/anti-CD3 bispecific antibody is about 10 mg; and (b) the second dosing cycle comprises:
 (i) a single dose (C2D1) of the anti-CD79b antibody drug conjugate; and
 (ii) a single dose (C2D1) of the anti-CD20/anti-CD3 bispecific antibody, wherein the C2D1 of the anti-CD20/anti-CD3 bispecific antibody is about 10 mg, about 16 mg, or about 30 mg.

48. Use of an anti-CD79b antibody drug conjugate and an anti-CD20/anti-CD3 bispecific antibody in the manufacture of a medicament for treating a subject having a CD20-positive cell proliferative disorder, wherein the anti-CD79b antibody drug conjugate and the anti-CD20/anti-CD3 bispecific antibody are administered to the subject in a dosing regimen comprising at least a first dosing cycle and a second dosing cycle, wherein:

(a) the first dosing cycle comprises:
 (i) a single dose (C1D1) of the anti-CD79b antibody drug conjugate; and
 (ii) a first dose (C1D1) of the anti-CD20/anti-CD3 bispecific antibody and a second dose (C1D2) of the anti-CD20/anti-CD3 bispecific antibody, wherein the C1D1 and the C1D2 of the anti-CD20/anti-CD3 bispecific antibody are each to be administered to the subject after the C1D1 of the anti-CD79b antibody drug conjugate, wherein the C1D1 of the anti-CD20/anti-CD3 bispecific antibody is about 2.5 mg, and the C1D2 of the anti-CD20/anti-CD3 bispecific antibody is about 10 mg; and (b) the second dosing cycle comprises:
 (i) a single dose (C2D1) of the anti-CD79b antibody drug conjugate; and
 (ii) a single dose (C2D1) of the anti-CD20/anti-CD3 bispecific antibody, wherein the C2D1 of the anti-CD20/anti-CD3 bispecific antibody is about 10 mg, about 16 mg, or about 30 mg.

49. The method, anti-CD79b antibody drug conjugate and bispecific antibody for use, or use of any one of embodiments 45-48, wherein the single dose C1D1 of the anti-CD79b antibody drug conjugate is from about 0.1 mg/kg to about 2.4 mg/kg and the single dose C2D1 of the anti-CD79b antibody drug conjugate is from about 0.1 mg/kg to about 2.4 mg/kg.

50. The method, anti-CD79b antibody drug conjugate and bispecific antibody for use, or use of embodiment 49, wherein the single dose C1D1 of the anti-CD79b antibody drug conjugate is about 1.8 mg/kg and the single dose C2D1 of the anti-CD79b antibody drug conjugate is about 1.8 mg/kg.

51. The method, anti-CD79b antibody drug conjugate and bispecific antibody for use, or use of any one of embodiments 45-50, wherein the C1D1 of the anti-CD20/anti-CD3 bispecific antibody and the C1D2 of the anti-CD20/anti-CD3 bispecific antibody are administered or are to be administered to the subject on or about Days 8 and 15, respectively, of the first dosing cycle.

52. The method, anti-CD79b antibody drug conjugate and bispecific antibody for use, or use of any one of embodiments 45-51, wherein the C2D1 of the anti-CD20/anti-CD3 bispecific antibody is administered or is to be administered to the subject on or about Day 1 of the second dosing cycle.

53. The method, anti-CD79b antibody drug conjugate and bispecific antibody for use, or use of any one of embodiments 45-52, wherein the C1D1 of the anti-CD79b antibody drug conjugate is administered or is to be administered to the subject on or about Day 2 of the first dosing cycle and the C2D1 of the anti-CD79b antibody drug conjugate is administered or is to be administered to the subject on or about Day 1 of the second dosing cycle.

54. The method, anti-CD79b antibody drug conjugate and bispecific antibody for use, or use of any one of embodiments 45-50, wherein the first and second dosing cycles are 14-day dosing cycles.

55. The method, anti-CD79b antibody drug conjugate and bispecific antibody for use, or use of any one of embodiments 45-53, wherein the first and second dosing cycles are 21-day dosing cycles.

56. The method, anti-CD79b antibody drug conjugate and bispecific antibody for use, or use of any one of embodiments 45-55, wherein the dosing regimen comprises one or more additional dosing cycles.

57. The method, anti-CD79b antibody drug conjugate and bispecific antibody for use, or use of embodiment 56, wherein the dosing regimen comprises six to ten additional dosing cycles.

58. The method, anti-CD79b antibody drug conjugate and bispecific antibody for use, or use of embodiment 57, wherein the dosing regimen comprises ten additional dosing cycles.

59. The method, anti-CD79b antibody drug conjugate and bispecific antibody for use, or use of any one of embodiments 56-58, wherein the additional dosing cycles are 21-day dosing cycles.

60. The method, anti-CD79b antibody drug conjugate and bispecific antibody for use, or use of any one of embodiments 45-50, wherein the dosing regimen comprises one or more additional dosing cycles.

61. The method, anti-CD79b antibody drug conjugate and bispecific antibody for use, or use of embodiment 60, wherein the dosing regimen comprises six to ten additional dosing cycles.

62. The method, anti-CD79b antibody drug conjugate and bispecific antibody for use, or use of embodiment 61, wherein the dosing regimen comprises ten additional dosing cycles.

63. The method, anti-CD79b antibody drug conjugate and bispecific antibody for use, or use of any one of embodiments 60-62, wherein the additional dosing cycles are 14-day dosing cycles.

64. The method, anti-CD79b antibody drug conjugate and bispecific antibody for use, or use of any one of embodiments 56-63, wherein one or more of the additional dosing cycles comprise an additional single dose of the anti-CD20/anti-CD3 bispecific antibody and an additional single dose of the anti-CD79b antibody drug conjugate.

65. The method, anti-CD79b antibody drug conjugate and bispecific antibody for use, or use of embodiment 64, wherein the additional single dose of the anti-CD79b antibody drug conjugate is about equivalent in amount to the C2D1 of the anti-CD79b antibody drug conjugate.

66. The method, anti-CD79b antibody drug conjugate and bispecific antibody for use, or use of embodiment 64 or 65, wherein the additional single dose of the anti-CD79b antibody drug conjugate is administered or is to be administered to the subject on or about Day 1 of each additional dosing cycle comprising an additional dose of the anti-CD79b antibody drug conjugate.

67. The method, anti-CD79b antibody drug conjugate and bispecific antibody for use, or use of any one of embodiments 64-66, wherein the additional single dose of the anti-CD20/anti-CD3 bispecific antibody of each additional dosing cycle comprising an additional dose of the anti-CD79b antibody drug conjugate is administered or is to be administered after the administration of the additional single dose of the anti-CD79b antibody drug conjugate has completed.

68. The method, anti-CD79b antibody drug conjugate and bispecific antibody for use, or use of embodiment 67, wherein the additional single dose of the anti-CD20/anti-CD3 bispecific antibody of each additional dosing cycle comprising an additional dose of the anti-CD79b antibody drug conjugate is administered or is to be administered between about 60-120 minutes after the administration of the additional single dose of the anti-CD79b antibody drug conjugate has completed.

69. The method, anti-CD79b antibody drug conjugate and bispecific antibody for use, or use of embodiment 68, wherein the additional single dose of the anti-CD20/anti-CD3 bispecific antibody of each additional dosing cycle comprising an additional dose of the anti-CD79b antibody drug conjugate is administered or is to be administered about 90 minutes after the administration of the additional single dose of the anti-CD79b antibody drug conjugate has completed.

70. The method, anti-CD79b antibody drug conjugate and bispecific antibody for use, or use of any one of embodiments 64-69, wherein the dosing regimen comprises at least four additional dosing cycles comprising an additional single dose of the anti-CD20/anti-CD3 bispecific antibody and an additional single dose of the anti-CD79b antibody drug conjugate.

71. The method, anti-CD79b antibody drug conjugate and bispecific antibody for use, or use of embodiment 70, wherein the dosing regimen comprises between four to ten additional dosing cycles comprising an additional single dose of the anti-CD20/anti-CD3 bispecific antibody and an additional single dose of the anti-CD79b antibody drug conjugate.

72. The method, anti-CD79b antibody drug conjugate and bispecific antibody for use, or use of any one of embodiments 56-63, wherein one or more of the additional dosing cycles comprise an additional single dose of the anti-CD20/anti-CD3 bispecific antibody and do not comprise administration of the anti-CD79b antibody drug conjugate.

73. The method, anti-CD79b antibody drug conjugate and bispecific antibody for use, or use of embodiment 72, wherein the dosing regimen comprises at least two additional dosing cycles comprising an additional single dose of the anti-CD20/anti-CD3 bispecific antibody and not comprising administration of the anti-CD79b antibody drug conjugate.

74. The method, anti-CD79b antibody drug conjugate and bispecific antibody for use, or use of embodiment 73, wherein the dosing regimen comprises between two and ten additional dosing cycles comprising an additional single dose of the anti-CD20/anti-CD3 bispecific antibody and not comprising administration of the anti-CD79b antibody drug conjugate.

75. The method, anti-CD79b antibody drug conjugate and bispecific antibody for use, or use of any one of embodiments 64-74, wherein the additional single dose of the anti-CD20/anti-CD3 bispecific antibody is about equivalent in amount to the C2D1 of the anti-CD20/anti-CD3 bispecific antibody.

76. The method, anti-CD79b antibody drug conjugate and bispecific antibody for use, or use of embodiment 75, wherein the additional single dose of the anti-CD20/anti-CD3 bispecific antibody is about 30 mg.

77. The method, anti-CD79b antibody drug conjugate and bispecific antibody for use, or use of any one of embodiments 64-76, wherein the additional single dose of the anti-CD20/anti-CD3 bispecific antibody is administered or is to be administered to the subject on or about Day 1 of each additional dosing cycle comprising an additional dose of the anti-CD20/anti-CD3 bispecific antibody.

78. The method, anti-CD79b antibody drug conjugate and bispecific antibody for use, or use of any one of embodiments 56-71 and 75-77, wherein the dosing regimen comprises six or more additional dosing cycles, wherein each of the six or more additional dosing cycles comprises a single dose of the anti-CD20/anti-CD3 bispecific antibody, and wherein no more than four of the six or more additional dosing cycles comprise administration of the anti-CD79b antibody drug conjugate.

79. The method, anti-CD79b antibody drug conjugate and bispecific antibody for use, or use of embodiment 78, wherein the dosing regimen comprises six to ten additional dosing cycles, wherein each of the six to ten additional dosing cycles comprises a single dose of the anti-CD20/anti-CD3 bispecific antibody, and wherein no more than four of the six to ten additional dosing cycles comprise administration of the anti-CD79b antibody drug conjugate.

80. The method, anti-CD79b antibody drug conjugate and bispecific antibody for use, or use of embodiment 79, wherein the dosing regimen comprises ten additional dosing cycles, wherein each of the ten additional dosing cycles comprises a single dose of the anti-CD20/anti-CD3 bispecific antibody, and wherein no more than four of the ten additional dosing cycles comprise administration of the anti-CD79b antibody drug conjugate.

81. The method, anti-CD79b antibody drug conjugate and bispecific antibody for use, or use of any one of embodiments 56-71 and 75-77, wherein the dosing regimen comprises ten additional dosing cycles, wherein each of the ten additional dosing cycles comprises a single dose of the anti-CD20/anti-CD3 bispecific antibody, and wherein each of the ten additional dosing cycles comprises administration of the anti-CD79b antibody drug conjugate.

82. A method of treating a subject having a CD20-positive cell proliferative disorder comprising administering to the subject an anti-CD79b antibody drug conjugate and an anti-CD20/anti-CD3 bispecific antibody in a dosing regimen comprising 12 dosing cycles, wherein:
  (a) the first dosing cycle comprises:
    (i) a first dose (C1D1) of the anti-CD20/anti-CD3 bispecific antibody and a second dose (C1D2) of the anti-CD20/anti-CD3 bispecific antibody, wherein the C1D1 of the anti-CD20/anti-CD3 bispecific antibody is about 2.5 mg, and the C1D2 of the anti-CD20/anti-CD3 bispecific antibody is about 10 mg; and
    (ii) a single dose (C1D1) of the anti-CD79b antibody drug conjugate;
  (b) the second to sixth dosing cycles each comprises a single dose (C2D1-C6D1) of the anti-CD20/anti-CD3 bispecific antibody and a single dose (C2D1-C6D1) of the anti-CD79b antibody drug conjugate; and
  (c) the seventh to $12^{th}$ dosing cycles each comprises a single dose (C7D1-C12D1) of the anti-CD20/anti-CD3 bispecific antibody and does not comprise administration of the anti-CD79b antibody drug conjugate, and
wherein each single dose C2D1-C12D1 of the anti-CD20/anti-CD3 bispecific antibody is about 10 mg, about 16 mg, or about 30 mg.

83. An anti-CD79b antibody drug conjugate and an anti-CD20/anti-CD3 bispecific antibody for use in a method of treating a subject having a CD20-positive cell proliferative disorder, wherein the anti-CD79b antibody drug conjugate and the anti-CD20/anti-CD3 bispecific antibody are administered in a dosing regimen comprising 12 dosing cycles, wherein:
  (a) the first dosing cycle comprises:
    (i) a first dose (C1D1) of the anti-CD20/anti-CD3 bispecific antibody and a second dose (C1D2) of the anti-CD20/anti-CD3 bispecific antibody, wherein the C1D1 of the anti-CD20/anti-CD3 bispecific antibody is about 2.5 mg, and the C1D2 of the anti-CD20/anti-CD3 bispecific antibody is about 10 mg; and
    (ii) a single dose (C1D1) of the anti-CD79b antibody drug conjugate;
  (b) the second to sixth dosing cycles each comprises a single dose (C2D1-C6D1) of the anti-CD20/anti-CD3 bispecific antibody and a single dose (C2D1-C6D1) of the anti-CD79b antibody drug conjugate; and
  (c) the seventh to 12$^{th}$ dosing cycles each comprises a single dose (C7D1-C12D1) of the anti-CD20/anti-CD3 bispecific antibody and does not comprise administration of the anti-CD79b antibody drug conjugate, and
  wherein each single dose C2D1-C12D1 of the anti-CD20/anti-CD3 bispecific antibody is about 10 mg, about 16 mg, or about 30 mg.

84. Use of an anti-CD79b antibody drug conjugate and an anti-CD20/anti-CD3 bispecific antibody in treating a subject having a CD20-positive cell proliferative disorder, wherein the anti-CD79b antibody drug conjugate and the anti-CD20/anti-CD3 bispecific antibody are administered in a dosing regimen comprising 12 dosing cycles, wherein:
  (a) the first dosing cycle comprises:
    (i) a first dose (C1D1) of the anti-CD20/anti-CD3 bispecific antibody and a second dose (C1D2) of the anti-CD20/anti-CD3 bispecific antibody, wherein the C1D1 of the anti-CD20/anti-CD3 bispecific antibody is about 2.5 mg, and the C1D2 of the anti-CD20/anti-CD3 bispecific antibody is about 10 mg; and
    (ii) a single dose (C1D1) of the anti-CD79b antibody drug conjugate;
  (b) the second to sixth dosing cycles each comprises a single dose (C2D1-C6D1) of the anti-CD20/anti-CD3 bispecific antibody and a single dose (C2D1-C6D1) of the anti-CD79b antibody drug conjugate; and
  (c) the seventh to 12$^{th}$ dosing cycles each comprises a single dose (C7D1-C12D1) of the anti-CD20/anti-CD3 bispecific antibody and does not comprise administration of the anti-CD79b antibody drug conjugate, and
  wherein each single dose C2D1-C12D1 of the anti-CD20/anti-CD3 bispecific antibody is about 10 mg, about 16 mg, or about 30 mg.

85. Use of an anti-CD79b antibody drug conjugate and an anti-CD20/anti-CD3 bispecific antibody in the manufacture of a medicament for treating a subject having a CD20-positive cell proliferative disorder, wherein the anti-CD79b antibody drug conjugate and the anti-CD20/anti-CD3 bispecific antibody are administered in a dosing regimen comprising 12 dosing cycles, wherein:
  (a) the first dosing cycle comprises:
    (i) a first dose (C1D1) of the anti-CD20/anti-CD3 bispecific antibody and a second dose (C1D2) of the anti-CD20/anti-CD3 bispecific antibody, wherein the C1D1 of the anti-CD20/anti-CD3 bispecific antibody is about 2.5 mg, and the C1D2 of the anti-CD20/anti-CD3 bispecific antibody is about 10 mg; and
    (ii) a single dose (C1D1) of the anti-CD79b antibody drug conjugate;
  (b) the second to sixth dosing cycles each comprises a single dose (C2D1-C6D1) of the anti-CD20/anti-CD3 bispecific antibody and a single dose (C2D1-C6D1) of the anti-CD79b antibody drug conjugate; and
  (c) the seventh to 12$^{th}$ dosing cycles each comprises a single dose (C7D1-C12D1) of the anti-CD20/anti-CD3 bispecific antibody and does not comprise administration of the anti-CD79b antibody drug conjugate, and
  wherein each single dose C2D1-C12D1 of the anti-CD20/anti-CD3 bispecific antibody is about 10 mg, about 16 mg, or about 30 mg.

86. The method, anti-CD79b antibody drug conjugate and bispecific antibody for use, or use of any one of embodiments 82-85, wherein the C2D1-C12D1 of the anti-CD20/anti-CD3 bispecific antibody are about equivalent in amount.

87. The method, anti-CD79b antibody drug conjugate and bispecific antibody for use, or use of embodiment 86, wherein the C2D1 of the anti-CD20/anti-CD3 bispecific antibody is about 30 mg.

88. The method, anti-CD79b antibody drug conjugate and bispecific antibody for use, or use of any one of embodiments 82-87, wherein the C1D1-C6D1 of the anti-CD79b antibody drug conjugate are about equivalent in amount.

89. The method, anti-CD79b antibody drug conjugate and bispecific antibody for use, or use of embodiment 88, wherein each of the C1D1-C6D1 of the anti-CD79b antibody drug conjugate is from about 0.1 mg/kg to about 2.4 mg/kg.

90. The method, anti-CD79b antibody drug conjugate and bispecific antibody for use, or use of embodiment 89, wherein each of the C1D1-C6D1 of the anti-CD79b antibody drug conjugate is about 1.8 mg/kg.

91. The method, anti-CD79b antibody drug conjugate and bispecific antibody for use, or use of any one of embodiments 82-90, wherein the C1D1 of the anti-CD20/anti-CD3 bispecific antibody and the C1D2 of the anti-CD20/anti-CD3 bispecific antibody are administered or are to be administered to the subject on or about Days 8 and 15, respectively, of the first dosing cycle.

92. The method, anti-CD79b antibody drug conjugate and bispecific antibody for use, or use of any one of embodiments 82-91, wherein the C2D1-C12D1 of the anti-CD20/anti-CD3 bispecific antibody is administered or is to be administered to the subject on or about Day 1 of each dosing cycle.

93. The method, anti-CD79b antibody drug conjugate and bispecific antibody for use, or use of any one of embodiments 82-92, wherein the C1D1 of the anti-CD79b antibody drug conjugate is administered or is to be administered to the subject on or about Day 2 of the first dosing cycle and the C2D1-C6D1 of the anti-CD79b antibody drug conjugate is administered or is to be administered to the subject on or about Day 1 of each dosing cycle comprising administration of the anti-CD79b antibody drug conjugate.

94. The method, anti-CD79b antibody drug conjugate and bispecific antibody for use, or use of any one of embodiments 82-93, wherein the C2D1-C6D1 of the anti-CD20/anti-CD3 bispecific antibody is administered or is to be administered after the administration the C2D1-C6D1 of the anti-CD79b antibody drug conjugate has completed.

95. The method, anti-CD79b antibody drug conjugate and bispecific antibody for use, or use of embodiment 94, wherein the C2D1-C6D1 of the anti-CD20/anti-CD3 bispecific antibody is administered or is to be administered between about 60-120 minutes after the administration of the C2D1-C6D1 of the anti-CD79b antibody drug conjugate has completed.

96. The method, anti-CD79b antibody drug conjugate and bispecific antibody for use, or use of embodiment 95, wherein the C2D1-C6D1 of the anti-CD20/anti-CD3 bispecific antibody is administered or is to be administered about 90 minutes after the administration of the C2D1-C6D1 anti-CD79b antibody drug conjugate has completed.

97. The method, anti-CD79b antibody drug conjugate and bispecific antibody for use, or use of any one of embodiments 82-990, wherein each dosing cycle is a 14-day dosing cycle.

98. The method, anti-CD79b antibody drug conjugate and bispecific antibody for use, or use of any one of embodiments 82-96, wherein each dosing cycle is a 21-day dosing cycle.

99. The method, anti-CD79b antibody drug conjugate and bispecific antibody for use, or use of any one of embodiments 82-98, wherein the dosing regimen comprises an additional re-treatment regimen after the completion of the 12 dosing cycles of the dosing regimen.

100. The method, anti-CD79b antibody drug conjugate and bispecific antibody for use, or use of embodiment 99, wherein the additional re-treatment regimen comprises 12 additional dosing cycles, wherein:
  (a) the first additional dosing cycle comprises:
    (i) a first dose (C13D1) of the anti-CD20/anti-CD3 bispecific antibody and a second dose (C13D2) of the anti-CD20/anti-CD3 bispecific antibody, wherein the C13D1 of the anti-CD20/anti-CD3 bispecific antibody is about 2.5 mg, and the C13D2 of the anti-CD20/anti-CD3 bispecific antibody is about 10 mg; and
    (ii) a single dose (C13D1) of the anti-CD79b antibody drug conjugate;
  (b) the second to sixth additional dosing cycles each comprises a single dose (C14D1-C18D1) of the anti-CD20/anti-CD3 bispecific antibody and a single dose (C14D1-C18D1) of the anti-CD79b antibody drug conjugate; and
  (c) the seventh to 12$^{th}$ additional dosing cycles each comprises a single dose (C19D1-C24D1) of the anti-CD20/anti-CD3 bispecific antibody and does not comprise administration of the anti-CD79b antibody drug conjugate, and
wherein each single dose C14D1-C24D1 of the anti-CD20/anti-CD3 bispecific antibody is about 10 mg, about 16 mg, or about 30 mg.

101. The method, anti-CD79b antibody drug conjugate and bispecific antibody for use, or use of embodiment 104, wherein:
  (a) the first additional dosing cycle comprises:
    (i) a first dose (C13D1) of the anti-CD20/anti-CD3 bispecific antibody administered or to be administered on Day 8 of the first additional dosing cycle and a second dose (C13D2) of the anti-CD20/anti-CD3 bispecific antibody administered or to be administered on Day 15 of the first additional dosing cycle, wherein the C13D1 of the anti-CD20/anti-CD3 bispecific antibody is about 2.5 mg, and the C13D2 of the anti-CD20/anti-CD3 bispecific antibody is about 10 mg; and
    (ii) a single dose (C13D1) of the anti-CD79b antibody drug conjugate administered or to be administered on Day 2 of the first additional dosing cycle;
  (b) the second to sixth additional dosing cycles each comprises a single dose (C14D1-C18D1) of the anti-CD20/anti-CD3 bispecific antibody and a single dose (C14D1-C18D1) of the anti-CD79b antibody drug conjugate; and
  (c) the seventh to 12$^{th}$ additional dosing cycles each comprises a single dose (C19D1-C24D1) of the anti-CD20/anti-CD3 bispecific antibody and does not comprise administration of the anti-CD79b antibody drug conjugate, and
wherein the C14D1-C24D1 of the anti-CD20/anti-CD3 bispecific antibody are administered or are to be administered on Day 1 of each additional dosing cycle and the C14D1-C18D1 of the anti-CD79b antibody drug conjugate are administered or are to be administered on Day 1 of each additional dosing cycle, and wherein each single dose C14D1-C24D1 of the anti-CD20/anti-CD3 bispecific antibody is about 30 mg and each single dose C13D1-C18D1 of the anti-CD79b antibody drug conjugate is about 1.8 mg/kg.

102. The method, anti-CD79b antibody drug conjugate and bispecific antibody for use, or use of any one of embodiments 99-101, wherein there is a waiting period between the completion of the 12 dosing cycles of the dosing regimen and the start of the 12 additional dosing cycles of the additional re-treatment regimen.

103. The method, anti-CD79b antibody drug conjugate and bispecific antibody for use, or use of embodiment 102, wherein the waiting period is between about one to about eight weeks.

104. The method, anti-CD79b antibody drug conjugate and bispecific antibody for use, or use of any one of embodiments 99-103, wherein each additional dosing cycle of the additional re-treatment regimen is a 14-day dosing cycle.

105. The method, anti-CD79b antibody drug conjugate and bispecific antibody for use, or use of any one of embodiments 99-103, wherein each additional dosing cycle of the additional re-treatment regimen is a 21-day dosing cycle.

106. The method of any one of embodiments 1, 5-45, 49-82, and 86-105, wherein the method further comprises administering to the subject one or more additional therapeutic agents.

107. The anti-CD79b antibody drug conjugate and bispecific antibody for use or use of any one of embodiments 2-44, 46-81, and 83-105, wherein the anti-CD79b antibody drug conjugate and bispecific antibody are administered with one or more additional therapeutic agents.

108. The method, anti-CD79b antibody drug conjugate and bispecific antibody for use, or use of embodiment 106 or 107, wherein the one or more additional therapeutic agents comprise one or more chemotherapeutic agents.

109. The method, anti-CD79b antibody drug conjugate and bispecific antibody for use, or use of embodiment 108, wherein the one or more chemotherapeutic agents comprise cyclophosphamide, doxorubicin, and rituximab.

110. The method, anti-CD79b antibody drug conjugate and bispecific antibody for use, or use of embodiment 106 or 107, wherein the one or more additional therapeutic agents is tocilizumab.

111. The method, anti-CD79b antibody drug conjugate and bispecific antibody for use, or use of embodiment 106 or 107, wherein the one or more additional therapeutic agents is a corticosteroid.

112. The method, anti-CD79b antibody drug conjugate and bispecific antibody for use, or use of embodiment 111, wherein the corticosteroid comprises prednisone, prednisolone, methylprednisolone and dexamethasone.

113. The method of any one of embodiments 1, 5-45, 49-82, and 86-105, wherein the method further comprises administering to the subject rituximab, cyclophosphamide, doxorubicin, and prednisone (R-CHP).

114. The anti-CD79b antibody drug conjugate and bispecific antibody for use or use of any one of embodiments 2-44, 46-81, and 83-105, wherein the anti-CD79b antibody drug conjugate and bispecific antibody are administered with rituximab, cyclophosphamide, doxorubicin, and prednisone (R-CHP).

115. The method, anti-CD79b antibody drug conjugate and bispecific antibody for use, or use of embodiment 106 or 107, wherein the one or more additional therapeutic agents is an antihistamine.

116. The method, anti-CD79b antibody drug conjugate and bispecific antibody for use, or use of embodiment 115, wherein the antihistamine is diphenhydramine.

117. The method, anti-CD79b antibody drug conjugate and bispecific antibody for use, or use of embodiment 106 or 107, wherein the one or more additional therapeutic agents comprises allopurinol and rasburicase.

118. The method, anti-CD79b antibody drug conjugate and bispecific antibody for use, or use of embodiment 106 or 107, wherein the one or more additional therapeutic agents is an antipyretic.

119. The method, anti-CD79b antibody drug conjugate and bispecific antibody for use, or use of embodiment 106 or 107, wherein the one or more additional therapeutic agents is obinutuzumab.

120. The method, anti-CD79b antibody drug conjugate and bispecific antibody for use, or use of embodiment 119, wherein obinutuzumab is administered or is to be administered prior to administration of the anti-CD20/anti-CD3 bispecific antibody.

121. The method, anti-CD79b antibody drug conjugate and bispecific antibody for use, or use of embodiment 120, wherein obinutuzumab is administered or is to be administered about seven days prior to administration of the anti-CD20/anti-CD3 bispecific antibody.

122. The method, anti-CD79b antibody drug conjugate and bispecific antibody for use, or use of any one of embodiments 119-121, wherein obinutuzumab is administered or is to be administered as a single dose of about 1000 mg.

123. The method, anti-CD79b antibody drug conjugate and bispecific antibody for use, or use of embodiment 119 or 120, wherein obinutuzumab is administered at a first dose of about 1000 and a second dose of about 1000 mg.

124. The method, anti-CD79b antibody drug conjugate and bispecific antibody for use, or use of embodiment 123, wherein the first dose of obinutuzumab is administered about seven days prior to administration of the C1D1 of the anti-CD20/anti-CD3 bispecific antibody.

125. The method, anti-CD79b antibody drug conjugate and bispecific antibody for use, or use of embodiment 123 or 124, wherein the second dose of obinutuzumab is administered about one day prior to administration of the C1D1 of the anti-CD20/anti-CD3 bispecific antibody.

126. The method, anti-CD79b antibody drug conjugate and bispecific antibody for use, or use of any one of embodiments 1-125, wherein the anti-CD79b antibody drug conjugate is polatuzumab vedotin or anti-CD79b-MC-vc-PAB-MMAE.

127. The method, anti-CD79b antibody drug conjugate and bispecific antibody for use, or use of embodiment 126, wherein the anti-CD79b antibody drug conjugate is polatuzumab vedotin.

128. The method, anti-CD79b antibody drug conjugate and bispecific antibody for use, or use of any one of embodiments 1-127, wherein the anti-CD20/anti-CD3 bispecific antibody comprises at least one Fab molecule which specifically binds to CD20 comprising the following six hypervariable regions (HVRs):
(a) an HVR-H1 comprising the amino acid sequence of YSWIN (SEQ ID NO: 1);
(b) an HVR-H2 comprising the amino acid sequence of RIFPGDGDTDYNGKFKG (SEQ ID NO: 2);
(c) an HVR-H3 comprising the amino acid sequence of NVFDGYWLVY (SEQ ID NO:3);
(d) an HVR-L1 comprising the amino acid sequence of RSSKSLLHSNGITYLY (SEQ ID NO: 4);
(e) an HVR-L2 comprising the amino acid sequence of QMSNLVS (SEQ ID NO: 5); and
(f) an HVR-L3 comprising the amino acid sequence of AQNLELPYT (SEQ ID NO: 6).

129. The method, anti-CD79b antibody drug conjugate and bispecific antibody for use, or use of any one of embodiments 1-128, wherein the anti-CD20/anti-CD3 bispecific antibody comprises at least one Fab molecule which specifically binds to CD20 comprising (a) a heavy chain variable VH domain comprising an amino acid sequence having at least 95% sequence identity to the amino acid sequence of SEQ ID NO: 7; (b) a variable light (VL) domain comprising an amino acid sequence having at least 95% sequence identity to the amino acid sequence of SEQ ID NO: 8; or (c) a VH domain as in (a) and a VL domain as in (b).

130. The method, anti-CD79b antibody drug conjugate and bispecific antibody for use, or use of embodiment 129, wherein the Fab molecule which specifically binds to CD20 comprises (a) a VH domain comprising an amino acid sequence of SEQ ID NO: 7 and (b) a VL domain comprising an amino acid sequence of SEQ ID NO: 8.

131. The method, anti-CD79b antibody drug conjugate and bispecific antibody for use, or use of any one of embodiments 1-130, wherein the anti-CD20/anti-CD3 bispecific antibody comprises at least one Fab molecule which specifically binds to CD3 comprising the following six HVRs:
(a) an HVR-H1 comprising the amino acid sequence of TYAMN (SEQ ID NO: 9);
(b) an HVR-H2 comprising the amino acid sequence of RIRSKYNNYATYYADSVKG (SEQ ID NO: 10);
(c) an HVR-H3 comprising the amino acid sequence of HGNFGNSYVSWFAY (SEQ ID NO: 11);
(d) an HVR-L1 comprising the amino acid sequence of GSSTGAVTTSNYAN (SEQ ID NO: 12);
(e) an HVR-L2 comprising the amino acid sequence of GTNKRAP (SEQ ID NO: 13); and
(f) an HVR-L3 comprising the amino acid sequence of ALWYSNLWV (SEQ ID NO: 14).

132. The method, anti-CD79b antibody drug conjugate and bispecific antibody for use, or use of any one of embodiments 1-131, wherein the anti-CD20/anti-CD3 bispecific antibody comprises at least one Fab molecule which specifically binds to CD3 comprising (a) a heavy chain variable VH domain comprising an amino acid sequence having at least 95% sequence identity to the amino acid sequence of SEQ ID NO: 15; (b) a variable light (VL) domain comprising an amino acid sequence having at least 95% sequence identity to the amino acid sequence of SEQ ID NO: 16; or (c) a VH domain as in (a) and a VL domain as in (b).

133. The method, anti-CD79b antibody drug conjugate and bispecific antibody for use, or use of embodiment 132, wherein the Fab molecule which specifically binds to CD3 comprises (a) a VH domain comprising an amino acid sequence of SEQ ID NO: 15 and (b) a VL domain comprising an amino acid sequence of SEQ ID NO: 16.

134. The method, anti-CD79b antibody drug conjugate and bispecific antibody for use, or use of any one of embodiments 1-133, wherein the anti-CD20/anti-CD3 bispecific antibody comprises a Fab molecule which specifically binds to CD3, wherein (a) the variable domains of the Fab heavy and light chain are exchanged or (b) the constant domains of the Fab heavy and light chain are exchanged.

135. The method, anti-CD79b antibody drug conjugate and bispecific antibody for use, or use of any one of embodiments 1-134, wherein the anti-CD20/anti-CD3 bispecific antibody comprises at least one Fab molecule which specifically binds to CD20, wherein in the constant domain CL of the Fab molecule the amino acid at position 124 is substituted by lysine (K) (numbering according to Kabat) and the amino acid at position 123 is substituted by arginine (R) or lysine (K) (numbering according to Kabat), and wherein in the constant domain CH1 of the Fab molecule the amino acid at position 147 is substituted by glutamic acid (E) (EU numbering) and the amino acid at position 213 is substituted by glutamic acid (E) (EU numbering).

136. The method, anti-CD79b antibody drug conjugate and bispecific antibody for use, or use of any one of embodiments 1-135, wherein the anti-CD20/anti-CD3 bispecific antibody is bivalent for CD20 and monovalent for CD3.

137. The method, anti-CD79b antibody drug conjugate and bispecific antibody for use, or use of any one of embodiments 1-136, wherein the anti-CD20/anti-CD3 bispecific antibody comprises two Fab molecule which specifically bind to CD20 and one Fab molecule which specifically binds to CD3.

138. The method, anti-CD79b antibody drug conjugate and bispecific antibody for use, or use of any one of embodiments 1-137, wherein the anti-CD20/anti-CD3 bispecific antibody comprises
(a) a first Fab molecule which specifically binds to CD20;
(b) a second Fab molecule which specifically binds to CD3;
(c) a third Fab molecule which specifically binds to CD20; and
(d) an Fc domain composed of a first and a second subunit capable of stable association;
wherein the third Fab molecule under (c) is identical to the first Fab molecule under (a); wherein in the constant domain CL of the first Fab molecule under (a) and the third Fab molecule under (c) the amino acid at position 124 is substituted by lysine (K) (numbering according to Kabat) and the amino acid at position 123 is substituted by arginine (R) or lysine (K) (numbering according to Kabat); and wherein in the constant domain CH1 of the first Fab molecule under (a) and the third Fab molecule under (c) the amino acid at position 147 is substituted by glutamic acid (E) (EU numbering) and the amino acid at position 213 is substituted by glutamic acid (E) (EU numbering); and wherein the first Fab molecule under (a) is fused at the C-terminus of the Fab heavy chain to the N-terminus of the Fab heavy chain of the second Fab molecule under (b), and the second Fab molecule under (b) and the third Fab molecule under (c) are each fused at the C-terminus of the Fab heavy chain to the N-terminus of one of the subunits of the Fc domain under (d).

139. The method, anti-CD79b antibody drug conjugate and bispecific antibody for use, or use of any one of embodiments 1-138, wherein the anti-CD20/anti-CD3 bispecific antibody is a humanized antibody.

140. The method, anti-CD79b antibody drug conjugate and bispecific antibody for use, or use of any one of embodiments 1-139, wherein the anti-CD20/anti-CD3 bispecific antibody is a chimeric antibody.

141. The method, anti-CD79b antibody drug conjugate and bispecific antibody for use, or use of any one of embodiments 1-140, wherein the anti-CD20/anti-CD3 bispecific antibody comprises an Fc domain, wherein the Fc domain is an IgG Fc domain.

142. The method, anti-CD79b antibody drug conjugate and bispecific antibody for use, or use of embodiment 141, wherein the IgG Fc domain is an IgG1 Fc domain.

143. The method, anti-CD79b antibody drug conjugate and bispecific antibody for use, or use of embodiment 141 or 142, wherein the IgG Fc domain comprises a mutation at amino acid residue N297 (EU numbering) that results in the absence of glycosylation.

144. The method, anti-CD79b antibody drug conjugate and bispecific antibody for use, or use of embodiment 143, wherein the mutation at amino acid residue N297 is a substitution mutation.

145. The method, anti-CD79b antibody drug conjugate and bispecific antibody for use, or use of embodiment 143 or 144, wherein the mutation at amino acid residue N297 reduces effector function of the Fc region.

146. The method, anti-CD79b antibody drug conjugate and bispecific antibody for use, or use of any one of embodiments 142-145, wherein the mutation is an N297G or N297A mutation.

147. The method, anti-CD79b antibody drug conjugate and bispecific antibody for use, or use of any one of embodiments 142-146, wherein the anti-CD20/anti-CD3 bispecific antibody comprises a mutation in the Fc region that reduces effector function.

148. The method, anti-CD79b antibody drug conjugate and bispecific antibody for use, or use of embodiment 147, wherein the mutation is a substitution mutation.

149. The method, anti-CD79b antibody drug conjugate and bispecific antibody for use, or use of embodiment 148, wherein the substitution mutation is at amino acid residue L234, L235, D265, and/or P329 (EU numbering).

150. The method, anti-CD79b antibody drug conjugate and bispecific antibody for use, or use of embodiment 149, wherein the substitution mutation is selected from the group consisting of L234A, L235A, D265A, and P329G.

151. The method, anti-CD79b antibody drug conjugate and bispecific antibody for use, or use of any one of embodiments 1-150, wherein the anti-CD20/anti-CD3 bispecific antibody comprises one or more heavy chain constant domains, wherein the one or more heavy chain constant domains are selected from a first CH1 ($CH1_1$) domain, a first CH2 ($CH2_1$) domain, a first CH3 ($CH3_1$) domain, a second CH1 ($CH1_2$) domain, second CH2 ($CH2_2$) domain, and a second CH3 ($CH3_2$) domain.

152. The method, anti-CD79b antibody drug conjugate and bispecific antibody for use, or use of embodiment 151, wherein at least one of the one or more heavy chain constant domains is paired with another heavy chain constant domain.

153. The method, anti-CD79b antibody drug conjugate and bispecific antibody for use, or use of embodiment 151 or 152, wherein the CH3, and CH3$_2$ domains each comprise a protuberance or cavity, and wherein the protuberance or cavity in the CH3$_1$ domain is positionable in the cavity or protuberance, respectively, in the CH3$_2$ domain.

154. The method, anti-CD79b antibody drug conjugate and bispecific antibody for use, or use of embodiment 153, wherein the CH3, and CH3$_2$ domains meet at an interface between the protuberance and cavity.

155. The method, anti-CD79b antibody drug conjugate and bispecific antibody for use, or use of any one of embodiments 151-154, wherein the CH2, and CH2$_2$ domains each comprise a protuberance or cavity, and wherein the protuberance or cavity in the CH2$_1$ domain is positionable in the cavity or protuberance, respectively, in the CH2$_2$ domain.

156. The method, anti-CD79b antibody drug conjugate and bispecific antibody for use, or use of embodiment 155, wherein the CH2, and CH2$_2$ domains meet at an interface between said protuberance and cavity.

157. The method, anti-CD79b antibody drug conjugate and bispecific antibody for use, or use of embodiments 1-156, wherein the anti-CD20/anti-CD3 bispecific antibody is glofitamab.

158. The method, anti-CD79b antibody drug conjugate and bispecific antibody for use, or use of any one of embodiments 1-157, wherein the anti-CD20/anti-CD3 bispecific antibody is administered or is administered intravenously.

159. The method, anti-CD79b antibody drug conjugate and bispecific antibody for use, or use of any one of embodiments 1-158, wherein the anti-CD79b antibody drug conjugate is administered or is administered intravenously.

160. The method, anti-CD79b antibody drug conjugate and bispecific antibody for use, or use of any one of embodiments 1-159, wherein if the anti-CD20/anti-CD3 bispecific antibody and the anti-CD79b antibody drug conjugate are administered or are to be administered on the same day, then the anti-CD20/anti-CD3 bispecific antibody is administered or is to be administered after the administration of the anti-CD79b antibody drug conjugate has completed.

161. The method, anti-CD79b antibody drug conjugate and bispecific antibody for use, or use of embodiment 160, wherein the anti-CD20/anti-CD3 bispecific antibody is administered or is to be administered between about 60-120 minutes after the administration of the anti-CD79b antibody drug conjugate has completed.

162. The method, anti-CD79b antibody drug conjugate and bispecific antibody for use, or use of embodiment 161, wherein the anti-CD20/anti-CD3 bispecific antibody is administered or is to be administered about 90 minutes after the administration of the anti-CD79b antibody drug conjugate has completed.

163. A method of treating a subject having a CD20-positive cell proliferative disorder comprising administering to the subject polatuzumab vedotin and glofitamab in a dosing regimen comprising at least a first dosing cycle and a second dosing cycle, wherein:
  (a) the first dosing cycle comprises a first dose (C1D1) of glofitamab administered on Day 8 of the first dosing cycle and a second dose (C1D2) of glofitamab administered on Day 15 of the first dosing cycle, wherein the C1D1 of glofitamab is about 2.5 mg, the C1D2 of glofitamab is about 10 mg; and
  (b) the second dosing cycle comprises a single dose (C2D1) of glofitamab administered on Day 1 of the second dosing cycle and a single dose (C2D1) of polatuzumab vedotin administered on Day 1 of the second dosing cycle, wherein the C2D1 of glofitamab is about 10 mg, about 16 mg, or about 30 mg.

164. Polatuzumab vedotin and glofitamab for use in a method of treating a subject having a CD20-positive cell proliferative disorder, wherein polatuzumab vedotin and glofitamab are administered in a dosing regimen comprising at least a first dosing cycle and a second dosing cycle, wherein:
  (a) the first dosing cycle comprises a first dose (C1D1) of glofitamab to be administered on Day 8 of the first dosing cycle and a second dose (C1D2) of glofitamab to be administered on Day 15 of the first dosing cycle, wherein the C1D1 of glofitamab is about 2.5 mg, the C1D2 of glofitamab is about 10 mg; and
  (b) the second dosing cycle comprises a single dose (C2D1) of glofitamab to be administered on Day 1 of the second dosing cycle and a single dose (C2D1) of polatuzumab vedotin to be administered on Day 1 of the second dosing cycle, wherein the C2D1 of glofitamab is about 10 mg, about 16 mg, or about 30 mg.

165. Use of Polatuzumab vedotin and glofitamab for treating a subject having a CD20-positive cell proliferative disorder, wherein polatuzumab vedotin and glofitamab are administered in a dosing regimen comprising at least a first dosing cycle and a second dosing cycle, wherein:
  (a) the first dosing cycle comprises a first dose (C1D1) of glofitamab to be administered on Day 8 of the first dosing cycle and a second dose (C1D2) of glofitamab to be administered on Day 15 of the first dosing cycle, wherein the C1D1 of glofitamab is about 2.5 mg, the C1D2 of glofitamab is about 10 mg; and
  (b) the second dosing cycle comprises a single dose (C2D1) of glofitamab to be administered on Day 1 of the second dosing cycle and a single dose (C2D1) of polatuzumab vedotin to be administered on Day 1 of the second dosing cycle, wherein the C2D1 of glofitamab is about 10 mg, about 16 mg, or about 30 mg.

166. Use of Polatuzumab vedotin and glofitamab in the manufacture of a medicament for treating a subject having a CD20-positive cell proliferative disorder, wherein polatuzumab vedotin and glofitamab are administered in a dosing regimen comprising at least a first dosing cycle and a second dosing cycle, wherein:
  (a) the first dosing cycle comprises a first dose (C1D1) of glofitamab to be administered on Day 8 of the first dosing cycle and a second dose (C1D2) of glofitamab to be administered on Day 15 of the first dosing cycle, wherein the C1D1 of glofitamab is about 2.5 mg, the C1D2 of glofitamab is about 10 mg; and
  (b) the second dosing cycle comprises a single dose (C2D1) of glofitamab to be administered on Day 1 of the second dosing cycle and a single dose (C2D1) of polatuzumab vedotin to be administered on Day 1 of the second dosing cycle, wherein the C2D1 of glofitamab is about 10 mg, about 16 mg, or about 30 mg.

167. A method of treating a subject having a CD20-positive cell proliferative disorder comprising administering to the subject polatuzumab vedotin and glofitamab in a dosing regimen comprising at least a first dosing cycle and a second dosing cycle, wherein:
(a) the first dosing cycle comprises:
(i) a single dose (C1D1) of polatuzumab vedotin administered on Day 2 of the first dosing cycle; and
(ii) a first dose (C1D1) of glofitamab administered on Day 8 of the first dosing cycle and a second dose (C1D2) of glofitamab administered on Day 15 of the first dosing cycle, wherein the C1D1 of glofitamab is about 2.5 mg, and the C1D2 of glofitamab is about 10 mg; and
(b) the second dosing cycle comprises:
(i) a single dose (C2D1) of polatuzumab vedotin administered on Day 1 of the second dosing cycle; and
(ii) a single dose (C2D1) of glofitamab administered on Day 1 of the second dosing cycle, wherein the C2D1 of glofitamab is about 10 mg, about 16 mg, or about 30 mg, and the C1D1 and C2D1 of polatuzumab vedotin are each about 1.8 mg/kg.

168. Polatuzumab vedotin and glofitamab for use in a method of treating a subject having a CD20-positive cell proliferative disorder, wherein polatuzumab vedotin and glofitamab are administered in a dosing regimen comprising at least a first dosing cycle and a second dosing cycle, wherein:
(a) the first dosing cycle comprises:
(i) a single dose (C1D1) of polatuzumab vedotin to be administered on Day 2 of the first dosing cycle; and
(ii) a first (C1D1) of glofitamab to be administered on Day 8 of the first dosing cycle and a second dose (C1D2) of glofitamab to be administered on Day 15 of the first dosing cycle, wherein the C1D1 of glofitamab is about 2.5 mg, and the C1D2 of glofitamab is about 10 mg; and
(b) the second dosing cycle comprises:
(i) a single dose (C2D1) of polatuzumab vedotin to be administered on Day 1 of the second dosing cycle; and
(ii) a single dose (C2D1) of glofitamab to be administered on Day 1 of the second dosing cycle, wherein the C2D1 of glofitamab is about 10 mg, about 16 mg, or about 30 mg, and the C1D1 and C2D1 of polatuzumab vedotin are each about 1.8 mg/kg.

169. Use of polatuzumab vedotin and glofitamab in treating a subject having a CD20-positive cell proliferative disorder, wherein polatuzumab vedotin and glofitamab are administered in a dosing regimen comprising at least a first dosing cycle and a second dosing cycle, wherein:
(a) the first dosing cycle comprises:
(i) a single dose (C1D1) of polatuzumab vedotin to be administered on Day 2 of the first dosing cycle; and
(ii) a first dose (C1D1) of glofitamab to be administered on Day 8 of the first dosing cycle and a second dose (C1D2) of glofitamab to be administered on Day 15 of the first dosing cycle, wherein the C1D1 of glofitamab is about 2.5 mg, and the C1D2 of glofitamab is about 10 mg; and
(b) the second dosing cycle comprises:
(i) a single dose (C2D1) of polatuzumab vedotin to be administered on Day 1 of the second dosing cycle; and
(ii) a single dose (C2D1) of glofitamab to be administered on Day 1 of the second dosing cycle, wherein the C2D1 of glofitamab is about 10 mg, about 16 mg, or about 30 mg, and the C1D1 and C2D1 of polatuzumab vedotin are each about 1.8 mg/kg.

170. Use of polatuzumab vedotin and glofitamab in the manufacture of a medicament for treating a subject having a CD20-positive cell proliferative disorder, wherein polatuzumab vedotin and glofitamab are administered in a dosing regimen comprising at least a first dosing cycle and a second dosing cycle, wherein:
(a) the first dosing cycle comprises:
(i) a single dose (C1D1) of polatuzumab vedotin to be administered on Day 2 of the first dosing cycle; and
(ii) a first dose (C1D1) of glofitamab to be administered on Day 8 of the first dosing cycle and a second dose (C1D2) of glofitamab to be administered on Day 15 of the first dosing cycle, wherein the C1D1 of glofitamab is about 2.5 mg, and the C1D2 of glofitamab is about 10 mg; and
(b) the second dosing cycle comprises:
(i) a single dose (C2D1) of polatuzumab vedotin to be administered on Day 1 of the second dosing cycle; and
(ii) a single dose (C2D1) of glofitamab to be administered on Day 1 of the second dosing cycle, wherein the C2D1 of glofitamab is about 10 mg, about 16 mg, or about 30 mg, and the C1D1 and C2D1 of polatuzumab vedotin are each about 1.8 mg/kg.

171. A method of treating a subject having a CD20-positive cell proliferative disorder comprising administering to the subject polatuzumab vedotin and glofitamab in a dosing regimen comprising 12 dosing cycles, wherein:
(a) the first dosing cycle comprises a first dose (C1D1) of glofitamab administered on Day 8 of the first dosing cycle, a second dose (C1D2) of glofitamab administered on Day 15 of the first dosing cycle, and a single dose (C1D1) of polatuzumab vedotin administered on Day 2 of the first dosing cycle, wherein the C1D1 of glofitamab is about 2.5 mg, and the C1D2 of glofitamab is about 10 mg;
(b) the second to sixth dosing cycles each comprises a single dose (C2D1-C6D1) of glofitamab and a single dose (C2D1-C6D1) of polatuzumab vedotin, wherein the C2D1 of glofitamab is about 10 mg, about 16 mg, or about 30 mg; and
(c) the seventh to 12$^{th}$ dosing cycles each comprises a single dose (C7D1-C12D1) of glofitamab and does not comprise administration of polatuzumab vedotin, and
wherein each single dose C2D1-C12D1 of glofitamab is administered on Day 1 of each dosing cycle, and each single dose C2D1-C6D1 of polatuzumab vedotin is administered on Day 1 of each dosing cycle, and wherein each single dose C3D1-C12D1 of glofitamab is about equal in amount to the C2D1 of glofitamab, and each single dose C1D1-C6D1 of polatuzumab vedotin is about 1.8 mg/kg.

172. Polatuzumab vedotin and glofitamab for use in a method of treating a subject having a CD20-positive cell proliferative disorder, wherein polatuzumab vedotin and glofitamab are administered in a dosing regimen comprising 12 dosing cycles, wherein:
(a) the first dosing cycle comprises a first dose (C1D1) of glofitamab to be administered on Day 8 of the first dosing cycle, a second dose (C1D2) of glofitamab to be administered on Day 15 of the first dosing cycle, and a single dose (C1D1) of polatuzumab vedotin to be administered on Day 2 of the first dosing cycle, wherein the C1D1 of glofitamab is about 2.5 mg, and the C1D2 of glofitamab is about 10 mg;
(b) the second to sixth dosing cycles each comprises a single dose (C2D1-C6D1) of glofitamab and a single dose (C2D1-C6D1) of polatuzumab vedotin, wherein the C2D1 of glofitamab is about 10 mg, about 16 mg, or about 30 mg; and (c) the seventh to 12$^{th}$ dosing cycles each comprises a single dose (C7D1-C12D1) of glofitamab and does not comprise administration of polatuzumab vedotin, and wherein each single dose C2D1-C12D1 of glofitamab is to be administered on Day 1 of each dosing cycle, and each single dose C2D1-C6D1 of polatuzumab vedotin is to be administered on Day 1 of each dosing cycle, and wherein each single dose C3D1-C12D1 of glofitamab is about equal in amount to the C2D1 of glofitamab, and each single dose C1D1-C6D1 of polatuzumab vedotin is about 1.8 mg/kg.

173. Use of polatuzumab vedotin and glofitamab in treating a subject having a CD20-positive cell proliferative disorder, wherein polatuzumab vedotin and glofitamab are administered in a dosing regimen comprising 12 dosing cycles, wherein:
 (a) the first dosing cycle comprises a first dose (C1D1) of glofitamab to be administered on Day 8 of the first dosing cycle, a second dose (C1D2) of glofitamab to be administered on Day 15 of the first dosing cycle, and a single dose (C1D1) of polatuzumab vedotin to be administered on Day 2 of the first dosing cycle, wherein the C1D1 of glofitamab is about 2.5 mg, and the C1D2 of glofitamab is about 10 mg;
 (b) the second to sixth dosing cycles each comprises a single dose (C2D1-C6D1) of glofitamab and a single dose (C2D1-C6D1) of polatuzumab vedotin, wherein the C2D1 of glofitamab is about 10 mg, about 16 mg, or about 30 mg; and
 (c) the seventh to 12$^{th}$ dosing cycles each comprises a single dose (C7D1-C12D1) of glofitamab and does not comprise administration of polatuzumab vedotin, and
 wherein each single dose C2D1-C12D1 of glofitamab is to be administered on Day 1 of each dosing cycle, and each single dose C2D1-C6D1 of polatuzumab vedotin is to be administered on Day 1 of each dosing cycle, and wherein each single dose C3D1-C12D1 of glofitamab is about equal in amount to the C2D1 of glofitamab, and each single dose C1D1-C6D1 of polatuzumab vedotin is about 1.8 mg/kg.

174. Use of polatuzumab vedotin and glofitamab in the manufacture of a medicament for treating a subject having a CD20-positive cell proliferative disorder, wherein polatuzumab vedotin and glofitamab are administered in a dosing regimen comprising 12 dosing cycles, wherein:
 (a) the first dosing cycle comprises a first dose (C1D1) of glofitamab to be administered on Day 8 of the first dosing cycle, a second dose (C1D2) of glofitamab to be administered on Day 15 of the first dosing cycle, and a single dose (C1D1) of polatuzumab vedotin to be administered on Day 2 of the first dosing cycle, wherein the C1D1 of glofitamab is about 2.5 mg, and the C1D2 of glofitamab is about 10 mg;
 (b) the second to sixth dosing cycles each comprises a single dose (C2D1-C6D1) of glofitamab and a single dose (C2D1-C6D1) of polatuzumab vedotin, wherein the C2D1 of glofitamab is about 10 mg, about 16 mg, or about 30 mg; and
 (c) the seventh to 12$^{th}$ dosing cycles each comprises a single dose (C7D1-C12D1) of glofitamab and does not comprise administration of polatuzumab vedotin, and
 wherein each single dose C2D1-C12D1 of glofitamab is to be administered on Day 1 of each dosing cycle, and each single dose C2D1-C6D1 of polatuzumab vedotin is to be administered on Day 1 of each dosing cycle, and wherein each single dose C3D1-C12D1 of glofitamab is about equal in amount to the C2D1 of glofitamab, and each single dose C1D1-C6D1 of polatuzumab vedotin is about 1.8 mg/kg.

175. A method of treating a subject having a CD20-positive cell proliferative disorder comprising administering to the subject polatuzumab vedotin and glofitamab in a dosing regimen comprising 12 dosing cycles, wherein:
 (a) the first dosing cycle comprises:
  (i) a first dose (C1D1) of glofitamab administered on Day 8 of the first dosing cycle and a second dose (C1D2) of glofitamab administered on Day 15 of the first dosing cycle, wherein the C1D1 of glofitamab is about 2.5 mg and the C1D2 of glofitamab is about 10 mg; and
  (ii) a single dose (C1D1) of polatuzumab vedotin administered on Day 2 of the first dosing cycle;
 (b) the second to sixth dosing cycles each comprises a single dose (C2D1-C6D1) of glofitamab and a single dose (C2D1-C6D1) of polatuzumab vedotin, wherein the C2D1 of glofitamab is about 10 mg, about 16 mg, or about 30 mg; and
 (c) the seventh to 12$^{th}$ dosing cycles each comprises a single dose (C7D1-C12D1) of glofitamab and does not comprise administration of polatuzumab vedotin, and
 wherein each single dose C2D1-C12D1 of glofitamab is administered on Day 1 of each dosing cycle, and each single dose C2D1-C6D1 of polatuzumab vedotin is administered on Day 1 of each dosing cycle, and wherein each single dose C3D1-C12D1 of glofitamab is about equal in amount to the C2D1 of glofitamab, and each single dose C1D1-C6D1 of polatuzumab vedotin is about 1.8 mg/kg.

176. Polatuzumab vedotin and glofitamab for use in a method of treating a subject having a CD20-positive cell proliferative disorder, wherein polatuzumab vedotin and glofitamab are administered in a dosing regimen comprising 12 dosing cycles, wherein:
 (a) the first dosing cycle comprises:
  (i) a first dose (C1D1) of glofitamab to be administered on Day 8 of the first dosing cycle and a second dose (C1D2) of glofitamab to be administered on Day 15 of the first dosing cycle, wherein the C1D1 of glofitamab is about 2.5 mg and the C1D2 of glofitamab is about 10 mg; and
  (ii) a single dose (C1D1) of polatuzumab vedotin to be administered on Day 2 of the first dosing cycle;
 (b) the second to sixth dosing cycles each comprises a single dose (C2D1-C6D1) of glofitamab and a single dose (C2D1-C6D1) of polatuzumab vedotin, wherein the C2D1 of glofitamab is about 10 mg, about 16 mg, or about 30 mg; and
 (c) the seventh to 12$^{th}$ dosing cycles each comprises a single dose (C7D1-C12D1) of glofitamab and does not comprise administration of polatuzumab vedotin, and
 wherein each single dose C2D1-C12D1 of glofitamab is to be administered on Day 1 of each dosing cycle, and each single dose C2D1-C6D1 of polatuzumab vedotin is to be administered on Day 1 of each dosing cycle, and wherein each single dose C3D1-C12D1 of glofitamab is about equal in amount to the C2D1 of glofitamab, and each single dose C1D1-C6D1 of polatuzumab vedotin is about 1.8 mg/kg.

177. Use of polatuzumab vedotin and glofitamab in treating a subject having a CD20-positive cell proliferative disorder, wherein polatuzumab vedotin and glofitamab are administered in a dosing regimen comprising 12 dosing cycles, wherein:
 (a) the first dosing cycle comprises:
  (i) a first dose (C1D1) of glofitamab to be administered on Day 8 of the first dosing cycle and a second dose (C1D2) of glofitamab to be administered on Day 15 of the first dosing cycle, wherein the C1D1 of glofitamab is about 2.5 mg and the C1D2 of glofitamab is about 10 mg; and (ii) a single dose (C1D1) of polatuzumab vedotin to be administered on Day 2 of the first dosing cycle;

(b) the second to sixth dosing cycles each comprises a single dose (C2D1-C6D1) of glofitamab and a single dose (C2D1-C6D1) of polatuzumab vedotin, wherein the C2D1 of glofitamab is about 10 mg, about 16 mg, or about 30 mg; and (c) the seventh to $12^{th}$ dosing cycles each comprises a single dose (C7D1-C12D1) of glofitamab and does not comprise administration of polatuzumab vedotin, and wherein each single dose C2D1-C12D1 of glofitamab is to be administered on Day 1 of each dosing cycle, and each single dose C2D1-C6D1 of polatuzumab vedotin is to be administered on Day 1 of each dosing cycle, and wherein each single dose C3D1-C12D1 of glofitamab is about equal in amount to the C2D1 of glofitamab, and each single dose C1D1-C6D1 of polatuzumab vedotin is about 1.8 mg/kg.

178. Use of polatuzumab vedotin and glofitamab in the manufacture of a medicament for treating a subject having a CD20-positive cell proliferative disorder, wherein polatuzumab vedotin and glofitamab are administered in a dosing regimen comprising 12 dosing cycles, wherein:

(a) the first dosing cycle comprises:
  (i) a first dose (C1D1) of glofitamab to be administered on Day 8 of the first dosing cycle and a second dose (C1D2) of glofitamab to be administered on Day 15 of the first dosing cycle, wherein the C1D1 of glofitamab is about 2.5 mg and the C1D2 of glofitamab is about 10 mg; and
  (ii) a single dose (C1D1) of polatuzumab vedotin to be administered on Day 2 of the first dosing cycle;

(b) the second to sixth dosing cycles each comprises a single dose (C2D1-C6D1) of glofitamab and a single dose (C2D1-C6D1) of polatuzumab vedotin, wherein the C2D1 of glofitamab is about 10 mg, about 16 mg, or about 30 mg; and (c) the seventh to $12^{th}$ dosing cycles each comprises a single dose (C7D1-C12D1) of glofitamab and does not comprise administration of polatuzumab vedotin, and wherein each single dose C2D1-C12D1 of glofitamab is to be administered on Day 1 of each dosing cycle, and each single dose C2D1-C6D1 of polatuzumab vedotin is to be administered on Day 1 of each dosing cycle, and wherein each single dose C3D1-C12D1 of glofitamab is about equal in amount to the C2D1, and each single dose C1D1-C6D1 of polatuzumab vedotin is about 1.8 mg/kg.

179. A method of treating a subject having a CD20-positive cell proliferative disorder comprising administering to the subject polatuzumab vedotin and glofitamab in a dosing regimen comprising 12 dosing cycles, wherein:

(a) the first dosing cycle comprises:
  (i) a first dose (C1D1) of glofitamab administered on Day 8 of the first dosing cycle and a second dose (C1D2) of glofitamab administered on Day 15 of the first dosing cycle, wherein the C1D1 of glofitamab is about 2.5 mg and the C1D2 of glofitamab is about 10 mg; and
  (ii) a single dose (C1D1) of polatuzumab vedotin administered on Day 2 of the first dosing cycle;

(b) the second to sixth dosing cycles each comprises a single dose (C2D1-C6D1) of glofitamab and a single dose (C2D1-C6D1) of polatuzumab vedotin, wherein the C2D1 of glofitamab is about 30 mg; and (c) the seventh to $12^{th}$ dosing cycles each comprises a single dose (C7D1-C12D1) of glofitamab and does not comprise administration of polatuzumab vedotin, and wherein each single dose C2D1-C12D1 of glofitamab is administered on Day 1 of each dosing cycle, and each single dose C2D1-C6D1 of polatuzumab vedotin is administered on Day 1 of each dosing cycle, and wherein each single dose C3D1-C12D1 of glofitamab is about equal in amount to the C2D1 of glofitamab, and each single dose C1D1-C6D1 of polatuzumab vedotin is about 1.8 mg/kg.

180. Polatuzumab vedotin and glofitamab for use in a method of treating a subject having a CD20-positive cell proliferative disorder, wherein polatuzumab vedotin and glofitamab are administered in a dosing regimen comprising 12 dosing cycles, wherein:

(a) the first dosing cycle comprises:
  (i) a first dose (C1D1) of glofitamab to be administered on Day 8 of the first dosing cycle and a second dose (C1D2) of glofitamab to be administered on Day 15 of the first dosing cycle, wherein the C1D1 of glofitamab is about 2.5 mg and the C1D2 of glofitamab is about 10 mg; and
  (ii) a single dose (C1D1) of polatuzumab vedotin to be administered on Day 2 of the first dosing cycle;

(b) the second to sixth dosing cycles each comprises a single dose (C2D1-C6D1) of glofitamab and a single dose (C2D1-C6D1) of polatuzumab vedotin, wherein the C2D1 of glofitamab is about 30 mg; and (c) the seventh to $12^{th}$ dosing cycles each comprises a single dose (C7D1-C12D1) of glofitamab and does not comprise administration of polatuzumab vedotin, and wherein each single dose C2D1-C12D1 of glofitamab is to be administered on Day 1 of each dosing cycle, and each single dose C2D1-C6D1 of polatuzumab vedotin is to be administered on Day 1 of each dosing cycle, and wherein each single dose C3D1-C12D1 of glofitamab is about equal in amount to the C2D1 of glofitamab, and each single dose C1D1-C6D1 of polatuzumab vedotin is about 1.8 mg/kg.

181. Use of polatuzumab vedotin and glofitamab in treating a subject having a CD20-positive cell proliferative disorder, wherein polatuzumab vedotin and glofitamab are administered in a dosing regimen comprising 12 dosing cycles, wherein:

(a) the first dosing cycle comprises:
  (i) a first dose (C1D1) of glofitamab to be administered on Day 8 of the first dosing cycle and a second dose (C1D2) of glofitamab to be administered on Day 15 of the first dosing cycle, wherein the C1D1 of glofitamab is about 2.5 mg and the C1D2 of glofitamab is about 10 mg; and
  (ii) a single dose (C1D1) of polatuzumab vedotin to be administered on Day 2 of the first dosing cycle;

(b) the second to sixth dosing cycles each comprises a single dose (C2D1-C6D1) of glofitamab and a single dose (C2D1-C6D1) of polatuzumab vedotin, wherein the C2D1 of glofitamab is about 30 mg; and (c) the seventh to $12^{th}$ dosing cycles each comprises a single dose (C7D1-C12D1) of glofitamab and does not comprise administration of polatuzumab vedotin, and wherein each single dose C2D1-C12D1 of glofitamab is to be administered on Day 1 of each dosing cycle, and each single dose C2D1-C6D1 of polatuzumab vedotin is to be administered on Day 1 of each dosing cycle, and wherein each single dose C3D1-C12D1 of glofitamab is about equal in amount to the C2D1 of glofitamab, and each single dose C1D1-C6D1 of polatuzumab vedotin is about 1.8 mg/kg.

182. Use of polatuzumab vedotin and glofitamab in the manufacture of a medicament for treating a subject having a CD20-positive cell proliferative disorder, wherein polatuzumab vedotin and glofitamab are administered in a dosing regimen comprising 12 dosing cycles, wherein:
(a) the first dosing cycle comprises:
(i) a first dose (C1D1) of glofitamab to be administered on Day 8 of the first dosing cycle and a second dose (C1D2) of glofitamab to be administered on Day 15 of the first dosing cycle, wherein the C1D1 of glofitamab is about 2.5 mg and the C1D2 of glofitamab is about 10 mg; and
(ii) a single dose (C1D1) of polatuzumab vedotin to be administered on Day 2 of the first dosing cycle;
(b) the second to sixth dosing cycles each comprises a single dose (C2D1-C6D1) of glofitamab and a single dose (C2D1-C6D1) of polatuzumab vedotin, wherein the C2D1 of glofitamab is about 30 mg; and
(c) the seventh to $12^{th}$ dosing cycles each comprises a single dose (C7D1-C12D1) of glofitamab and does not comprise administration of polatuzumab vedotin, and wherein each single dose C2D1-C12D1 of glofitamab is to be administered on Day 1 of each dosing cycle, and each single dose C2D1-C6D1 of polatuzumab vedotin is to be administered on Day 1 of each dosing cycle, and wherein each single dose C3D1-C12D1 of glofitamab is about equal in amount to the C2D1, and each single dose C1D1-C6D1 of polatuzumab vedotin is about 1.8 mg/kg.

183. The method, polatuzumab vedotin and glofitamab for use, or use of any one of embodiments 163-182, wherein the dosing cycles are 14-day dosing cycles.

184. The method, polatuzumab vedotin and glofitamab for use, or use of any one of embodiments 163-182, wherein the dosing cycles are 21-day dosing cycles.

185. The method, polatuzumab vedotin and glofitamab for use, or use of any one of embodiments 163-184, wherein glofitamab is administered intravenously.

186. The method, polatuzumab vedotin and glofitamab for use, or use of any one of embodiments 163-185, wherein polatuzumab vedotin is administered intravenously.

187. The method, polatuzumab vedotin and glofitamab for use, or use of any one of embodiments 163-186, wherein if glofitamab and polatuzumab vedotin are administered or are to be administered on the same day, then glofitamab is administered or is to be administered after the administration of polatuzumab vedotin has completed.

188. The method, polatuzumab vedotin and glofitamab for use, or use of embodiment 187, wherein glofitamab is administered or is to be administered between about 60-120 minutes after the administration of polatuzumab has completed.

189. The method, polatuzumab vedotin and glofitamab for use, or use of embodiment 188, wherein glofitamab is administered or is to be administered about 90 minutes after the administration of polatuzumab vedotin has completed.

190. The method of any one of embodiments 163, 167, 171, 175, 179, and 183-189, wherein the method further comprises administering to the subject obinutuzumab.

191. The polatuzumab vedotin and glofitamab for use or use of any one of embodiments 164-166, 168-170, 172-174, 176-178, and 180-189, wherein polatuzumab vedotin and glofitamab are administered with obinutuzumab.

192. The method, polatuzumab vedotin and glofitamab for use, or use of embodiment 190 or 191, wherein obinutuzumab is administered or is to be administered prior to administration of glofitamab.

193. The method, polatuzumab vedotin and glofitamab for use, or use of embodiment 192, wherein obinutuzumab is administered or is to be administered about seven days prior to administration of glofitamab.

194. The method, polatuzumab vedotin and glofitamab for use, or use of embodiment 192 or 193, wherein obinutuzumab is administered or is to be administered as a single dose of about 1000 mg.

195. The method, anti-CD79b antibody drug conjugate and bispecific antibody for use, or use of any one of embodiments 1-125, wherein the CD20-positive cell proliferative disorder is a B cell proliferative disorder.

196. The method, anti-CD79b antibody drug conjugate and bispecific antibody for use, or use of embodiment 195, wherein the B cell proliferative disorder is a non-Hodgkin's lymphoma (NHL) or a central nervous system lymphoma (CNSL).

197. The method, anti-CD79b antibody drug conjugate and bispecific antibody for use, or use of embodiment 196, wherein the NHL is relapsed and/or refractory.

198. The method, anti-CD79b antibody drug conjugate and bispecific antibody for use, or use of embodiment 196, wherein the NHL is a diffuse-large B cell lymphoma (DLBCL), a follicular lymphoma (FL), a mantle cell lymphoma (MCL), a marginal zone lymphoma (MZL), a high-grade B cell lymphoma, a primary mediastinal (thymic) large B cell lymphoma (PMLBCL), a diffuse B cell lymphoma, or a small lymphocytic lymphoma.

199. The method, anti-CD79b antibody drug conjugate and bispecific antibody for use, or use of embodiment 198, wherein the NHL is a DLBCL.

200. The method, anti-CD79b antibody drug conjugate and bispecific antibody for use, or use of embodiment 199, wherein the DLBCL is a relapsed or refractory DLBCL.

201. The method, anti-CD79b antibody drug conjugate and bispecific antibody for use, or use of embodiment 198, wherein the NHL is an FL.

202. The method, anti-CD79b antibody drug conjugate and bispecific antibody for use, or use of embodiment 201, wherein the FL is a relapsed or refractory FL.

203. The method, anti-CD79b antibody drug conjugate and bispecific antibody for use, or use of embodiment 201 or 2002, wherein the FL is a transformed FL.

204. The method, anti-CD79b antibody drug conjugate and bispecific antibody for use, or use of embodiment 198, wherein the NHL is an MCL.

205. The method, anti-CD79b antibody drug conjugate and bispecific antibody for use, or use of embodiment 204, wherein the MCL is a relapsed or refractory MCL.

206. The method, anti-CD79b antibody drug conjugate and bispecific antibody for use, or use of any one of embodiments 1-125, wherein the CD20-positive cell proliferative disorder is not a chronic lymphoid leukemia (CLL), an acute lymphoblastic leukemia (ALL), a Richter's transformation, a Burkitt lymphoma, or a lymphoplasmacytic lymphoma.

207. The method, polatuzumab vedotin and glofitamab for use, or use of any one of embodiments 163-194, wherein the CD20-positive cell proliferative disorder is a B cell proliferative disorder.

208. The method, polatuzumab vedotin and glofitamab for use, or use of embodiment 207, wherein the B cell proliferative disorder is a non-Hodgkin's lymphoma (NHL) or a central nervous system lymphoma (CNSL).

209. The method, polatuzumab vedotin and glofitamab for use, or use of embodiment 208, wherein the NHL is relapsed and/or refractory.

210. The method, polatuzumab vedotin and glofitamab for use, or use of embodiment 208, wherein the NHL is a diffuse-large B cell lymphoma (DLBCL), a follicular lymphoma (FL), a mantle cell lymphoma (MCL), a marginal zone lymphoma (MZL), a high-grade B cell lymphoma, a primary mediastinal (thymic) large B cell lymphoma (PMLBCL), a diffuse B cell lymphoma, or a small lymphocytic lymphoma.

211. The method, polatuzumab vedotin and glofitamab for use, or use of embodiment 210, wherein the NHL is a DLBCL.

212. The method, polatuzumab vedotin and glofitamab for use, or use of embodiment 211, wherein the DLBCL is a relapsed or refractory DLBCL.

213. The method, polatuzumab vedotin and glofitamab for use, or use of embodiment 210, wherein the NHL is an FL.

214. The method, polatuzumab vedotin and glofitamab for use, or use of embodiment 213, wherein the FL is a relapsed or refractory FL.

215. The method, polatuzumab vedotin and glofitamab for use, or use of embodiment 213 or 214, wherein the FL is a transformed FL.

216. The method, polatuzumab vedotin and glofitamab for use, or use of embodiment 120, wherein the NHL is an MCL.

217. The method, polatuzumab vedotin and glofitamab for use, or use of embodiment 216, wherein the MCL is a relapsed or refractory MCL.

218. The method, polatuzumab vedotin and glofitamab for use, or use of any one of embodiments 163-194, wherein the CD20-positive cell proliferative disorder is not a chronic lymphoid leukemia (CLL), an acute lymphoblastic leukemia (ALL), a Richter's transformation, a Burkitt lymphoma, or a lymphoplasmacytic lymphoma.

219. A method of treating a population of subjects having a R/R NHL comprising administering to the subjects an anti-CD79b antibody drug conjugate and an anti-CD20/anti-CD3 bispecific antibody in a dosing regimen comprising at least a first dosing cycle and a second dosing cycle, wherein:
(a) the first dosing cycle comprises a first dose (C1D1) of the anti-CD20/anti-CD3 bispecific antibody administered on Day 8 of the first dosing cycle, a second dose (C1D2) of the anti-CD20/anti-CD3 bispecific antibody administered on Day 15 of the first dosing cycle, and a single dose (C1D1) of the polatuzumab vedotin administered on Day 2 of the first dosing cycle, wherein the C1D1 of the anti-CD20/anti-CD3 bispecific antibody is about 2.5 mg, and the C1D2 of the anti-CD20/anti-CD3 bispecific antibody is about 10 mg; and
(b) the second dosing cycle comprises a single dose (C2D1) of the anti-CD20/anti-CD3 bispecific antibody administered on Day 1 of the second dosing cycle and a single dose (C2D1) of polatuzumab vedotin administered on Day 1 of the second dosing cycle, wherein the C2D1 of the anti-CD20/anti-CD3 bispecific antibody is about 30 mg, and
wherein the C1D1 and the C1D2 of the anti-CD79b antibody drug conjugate are each about 1.8 mg/kg.

220. An anti-CD79b antibody drug conjugate and an anti-CD20/anti-CD3 bispecific antibody for use in a method of treating a population of subjects having a R/R NHL, wherein the anti-CD79b antibody drug conjugate and the anti-CD20/anti-CD3 bispecific antibody are administered in a dosing regimen comprising at least a first dosing cycle and a second dosing cycle, wherein:
(a) the first dosing cycle comprises a first dose (C1D1) of the anti-CD20/anti-CD3 bispecific antibody to be administered on Day 8 of the first dosing cycle, a second dose (C1D2) of the anti-CD20/anti-CD3 bispecific antibody to be administered on Day 15 of the first dosing cycle, and a single dose (C1D1) of polatuzumab vedotin to be administered on Day 2 of the first dosing cycle, wherein the C1D1 of the anti-CD20/anti-CD3 bispecific antibody is about 2.5 mg, and the C1D2 of the anti-CD20/anti-CD3 bispecific antibody is about 10 mg; and
(b) the second dosing cycle comprises a single dose (C2D1) of the anti-CD20/anti-CD3 bispecific antibody to be administered on Day 1 of the second dosing cycle and a single dose (C2D1) of polatuzumab vedotin to be administered on Day 1 of the second dosing cycle, wherein the C2D1 of the anti-CD20/anti-CD3 bispecific antibody is about 30 mg, and
wherein the C1D1 and the C1D2 of the anti-CD79b antibody drug conjugate are each about 1.8 mg/kg.

221. Use of an anti-CD79b antibody drug conjugate and an anti-CD20/anti-CD3 bispecific antibody for treating a population of subjects having a R/R NHL, wherein the anti-CD79b antibody drug conjugate and the anti-CD20/anti-CD3 bispecific antibody are administered in a dosing regimen comprising at least a first dosing cycle and a second dosing cycle, wherein:
(a) the first dosing cycle comprises a first dose (C1D1) of the anti-CD20/anti-CD3 bispecific antibody to be administered on Day 8 of the first dosing cycle, a second dose (C1D2) of the anti-CD20/anti-CD3 bispecific antibody to be administered on Day 15 of the first dosing cycle, and a single dose (C1D1) of polatuzumab vedotin to be administered on Day 2 of the first dosing cycle, wherein the C1D1 of the anti-CD20/anti-CD3 bispecific antibody is about 2.5 mg, and the C1D2 of the anti-CD20/anti-CD3 bispecific antibody is about 10 mg; and
(b) the second dosing cycle comprises a single dose (C2D1) of the anti-CD20/anti-CD3 bispecific antibody to be administered on Day 1 of the second dosing cycle and a single dose (C2D1) of polatuzumab vedotin to be administered on Day 1 of the second dosing cycle, wherein the C2D1 of the anti-CD20/anti-CD3 bispecific antibody is about 30 mg, and
wherein the C1D1 and the C1D2 of the anti-CD79b antibody drug conjugate are each about 1.8 mg/kg.

222. Use of an anti-CD79b antibody drug conjugate and an anti-CD20/anti-CD3 bispecific antibody in the manufacture of a medicament for treating a population of subjects having a R/R NHL, wherein the anti-CD79b antibody drug conjugate and the anti-CD20/anti-CD3 bispecific antibody are administered in a dosing regimen comprising at least a first dosing cycle and a second dosing cycle, wherein:
(a) the first dosing cycle comprises a first dose (C1D1) of the anti-CD20/anti-CD3 bispecific antibody to be administered on Day 8 of the first dosing cycle, a second dose (C1D2) of the anti-CD20/anti-CD3 bispecific antibody to be administered on Day 15 of the first dosing cycle, and a single dose (C1D1) of polatuzumab vedotin to be administered on Day 2 of the first dosing cycle, wherein the C1D1 of the anti-CD20/anti-CD3 bispecific antibody is about 2.5 mg, and the C1D2 of the anti-CD20/anti-CD3 bispecific antibody is about 10 mg; and
(b) the second dosing cycle comprises a single dose (C2D1) of the anti-CD20/anti-CD3 bispecific antibody to be administered on Day 1 of the second dosing cycle and a single dose (C2D1) of polatuzumab vedotin to be administered on Day 1 of the second dosing cycle, wherein the C2D1 of the anti-CD20/anti-CD3 bispecific antibody is about 30 mg, and wherein the C1D1 and the C1D2 of the anti-CD79b antibody drug conjugate are each about 1.8 mg/kg.

223. A method of treating a population of subjects having a R/R NHL comprising administering to the subjects an anti-CD79b antibody drug conjugate and an anti-CD20/anti-CD3 bispecific antibody in a dosing regimen comprising 12 dosing cycles, wherein:
 (a) the first dosing cycle comprises:
  (i) a first dose (C1D1) of the anti-CD20/anti-CD3 bispecific antibody administered on Day 8 of the first dosing cycle and a second dose (C1D2) of the anti-CD20/anti-CD3 bispecific antibody to be administered on Day 15 of the first dosing cycle, wherein the C1D1 of the anti-CD20/anti-CD3 bispecific antibody is about 2.5 mg, and the C1D2 of the anti-CD20/anti-CD3 bispecific antibody is about 10 mg; and
  (ii) a single dose (C1D1) of the anti-CD79b antibody drug conjugate administered on Day 2 of the first dosing cycle;
 (b) the second to sixth dosing cycles each comprises a single dose (C2D1-C6D1) of the anti-CD20/anti-CD3 bispecific antibody and a single dose (C2D1-C6D1) of the anti-CD79b antibody drug conjugate; and
 (c) the seventh to 12$^{th}$ dosing cycles each comprises a single dose (C7D1-C12D1) of the anti-CD20/anti-CD3 bispecific antibody and does not comprise administration of the anti-CD79b antibody drug conjugate, and
wherein each single dose C2D1-C12D1 of the anti-CD20/anti-CD3 bispecific antibody is administered on Day 1 of each dosing cycle, and each single dose C2D1-C6D1 of the anti-CD79b antibody drug conjugate is administered on Day 1 of each dosing cycle, and wherein each single dose C2D1-C12D1 of the anti-CD20/anti-CD3 bispecific antibody is about 30 mg and each single dose C1D1-C6D1 of the anti-CD79b antibody drug conjugate is about 1.8 mg/kg.

224. An anti-CD79b antibody drug conjugate and an anti-CD20/anti-CD3 bispecific antibody for use in a method of treating a population of subjects having a R/R NHL, wherein the anti-CD79b antibody drug conjugate and the anti-CD20/anti-CD3 bispecific antibody are administered in a dosing regimen comprising 12 dosing cycles, wherein:
 (a) the first dosing cycle comprises:
  (i) a first dose (C1D1) of the anti-CD20/anti-CD3 bispecific antibody to be administered on Day 8 of the first dosing cycle and a second dose (C1D2) of the anti-CD20/anti-CD3 bispecific antibody to be administered on Day 15 of the first dosing cycle, wherein the C1D1 of the anti-CD20/anti-CD3 bispecific antibody is about 2.5 mg, and the C1D2 of the anti-CD20/anti-CD3 bispecific antibody is about 10 mg; and
  (ii) a single dose (C1D1) of the anti-CD79b antibody drug conjugate to be administered on Day 2 of the first dosing cycle;
 (b) the second to sixth dosing cycles each comprises a single dose (C2D1-C6D1) of the anti-CD20/anti-CD3 bispecific antibody and a single dose (C2D1-C6D1) of the anti-CD79b antibody drug conjugate; and
 (c) the seventh to 12$^{th}$ dosing cycles each comprises a single dose (C7D1-C12D1) of the anti-CD20/anti-CD3 bispecific antibody and does not comprise administration of the anti-CD79b antibody drug conjugate, and
wherein each single dose C2D1-C12D1 of the anti-CD20/anti-CD3 bispecific antibody is to be administered on Day 1 of each dosing cycle, and each single dose C2D1-C6D1 of the anti-CD79b antibody drug conjugate is to be administered on Day 1 of each dosing cycle, and wherein each single dose C2D1-C12D1 of the anti-CD20/anti-CD3 bispecific antibody is about 30 mg and each single dose C1D1-C6D1 of the anti-CD79b antibody drug conjugate is about 1.8 mg/kg.

225. Use of an anti-CD79b antibody drug conjugate and an anti-CD20/anti-CD3 bispecific antibody for treating a population of subjects having a R/R NHL, wherein the anti-CD79b antibody drug conjugate and the anti-CD20/anti-CD3 bispecific antibody are administered in a dosing regimen comprising 12 dosing cycles, wherein:
 (a) the first dosing cycle comprises:
  (i) a first dose (C1D1) of the anti-CD20/anti-CD3 bispecific antibody to be administered on Day 8 of the first dosing cycle and a second dose (C1D2) of the anti-CD20/anti-CD3 bispecific antibody to be administered on Day 15 of the first dosing cycle, wherein the C1D1 of the anti-CD20/anti-CD3 bispecific antibody is about 2.5 mg, and the C1D2 of the anti-CD20/anti-CD3 bispecific antibody is about 10 mg; and
  (ii) a single dose (C1D1) of the anti-CD79b antibody drug conjugate to be administered on Day 2 of the first dosing cycle;
 (b) the second to sixth dosing cycles each comprises a single dose (C2D1-C6D1) of the anti-CD20/anti-CD3 bispecific antibody and a single dose (C2D1-C6D1) of the anti-CD79b antibody drug conjugate; and
 (c) the seventh to 12$^{th}$ dosing cycles each comprises a single dose (C7D1-C12D1) of the anti-CD20/anti-CD3 bispecific antibody and does not comprise administration of the anti-CD79b antibody drug conjugate, and
wherein each single dose C2D1-C12D1 of the anti-CD20/anti-CD3 bispecific antibody is to be administered on Day 1 of each dosing cycle, and each single dose C2D1-C6D1 of the anti-CD79b antibody drug conjugate is to be administered on Day 1 of each dosing cycle, and wherein each single dose C2D1-C12D1 of the anti-CD20/anti-CD3 bispecific antibody is about 30 mg and each single dose C1D1-C6D1 of the anti-CD79b antibody drug conjugate is about 1.8 mg/kg.

226. Use of an anti-CD79b antibody drug conjugate and an anti-CD20/anti-CD3 bispecific antibody in the manufacture of a medicament for treating a population of subjects having a R/R NHL, wherein the anti-CD79b antibody drug conjugate and the anti-CD20/anti-CD3 bispecific antibody are administered in a dosing regimen comprising 12 dosing cycles, wherein:
 (a) the first dosing cycle comprises:
  (i) a first dose (C1D1) of the anti-CD20/anti-CD3 bispecific antibody to be administered on Day 8 of the first dosing cycle and a second dose (C1D2) of the anti-CD20/anti-CD3 bispecific antibody to be administered on Day 15 of the first dosing cycle, wherein the C1D1 of the anti-CD20/anti-CD3 bispecific antibody is about 2.5 mg, and the C1D2 of the anti-CD20/anti-CD3 bispecific antibody is about 10 mg; and
  (ii) a single dose (C1D1) of the anti-CD79b antibody drug conjugate to be administered on Day 2 of the first dosing cycle;
 (b) the second to sixth dosing cycles each comprises a single dose (C2D1-C6D1) of the anti-CD20/anti-CD3 bispecific antibody and a single dose (C2D1-C6D1) of the anti-CD79b antibody drug conjugate; and
 (c) the seventh to 12$^{th}$ dosing cycles each comprises a single dose (C7D1-C12D1) of the anti-CD20/anti-CD3 bispecific antibody and does not comprise administration of the anti-CD79b antibody drug conjugate, and
wherein each single dose C2D1-C12D1 of the anti-CD20/anti-CD3 bispecific antibody is to be administered on Day 1 of each dosing cycle, and each single dose C2D1-C6D1 of the anti-CD79b antibody drug conjugate is to be administered on Day 1 of each dosing cycle, and wherein each single dose C2D1-C12D1 of the anti-CD20/anti-CD3 bispecific antibody is about 30 mg and each single dose C1D1-C6D1 of the anti-CD79b antibody drug conjugate is about 1.8 mg/kg.

227. A method of treating a population of subjects having a R/R NHL comprising administering to the subjects polatuzumab vedotin and glofitamab in a dosing regimen comprising at least a first dosing cycle and a second dosing cycle, wherein:
(a) the first dosing cycle comprises a first dose (C1D1) of glofitamab administered on Day 8 of the first dosing cycle, a second dose (C1D2) of glofitamab administered on Day 15 of the first dosing cycle, and a single dose (C1D1) of polatuzumab vedotin administered on Day 2 of the first dosing cycle, wherein the C1D1 of glofitamab is about 2.5 mg, and the C1D2 of glofitamab is about 10 mg; and
(b) the second dosing cycle comprises a single dose (C2D1) of glofitamab administered on Day 1 of the second dosing cycle and a single dose (C2D1) of polatuzumab vedotin administered on Day 1 of the second dosing cycle, wherein the C2D1 of glofitamab is about 30 mg, and
wherein the C1D1 and the C2D1 of polatuzumab vedotin are each about 1.8 mg/kg.

228. Polatuzumab vedotin and glofitamab for use in a method of treating a population of subjects having a R/R NHL, wherein polatuzumab vedotin and glofitamab are administered in a dosing regimen comprising at least a first dosing cycle and a second dosing cycle, wherein:
(a) the first dosing cycle comprises a first dose (C1D1) of glofitamab to be administered on Day 8 of the first dosing cycle, a second dose (C1D2) of glofitamab to be administered on Day 15 of the first dosing cycle, and a single dose (C1D1) of polatuzumab vedotin to be administered on Day 2 of the first dosing cycle, wherein the C1D1 of glofitamab is about 2.5 mg, and the C1D2 of glofitamab is about 10 mg; and
(b) the second dosing cycle comprises a single dose (C2D1) of glofitamab to be administered on Day 1 of the second dosing cycle and a single dose (C2D1) of polatuzumab vedotin to be administered on Day 1 of the second dosing cycle, wherein the C2D1 of glofitamab is about 30 mg, and
wherein the C1D1 and the C2D1 of polatuzumab vedotin are each about 1.8 mg/kg.

229. Use of polatuzumab vedotin and glofitamab in treating a population of subjects having a R/R NHL, wherein polatuzumab vedotin and glofitamab are administered in a dosing regimen comprising at least a first dosing cycle and a second dosing cycle, wherein:
(a) the first dosing cycle comprises a first dose (C1D1) of glofitamab to be administered on Day 8 of the first dosing cycle, a second dose (C1D2) of glofitamab to be administered on Day 15 of the first dosing cycle, and a single dose (C1D1) of polatuzumab vedotin to be administered on Day 2 of the first dosing cycle, wherein the C1D1 of glofitamab is about 2.5 mg, and the C1D2 of glofitamab is about 10 mg; and
(b) the second dosing cycle comprises a single dose (C2D1) of glofitamab to be administered on Day 1 of the second dosing cycle and a single dose (C2D1) of polatuzumab vedotin to be administered on Day 1 of the second dosing cycle, wherein the C2D1 of glofitamab is about 30 mg, and
wherein the C1D1 and the C2D1 of polatuzumab vedotin are each about 1.8 mg/kg.

230. Use of polatuzumab vedotin and glofitamab in the manufacture of a medicament for treating a population of subjects having a R/R NHL, wherein polatuzumab vedotin and glofitamab are administered in a dosing regimen comprising at least a first dosing cycle and a second dosing cycle, wherein:
(a) the first dosing cycle comprises a first dose (C1D1) of glofitamab to be administered on Day 8 of the first dosing cycle, a second dose (C1D2) of glofitamab to be administered on Day 15 of the first dosing cycle, and a single dose (C1D1) of polatuzumab vedotin to be administered on Day 2 of the first dosing cycle, wherein the C1D1 of glofitamab is about 2.5 mg, and the C1D2 of glofitamab is about 10 mg; and
(b) the second dosing cycle comprises a single dose (C2D1) of glofitamab to be administered on Day 1 of the second dosing cycle and a single dose (C2D1) of polatuzumab vedotin to be administered on Day 1 of the second dosing cycle, wherein the C2D1 of glofitamab is about 30 mg, and
wherein the C1D1 and the C2D1 of polatuzumab vedotin are each about 1.8 mg/kg.

231. A method of treating a population of subjects having a R/R NHL comprising administering to the subjects polatuzumab vedotin and glofitamab in a dosing regimen comprising 12 dosing cycles, wherein:
(a) the first dosing cycle comprises:
(i) a first dose (C1D1) of glofitamab administered on Day 8 of the first dosing cycle and a second dose (C1D2) of glofitamab administered on Day 15 of the first dosing cycle, wherein the C1D1 of glofitamab is about 2.5 mg, and the C1D2 of glofitamab is about 10 mg; and
(ii) a single dose (C1D1) of polatuzumab vedotin administered on Day 2 of the first dosing cycle;
(b) the second to sixth dosing cycles each comprises a single dose (C2D1-C6D1) of glofitamab and a single dose (C2D1-C6D1) of polatuzumab vedotin; and
(c) the seventh to 12$^{th}$ dosing cycles each comprises a single dose (C7D1-C12D1) of glofitamab and does not comprise administration of polatuzumab vedotin, and
wherein each single dose C2D1-C12D1 of glofitamab is administered on Day 1 of each dosing cycle, and each single dose C2D1-C6D1 of polatuzumab vedotin is administered on Day 1 of each dosing cycle, and wherein each single dose C2D1-C12D1 of glofitamab is about 30 mg and each single dose C1D1-C6D1 of polatuzumab vedotin is about 1.8 mg/kg.

232. Polatuzumab vedotin and glofitamab for use in a method of treating a population of subjects having a R/R NHL, wherein polatuzumab vedotin and glofitamab are administered in a dosing regimen comprising 12 dosing cycles, wherein:
(a) the first dosing cycle comprises:
(i) a first dose (C1D1) of glofitamab to be administered on Day 8 of the first dosing cycle and a second dose (C1D2) of glofitamab to be administered on Day 15 of the first dosing cycle, wherein the C1D1 of glofitamab is about 2.5 mg, and the C1D2 of glofitamab is about 10 mg; and
(ii) a single dose (C1D1) of polatuzumab vedotin to be administered on Day 2 of the first dosing cycle;
(b) the second to sixth dosing cycles each comprises a single dose (C2D1-C6D1) of glofitamab and a single dose (C2D1-C6D1) of polatuzumab vedotin; and
(c) the seventh to 12$^{th}$ dosing cycles each comprises a single dose (C7D1-C12D1) of glofitamab and does not comprise administration of polatuzumab vedotin, and
wherein each single dose C2D1-C12D1 of glofitamab is to be administered on Day 1 of each dosing cycle, and each single dose C2D1-C6D1 of polatuzumab vedotin is to be administered on Day 1 of each dosing cycle, and wherein each single dose C2D1-C12D1 of glofitamab is about 30 mg and each single dose C1D1-C6D1 of polatuzumab vedotin is about 1.8 mg/kg.

233. Use of polatuzumab vedotin and glofitamab in treating a population of subjects having a R/R NHL, wherein polatuzumab vedotin and glofitamab are administered in a dosing regimen comprising 12 dosing cycles, wherein:
(a) the first dosing cycle comprises:
(i) a first dose (C1D1) of glofitamab to be administered on Day 8 of the first dosing cycle and a second dose (C1D2) of glofitamab to be administered on Day 15 of the first dosing cycle, wherein the C1D1 of glofitamab is about 2.5 mg, and the C1D2 of glofitamab is about 10 mg; and
(ii) a single dose (C1D1) of polatuzumab vedotin to be administered on Day 2 of the first dosing cycle;
(b) the second to sixth dosing cycles each comprises a single dose (C2D1-C6D1) of glofitamab and a single dose (C2D1-C6D1) of polatuzumab vedotin; and
(c) the seventh to 12$^{th}$ dosing cycles each comprises a single dose (C7D1) of glofitamab and does not comprise administration of polatuzumab vedotin, and
wherein each single dose C2D1-C12D1 of glofitamab is to be administered on Day 1 of each dosing cycle, and each single dose C2D1-C6D1 of polatuzumab vedotin is to be administered on Day 1 of each dosing cycle, and wherein each single dose C2D1-C12D1 of glofitamab is about 30 mg and each single dose C1D1-C6D1 of polatuzumab vedotin is about 1.8 mg/kg.

234. Use of polatuzumab vedotin and glofitamab in the manufacture of a medicament for treating a population of subjects having a R/R NHL, wherein polatuzumab vedotin and glofitamab are administered in a dosing regimen comprising 12 dosing cycles, wherein:
(a) the first dosing cycle comprises:
(i) a first dose (C1D1) of glofitamab to be administered on Day 8 of the first dosing cycle and a second dose (C1D2) of glofitamab to be administered on Day 15 of the first dosing cycle, wherein the C1D1 of glofitamab is about 2.5 mg, and the C1D2 of glofitamab is about 10 mg; and
(ii) a single dose (C1D1) of polatuzumab vedotin to be administered on Day 2 of the first dosing cycle;
(b) the second to sixth dosing cycles each comprises a single dose (C2D1-C6D1) of glofitamab and a single dose (C2D1-C6D1) of polatuzumab vedotin; and
(c) the seventh to 12$^{th}$ dosing cycles each comprises a single dose (C7D1) of glofitamab and does not comprise administration of polatuzumab vedotin, and
wherein each single dose C2D1-C12D1 of glofitamab is to be administered on Day 1 of each dosing cycle, and each single dose C2D1-C6D1 of polatuzumab vedotin is to be administered on Day 1 of each dosing cycle, and wherein each single dose C2D1-C12D1 of glofitamab is about 30 mg and each single dose C1D1-C6D1 of polatuzumab vedotin is about 1.8 mg/kg.

235. The method, anti-CD79b antibody drug conjugate and bispecific antibody for use, or use of any one of embodiments 219-226, wherein the complete response rate is at least 20%.

236. The method, anti-CD79b antibody drug conjugate and bispecific antibody for use, or use of embodiment 235, wherein the complete response rate is at least 40%.

237. The method, anti-CD79b antibody drug conjugate and bispecific antibody for use, or use of any one of embodiments 219-226, wherein the overall response rate is at least 30%.

238. The method, anti-CD79b antibody drug conjugate and bispecific antibody for use, or use of embodiment 237, wherein the overall response rate is at least 50%.

239. The method, anti-CD79b antibody drug conjugate and bispecific antibody for use, or use of any one of embodiments 219-226, wherein the B cell proliferative disorder is a R/R MCL.

240. The method, anti-CD79b antibody drug conjugate and bispecific antibody for use, or use of embodiment 239, wherein the complete response rate is at least 60%.

241. The method, anti-CD79b antibody drug conjugate and bispecific antibody for use, or use of embodiment 240, wherein the complete response rate is at least 80%.

242. The method, anti-CD79b antibody drug conjugate and bispecific antibody for use, or use of embodiment 239, wherein the overall response rate is at least 60%.

243. The method, anti-CD79b antibody drug conjugate and bispecific antibody for use, or use of embodiment 242, wherein the overall response rate is at least 80%.

244. The method, anti-CD79b antibody drug conjugate and bispecific antibody for use, or use of any one of embodiments 219-226, wherein the B cell proliferative disorder is a R/R DLBCL.

245. The method, anti-CD79b antibody drug conjugate and bispecific antibody for use, or use of embodiment 244, wherein the complete response rate is at least 35%.

246. The method, anti-CD79b antibody drug conjugate and bispecific antibody for use, or use of embodiment 245, wherein the complete response rate is at least 45%.

247. The method, anti-CD79b antibody drug conjugate and bispecific antibody for use, or use of embodiment 246, wherein the complete response rate is at least 55%.

248. The method, anti-CD79b antibody drug conjugate and bispecific antibody for use, or use of embodiment 247, wherein the complete response rate is at least 60%.

249. The method, anti-CD79b antibody drug conjugate and bispecific antibody for use, or use of embodiment 248, wherein the complete response rate is at least 65%.

250. The method, anti-CD79b antibody drug conjugate and bispecific antibody for use, or use of embodiment 249, wherein the complete response rate is at least 70%.

251. The method, anti-CD79b antibody drug conjugate and bispecific antibody for use, or use of embodiment 250, wherein the complete response rate is at least 75%.

252. The method, anti-CD79b antibody drug conjugate and bispecific antibody for use, or use of embodiment 251, wherein the complete response rate is at least 85%.

253. The method, anti-CD79b antibody drug conjugate and bispecific antibody for use, or use of embodiment 252, wherein the complete response rate is at least 90%.

254. The method, anti-CD79b antibody drug conjugate and bispecific antibody for use, or use of embodiment 244, wherein the overall response rate is at least 60%.

255. The method, anti-CD79b antibody drug conjugate and bispecific antibody for use, or use of embodiment 254, wherein the overall response rate is at least 70%.

256. The method, anti-CD79b antibody drug conjugate and bispecific antibody for use, or use of embodiment 255, wherein the overall response rate is at least 80%.

257. The method, anti-CD79b antibody drug conjugate and bispecific antibody for use, or use of embodiment 256, wherein the overall response rate is at least 85%.

258. The method, anti-CD79b antibody drug conjugate and bispecific antibody for use, or use of embodiment 257, wherein the overall response rate is at least 90%.

259. The method, anti-CD79b antibody drug conjugate and bispecific antibody for use, or use of any one of embodiments 219-226, wherein the complete response rate is higher than a reference complete response rate in a reference population of subjects treated with a combination therapy comprising an anti-CD20/anti-CD3 bispecific antibody and an anti-PD-L1 antagonist antibody and not comprising an anti-CD79b antibody drug conjugate.

260. The method, anti-CD79b antibody drug conjugate and bispecific antibody for use, or use of any one of embodiments 219-226, wherein the objective response rate is higher than a reference objective response rate in a reference population of subjects treated with a combination therapy comprising an anti-CD20/anti-CD3 bispecific antibody and an anti-PD-L1 antagonist antibody and not comprising an anti-CD79b antibody drug conjugate.

261. The method, polatuzumab vedotin and glofitamab for use, or use of any one of embodiments 227-234, wherein the complete response rate is at least 20%.

262. The method, polatuzumab vedotin and glofitamab for use, or use of embodiment 261, wherein the complete response rate is at least 40%.

263. The method, polatuzumab vedotin and glofitamab for use, or use of any one of embodiments 227-234, wherein the overall response rate is at least 30%.

264. The method, polatuzumab vedotin and glofitamab for use, or use of embodiment 263, wherein the overall response rate is at least 50%.

265. The method, polatuzumab vedotin and glofitamab for use, or use of any one of embodiments 227-234, wherein the R/R NHL is a R/R MCL.

266. The method, polatuzumab vedotin and glofitamab for use, or use of embodiment 265, wherein the complete response rate is at least 60%.

267. The method, polatuzumab vedotin and glofitamab for use, or use of embodiment 266, wherein the complete response rate is at least 80%.

268. The method, polatuzumab vedotin and glofitamab for use, or use of embodiment 265, wherein the overall response rate is at least 60%.

269. The method, polatuzumab vedotin and glofitamab for use, or use of embodiment 268, wherein the overall response rate is at least 80%.

270. The method, polatuzumab vedotin and glofitamab for use, or use of any one of embodiments 227-234, wherein the R/R NHL is a R/R DLBCL.

271. The method, polatuzumab vedotin and glofitamab for use, or use of embodiment 270, wherein the complete response rate is at least 35%.

272. The method, polatuzumab vedotin and glofitamab for use, or use of embodiment 271, wherein the complete response rate is at least 45%.

273. The method, polatuzumab vedotin and glofitamab for use, or use of embodiment 272, wherein the complete response rate is at least 55%.

274. The method, polatuzumab vedotin and glofitamab for use, or use of embodiment 274, wherein the complete response rate is at least 60%.

275. The method, polatuzumab vedotin and glofitamab for use, or use of embodiment 274, wherein the complete response rate is at least 65%.

276. The method, polatuzumab vedotin and glofitamab for use, or use of embodiment 275, wherein the complete response rate is at least 70%.

277. The method, polatuzumab vedotin and glofitamab for use, or use of embodiment 276, wherein the complete response rate is at least 75%.

278. The method, polatuzumab vedotin and glofitamab for use, or use of embodiment 277, wherein the complete response rate is at least 85%.

279. The method, polatuzumab vedotin and glofitamab for use, or use of embodiment 278, wherein the complete response rate is at least 90%.

280. The method, polatuzumab vedotin and glofitamab for use, or use of embodiment 270, wherein the overall response rate is at least 60%.

281. The method, polatuzumab vedotin and glofitamab for use, or use of embodiment 280, wherein the overall response rate is at least 70%.

282. The method, polatuzumab vedotin and glofitamab for use, or use of embodiment 281, wherein the overall response rate is at least 80%.

283. The method, anti-CD79b antibody drug conjugate and bispecific antibody for use, polatuzumab vedotin and glofitamab for use, or use of embodiment 282, wherein the overall response rate is at least 85%.

284. The method, anti-CD79b antibody drug conjugate and bispecific antibody for use, polatuzumab vedotin and glofitamab for use, or use of embodiment 283, wherein the overall response rate is at least 90%.

285. The method, polatuzumab vedotin and glofitamab for use, or use of any one of embodiments 227-234, wherein the complete response rate is higher than a reference complete response rate in a reference population of subjects treated with a combination therapy comprising glofitamab and atezolizumab and not comprising polatuzumab vedotin.

286. The method, polatuzumab vedotin and glofitamab for use, or use of any one of embodiments 227-234, wherein the objective response rate is higher than a reference objective response rate in a reference population of subjects treated with a combination therapy comprising glofitamab and atezolizumab and not comprising polatuzumab vedotin.

287. The method, polatuzumab vedotin and glofitamab for use, or use of any one of embodiments 163-194, 207-218, 227-234, and 261-286, wherein the subject or population of subjects is human.

288. The method, anti-CD79b antibody drug conjugate and bispecific antibody for use, or use of any one of embodiments 1-162, 195-206, 219-226, and 235-260, wherein the subject or population of subjects is human.

289. The method, anti-CD79b antibody drug conjugate and bispecific antibody for use, polatuzumab vedotin and glofitamab for use, or use of any one of the preceeding embodiments, wherein the subject or population of subjects has received at least two prior systemic therapies.

290. The method, anti-CD79b antibody drug conjugate and bispecific antibody for use, or polatuzumab vedotin and glofitamab for use of any one of the preceeding embodiments, wherein the subject or population of subjects is ineligible for autologous stem cell transplant (SCT).

EXAMPLES

The following are examples of methods and compositions of the invention. It is understood that various other embodiments may be practiced, given the general description provided above.

Example 1. An Open-Label, Multi-Center, Phase Ib Study of Glofitamab and Atezolizumab or Polatuzumab Vedotin (Plus a Single Pre-Treatment Dose of Obinutuzumab) in Adult Patients with Relapsed/Refractory B-Cell Non-Hodgkin's Lymphoma Objectives This study evaluates the safety, tolerability, pharmacokinetics, and efficacy of glofitamab, a T-cell-engaging bispecific (TCB) antibody, in combination with polatuzumab vedotin in patients with B-cell NHL. Specific objectives and corresponding endpoints for the study are outlined in Table 7.

TABLE 7

Objectives and Endpoints

| Objectives | Corresponding Endpoints |
|---|---|
| Primary Objectives: | |
| To determine the maximum tolerated dose (MTD) and/or recommended Phase II dose (RP2D) for glofitamab in combination with atezolizumab (including a single pre-treatment dose of obinutuzumab) To determine the MTD and/or recommended Phase II dose (RP2D) for glofitamab in combination with polatuzumab vedotin (including a single pre-treatment dose of obinutuzumab) | Incidence and nature of dose-limiting toxicities (DLTs) during the DLT observation period |
| Safety Objective: | |
| To evaluate the safety and tolerability of glofitamab in combination with atezolizumab or polatuzumab vedotin (including a single pre-treatment dose of obinutuzumab) To explore Relationship between patient's baseline disease characteristics with AEs including CRS | Incidence, nature, frequency, severity, and timing of adverse events (AEs) and serious adverse events (SAEs). AEs/SAEs are graded according to NCI-CTCAE V4 Changes in vital signs (VS), electrocardiograms (ECGs), and clinical laboratory results during and following study treatment administration Incidence of anti-drug antibody (ADA) formation |
| Efficacy Objectives: | |
| To assess preliminary anti-tumor activity of glofitamab in combination with atezolizumab or polatuzumab vedotin (including a single pre-treatment dose of obinutuzumab) To determine preliminary anti-tumor activity of glofitamab in combination with atezolizumab or polatuzumab vedotin (including a single pre-treatment dose of obinutuzumab) for CR patients with re-treatment at time of disease progression. To evaluate preliminary anti-tumor activity of glofitamab in combination with atezolizumab or polatuzumab vedotin (including a single pre-treatment dose of obinutuzumab) when using the LYRIC criteria | Complete response (CR) rate as assessed by FDG-PET/CT-scan Objective response rate (ORR) Disease control rate (DCR) Duration of response (DOR) Duration of complete response Time to first complete response (TFCR) Time to first overall response (TFOR) Progression-free survival (PFS) Overall survival (OS) Efficacy endpoints are assessed according to Lugano Classification (Cheson et al., 2014) or LYRIC criteria (Cheson et al. 2016) |
| Pharmacokinetics Objectives | |
| To characterize the pharmacokinetics (PK) of glofitamab when administered in combination with atezolizumab or polatuzumab vedotin To characterize the PK of atezolizumab when administered in combination with glofitamab To characterize the PK of polatuzumab vedotin when administered in combination with glofitamab | The following PK parameters are derived from the serum concentration-time profile of glofitamab following administration when appropriate, as data allow: Elimination half-life ($T_{1/2}$) Total serum exposure - Area under the concentration-time curve (AUC) Time to maximum observed serum concentration ($T_{max}$) Maximum serum concentration observed ($C_{max}$) Minimum serum concentration ($C_{min}$) under steady-state conditions within a dosing interval Other PK parameters such as clearance (CL), and volume of distribution at steady-state ($V_{ss}$), may also be calculated as data allow. For atezolizumab and polatuzumab vedotin, key PK parameters are derived from serum concentration-time profile of atezolizumab and polatuzumab vedotin following administration. |
| Biomarker/Pharmacodynamics Objectives: | |
| To assess mode of action of glofitamab in combination with atezolizumab or polatuzumab vedotin To investigate pharmacodynamic (PD) effects of glofitamab in combination with atezolizumab or polatuzumab vedotin To assess biomarkers that might predict response or resistance to glofitamab in combination with atezolizumab or polatuzumab vedotin To explore minimal residual disease (MRD) as a potential prognostic marker in patients who receive glofitamab in combination with atezolizumab or polatuzumab vedotin | Immune cell changes in blood and tumor tissue (e.g., T-cell activation/exhaustion/reinvigoration, CD4/CD8 T-cell ratio), pro-inflammatory cytokine release. PD-L1 status Genetic and transcriptomic markers (e.g., mutational status, mutational load, cell-of-origin [COO], gene expression) MRD Additional biomarkers may be explored depending on emerging data |

TABLE 7-continued

Objectives and Endpoints

| Objectives | Corresponding Endpoints |
|---|---|
| Tocilizumab Objectives: | |
| To make a preliminary assessment of the efficacy of tocilizumab (ACTEMRA ®/ ROACTEMRA ®) in ameliorating the symptoms of severe CRS following glofitamab treatment | Changes in the nature and severity of severe CRS following administration of tocilizumab for severe CRS and changes in cytokine levels and clinical laboratory values following administration of tocilizumab for CRS |
| To characterize the PK of tocilizumab when administered together with glofitamab or in combination with glofitamab and atezolizumab or in combination with glofitamab and polatuzumab vedotin | The following PK parameters are derived from the serum concentration-time profile of tocilizumab following administration when appropriate, as data allow: $C_{max}$ $C_{trough}$ |

Study Design

This is an open-label, single arm, multicenter, dose finding, Phase Ib study in order to assess the MTD and/or recommended Phase II dose (RP2D) for the combination treatment of glofitamab plus atezolizumab (atezolizumab arm) or glofitamab plus polatuzumab vedotin (polatuzumab vedotin arm) and to evaluate the general safety, tolerability, PK, pharmacodynamic, and preliminary anti-tumor activity of both combination treatments in adult patients.

Overall Design

Figure 3:
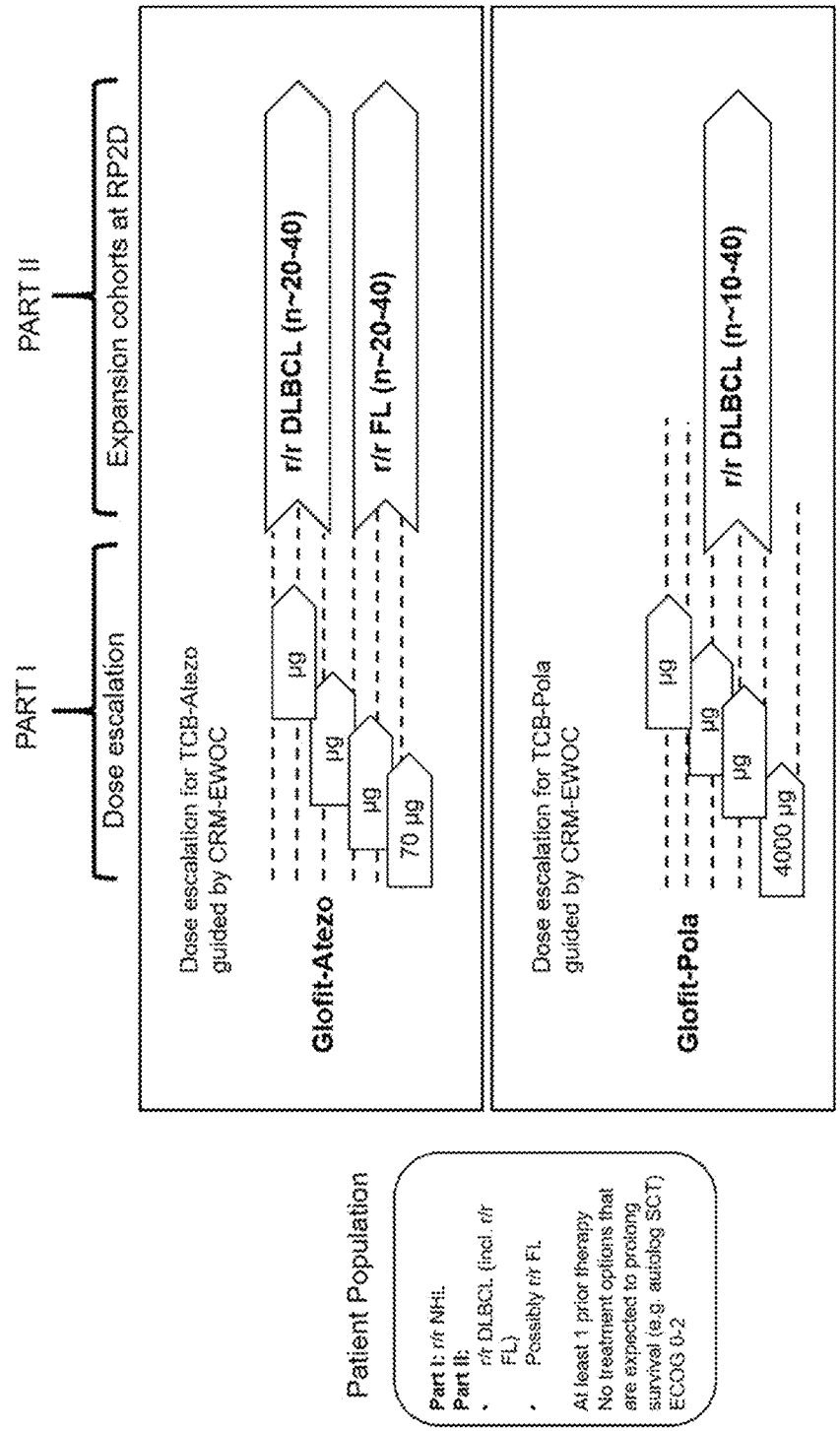
FIG. 3 is a schematic showing the overview of the study design as described in Example 1. Atezo=atezolizumab; CRM=continual reassessment method; DLBCL=diffuse large B-cell lymphoma; ECOG=Eastern Cooperative Oncology Group; EWOC=escalation with overdose control; FL=follicular lymphoma; Pola=polatuzumab vedotin; R/R=relapsed and/or refractory; SCT=Society for Clinical Trials; TCB=glofitamab.

An overview of the study design is provided in FIG. 3.

Study treatment consists of escalating doses of glofitamab in combination with:

Atezolizumab arm: Fixed doses of atezolizumab (1200 mg) starting from Cycle 2 onwards.

Polatuzumab vedotin arm: Polatuzumab vedotin dose of 1.8 mg/kg starting from Cycle 1 onwards The treatment in both combination arms includes one fixed dose of obinutuzumab given seven days before first dose of glofitamab in order to prevent/reduce cytokine release when glofitamab is administered first time.

The study has 2 parts: a dose-escalation and an expansion part:

A) Dose-Escalation Part:

The dose-escalation part was conducted in patients with relapsed/refractory (R/R) B-cell malignancies expected to express CD20 (no CD20 expression profiling required). Patients with CLL, acute lymphoblastic leukemia (including CD20+ ALL), Burkitt lymphoma, Richter's transformation, and lymphoplasmacytic lymphoma were excluded.

Atezolizumab arm: Starting dose 70 µg glofitamab. Dose-escalation continued until the MTD, and/or preliminary RP2D was defined.

Polatuzumab vedotin arm: Starting dose 4 mg glofitamab or below. Dose-escalation continued until the MTD, and/or preliminary RP2D was defined.

B) Expansion Part

The expansion part is conducted upon clearance of the dose escalation cohorts at the RP2D. Based on the available data from this as well as other glofitamab studies, the following dose expansion cohorts per NHL entity is conducted in patients with R/R DLBCL and R/R FL in patients with at least one prior treatment regimen.

Atezolizumab arm: Up to 40 patients with R/R FL and up to 40 patients with R/R DLBCL are enrolled in the atezolizumab arm of the expansion part of the study and treated at the preliminary RP2D in order to confirm this dose for future studies and to investigate the preliminary anti-tumor activity in this patient population in a larger number of patients.

Polatuzumab vedotin arm: Approximately 10 to 40 patients with R/RDLBCL are enrolled in the polatuzumab vedotin arm of the expansion part of the study and treated at the preliminary RP2D in order to confirm this dose for future studies. In addition, an exploratory evaluation of efficacy is performed.

Figure 4A:
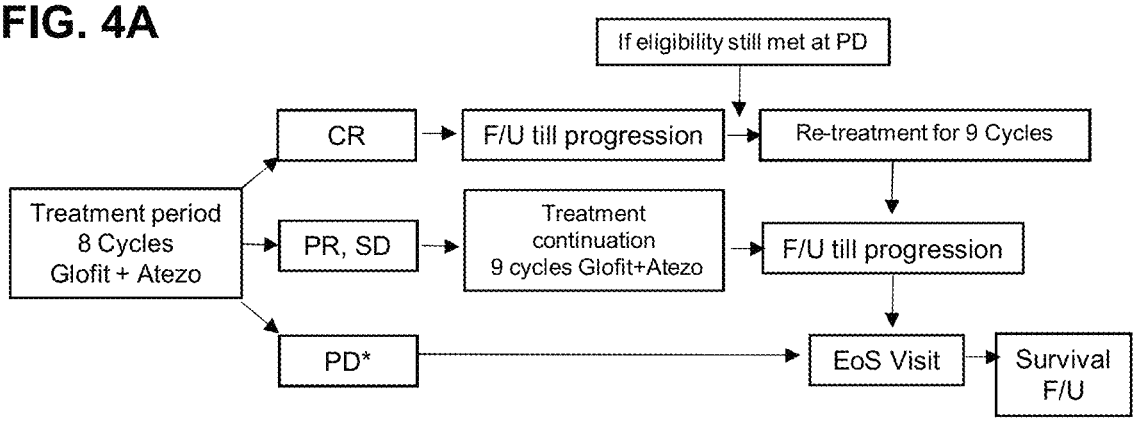
FIG. 4A-FIG. 4C are schematics showing the study design for the atezolizumab arm (FIG. 4A), dose escalation phase of the polatuzumab arm (FIG. 4B), and expansion phase of the polatuzumab arm (FIG. 4C) as described in Example 1. Atezo=atezolizumab; CR=complete response; DE=dose escalation; DLBCL=diffuse large B cell lymphoma; EoS=end of study; F/U=follow-up; Glofit=glofitamab; NHL=non-Hodgkin's lymphoma; Pola=polatuzumab vedotin; PD=progressive disease; PR=partial response; Pts=patients; RP2D=recommended Phase II dose; R/R=relapsed and/or refractory; SD=stable disease.
Figure 4B:
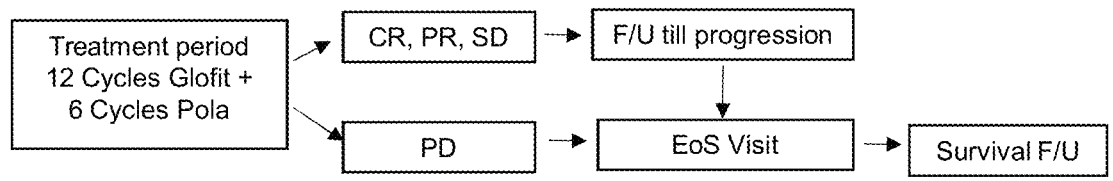
Figure 4C:
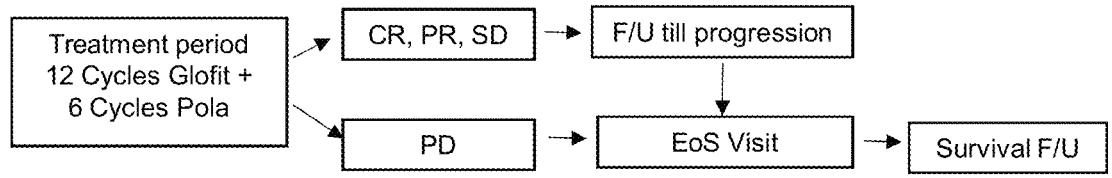

An overview of the current study design for the atezolizumab arm is provided in FIG. 4A. An overview of the current study design for the polatuzumab vedotin arm is provided in FIG. 4B, and an overview of the planned study design for the expansion phase of polatuzumab vedotin is provided in FIG. 4C. The study designs for the two arms are described below:

Atezolizumab Arm:

Eight dosing cycles of glofitamab with atezolizumab are administered on a 3-weekly (Q3W) schedule of study treatment, unless patients discontinue study treatment and/or discontinue the study earlier due to disease progression, unacceptable toxicities, or withdrawal of consent. After completion of 8 dosing cycles, patients then undergo a tumor assessment to determine if additional treatment can be given.

Based upon their treatment response in Cycle 8, the following occurs:

Complete response (CR): Patients who have achieved CR after 8 treatment cycles end treatment but continue to be followed. At the time of disease progression, the patients have the possibility to receive re-treatment with 9 additional cycles of glofitamab and atezolizumab Partial response (PR) or stable disease (SD): Patients who achieved PR or SD after 8 treatment cycles continue combination treatment with atezolizumab and glofitamab for an additional 9 dosing cycles Progressive disease (PD): Patients with progressive disease after 8 treatment cycles (or earlier in case of rapid progression) discontinue from the study and go into survival follow-up and are not treated anymore with this combination regimen.

Polatuzumab Vedotin Arm:

Six dosing cycles of polatuzumab vedotin and 12 dosing cycles of glofitamab are administered on a Q3W schedule of study treatment, unless patients discontinue study treatment and/or discontinue the study earlier due to disease progression, unacceptable toxicities, or withdrawal of consent.

Both Arms:

In the event of a delayed response, i.e., patients have been withdrawn from study treatment due to progression or pseudoprogression, who later achieve PR or CR without receiving any other therapy after last dose of combination treatment with glofitamab plus atezolizumab or polatuzumab vedotin, patients are allowed to continue the study if Investigator and Sponsor considers this in the best interest of the patient and if they still meet the eligibility criteria. Continuation of the study is independent from the duration of the dose delay, i.e., the allowed treatment delay of maximum 3 weeks is not applied in such a case. However, as a safety measure, Gpt may be given 7 days prior to resuming treatment with glofitamab after discussion and agreement with Investigator and Sponsor.

All patients attend an End of Treatment (EoT) visit after receiving the last administration of study drug (note: patients achieving a CR have an EoT visit and if they are retreated, an End of Re-treatment visit after completion of retreatment). In case of progressive disease (PD), this is also considered as the End of Study (EoS) visit.

Patients with evidence of disease control (CR, PR, SD) enter the "follow-up until progression" period, where they are followed until disease progression. At time of disease progression, the patients undergo the EoS visit (note: patients achieving a CR do not have an EoS visit at the time of progression; they have the possibility to be retreated and in this case only enter the EoS visit at time of second progression). After study completion all patients enter the Survival Follow-up Period with assessments (phone calls or clinic visits) every 3 months The treatment period for this protocol may be modified if emerging data suggest a benefit.

Step Up Dosing

Both study parts (dose-escalation and expansion) started exploring a step-up dosing regimen in which an initial lower dose of glofitamab is be administered first followed by a higher dose administered 1 week later. This applies for both: the initial treatment phase and—if the patient is eligible for re-treatment—also for Cycle 9 of the re-treatment phase in the atezolizumab cohort. If emerging data from the first patients under this regimen suggest that this is not sufficient to prevent/reduce CRS, another step may be implemented for the atezolizumab arm on Day 15. The total dose administered in Cycle 1 does not exceed the dose previously cleared for safety within the Sponsor's EIH study NP30179 Higher doses may be explored from Cycle 2 onward.

Step up dosing initially requires hospitalization. Patients also remain hospitalized for Cycle 2 as this is the first time when both agents (glofitamab plus atezolizumab or polatuzumab vedotin) are administered together. Hospitalization guidelines are as follows:

Atezolizumab arm: on Day 1 of Cycle 1, Day 8 of Cycle 1, and Day 1 of Cycle 2 (as well as Day 1 of Cycle 9, Day 8 of Cycle 9, and Day 1 of Cycle 10 in case of re-treatment)

Polatuzumab vedotin arm: on Day 8 of Cycle 1, Day 15 of Cycle 1, and Day 1 of Cycle 2 until the IMC together with study investigators determine that mandatory hospitalization on any of these days is no longer required.

Infusion Duration

For the first 2 dosing cycles, the infusion duration for glofitamab is 4 hours.

In the absence of infusion-related reactions (IRRs)/CRS, the infusion time from Cycle 3 onwards may be reduced to two hours.

In patients who may be at increased risk of CRS, patients who experience IRRs or CRS with their previous dose of glofitamab or who are at increased risk of recurrent IRR/CRS with subsequent doses, the next dose and time of infusion may be extended to up to 8 hours. Modifications to infusion time in these circumstances should be discussed with the Medical Monitor.

Administration of Glofitamab and Polatuzumab Vedotin

Glofitamab is administered by IV infusion at escalating doses on Day 1 of each Cycle with the exception of Cycle 1 where glofitamab is administered in 2 steps on Day 8 and Day 15. Polatuzumab vedotin is administered by IV infusion with a fixed dose of 1.8 mg/kg on Day 2 of Cycle 1 and on Day 1 of each subsequent dosing cycle. When both agents are administered on the same day, polatuzumab vedotin is administered first, followed by glofitamab, with glofitamab infusion to begin at least 90 minutes after the completion of the polatuzumab vedotin infusion, provided that patients have recovered from any acute toxicity mediated by the preceding administration. If prior polatuzumab vedotin infusion has been well tolerated, the time interval between the end of infusion of polatuzumab vedotin and the start of glofitamab infusion can be reduced but should be at least 1 hour. In case of acute toxicity preventing from dosing both agents on the same day, the administration of glofitamab may be delayed up to a maximum of 36 hours (starting from end of polatuzumab vedotin infusion).

All glofitamab infusions should be administered to patients after pre-medication with oral acetaminophen (e.g., 650-1000 mg), an antihistamine such as diphenhydramine hydrochloride (50-100 mg), and a glucocorticoid (e.g., 100 mg intravenous prednisolone or equivalent) 30-60 minutes prior to starting each infusion. For patients who do not experience Grade 2 infusion-related symptoms with their previous infusion, pre-medication at subsequent infusions may be omitted at the investigator's discretion. For polatuzumab vedotin the following applies: Premedication (e.g., 500-1000 mg of oral acetaminophen or paracetamol and 50-100 mg diphenhydramine as per institutional standard practice) may be administered to an individual patient before administration of polatuzumab vedotin. Administration of corticosteroids is permitted at the discretion of the treating physician. If infusion-related reactions (IRRs) are observed with the first infusion in the absence of premedication, premedication must be administered before subsequent doses.

Length of Study

The total duration of the study for each patient is approximately 13-14 months from screening until the EoT visit plus an undefined time thereafter (individual for each patient) and is divided as follows:

Screening: Up to 4 weeks (screening period starts with date of Informed Consent Form).

Hospitalization for 48 hours in Cycle 1 (for both step-up doses) and Cycle 2.

Atezolizumab arm: on day 1 of dosing cycle 1, day 8 of dosing cycle 1, and day 1 of dosing cycle 2 (as well as day 1 of dosing cycle 9, day 8 of dosing cycle 9, and day 1 of dosing cycle 10 in case of re-treatment)

Polatuzumab vedotin arm: on day 8 of dosing cycle 1, day 15 of dosing cycle 1, and day 1 of dosing cycle 2

Treatment Period: approximately 6-12 months.

EoT visit: At 4 (±2) weeks after receiving the last administration of study drug. Follow-up until progression period: Patients undergo visits approximately every 3 months until disease progression.

EoS visit: To be performed within 4 weeks after disease progression or also performed within 4 weeks due to unacceptable toxicity, Investigator's decision or withdrawal of consent.

Survival Follow-up period: After the EoS visit, all patients are followed for survival and subsequent anti-cancer therapy approximately every 3 months (e.g., by phone call or clinic visit) until death, loss to follow-up or study termination by Roche, whichever occurs first.

Dose-Escalation

Dose-escalation is guided by the modified continual reassessment method escalation with overdose control (mCRM-EWOC) model (Neuenschwander et al., 2008). During the dose-escalation phase, at least 3 patients are enrolled in each cohort, which, if required, may be expanded with additional patients in order to collect additional data on PK, pharmacodynamics or safety. Patients who discontinue from the study prior to completing the dose-limiting toxicities (DLT) observation window for reasons other than drug-related toxicity are replaced. The starting dose-level for glofitamab is 70 µg for the atezolizumab arm and 4 mg or below for the polatuzumab vedotin arm.

Dose-escalation is explored in step-up dosing regimens in which initial low glofitamab doses are administered:

for the atezolizumab arm on Day 1 of Cycle 1 (7 days after obinutuzumab administration) followed by a higher dose administered on Day 8 of Cycle 1, and a target dose on Day 15 of Cycle 1 and for the polatuzumab vedotin arm on Day 8 of Cycle 1 (7 days after obinutuzumab administration) followed by a higher dose administered on Day 15 of Cycle 1 and a target dose administered on Day 1 of Cycle 2.

The total dose administered in Cycle 1 does not exceed the determined MTD for single agent glofitamab, but increased doses may be explored from Cycle 2 onward.

Due to the fact, that in the polatuzumab vedotin arm the DLT period starts with step-up dosing on Day 8 of Cycle 1, the mCRM-EWOC model may be used to guide dose-escalation in C2 after step-up dosing in C1. It is expected that step-up dosing in Cycle 1 does help to reduce the occurrence and severity of first-cycle CRS (DLTs); therefore, the probability of DLT predicted by the CRM model is likely to be overestimated for Cycle 2 dosing. Consequently, the model is considered conservative and protective of patient safety. Estimates of the probability of DLT produced by the CRM model evolve over time to more closely match the risk appropriate to the new dosing regimen as further information is collected.

In the atezolizumab arm, the DLT period starts in Cycle 2. Therefore, in order to evaluate the overall tolerability including the step-up dosing with glofitamab, any glofitamab-related safety events observed during step-up dosing are taken into account, i.e., the MTD/RP2D for C1 is not based on the mCRM-EWOC model but on the overall observed tolerability.

Once a minimum of 3 patients have completed the DLT observation period, further treatment of the next cohort only resumes after the IMC in consultation with the Investigators have evaluated the next recommended dose calculated by the mCRM-EWOC model and recommends the dose for the subsequent cohort.

Dose-escalation decisions and selection of the dose for the next cohort of patients are made following review of all relevant available data (e.g., safety, PK, pharmacodynamic, activity) and not solely on DLT type and frequency. At each dose-escalation step, the dose can be escalated, de-escalated, or further investigated by expansion of the current dose-level cohort. For safety constraints, the maximum allowable dose increment is 250% of the full C1 dose for Part I. In addition, escalating doses calculated by the model can be overruled by the IMC (either downward or upward) after consultation with the study Investigators, i.e., clinical judgment always overrides model estimates when selecting the next dose.

Upon discussion and agreement between the Sponsor and the Investigator individual patients may switch to a higher dose of glofitamab, however, only up to the dose level that has been considered as safe when given in combination with atezolizumab or polatuzumab vedotin (i.e., at least one dose-level below the actual tested dose level in study NP39488). Based on the model, dose-escalation continues in both arms until a tentative MTD, and/or preliminary RP2D is defined. Note: In case of concerns regarding the tolerability of a reached dose-level, an alternative dosing schedule for the combination of glofitamab and atezolizumab or polatuzumab vedotin may be explored (e.g., a lower dose of glofitamab for the first dosing cycle followed by higher doses for subsequent dosing cycles).

For determination of preliminary RP2D, additional patients might be enrolled to ensure that at least six patients are treated at or near (±20%) this dose-level. The tentative MTD is defined based on occurrence of DLTs and as a dose that is defined as having a probability of 20-35% of a DLT occurring during the DLT observation period in Part I. The MTD is confirmed or can be adjusted based on the safety data observed in Part II of the study, taking into account of toxicities during the treatment period. The RP2D is defined as the quantity of a drug that most effectively produce the desired effect while remaining in the range of acceptable toxicity and is selected based on the overall clinical safety and activity, as well as the PK and available pharmacodynamic profiles of glofitamab plus atezolizumab.

Dose-Limiting Toxicity Observation Period

The DLT observation period is based on the timing of first administration of glofitamab in the presence of polatuzumab vedotin and therefore starts on Day 8 of Cycle 1 with first administration of glofitamab and ends on Day 21 of Cycle 2 as both agents are administered on Day 1 of Cycle 2 for the first time together on the same day. During the DLT period, no more than one treatment delay for up to 21 days is allowed for resolution of toxicities to CTCAE Grade ≤1, unless otherwise specified.

Whenever a patient experiences a toxicity that fulfills the DLT criteria, the following applies:

Treatment with glofitamab and atezolizumab or polatuzumab vedotin is permanently discontinued and the toxicity is followed up as needed, unless the DLT resolves to Grade ≤1 within 3 weeks and it is determined to be in the patient's best interest to continue study treatment. The patient may continue to receive study treatment provided that the study treatment dose modifications are made and/or measures to manage toxicity can be applied, as agreed to between the Investigator(s) and the Medical Monitor.

If a DLT occurs in the first patient enrolled in a cohort during the first 7 days, and no subsequent patient has been treated yet, then the IMC in consultation with the Investigators decides whether subsequent patients are enrolled in this cohort or receive a lower dose-level (in which case this is considered a new cohort).

All DLTs that occur during the DLT period must be reported immediately, i.e., no more than 24 hours after learning of the event All adverse events, including DLTs, are graded according to NCI CTCAE v4.0 unless otherwise indicated. Although CRS is graded based on published American Society for Transplantation and Cellular Therapy (ASTCT) criteria (Lee et al., 2019), for dose-escalation decisions, DLTs related to CRS are defined based on individual signs and symptoms and laboratory data according to NCI CTCAE v4.0. DLTs are treated according to clinical practice and are monitored through their resolution. Decreases in B-cells, lymphopenia, and/or leukopenia due to decreases in B-cells are not considered DLTs, as they are expected pharmacodynamic outcomes of glofitamab treatment.

Criteria for Continuing Treatment During Possible Pseudoprogression

Patients with radiographic disease progression as defined by Lugano Classification (Cheson et al., 2014), prior to the completion of the study treatment period, are generally ineligible to receive further glofitamab treatment.

However, in limited cases, treatment after apparent radiographic disease progression may be allowed, as "pseudoprogression" due to infiltration of immune cells may occur with this category of immunologic treatments. Identification of pseudoprogression by the use of LYRIC criteria may therefore prevent early treatment discontinuation in patients who are deriving benefit.

The LYRIC criteria introduces the new term, "Indeterminate Response (IR)", which provides the flexibility to allow patients to continue treatment past IR in some circumstances with a mandatory subsequent evaluation within 6 to 12 weeks to confirm or refute true progressive disease (PD).

A patient is considered to have Indeterminate Response (IR) in one or more of the three following circumstances:
1. Category IR1: Increase in overall tumor burden (as assessed by the sum of the product of the perpendicular diameters [SPD]) of ≥50% of ≤6 measurable target lesions in the first 12 weeks of therapy, without clinical deterioration.
2. Category IR2: Appearance of new lesions or growth of one or more existing lesion(s) ≤50% at any time during treatment; occurring in the context of lack of overall progression (<50% increase) of overall tumor burden, as measured by SPD of up to 6 lesions at any time during the treatment.
3. Category IR3: Increase in FDG uptake of one or more lesion(s) without a concomitant increase in lesion size or number.

In patients categorized as having any of the above types of IR, it is mandatory to obtain a repeat imaging scan. At that time, response should be re-evaluated and the patient should be considered to have true progressive disease (PD) if the SPD of target lesion has increased further, with the considerations outlined in detail in the section "Follow-up of IR" in patients continuing study therapy, despite apparent radiographic progression, is encouraged to undergo a tumor biopsy to assess whether increases in tumor volume are due to immune cell infiltration or neoplastic proliferation, provided that such a biopsy can be performed safely on a non-target lesion. If true progression is suspected based on the Investigator's judgment, clinical factors, or biopsy findings that are consistent with neoplastic proliferation, the patient is ineligible to receive further study treatment. If the Investigator believes that a patient is deriving clinical benefit, but IR cannot be determined for whatever reason, the patient may continue study treatment, provided the following criteria are met:
   There is an absence of symptoms and signs (including worsening of laboratory values) indicating progression of disease.
   There is no decline in Eastern Cooperative Oncology Group (ECOG) performance status.
   There is an absence of tumor progression at critical anatomical sites, including the central airway, the great vessels, and other organs or tissues where compromised function secondary to tumor progression would be expected to result acutely in severe and/or irreversible disability or death.

Patients for whom approved therapies exist must provide written consent to acknowledge deferring these treatment options in favor of continuing study treatment at the time of initial apparent progression.

If radiographic disease progression is confirmed at a subsequent tumor assessment, the patient is ineligible to receive further combination treatment.

Inclusion Criteria

Patients meet the following criteria for study entry:
   Able and willing to provide written informed consent and to comply with the study protocol and protocol mandated hospitalizations according to ICH and local regulations.
   Age ≥18 years.
   Histologically-confirmed hematologic malignancy that is expected to express CD20:
      Relapsed after or refractory to at least one prior treatment regimen
      No available treatment options that are expected to prolong survival (e.g., standard chemotherapy or autologous stem cell transplant (SCT)) or patients refusing chemotherapy or autologous SCT.
   A) Dose escalation Part
      Eligible patients include: Grade 1-3b R/R follicular lymphoma (FL) or marginal zone lymphoma (MZL) (nodal; extra-nodal; or splenic), mantle cell lymphoma (MCL), diffuse large B-cell lymphoma (DLBCL), primary mediastinal large B-cell lymphoma (PMBCL), high-grade B cell lymphoma with MYC and BCL2 and/or BCL6 rearrangements (double-hit lymphoma), high-grade B cell lymphoma NOS.
   B) Expansion Part
      Relapsed/refractory DLBCL, including transformed from FL
      Note: Refractory is defined as having relapsed within 6 months to the previous treatment.
   At least one measurable target lesion, measurable as defined by Lugano classification (node: >1.5 cm longest transverse diameter; extra-nodal: >1 cm longest transverse diameter) by computerized tomography (CT) scan. The following lesions should not be counted as target lesions:
      Previously irradiated lesions
      Lesions that are intended to be used to collect tissue samples for biopsy
      Bone lesions
   Note: in case patient has just one target lesion, no baseline and/or on treatment biopsy is required as this would exclude the patient from study participation.
   Tumor tissue:
      Able to provide a fresh pre-treatment biopsy during the screening period. If a fresh pre-treatment biopsy cannot be safely taken per Investigator's determination, provide a previously archived biopsy that is preferably not older than 6 months and preferably not confounded by major events (e.g., treatment or progression since the biopsy was taken), if available. A formalin-fixed paraffin embedded (FFPE) block is preferred. If an FFPE block is not available, slides are acceptable.

Willingness to provide biopsies.

ECOG performance status of ≤2.

Life expectancy (in the opinion of the Investigator) of 12 weeks.

Adequate liver function:
Total bilirubin ≤1.5×ULN (≤3×ULN in patients with Gilbert's syndrome).
AST (aspartate aminotransferase)/ALT (alanine aminotransferase), ALP (alkaline phosphatase) ≤3×ULN.
Patients with bone marrow or liver involvement ALP≤5×ULN.
Patients with documented liver involvement: AST and/or ALT≤5×ULN.
Albumin ≥2.5 g/dL Adequate hematological function:
Neutrophil count of ≥1.5≥$10^9$ cells/L (1,500/μL).
Platelet count of ≥75≥$10^9$ cells/L (75,000/μL).
Hemoglobin (Hb) ≥9.0 g/dL; (platelet and hemoglobin transfusion free within 14 days prior to first study administration on Day −7 of Cycle 1).
For patients not receiving therapeutic anti-coagulation: INR or aPTT ≤1.5×ULN.

Note: In case screening procedures are leading to situations which would exclude the patient from study participation (such as Hb value below entry criteria or blood transfusion given within 14 days prior to therapy due to a bleeding event caused by the screening biopsy), the patient may still be enrolled into the trial after consultation with the Medical Monitor.

Adequate renal function:
Creatinine ≤1.5×ULN or Creatinine clearance (CrCl) calculated by Cockroft-Gault formula of 50 ml/min for patients in whom serum creatinine levels do not adequately reflect renal function.

Negative serologic and/or polymerase chain reaction (PCR) test results for acute or chronic hepatitis B virus (HBV) infection. Note: Patients whose HBV infection status cannot be determined by serologic test results must be negative for HBV by PCR to be eligible for study participation.

Negative test results for hepatitis C virus (HCV) and human immunodeficiency virus (HIV). Note: Patients who are positive for HCV antibody must be negative for HCV by PCR to be eligible for study participation Patients must agree to either remain completely abstinent or to use two effective contraceptive methods that result in a failure rate of <1% per year from screening until: (a) at least 3 months after pre-treatment with obinutuzumab, 5 months after the last dose of polatuzumab vedotin, or 2 months after the last dose of glofitamab, whichever is longer, if the patient is a male or (b) until at least 18 months after pre-treatment with obinutuzumab, 5 months after the last dose of polatuzumab vedotin, or 2 months after the last dose of glofitamab, whichever is longer, if patient is a female. Male patients must also agree to refrain from donating sperm during this same period. Female patients must not be pregnant or breastfeeding during study period.

Exclusion Criteria

Patients who meet any of the following criteria are excluded from the study:

Patients with CLL, acute lymphoblastic leukemia (including CD20+ ALL), lymphoblastic lymphoma, Richter's transformation, Burkitt lymphoma, or lymphoplasmacytic lymphoma.

Patients with known active infection, or reactivation of a latent infection, whether bacterial (e.g., tuberculosis), viral (including, but not limited to severe pneumonia, Epstein-Barr virus (EBV), fungal, mycobacterial, or other pathogens (excluding fungal infections of nail beds) or any major episode of infection requiring hospitalization or treatment with IV antibiotics (for IV antibiotics this pertains to completion of last course of antibiotic treatment) within 4 weeks prior to Gpt infusion. Note: Patients receiving prophylactic antibiotics (e.g., to prevent a urinary tract infection or chronic obstructive pulmonary disease exacerbation) are eligible for the study. Note: Exclusion of patients with mycobacterial infections on the basis of chest X-ray or CT or on the basis of a positive Quantiferon or Mantoux test.

Current >Grade 1 peripheral neuropathy (only for patients being treated in the polatuzumab vedotin arm).

Patient with history of confirmed progressive multifocal leukoencephalopathy (PML).

History of leptomeningeal disease.

Current or past history of CNS lymphoma.

Current or past history of CNS disease, such as stroke, epilepsy, CNS vasculitis, or neurodegenerative disease. Note: Patients with a history of stroke who have not experienced a stroke or transient ischemic attack in the past 2 years and have no residual neurologic deficits, as judged by the Investigator, are allowed.

Major surgery or significant traumatic injury ≤28 days prior to Gpt infusion (excluding biopsies) or anticipation of the need for major surgery during study treatment. Note: Placement of central venous access catheter (e.g., port or similar) is not considered a major surgical procedure and is therefore permitted.

Patients with another invasive malignancy in the last 2 years (with the exception of basal cell carcinoma and tumors deemed by the Investigator to be of low likelihood for recurrence), with the exception of malignancies with a negligible risk of metastasis or death (e.g., 5-year OS rate 90%), such as adequately-treated carcinoma in situ of the cervix, non-melanoma skin carcinoma, localized prostate cancer, ductal carcinoma in situ, or Stage I uterine cancer.

Significant cardiovascular disease (such as New York Heart Association (NYHA) Class ≥II cardiac disease, congestive heart failure, myocardial infarction or cerebrovascular accident within the past 3 months, unstable arrhythmias, or unstable angina) or significant pulmonary disease (including obstructive pulmonary disease and history of bronchospasm).

Active or history of autoimmune disease or immune deficiency, including, but not limited to, myasthenia gravis, myositis, autoimmune hepatitis, systemic lupus erythematosus, rheumatoid arthritis, inflammatory bowel disease, antiphospholipid antibody syndrome, Wegener granulomatosis, Sjögren syndrome, Guillain-Barré syndrome, or multiple sclerosis, with the following exceptions:

Patients with a history of autoimmune-related hypothyroidism who are on thyroid-replacement hormone are eligible for the study.

Patients with controlled Type 1 diabetes mellitus who are on an insulin regimen are eligible for the study.

Patients with eczema, psoriasis, lichen simplex chronicus, or vitiligo with dermatologic manifestations only (e.g., patients with psoriatic arthritis are excluded) are eligible for the study provided all of following conditions are met:
  Rash must cover <10% of body surface area.
  Disease is well controlled at baseline and requires only low-potency topical corticosteroids.
  No occurrence of acute exacerbations of the underlying condition requiring psoralen plus ultraviolet A radiation, methotrexate, retinoids, biologic agents, oral calcineurin inhibitors, or high-potency or oral corticosteroids within the previous 12 months.
Uncontrolled tumor-related pain.
  Patients requiring pain medication must be on a stable regimen at study entry.
  Symptomatic lesions (e.g., bone metastases or metastases causing nerve impingement) amenable to palliative radiotherapy should be treated prior to treatment. Patients should be recovered from the effects of radiation. There is no required minimum recovery period.
  Asymptomatic lesions whose further growth would likely cause functional deficits or intractable pain (e.g., epidural lymphoma that is not currently associated with spinal cord compression) should be considered for locoregional therapy, if appropriate, prior to enrollment.
Uncontrolled pleural effusion, pericardial effusion, or ascites requiring recurrent drainage procedures (once monthly or more frequently). Note: Patients with indwelling catheters (e.g., PleurX®) are allowed.
Uncontrolled or symptomatic hypercalcemia (ionized calcium >1.5 mmol/L, calcium >12 mg/dL or corrected serum calcium >ULN).
History of idiopathic pulmonary fibrosis, organizing pneumonia (e.g., bronchiolitis obliterans), drug-induced pneumonitis, or idiopathic pneumonitis, or evidence of active pneumonitis on screening chest CT scan. Note: History of radiation pneumonitis in the radiation field (fibrosis) is permitted.
Evidence of significant, uncontrolled concomitant diseases that could affect compliance with the protocol or interpretation of results, including diabetes mellitus, history of relevant pulmonary disorders (bronchospasm, obstructive pulmonary disease) and known autoimmune diseases.
Any other diseases, metabolic dysfunction, physical examination finding, mental status or clinical laboratory finding giving reasonable suspicion of a disease or condition that would contraindicate the use of an investigational drug.
Treatment with any other standard anti-cancer radiotherapy/chemotherapy including investigational therapy (defined as treatment for which there is currently no regulatory authority approved indication) within 4 weeks prior to Gpt infusion.
Prior solid organ transplantation.
Prior allogenenic SCT.
Autologous SCT within 100 days prior to Gpt infusion.
Documented refractoriness to an obinutuzumab-monotherapy regimen.
Prior treatment with targeted therapies, e.g., tyrosine kinase inhibitors, systemic immunotherapeutic/immunostimulating agents, including, but not limited to, CD137 agonists or immune checkpoint blockade therapies, including anti-CTLA-4, anti-PD-1, and anti-PD-L1 therapeutic antibodies, radio-immunoconjugates, antibody drug conjugates, immune/cytokines and monoclonal antibodies within 4 weeks or five half-lives of the drug, whichever is shorter, prior to Gpt infusion.
Prior treatment with CAR T-cell therapy within 30 days before first study treatment administration.
Toxicities from prior anti-cancer therapy including immunotherapy that did not resolve to ≤Grade 1 with the exception of alopecia, endocrinopathy managed with replacement therapy and stable vitiligo.
Any history of immune related Grade ≥3 AE with the exception of endocrinopathy managed with replacement therapy.
Ongoing corticosteroid use >25 mg/day of prednisone or equivalent within 4 weeks prior and during study treatment.
  Patients who received corticosteroid treatment with >25 mg/day of prednisone or equivalent must be documented to be on a stable dose of at least 4-week duration prior to Day −7 of Cycle 1.
  Patients may have received a brief (<7 days) course of systemic steroids (≤100 mg prednisone equivalent per day) prior to initiation of study therapy for control of lymphoma-related symptoms.
Treatment with systemic immunosuppressive medication (including, but not limited to, cyclophosphamide, azathioprine, methotrexate, thalidomide, and anti-TNF-α agents) within 2 weeks prior to initiation of study treatment, or anticipation of need for systemic immunosuppressive medication during study treatment, with the following exceptions:
  Patients who received mineralocorticoids (e.g., fludrocortisone), corticosteroids for chronic obstructive pulmonary disease (COPD) or asthma, or low-dose corticosteroids for orthostatic hypotension or adrenal insufficiency are eligible for the study.
Ongoing corticosteroid use >25 mg/day of prednisone or equivalent within 4 weeks prior and during study treatment.
Administration of a live, attenuated vaccine within 4 weeks prior to Gpt infusion or anticipation that such a live attenuated vaccine is required during the study or within 5 months after last dose of study treatment. Note: Influenza vaccination should be given during influenza season only. Patients must not receive live, attenuated influenza vaccine (e.g., FLUMIST®) at any time during the study treatment period.
History of illicit drug or alcohol abuse within 12 months prior to screening.
History of severe allergic anaphylactic reactions to chimeric or humanized monoclonal antibodies or recombinant antibody-related fusion proteins. Note: Patients with IRRs are in general not excluded, only in case if IRR was accompanied by documented tryptase elevation.
Known hypersensitivity to Chinese hamster ovary cell products or to any component of the atezolizumab, polatuzumab vedotin, and/or glofitamab formulation and/or to the contrast agents used in the study.

Study Treatments

Study treatment is defined as any investigational treatment(s), marketed product(s), placebo, or medical device(s) intended to be administered to a study patient according to the study protocol. Study medication (glofitamab, atezolizumab, polatuzumab vedotin, and obinutuzumab) must be administered in a clinic or hospital equipped for systemic (IV) cancer treatment. Full emergency resuscitation facilities should be immediately available, and patients should be under close observation by the Investigator/site staff at all times. In case of infusion-associated adverse events in patients, the signs and symptoms should be fully resolved before the patient is discharged. Patients who use oral contraceptives, hormone-replacement therapy, or other maintenance therapy should continue their use. Tocilizumab should be administered when necessary. Study treatments are summarized below in Table 8.

TABLE 8

Summary of Study Treatments

| Study Treatment Name: | Glofitamab | Atezolizumab (Tecentriq ®) | Polatuzumab vedotin | Obinutuzumab (GAZYVA ®, GAZYVARO ®) | Tocilizumab (ACTEMRA ®) |
|---|---|---|---|---|---|
| Dosage Formulation: | Concentrate solution for infusion | Concentrate solution for infusion | Powder for concentrate solution for infusion | Concentrate solution for infusion | Refer to local prescribing information |
| Unit Dose Strength(s)/ Dosage Level(s): | Concentration of 5 mg/ml of glofitamab | Concentration of 60 mg/ml atezolizumab. | Concentration of 20 mg/ml polatuzumab vedotin after reconstitution | Concentration of 25 mg/ml obinutuzumab | Refer to local prescribing information |
| Dose: | Ascending flat doses with starting dose of 70 μg | 1200 mg flat | 1.8 mg/kg | 1000 mg flat | 8 mg/kg (for patients ≥30 kg); 12 mg/kg (for patients <30 kg) |
| Route of Administration: | IV | IV | IV | IV | IV |
| Schedule*: | Q3W at each Cycle; SUD: Q1W | Q3W from Cycle 2 onwards | Q3W at each cycle | Single dose 7 days ahead of first glofitamab dose | Only if needed for management of CRS |
| Dosing Instructions: | 4-Hour infusion for C1 and C2, which may be extended to prevent IRRs/ CRS to up to 8 hours. In the absence of IRRs/CRS the infusion time from Cycle 3 onwards may be reduced to two hours. | 60 (±15) minutes. Infusion may be slowed or interrupted for IRRs. In the absence of IRRs, the infusion time for subsequent dosing cycles should be infused over 30 (+10) minutes. | 90 (+10) minutes. Infusion may be slowed or interrupted for IRRs. In the absence of IRRs, the infusion time for subsequent dosing cycles should be infused over 30 (±10) minutes. | Refer to local prescribing information. Obinutuzumab dose may be split over 2 days if needed for management of infusion-related reactions. | Administer, if required, for the management of CRS |
| Packaging: (labeled as required per country requirement) | Provided in 6 ml glass vials containing 2 ml. | Provided in 20 ml glass vials containing 20 ml. | Provided in 20 ml glass vials containing powder for reconstitution with 7.2 ml sterile water for injection. | Provided in 50 ml glass vials containing 40 ml. | Refer to local prescribing information. |

*The schedule is Q3W, but depending on emerging PK and pharmacodynamic data, given an appropriate previously observed safety and tolerability profile, the treatment schedule may change. CRS = Cytokine release syndrome, IRR = infusion related reactions.

Figure 5A:
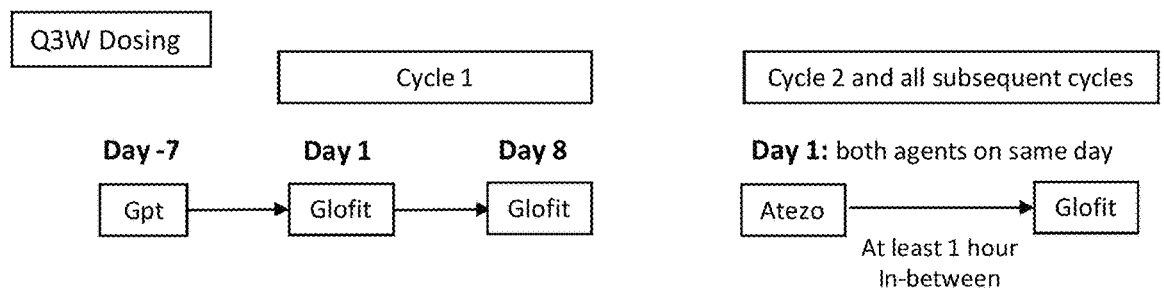
FIG. 5A and FIG. 5B are schematics showing the timing of dose administration in the study described in Example 1 for the atezolizumab arm (FIG. 5A) and for the polatuzumab vedotin arm (FIG. 5B). Atezo=atezolizumab; Glofit=glofitamab; Gpt=GAZVAYA® pre-treatment (obinutuzumab pre-treatment); Pola=polatuzumab vedotin.
Figure 5B:
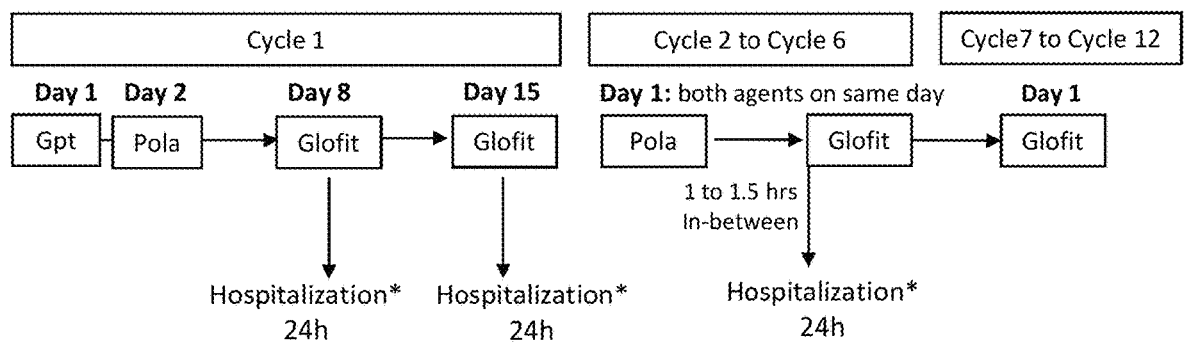

The sequence of treatment administration is summarized below (Schematic shown in FIG. 5A (atezolizumab arm) and FIG. 5B (polatuzumab vedotin arm)): Atezolizumab arm:

Day −7 of Cycle 1: obinutuzumab

Day 1 of Cycle 1: glofitamab—first (lower) step-up dose

Day 8 of Cycle 1: glofitamab—second (higher) step-up dose

Day 1 of Cycle 2 and each subsequent dosing cycle: atezolizumab plus glofitamab

In Cycle 2 and subsequent dosing cycles, atezolizumab is administered first, followed by glofitamab, with glofitamab infusion to begin at least one hour after the completion of the atezolizumab infusion, provided that patients have recovered from any acute toxicity mediated by the preceding administration. If dosing-related toxicity prohibits the dosing of both agents on the same day, the administration of glofitamab may be delayed up to a maximum of 36 hours.

Note: Patients with CR, starting re-treatment for 9 dosing cycles at time of disease progression receive study medication with Gpt on Day −7, step-up dosing in Cycle 9 identical to Cycle 1 and combination treatment starting from Cycle 10 onwards.

Polatuzumab Vedotin Arm:
Cycle 1:
Day 1: obinutuzumab
Day 2: polatuzumab vedotin
Day 8: glofitamab—first (lower) step-up dose
Day 15: glofitamab—second (higher) step-up dose
Day 1 of Cycle 2 to Day 1 of Cycle 6:
Polatuzumab vedotin followed by glofitamab
Day 1 of Cycle 7 to 12:
Glofitamab Following the initial dose of polatuzumab vedotin on C1D2, patients are observed for 90 minutes for fever, chills, rigors, hypotension, nausea, or other infusion associated symptoms. When both agents are administered on the same day for the first time, polatuzumab vedotin is administered first, followed by glofitamab, with glofitamab infusion to begin at least 90 minutes after the completion of the polatuzumab vedotin infusion, provided that patients have recovered from any acute toxicity mediated by the preceding administration. If the prior polatuzumab vedotin infusion has been well tolerated, the time interval between the end of infusion of polatuzumab vedotin and the start of glofitamab infusion can be reduced but should be at least 1 hour. If dosing-related toxicity prohibits the dosing of both agents on the same day, the administration of glofitamab may be delayed up to a maximum of 36 hours. The total dose of polatuzumab vedotin for each patient depends on the patient's weight. If the patient's weight increases or decreases >10% relative to the weight obtained during screening within 96 hours prior to treatment with polatuzumab vedotin, the actual weight is used to calculate the dose. The weight measurement that triggered a dose adjustment is taken as the new reference weight for future dose adjustments. All subsequent doses should be modified accordingly.

Pre-Medication and Prophylaxis

Since some patients may develop hypersensitivity or other infusion-related reactions to obinutuzumab, polatuzumab vedotin, or glofitamab, pre-medications and/or prophylaxis treatments may be required.

Pre-medications are required before treatment with glofitamab. The administration of corticosteroid premedication may be optional from Cycle 4 and beyond, based on investigator's assessment and with approval of the medical monitor. However, if the patient experiences CRS in earlier doses, premedication with steroids must be administered for subsequent doses until no additional CRS events are observed for at least 2 target doses. Be mindful of dose delay >7 days due to AE, in case of long delay. Hydrocortisone should not be used as premedication. Pre-medications include analgesics/anti-pyretics (e.g., paracetamol; at 500-1000 mg; orally (PO) or intravenously (IV)) approximately 30 minutes prior to glofitamab infusion, antihistamines (e.g., diphenhydramine; at 50-100 mg; PO or IV) approximately 30 minutes prior to glofitamab infusion, and corticosteroids (e.g., methylprednisolone at 80 mg, prednisone at 100 mg, or prednisolone at 100 mg; IV) approximately 1 hour prior to glofitamab infusion.

For polatuzumab vedotin (only applicable at Day 2 of Cycle 1, premedication (e.g., 500 to 1000 mg of oral acetaminophen or paracetamol and 50 to 100 mg diphenhydramine as per institutional standard practice) may be administered to an individual patient before administration of polatuzumab vedotin. Administration of corticosteroids is permitted at the discretion of the treating physician. If IRRs are observed with the first infusion in the absence of premedication, premedication must be administered before subsequent doses.

For combination treatment of glofitamab plus polatuzumab vedotin, pre-medications include analgesics/anti-pyretics (e.g., paracetamol; at 500-1000 mg; orally (PO) or intravenously (IV)) approximately 30 minutes prior to glofitamab infusion, antihistamines (e.g., diphenhydramine; at 50-100 mg; PO or IV) approximately 30 minutes prior to glofitamab infusion, and corticosteroids (e.g., methylprednisolone at 80 mg, prednisone at 100 mg, or prednisolone at 100 mg; IV) approximately 1 hour prior to glofitamab infusion. For combination treatment, pre-medications are only given prior to treatment with polatuzumab vedotin and are not repeated prior to start of glofitamab infusion.

For pre-medication for obinutuzumab, refer to the prescribing information of obinutuzumab. For atezolizumab, refer to the prescribing information for atezolizumab; currently no routine pre-medication is required for atezolizumab.

In general, for all patients, study medication should be administered to well-hydrated patients. Starting 1 or 2 days before the first dose of obinutuzumab, it is desirable to maintain a fluid intake of approximately 3 L/day. Prophylaxis medication is required for patients who are, in the opinion of the Investigator, at risk for tumor lysis syndrome (TLS). These are e.g., patients with bulky disease or patients with renal impairment. Those patients should be well-hydrated and should be treated with 300 mg/day of allopurinol PO or a suitable alternative treatment (e.g., 0.2 mg/kg/day rasburicase; IV) starting 48 to 72 hours prior to obinutuzumab pretreatment and prior to treatment on Day 1 of Cycle 1. Patients should continue to receive repeated prophylaxis with allopurinol and adequate hydration prior to each subsequent infusion, if deemed appropriate by the Investigator. Anti-infective prophylaxis for viral, fungal, bacterial or *pneumocystis* infections is permitted and should be instituted per institutional practice.

Safety Concerns and Management

Liver Toxicity

In the 2-week GLP study with glofitamab in cynomolgus monkeys, there were no changes in liver enzymes. The increases in bilirubin and decreases in albumin observed together with increases in C-reactive protein (CRP), fibrinogen and triglycerides and decreases in cholesterol were suggestive of an acute phase response secondary to post-dose increases in multiple cytokines. All findings showed evidence of reversibility. The risk of elevated liver enzymes of glofitamab in humans is not known. Patients with elevated LFTs at screening are excluded from trial.

Neurotoxicity

In the cynomolgus monkey studies, glofitamab administered with or without obinutuzumab pre-treatment was not associated with any histopathological signs of nervous system toxicity. Nevertheless, in Study NP39488, all patients must be without CNS lymphoma at baseline, and agree to close CNS monitoring while being treated with glofitamab. Also, to minimize the risk of CRS and neurologic events, all patients receive prophylactic dexamethasone for each glofitamab infusion. From Cycle 3 onwards, dexamethasone dose may be reduced based on clinical judgement and after discussion and approved by Medical Monitor. In case of neurologic events or signs of CRS, additional dexamethasone may be administered to treat the event.

Neutropenia

Neutropenia and febrile neutropenia, including Grade 4 neutropenic events, have been observed in patients receiving glofitamab. The frequency of febrile neutropenia or infections during neutropenic events appears to be very low. However, it may increase when glofitamab is combined with other agents including obinutuzumab and polatuzumab vedotin.

Pyrexia

Pyrexia frequently occurred in patients treated with glofitamab but never led to treatment discontinuation. When occurring within 24h from administration of glofitamab, pyrexia should be reported as symptom of CRS.

When pyrexia onset occurs with an interval longer than 24h from last administration of glofitamab, pyrexia should be managed with appropriate antipyretic treatment. It is important to perform differential diagnosis for infections and disease progression (B-symptoms). Hospitalization may be appropriate for these cases and becomes compelling in case of febrile neutropenia.

Tumor Lysis Syndrome (TLS)

Tumor lysis syndrome (TLS) has been reported with blinatumomab, CAR T-cell therapy, and other CD20-directed therapies. The inherent risk of TLS is dependent on the malignancy being treated and individual patient characteristics (Coiffier et al., 2008). The risk of TLS with glofitamab in NHL patients is predicted to be highest for those with bulky disease (defined as any lesion >10 cm on the screening CT scan) and elevated pre-treatment lactate dehydrogenase (LDH) levels, particularly in the presence of dehydration or compromised renal function. Whereas DLBCL, transformed lymphomas, and mantle cell lymphoma may be at higher risk of TLS as compared to follicular, marginal, and small cell lymphomas (Cairo et al., 2010), any risk assessment based on tumor type must be considered along with the effectiveness of therapy (Howard et al., 2011).

TLS is a medical emergency and requires immediate treatment with a multidisciplinary approach and involvement of hematologists, nephrologists and intensive care physicians. Potassium must not be added to the hydration fluid. Alkalinization of the urine is not recommended in the treatment of TLS. Allopurinol, whilst useful in the prophylactic setting, is not the drug of choice in established TLS except in the presence of glucose-6-phosphate dehydrogenase (G6PD) deficiency or allergy to rasburicase. In the absence of contraindications, patients with established TLS should be given rasburicase at a dose of 0.2 mg/kg/day.

The duration of treatment should be determined by the clinical response. Asymptomatic hypocalcemia should not be treated. Symptomatic hypocalcemia should be treated with a short infusion of calcium gluconate at a dose applicable to the age/weight of the patient and close monitoring of calcium levels, phosphate levels and renal function. Patients with potassium levels 6 mmol/L or having experienced a 25% increase in potassium level from baseline should have cardiac monitoring. Intractable fluid overload, hyperkalemia, hyperuricemia, hyperphosphatemia or hypocalcemia are indications for renal dialysis. Peritoneal dialysis is not recommended for the treatment of TLS. Dialysis should continue until there is adequate recovery of renal function, resolution of severe electrolyte imbalance and recovery of urine output. Balanced or isotonic solutions should be administered to maintain urine output >100 ml/m²/h.

Tumor Inflammation/Tumor Flare Events

The mechanism of action of glofitamab may result in a volumetric increase of lymphoma lesions leading to local compression and organ dysfunction. All patients should be carefully monitored for tumor flare/tumor inflammation events.

Cytokine Release Syndrome

Based on non-clinical data, glofitamab has the potential to cause rapid increases in plasma cytokine levels. Thus, infusion reactions may be clinically indistinguishable from manifestations of CRS given the expected human pharmacology of glofitamab, where T-cell engagement with B-cells results in T-cell activation and cytokine release.

This risk of glofitamab-induced CRS is anticipated to be reduced by a single dose of obinutuzumab 7 days ahead of glofitamab treatment, which should reduce circulating and tissue-resident B-cell targets, thereby abrogating immediate T-cell activation and subsequent cytokine release, particularly within the circulation. Furthermore, exploration of step-up dosing in Cycle 1 has been added as a possible additional safety measure to improve tolerability of glofitamab in Cycle 1 with regards to CRS.

Evidence of cytokine release was observed in a non-clinical toxicology study using cynomolgus monkeys where the MTD for intravenous glofitamab was 100 µg/kg in the absence of obinutuzumab pre-treatment. In contrast, when circulating B-cells were first depleted by administration of a single dose of obinutuzumab 4 days in advance of the first dose of glofitamab, doses up to 1000 µg/kg were well-tolerated (highest dose tested).

Severe or life-threatening presentations of infusion reactions and/or CRS, such as hypotension, tachycardia, dyspnea or chest discomfort, should be treated aggressively with supportive and resuscitative measures, including the use of high dose corticosteroids, tocilizumab, IV fluids, and other supportive measures, per institutional practice.

In this study, grading and treatment of the adverse event of CRS arising from treatment are based on published criteria of Lee et al. (2014) and are described in Table 9.

The American Society for Transplantation and Cellular Therapy (ASTCT) consensus grading for CRS is currently considered the most clinical relevant grading scale for CRS (Lee et al., 2019). Although the protocol specified CRS grading system for Study NP30179 is per Lee et al., 2014, the study electronic case report form (eCRF) collects details on the supportive management of hypoxia and hypotension which allows a programmatical derivation of the ASTCT grade for CRS events.

TABLE 9

Recommendations for Cytokine Release Syndrome Management
(Event Onset after the End of Infusion)

| Event[a] | Initial Management Recommendation[b] | Action to Be Taken with Glofitamab at Next Dose |
|---|---|---|
| Grade 1 Fever, constitutional symptoms | Treat symptomatically as indicated, including antihistamines, antipyretics, and/or analgesics as needed<br>Treat fever and neutropenia if present<br>Monitor fluid balance; administer IV fluids as clinically indicated<br>For prolonged CRS (>2 days) in patients with significant symptoms or comorbidities (per investigator discretion [e.g., impaired cardiovascular function, reduced pulmonary reserve]), consider IV corticosteroids[d] and tocilizumab[e] | Continue treatment with glofitamab, consider reduced rate of infusion<br>Hospitalize for next dose if prolonged CRS |
| Grade 2 Hypotension: Responds to fluids or a single low dose vasopressor[c]<br>Hypoxia: requires <40% FiO₂ to maintain adequate | No or minimal comorbidities<br>Follow all Grade 1 recommendations<br>Monitor cardiac and other organ function closely<br>Hemodynamic support as indicated<br>Oxygen for hypoxia<br>Admit to ICU as appropriate<br>Administer tocilizumab IV[e] | May receive the next dose of glofitamab if symptoms resolve to Grade ≤1 for 3 consecutive days with approval of Medical Monitor<br>Consider extending infusion time (slower infusion rate) for subsequent doses |

TABLE 9-continued

Recommendations for Cytokine Release Syndrome Management
(Event Onset after the End of Infusion)

| Event[a] | Initial Management Recommendation[b] | Action to Be Taken with Glofitamab at Next Dose |
|---|---|---|
| hemoglobin oxygen saturation Organ toxicity: Assessed as Grade 2 | Administer IV corticosteroids[d] If no improvement within 24 hours: a) Notify Medical Monitor b) Initiate work-up and assess for signs and symptoms of HLH Manage per Grade 3 if no improvement within 8-12 hours after starting tocilizumab Extensive comorbidities Follow Grade 3 management guidelines | Hospitalize for next dose |
| Grade 3 Hypotension: Requires multiple pressors or high dose vasopressor[c] Hypoxia: requires ≥40% FiO$_2$ to maintain adequate hemoglobin oxygen saturation Organ toxicity: Assessed as Grade 3 (Grade 4 transaminitis) | Strongly consider cardiopulmonary and organ function monitoring in Intensive Care Unit Closely monitor and maintain fluid balance; administer IV fluids as clinically indicated Oxygen for hypoxia Vasopressor support for hypotension at high and repeated doses if required Other supportive care as clinically indicated (e.g., fever and neutropenia, infection) Administer Tocilizumab as per Grade 2, If maximum dose not reached within a 24-hour period Administer IV corticosteroids[d] in addition to antihistamines, antipyretics and/or analgesics Initiate work-up and assess for signs And symptoms of HLH | Patient may receive the next dose of glofitamab if symptoms resolve to Grade 1 or better for 3 consecutive days with approval of Medical Monitor The dose of glofitamab for the subsequent administration must be discussed with the Medical Monitor Consider extending infusion time (slower infusion rate) for subsequent doses Hospitalize for next dose If Grade 3 CRS recurs with subsequent doses, consider permanent discontinuation of glofitamab |
| Grade 4 Hypxia: Mechanical ventilation required Organ toxicity: Grade 4 (excluding transaminitis) | ICU admission, follow all Grade 3 guidelines For patients refractory to tocilizumab, consider siltuximab, anakinra, dasatinib and emapalumab, based on discretion of the investigator; management should be discussed with the Medical Monitor[f] | Permanently discontinue glofitamab [g] |

HLH = Hemophagocytic lymphohistiocytosis; IV = intravenous
[a]Refer to the NCI-CTCAE, v4.03 scale for the grading of symptoms.
[b]Guidance for CRS management is based on Lee et al., 2014 (Lee D W, Gardner R, Porter D L, et al. Current concepts in the diagnosis and management of cytokine release syndrome. Blood 2014; 124(2): 188-95.) and Thompson et al. 2019 (Thompson J A, Schneider B J, Brahmer J, Andrews S, Armand P, Bhatia S, Budde L E, Costa L, Davies M, Dunnington D, Ernstoff M S. Management of Immunotherapy-Related Toxicities, Version 1.2019, NCCN Clinical Practice Guidelines in Oncology. J Natl Compr Cancer Netw. 2019: 17(3):).
[c]Vasopressor use is defined as low dose if:
Norepinephrine monotherapy <20 μg/min; or
Dopamine monotherapy <10 μg/min; or
Phenylephrine monotherapy <200 μg/min; or
Epinephrine monotherapy <10 μg/min; or
Vasopressin + Norepinephrine equivalent ≤10 μg/min; or
On a combination of vasopressors, Norepinephrine equivalent of <20 μg/min
Equivalent equation: norepinephrine equivalent dose = [norepinephrine (μg/min)] + [dopamine (μg/kg/min)] + [phenylephrine (μg/min)/10].
High dose vasopressor use is defined as all doses required for ≥3 hours:
Norepinephrine monotherapy ≥20 μg/min; or
Dopamine monotherapy ≥10 μg/min; or
Phenylephrine monotherapy ≥200 μg/min; or
Epinephrine monotherapy ≥10 μg/min; or
Vasopressin + Norepinephrine equivalent ≥10 μg/min; or
On a combination of vasopressors, Norepinephrine equivalent of ≥20 μg/min
Equivalent equation: norepinephrine equivalent dose = [norepinephrine (μg/min)] + [dopamine (μg/kg/min)] + [phenylephrine (μg/min)/10].
[d]IV corticosteroids (e.g., methylprednisolone 2 mg/kg/day or dexamethasone 10 mg).
[e]Tocilizumab IV (8 mg/kg for patients at or above 30-kg weight; 12 mg/kg for patients less than 30-kg weight, not to exceed 800 mg/dose).
[f]Reference: Riegler et al. 2019 (Riegler L L, Jones G P, Lee D W. Current approaches in the grading and management of cytokine release syndrome after chimeric antigen receptor T-cell therapy. Ther Clin Risk Manag. 2019; 15: 323.); Wu et al. 2019 (Wu B X, Song N J, Riesenberg B P, et al. Development of molecular and pharmacological switches for chimeric antigen receptor T cells. Experimental hematology & oncology. 2019 8: 27.).
[g] Resumption of glofitamab may be considered in patients who are deriving benefit and have fully recovered from the adverse event. Patients can be re-challenged with glofitamab only after approval has been documented by both the investigator (or an appropriate delegate) and the Medical Monitor.

Dose Modification

Should a patient experience a recurrence of a toxicity of the same or higher grade following re-exposure to glofitamab, the Investigator, after discussion with the IMC, have the option to reduce the dose of glofitamab once to a lower dose-level. This can be done to allow patients who could potentially benefit from glofitamab to remain on the study drug.

For patients who receive step-up dosing, if a treatment delay of glofitamab occurs for more than 7 days (>14 days between doses) due to toxicity following dosing on Day 8 of Cycle 1, Day 15 of Cycle 1, and/or Day 1 of Cycle 2, modification of the subsequent glofitamab dosing (i.e. repeating last tolerated dose) and/or addition of an additional dose of Gpt (obinutuzumab pre-treatment) may occur at the discretion of the investigator in consultation with the Medical Monitor.

For patients receiving polatuzumab vedotin, the dose of polatuzumab vedotin may be reduced stepwise to a maximum of two levels for management of drug-related toxicities. In particular, while polatuzumab vedotin is administered at a starting dose of 1.8 mg/kg per Cycle, it can be reduced to a first dose reduction level of 1.4 mg/kg per Cycle, further reduced to a second dose reduction level of 1.0 mg/kg per Cycle, or reduced to a third and final reduction level of discontinuation of polatuzumab administration. If further dose reduction is indicated after two dose reductions, the patient must discontinue polatuzumab vedotin but may continue treatment with the remaining study drugs at the investigator's discretion in consultation with the Medical Monitor.

Analyses
Efficacy Assessment
Tumor and Response Evaluations

Tumor and response evaluations are determined in regular intervals by the Investigator using the Lugano Classification (Cheson et al., 2014) and the exploratory LYRIC Criteria (Cheson et al., 2016). All measurable disease must be documented at screening and re-assessed at each subsequent tumor evaluation by both fluoro-D-glucose integrated with computed tomography (FDG-PET/CT) and diagnostic CT scans.

For patients with DLBCL, screening PET/CT scans may be utilized to assess bone marrow involvement; therefore, for DLBC patients bone marrow examinations are not required unless clinically indicated (Cheson et al., 2014). For all other indications enrolled in this study, bone marrow examinations (if appropriate) are required at screening. If positive at screening, a subsequent bone marrow examination is required only to confirm a CT-based complete response (CR). Clinical response assessment should include evaluation of the presence and degree of enlarged lymph nodes, hepatomegaly, and splenomegaly by physical examination.

Radiographic Assessments

At each imaging time-point both radiographic assessment methods are needed:
 1. FDG-PET/CT
 2. Diagnostic CT scan FDG-PET/CT scans and diagnostic CT scans should be acquired according to the standardized imaging manual, which are provided to all sites. In certain cases, e.g., due to technical issues, PET/CT scanners may be used to collect diagnostic CT scans as long as they are acquired according to the guidelines in the imaging manual.

FDG-PET/CT scans should include the base of the skull to mid-thigh. Full-body PET scans should be performed when clinically appropriate.

Diagnostic CT scans with oral and IV contrast should include chest, abdomen, and pelvic scans. CT scans of the neck should be included if clinically indicated (i.e., if evidence of disease upon physical examination) and must be repeated throughout the study if there is disease involvement at baseline.

There needs to be at least 7 days between the screening tumor biopsy and the subsequent imaging assessment in case biopsy was performed first. A full radiographic assessment must be performed any time disease progression or relapse is suspected.

Bone Marrow Assessments

Bone marrow assessments (if appropriate), consisting of bone marrow biopsy and aspirate, are required at screening for staging purposes in all patients except DLBCL and should be performed within approximately 3 months prior to Day −7 of Cycle 1 with no intervening therapy.

Summaries are carried out by dose-level, and/or disease cohort, and treatment arm.

Safety Assessments

Safety assessments consist of monitoring and recording adverse events, including serious adverse events and non-serious adverse events of special interest; measurement of protocol specified safety laboratory assessments; measurement of protocol-specified vital signs, ECGs; and other protocol-specified tests that are deemed critical to the safety evaluation of the study.

All safety analyses are based on the safety analysis population grouped according to dose-level, and/or disease cohort, and treatment arm.

The dose-determining population, which is used to recommend the next dose-level based on the mCRM-EWOC design, includes all patients from the safety population who received the assigned doses of glofitamab and have undergone the scheduled safety evaluations within the DLT period, or who discontinued earlier due to a DLT. Patients in the safety population who have not been treated by any dose of glofitamab are analyzed separately. Safety is determined by adverse events, laboratory tests, ADAs, auto-antibodies, vital signs, ECGs, physical examinations, and performance status, as well as by DLTs. As appropriate, listings, summary tables, and graphs are provided for safety and tolerability assessments.

Physical and Neurological Examinations

A complete physical examination should include an evaluation of the head & neck, eyes, ears, nose and throat in addition to cardiovascular; dermatological; musculoskeletal; respiratory; gastrointestinal; genitourinary and neurological systems. Assessment should include evaluation of the presence and degree of enlarged lymph nodes, hepatomegaly, and splenomegaly.

A complete neurological examination, which includes an evaluation of cranial nerves, muscle strength, sensation, mental status and coordination, should be performed and documented in the patient's chart. Mental status checks can be done without the need to complete a validated mental status questionnaire.

At subsequent visits (or as clinically indicated), targeted, symptom-directed physical examinations should be performed. Targeted physical examinations should be limited to systems of (if appropriate) primary relevance (i.e., cardiovascular, respiratory, neurologic, and any system that might be associated with tumor assessment (e.g., lymph nodes, liver, and spleen and those systems associated with symptoms), or potential drug-related toxicity).

Vital Signs

Vital Signs (VS), including, respiratory rate, diastolic and systolic BPs, pulse rate and temperature to be performed. Blood pressure and pulse measurements are assessed in a seated position with a completely automated device. Manual techniques are used only if an automated device is not available. When possible, the same arm should be used for all BP measurements. BP and pulse measurements should be preceded by at least 5 minutes of rest for the patient in a quiet setting Infusion Related Reactions (IRRs)/Cytokine Release Syndrome (CRS)

Following infusion of each dose of glofitamab, patients must also be observed clinically for at least 90 minutes for fever, chills, hypotension, nausea, or other signs and symptoms of IRRs.

At the end of the infusion, an IV line should remain in place for the full 90-minute window of observation. If no infusion-related adverse events have been observed during this 90-minute period of time, the infusion line may then be removed. If the IV line used for infusion must be removed prior to completing the 90-minute window, a temporary access line must be placed as a substitute until the 90-minute window is completed. If feasible, the line for drawing blood for PK samples (opposite extremity to the one for drug infusion) remains in place until the 24-hour sample is taken.

For subsequent infusions that occur without infusion-related signs and symptoms, the IV line should remain in place for 30 minutes from the end of the infusion, but patients should continue to be observed clinically for a full 90-minute window.

VS during the infusion are not required to be captured in the electronic case report form (eCRF) unless abnormalities are observed. VS should be measured more frequently in patients with disease factors that may indicate an increased risk of severe CRS. These patients should have vital signs recorded every 15 minutes during the infusion and up to 2 hours following the infusion.

Electrocardiograms (ECGs)

Triplicate 12-lead ECG recordings (i.e., three useful ECGs without artifacts) are collected. The triplicate ECG recordings are obtained within approximately 2-5 minutes at each specified time-point. Whenever possible, the same brand/model of a standard high-quality, high-fidelity electrocardiograph machine equipped with computer-based interval measurements is used for each patient. The average of the three readings is used to determine ECG intervals and characteristics (e.g., PR; QRS; QT), which are recorded on the electronic case report form (eCRF).

ECG characteristics, including heart rate, QRS duration, and PR, and QT intervals, are recorded on the eCRF. QTcB (Bazett's correction), QTcF (Fredericia's correction) and RR are recorded on the eCRF. Changes in T-wave and U-wave morphology and overall ECG interpretation are documented on the eCRF. T-wave information is captured as normal or abnormal. U-wave information is captured in two categories: absent/normal or abnormal.

Time Period and Frequency for Collecting Adverse Event (AE) and Serious Adverse Event (SAE) Information.

Investigators seek information on adverse events at each patient's contact. All adverse events, whether reported by the patient or noted by study personnel, are recorded in the patient's medical record and on the Adverse Event eCRF.

After initiation of Gpt, all adverse events, regardless of relationship to study drug, are reported until 90 days after the last dose of glofitamab.

After a period of 90 days from the last dose of study drug, investigators report any deaths, serious adverse events, or other adverse events of concern that are believed to be related to prior treatment with study drug.

Secondary malignancies are recorded indefinitely (even if the study has been closed). Study treatment-related SAEs are to be collected indefinitely from the last obinutuzumab, atezolizumab, polatuzumab vedotin, tocilizumab or glofitamab (even if the study has been closed).

Non-serious adverse events of special interest for this study include the following:

A) General
   Cases of an elevated ALT or AST in combination with either an elevated bilirubin or clinical jaundice, as defined in Appendix 3.
   Suspected transmission of an infectious agent by the study treatment, as defined below:
      Any organism, virus, or infectious particle (e.g., prion protein transmitting transmissible spongiform encephalopathy), pathogenic or non-pathogenic, is considered an infectious agent. A transmission of an infectious agent may be suspected from clinical symptoms or laboratory findings that indicate an infection in a patient exposed to a medicinal product. This term applies only when a contamination of the study treatment is suspected.

B) Glofitamab Specific
   Grade ≥2 neurologic adverse event
   Grade ≥2 CRS
   Tumor lysis syndrome (minimum Grade 3 by definition)
   Any suspected MAS/HLH
   Febrile neutropenia (minimum Grade 3 by definition)
   Grade ≥3 neutropenia
   Grade ≥2 tumor inflammation/flare (e.g., manifestation of signs/symptoms associated with an increase in size of known nodal or extranodal lesions by clinical or radiographic assessment
   Grade ≥2 AST, ALT, or total bilirubin elevation
   Any grade disseminated intravascular coagulation (minimum Grade 2 by definition)

C) Atezolizumab Specific
   Pneumonitis
   Colitis
   Endocrinopathies: diabetes mellitus, pancreatitis, adrenal insufficiency, hyperthyroidism, and hypophysitis
   Hepatitis, including AST or ALT>10×ULN
   Systemic lupus erythematosus
   Neurological disorders: Guillain-Barré syndrome, myasthenic syndrome or myasthenia gravis, and meningo-encephalitis.
   Events suggestive of hypersensitivity, infusion-related reactions, CRS, influenza-like illness, systemic inflammatory response syndrome, and systemic immune activation.
   Nephritis
   Ocular toxicities (e.g., uveitis, retinitis)
   Myositis
   Myopathies, including rhabdomyolysis
   Grade ≥2 cardiac disorders (e.g., atrial fibrillation, myocarditis, pericarditis)
   Vasculitis D) Obinutuzumab Specific
   Tumor lysis syndrome (irrespective of regulatory serious criteria)
   Serious IRR
   Serious neutropenia
   Serious infections
   Second malignancy E) Polatuzumab Vedotin Specific
   Grade 2 or higher peripheral neuropathy (sensory and/or motor)
   Grade 3 or higher Infections Management of Specific Adverse Events If scheduled dosing coincides with a holiday or other justifiable events, that precludes dosing, dosing should commence on the nearest following date, with subsequent dosing continuing on a 21-day schedule as applicable. This is permitted and not considered as a protocol violation.

Study treatment may be delayed as appropriate for management of toxicity:
  Delays in glofitamab treatment >3 weeks result in its discontinuation unless otherwise described in the toxicity management guidelines or otherwise discussed and agreed upon with Medical Monitor.
  Note: In case the first glofitamab dose needs to be delayed the following rule applies:
    If patient fully recovers within 2 weeks, i.e., delay is ≥2 weeks from the planned first dose (determined from the Gpt dosing date) then patient can be treated with glofitamab.
    If patient's recovery lasts for more than 2 weeks, i.e., delay is ≥2 weeks from the planned first dose (determined from the Gpt dosing date), pre-treatment with obinutuzumab needs to be repeated 7 days ahead of glofitamab dosing.
  Delays in atezolizumab treatment >12 weeks result in its discontinuation unless otherwise described in the toxicity management guidelines or otherwise discussed and agreed upon with Medical Monitor.
  Delays in polatuzumab vedotin treatment >3 weeks result in its discontinuation unless otherwise described in the toxicity management guidelines or otherwise discussed and agreed upon with Medical Monitor.
  During Cycle 3 and beyond, patients who experience adverse event that is clearly attributed to glofitamab or atezolizumab or polatuzumab vedotin may continue treatment with the other agent following initial improvement of the adverse event and after discussion with and approval of the Medical Monitor.

Pharmacokinetics

To determine the PK profile of glofitamab, obinutuzumab, polatuzumab vedotin, and atezolizumab in serum, serial whole blood samples are collected from all patients throughout the duration of the study and are analyzed by using validated assays. For polatuzumab serum samples for measurement of total antibody analyte concentrations for polatuzumab vedotin and lithium plasma for polatuzumab vedotin antibody conjugated MMAE (acMMAE) and unconjugated MMAE are required. Blood samples for measurement of serum concentrations of tocilizumab are collected before, during, and up to 8 days after administration of tocilizumab.

Standard non-compartmental analysis is applied for calculating PK parameters and/or population methods may be considered. Other parameters, such as accumulation ratio and dose-proportionality may also be calculated.

Analyses are carried out on the PK analysis population. All PK parameters are presented by listings and descriptive summary statistics (mean, standard deviation, coefficient of variation, median, minimum, and maximum) separately by group or cohorts.

Individual and mean serum glofitamab concentration versus time data are tabulated and plotted by dose-level. Graphical displays of PK data may also be provided. The PK of glofitamab is summarized by estimating total exposure (area under the curve [AUC]), maximum concentration ($C_{max}$), minimum concentration ($C_{min}$), total clearance (CL), volume of distribution at steady-state ($V_{ss}$), and terminal half-life ($t_{1/2}$). Estimates for these parameters are tabulated and summarized. Inter-patient variability and drug accumulation are evaluated.

Pharmacodynamics

The pharmacodynamic sampling schedule is designed to provide a detailed profile of the magnitude and kinetics of B-cell depletion, T-cell activation/proliferation/exhaustion and cytokine release following treatment. These data are used to understand the pharmacodynamic effect of glofitamab in combination with atezolizumab or polatuzumab vedotin and to demonstrate the mode-of-action.

Mandatory blood samples is collected for measurement of immune cell phenotype and functional status (including, but not limited to, flow cytometry on T-cell activation, proliferation and exhaustion markers such as CD3/CD4/CD8/4-1 BB/PD1), tumor cells (including, but not limited to, flow cytometry on CD19-positive cells), cytokines (including, but not limited to, IL-6, IL-10, INF-γ) at baseline and after glofitamab and atezolizumab or polatuzumab vedotin treatment.

Tumor tissue samples (at least 2 but preferably 4 cores) are collected for measurement of immune cells and tumor cells (including, but not limited to immunohistochemistry on proliferating T-cells CD8/Ki67 and B-cell markers CD20 and PD-L1, flow cytometry on T-cell activation and exhaustion markers, and CD3/CD8/4-1 BB/PD1), at baseline, after glofitamab and after combination treatment with glofitamab plus atezolizumab or polatuzumab vedotin.
  Parts I and II: Mandatory pre-treatment fresh biopsies are requested from all patients for response prediction analyses. If a fresh biopsy cannot be safely taken, a previously archived biopsy is acceptable (preferably not older than 6 months and preferably not confounded by major events, e.g., treatment or progression since the biopsy was taken).
  Part I: Mandatory on-treatment and end of study biopsies after glofitamab as well as after combined glofitamab/atezolizumab or polatuzumab vedotin treatment may be requested from patients in cohorts close to RP2D/MTD for MoA analyses. The final decision when to introduce mandatory biopsies is made after discussion between the Investigator and the Sponsor and takes into account the accrued safety and efficacy data.
  Part II: Mandatory on-treatment and end of study biopsies after glofitamab as well as after combined glofitamab/atezolizumab/polatuzumab vedotin treatment are requested from at least 10 DLBCL and at least 10 FL patients for MoA analyses.

All pharmacodynamic parameters are presented by listings and descriptive summary statistics separately by group or cohorts.

Genetics

Whole Genome/Exome/Targeted DNA Analysis

Archival, fresh tumor tissue samples and blood sample are collected at baseline and on-treatment for DNA and/or RNA extraction for exploratory research on genetic biomarkers (including, but not limited to, HLA genotyping, cancer-related genes and biomarkers associated with common molecular pathways [e.g., MYC, BCL2, CD79B, MYD88, CARD11, TNFAIP3], or immune-related markers [e.g., T-cell receptor sequence], microsatellite instability [MSI] and tumor mutation burden).

In addition, tumor tissue sample collected at the time of progression, if deemed clinically feasible, are used for DNA and/or RNA extraction for exploratory research on genetic biomarkers (including, but not limited to, cancer-related genes and biomarkers associated with common molecular pathways) to understand immune resistance mechanisms.

Transcriptome Analysis

Archival tissue, fresh tissue samples and blood are collected for RNA extraction and subsequent gene expression profiling to enable: identification of pharmacodynamic biomarkers, identification of response predictive biomarkers (including, but not limited to, cell-of-origin prognostic subgroups ABC/GCB), and assessment of treatment response and mode-of-action.

Biomarkers

Minimal Residual Disease (MRD) is assessed at baseline in archival tissue and blood samples and during study treatment in newly collected blood samples to monitor clinical response and predict efficacy.

Collection of blood samples for exploratory biomarker research is also part of this study. Blood samples for exploratory biomarker research are collected from all patients.

The specimens are stored and may be used for research purposes to identify biomarkers useful for predicting and monitoring response to glofitamab in combination with atezolizumab or polatuzumab vedotin, identifying biomarkers useful for predicting and monitoring the safety of glofitamab in combination with atezolizumab or polatuzumab vedotin, assessing pharmacodynamic effects of glofitamab in combination with atezolizumab or polatuzumab vedotin, and investigating mechanism of therapy resistance. Additional markers may be measured in case a strong scientific rationale develops.

Example 2. Anti-CD20/Anti-CD3 TCB (Glofitamab) in Combination with Atezolizumab

The anti-CD20/anti-CD3 T-cell-engaging bispecific (TCB) antibody, glofitamab (Glofit) (RG6026; glofitamab), and the anti-PD-L1 antibody, atezolizumab, were used in combination in NP39488 (NCT03533283), a Phase Ib, open-label, multicenter, dose-escalation and expansion study evaluating anti-CD20/anti-CD3 TCB (e.g., anti-CD20/anti-CD3 bispecific antibody, e.g., glofitamab)+atezolizumab (Atezo) (Hutchings et al., ASH 2019) in R/R B-NHL patients. This study provided the following preliminary safety and activity data.

Methods

Patients were aged ≥18 years with: CD20+B-NHL that was R/R to ≥1 prior therapy; ≥1 measurable target legion; and an ECOG PS of 0-2. A single 1000-mg dose of obinutuzumab was administered on Day 1 of Cycle 1 to mitigate cytokine release syndrome (CRS). Glofitamab was either administered with fixed dosing (in Cohorts 1-5 at 70 µg-6 mg dosing) or with step-up dosing (SUD: Cohort 6, at 2.5/10/10 mg dosing and Cohort 7, at 2.5/10/30 mg dosing). In the SUD, glofitamab was administered by SUD on Day 8 of Cycle 1 (C1 D1) and Day 15 of Cycle 1 (C1 D2), then at the target dose from Day 1 of Cycle 2, every 3 weeks for up to 17 dosing cycles. Atezolizumab was administered at 1200 mg starting from Cycle 2 onwards on Day 1 of each subsequent dosing cycle. Patients received 8 dosing cycles of glofitamab with atezolizumab on a 21-day dosing cycle [Q3W] schedule of study treatment, unless they discontinued study treatment early due to disease progression, unacceptable toxicities, or withdrawal of consent.

After completion of 8 dosing cycles, patients then underwent a tumor assessment to determine if additional treatment can be given. The primary objective was to establish the maximum tolerated dose (MTD) and/or recommended Phase II dose (RP2D) of anti-CD20/anti-CD3 TCB combined with atezolizumab.

Results

Efficacy results in Cohorts 1-7 of the glofitamab+atezolizumab study are reported below in Table 10.

TABLE 10

Efficacy Results in Glofitamab + Atezolizumab Cohorts Dosed
Atezolizumab + Glofitamab (n = 52)

|  | Cohort 1 | Cohort 2 | Cohort 3 | Cohort 4 | Cohort 5 | Cohort 6 | Cohort 7 |
|---|---|---|---|---|---|---|---|
| Dose | 70 µg | 300 µg | 1.8 mg | 4 mg | 6 mg | SUD 10 mg | SUD 30 mg |
| ORR | 0% | 17% | 37.5% | 43% | 20% | 22% | 60% |

Overall safety results in patients in Cohorts 1-7 of the glofitamab+atezolizumab study are reported below in Table 11. Cohorts 1-5 have been grouped together.

TABLE 11

Safety Overview in Glofitamab (Glofit) + Atezolizumab (Atezo) Cohorts

|  | Cohorts 1-5 (70 µg-6 mg) (n = 38) | Cohort 6 (2.5/10/10 mg) (n = 9) | Cohort 7 (2.5/10/30 mg) (n = 5) | All Cohorts (n = 52) |
|---|---|---|---|---|
| Median Glofit Cycles (range) | NA | 5 (0-8) | 5 (1-7) | 5 (0-8) |
| Patients with ≥1 adverse event (AE) | 38 (100%) | 7 (78%) | 5 (100%) | 50 (96%) |
| AE related to: Glofit | 27 (71%) | 7 (78%) | 5 (100%) | 39 (75%) |
| Atezo | 14 (37%) | 4 (44%) | 4 (80%) | 22 (42%) |
| Grade 3-4 AE | 27 (71%) | 4 (44%) | 5 (100%) | 36 (69%) |
| Grade 5 AE | 1 (3%) | 0 | 1 (20%) | 2 (4%) |
| Serious AE (SAE) | 23 (61%) | 6 (67%) | 5 (100%) | 34 (65%) |
| SAE related to: Glofit | 13 (34%) | 2 (22%) | 5 (100%) | 20 (38%) |
| Atezo | 4 (11%) | 2 (22%) | 5 (100%) | 11 (21%) |
| AE leading to treatment withdrawal | — | 1 (11%) | 1 (20%) | 2 (4%) |

CRS events experiences by patients in Glofitamab+Atezolizumab cohorts are summarized below in Table 12. Cohorts 1-5 have been grouped together.

Figure 6:
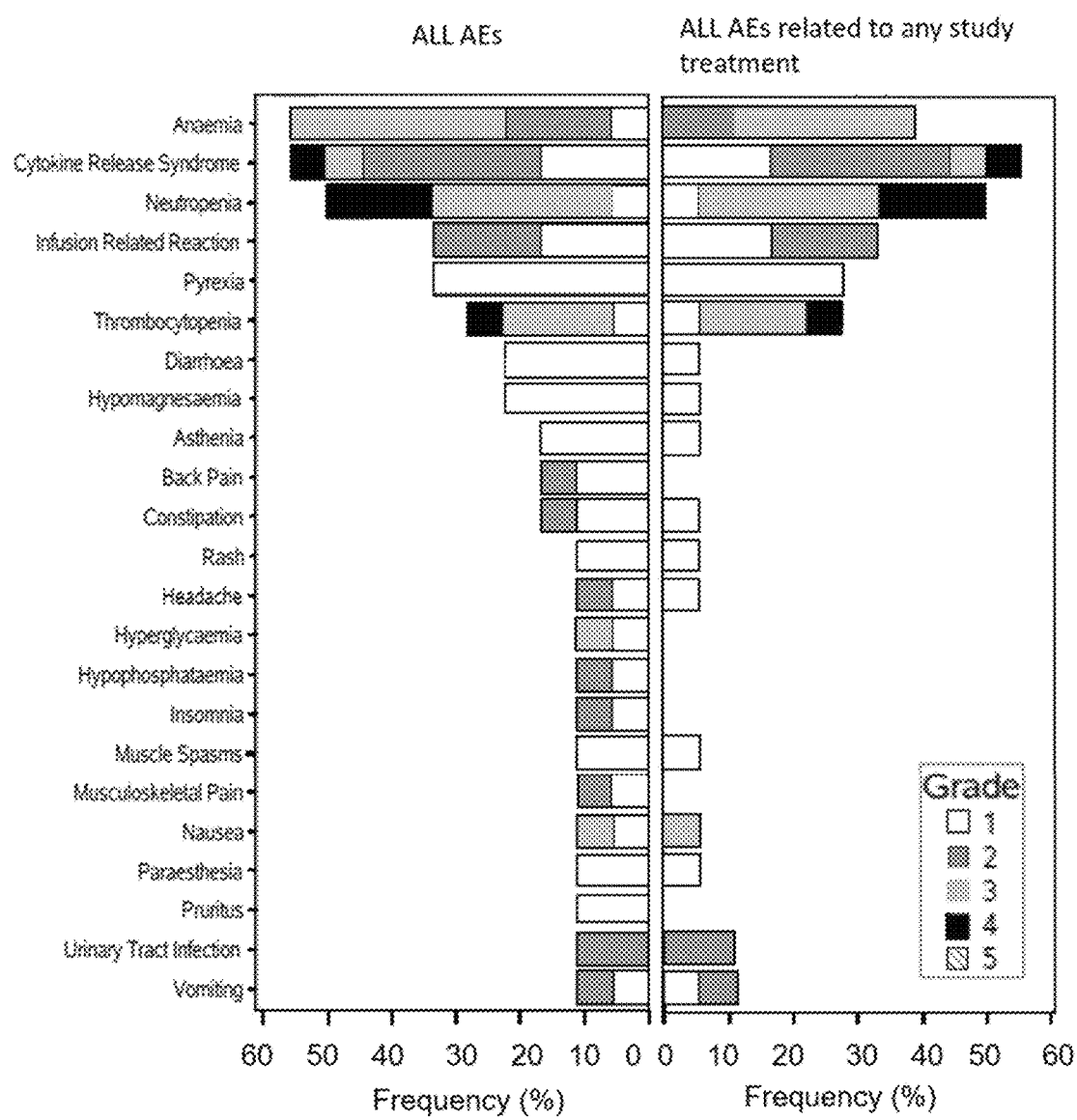
FIG. 6 is a chart reporting frequency of adverse events (AEs) with ≥10% incidence or NCI-CTCAE Grade of 5 for safety-evaluable patients in Cohorts 1 and 2 that have been treated with glofitamab+polatuzumab vedotin. Color indicates Grade of AE. Left side reports all AEs in study. Right side reports only AEs deemed to be related to study treatments (e.g., glofitamab or polatuzumab vedotin).

2 of n=5 patients. A summary of all adverse events (AEs) exhibited in Cohorts 1 and 2 with ≥10% incidence rate is provided in FIG. 6.

TABLE 12

CRS Events (ASTCT criteria) in the Glofitamab (Glofit) + Atezolizumab (Atezo) Cohorts

| | Cohorts 1-5 (70 µg-6 mg) N = 38 | Cohort 6 (2.5/10/10 mg) N = 9 | | | Cohort 7 (2.5/10/30 mg) N = 5 | | | | All Atezo Cohorts N = 52 |
|---|---|---|---|---|---|---|---|---|---|
| | 70 µg-6 mg N = 38 | 2.5 mg N = 9 | 10 mg N = 9 | Any dose N = 9 | 2.5 mg N = 5 | 10 mg N = 5 | 30 mg N = 5 | Any dose N = 5 | Any dose N = 52 |
| # of pts with highest CRS grade of any grade (%) | 16 (42%) | 3 (33%) | 2 (22%) | 5 (55%) | 3 (60%) | 0 | 0 | 3 (60%) | 25 (49%) |
| Grade 1 | 10 (26%) | 2 (22%) | 1 (11%) | 3 (33%) | 1 (20%) | 0 | 0 | 1 (20%) | 14 (27%) |
| Grade 2 | 5 (13%) | 1 (11%) | 0 | 1 (11%) | 0 | 0 | 0 | 0 | 6 (12%) |
| Grade 3 | 2 (5%) | 0 | 1 (11%) | 1 (11%) | 2 (40%) | 0 | 0 | 2 (40%) | 5 (10%) |
| Grade ≥4 | 0 | 0 | 0 | 0 | 0 | 0 | 0 | 0 | 0 |

Example 3. Safety and Efficacy of Anti-CD20/Anti-CD3 TCB (Glofitamab) in Combination with Polatuzumab Vedotin in Patients with R/R B-NHL A follow-on analysis of NP39488 (NCT03533283), including both safety and efficacy of the glofitamab (Glofit)+polatuzumab vedotin (Pola) combination treatment in R/R B-NHL patients, was conducted.

Methods

Patients were aged ≥18 years with: CD20+ B-NHL that was R/R to ≥1 prior therapy; ≥1 measurable target legion; and an ECOG PS of 0-2. A single 1000 mg dose of obinutuzumab was administered on Day 1 of Cycle 1 to mitigate cytokine release syndrome (CRS). Step-up dosing (SUD) of anti-CD20/anti-CD3 T-cell-engaging bispecific (TCB) antibody was also being used as a CRS mitigation strategy. Anti-CD20/anti-CD3 TCB was administered by SUD on Day 8 of Cycle 1 and Day 15 of Cycle 1, then at the target dose from Day 1 of Cycle 2, every 3 weeks for up to 17 dosing cycles. The two dosing regimens used for the anti-CD20/anti-CD3 TCB were either anti-CD20/anti-CD3 TCB at 2.5 mg (C1D1 on Day 8 of Cycle 1)/10 mg (C1D2 on Day 15 of Cycle 1)/10 mg (C2D1 onwards on Day 1 of Cycle 2 and onwards) (2.5/10/10 mg dosing; Cohort 1) or anti-CD20/anti-CD3 TCB at 2.5 mg (C1D1 on Day 8 of Cycle 1)/10 mg (C1D2 on Day 15 of Cycle 1)/30 mg (C2D1 onwards on Day 1 of Cycle 2 and onwards) (2.5/10/30 mg dosing; Cohort 2). Pola was administered at 1.8 mg/kg on Day 2 of Cycle 1 and then on Day 1 of each subsequent dosing cycle for six cycles.

Results

As of Nov. 3, 2020, 18 patients with R/R B-NHL (DLBCL n=10; FL=4; MCL=4) have been treated with either anti-CD20/anti-CD3 TCB at 2.5/10/10 mg dosing+Pola (Planned Cohort 1; n=12) or anti-CD20/anti-CD3 TCB 2.5/10/30 mg dosing+Pola (Planned Cohort 2; n=6). Planned Cohort 1 patients (75% male) had a median age of 62.5 years (range: 52-76) and had received a median of 3 prior lines (range: 1-5). Planned Cohort 2 patients (83% male) had a median age of 58.5 (range: 31-79) and had received a median of 2.5 prior lines (range: 2-4). One Planned Cohort 2 patient was dosed with 2.5/10/10 mg dosing of glofitamab rather than 2.5/10/30 mg dosing, and results in the Efficacy section below report data for Cohort 1 of n=13 patients and Cohort 2 of n=5 patients. A summary of all adverse events (AEs) exhibited in Cohorts 1 and 2 with ≥10% incidence rate is provided in FIG. 6.

Safety

A summary of Grade ≥3 adverse event (AE) rates and serious adverse event (SAE) rates that occurred in 2 or more patients from Cohorts 1 and 2 is provided below in Table 13.

TABLE 13

Rates of Grade ≥3 AE and SAEs in ≥2 Patients from Cohorts 1 and 2

| | Cohort 1 (2.5/10/10 mg) (N = 12) | Cohort 2 (2.5/10/30 mg) (N = 6) | All Pola + Glofit Step Up Dosing (N = 18) |
|---|---|---|---|
| All Gr ≥3 | 8 (67%) | 4 (67%) | 12 (67%) |
| Gr ≥3 SAE | 2 (17%) | 2 (33%) | 4 (22%) |
| Neutropenia* | 5 (42%) | 2 (33%) | 7 (39%) |
| Febrile Neutropenia (SAE) | 1 (8%) | — | 1 (6%) |
| Anemia* | 3 (25%) | 3 (50%) | 6 (33%) |
| Thrombocytopenia* | 3 (25%) | 1 (17%) | 4 (22%) |

Cohort 1

As of November 2020, the most frequent adverse event (AE) in Cohort 1 was CRS (50%; 6/12 patients): 17% Grade 1 (n=1), 8.3% Grade 2 (n=3), 25% Grade ≥3 (n=1), and 8% Grade 4 (n=1) (Lee et al. ASTCT 2019 criteria). Both patients who experienced Grade ≥3 CRS events were MCL patients, and the patient who exhibited the Grade 4 CRS event continued treatment and achieved CR. Other common AEs include neutropenia (42%), anemia (25%), and thrombocytopenia (25). Grade ≥3 AEs occurred in 8/12 patients (67%). There were no Grade 5 AEs or discontinuations due to AEs. Serious AEs occurred in 6 patients (50%).

Cohort 2

As of November 2020, one dose-limiting toxicity was reported (Grade 3 nausea during Cycle 1 dosing) in Cohort 2. The most frequent adverse event (AE) in Cohort 2 was CRS (67%; 4/6 patients): 33% Grade 1 (n=2) and 33% Grade 2 (n=2) (Lee et al. ASTCT 2019 criteria). No patients in Cohort 2 exhibited any Grade ≥3 or 4 CRS events. Other common AEs include anemia (50%), neutropenia (33%), and thrombocytopenia (17%). Grade ≥3 AEs occurred in 5/6 patients (83%). There were no Grade 5 AEs or discontinuations due to AEs. Serious AEs occurred in 4 patients (67%).

CRS

Nine out of the 10 patients who exhibited a CRS event from Cohorts 1 and 2 experienced their first CRS event at the C1D1 dose on Day 8 of Cycle 1 (2.5 mg). One patient experienced their first CRS event (Grade 1) at the C1D2 dose on Day 15 of Cycle 1 (10 mg). In total, there were 8 Grade 1 CRS events, 5 Grade 2 CRS events, 1 Grade 3 CRS event, and 1 Grade 4 CRS event. Treatments for 1 Grade 1 CRS event (13%), 4 Grade 2 CRS events (80%), and each of the Grade 3 (100%) and Grade 4 (100%) CRS events included tocilizumab. In DLBCL patients, 2/3 Grade 2 CRS events occurred within 24 hours of the patient being administered the first glofitamab dose (2.5 mg). The third Grade 2 CRS event in DLBCL patients occurred 1 hour after being administered the C3D1 dose (30 mg) and had also experienced CRS events at the previous doses of 2.5 mg and 10 mg (C1D1 and C1D2, respectively).
Efficacy Thirteen patients (7 with DLBCL, 2 with FL, and 4 with MCL) in Cohort 1 were efficacy-evaluable. Five DLBCL patients exhibited objective response (ORR=71%), with all 5 DLBCL patients exhibiting complete response (CR) (CR rate=71%), while 1 DLBCL patient exhibited stable disease (SD; 17%) and 1 DLBCL patient exhibited progressive disease (PD; 17%). Both FL patients exhibited objective response (ORR=100%), with 1 FL patient exhibiting a CR (50%) and 1 FL patient exhibiting a PR (50%). All 4 MCL patients exhibited objective response (ORR=100%), with all 4 MCL patients exhibiting CR (100%). Overall, in both Cohorts, 8 out of 10 patients with DLBCL were evaluable for efficacy, and 5 out of 8 efficacy-evaluable DLBCL patients exhibited ORR and CR (62.5%).
Conclusions Anti-CD20/anti-CD3 TCB (glofitamab)+Pola combination treatment showed encouraging preliminary efficacy and manageable safety in R/R B-NHL patients. In particular, no R/R DLBCL patients exhibited Grade >2 CRS events during treatment with a combination of glofitamab and polatuzumab vedotin. Cohort expansion can proceed with glofitamab+polatuzumab, with glofitamab dosing at 2.5/10/30 mg dosing (e.g., Cohort 2 dosing), and mandatory hospitalization length can decrease from 48 hours to 24 hours. For Expansion Cohort, dexamethasone is the highly recommended pre-dose corticosteroid for CRS mitigation.

Example 4. Safety and Efficacy of Anti-CD20/Anti-CD3 TCB (Glofitamab) in Combination with Polatuzumab Vedotin in Patients with R/R DLBCL The present analysis provides an update on NP39488 (NCT03533283), including both safety and efficacy of the glofitamab (Glofit)+polatuzumab vedotin (Pola) combination treatment in R/R DLBCL patients from Cohorts 1 and 2, as well as the Expansion Cohort.
Methods Patient characteristics for the 25 patients with R/R DLBCL in Cohort 1, Cohort 2, and the Expansion Cohort, that have been treated with the combination of glofitamab and polatuzumab vedotin as of Mar. 17, 2021, are described below in Table 14.

TABLE 14

Characteristics of R/R DLBCL Patients Treated with Glofitamab (Glofit) + Polatuzumab Vedotin (Pola) Combo

|  | Cohort 1 2.5/10/10 mg (N = 6) | Cohort 2 2.5/10/30 mg (N = 4) | Expansion Cohort 2.5/10/30 mg (N = 15) | All Glofit + Pola R/R DLBCL (N = 25) |
|---|---|---|---|---|
| Median age, (range), years | 66 (54-76) | 60.5 (47-79) | 62 (55-78) | 64.5 (47-79) |
| Male gender, n (%) | 3 (50%) | 3 (75%) | 10 (67%) | 16 (64%) |
| ECOG 0-1, n (%) | 6 (100%) | 4 (100%) | 14 (93%) | 24 (96%) |
| Histology |  |  |  |  |
| De-novo DLBCL | 6 (100%) | 4 (100%) | 12 (80%) | 22 (88%) |
| Transformed FL | — | — | 3 (20%) | 3 (12%) |
| aaIPI (0-3), n (%) |  |  |  |  |
| 0 | 2 (33%) | 0 | 1 (7%) | 3 (12%) |
| 1 | 1 (17%) | 1 (25%) | 2 (12%) | 4 (17%) |
| 2 | 3 (50%) | 3 (75%) | 10 (66%) | 16 (64%) |
| 3 | — | — | 2 (12%) | 2 (8%) |
| Ann Arbor Stage III-IV, n (%) | 4 (67%) | 3 (75%) | 14 (93%) | 21 (84%) |
| Prior lines of therapy, median (range) | 3 (1-4) | 2.5 (2-3) | 2 (1-5) | 2 (1-5) |
| Refractory status, n (%) |  |  |  |  |
| Refractory to any prior therapy | 3 (50%) | 1 (25%) | 7 (47%) | 11 (44%) |
| Refractory to most recent therapy line | 2 (33%) | 2 (50%) | 5 (33%) | 10 (40%) |
| Refractory to any prior anti-CD20 | 4 (67%) | 2 (50%) | 7 (47%) | 13 (52%) |
| Prior CAR-T | 1 (17%) | 2 (50%) | 3 (20%) | 6 (24%) |
| Prior ASCT | — | — | 1 (7%) | 1 (4%) |

A single 1000 mg dose of obinutuzumab was administered on Day 1 of Cycle 1 to mitigate cytokine release syndrome (CRS). Step-up dosing (SUD) of glofitamab was also being used as a CRS mitigation strategy. Glofitamab was administered by SUD on Day 8 of Cycle 1 and Day 15 of Cycle 1, then at the target dose from on Day 1 of Cycle 2, every 3 weeks for up to 17 dosing cycles. The two dosing regimens used for glofitamab were either glofitamab at 2.5 mg (C1D1 on Day 8 of Cycle 1)/10 mg (C1D2 on Day 15 of Cycle 1)/10 mg (C2D1 onwards on Day 1 of Cycle 2 and onwards) (2.5/10/10 mg dosing; Cohort 1; n=6) or glofitamab at 2.5 mg (C1D1 on Day 8 of Cycle 1)/10 mg (C1D2 on Day 15 of Cycle 1)/30 mg (C2D1 onwards on Day 1 of Cycle 2 and onwards) (2.5/10/30 mg dosing; Cohort 2 and Expansion Cohort; n=19). Pola was administered at 1.8 mg/kg on Day 2 of Cycle 1 and then on Day 1 of each subsequent dosing cycle for five dosing cycles. An overview of the treatment schedule is given in FIG. 5B.

Results

As of Mar. 17, 2021, 14 patients with R/R DLBCL/tr FL have been treated with either glofitamab at 2.5/10/10 mg dosing+polatuzumab vedotin (Pola) (Cohort 1; n=6) or glofitamab 2.5/10/30 mg dosing+Pola (Cohort 2 & Expansion; n=8).

Safety

Table 15 below summarizes the adverse events (AEs) and serious adverse events (SAEs) experienced by R/R DLBCL patients treated with at least 1 dose of glofitamab in the glofitamab (glofit)+polatuzumab vedotin (pola) combination treatment cohorts.

TABLE 15

Safety Overview in Step-Up Dosing (SUD) Glofit-Pola Cohorts

|  | Cohort 1 (2.5/10/10 mg) (N = 6) | Cohort 2 & Expansion (2.5/10/30 mg) (N = 19) | All Pola + Glofit DLBCL SUD (N = 25) |
|---|---|---|---|
| Median Glofit Cycles (range) | 8 (6-17) | 3 (0-10) | 3 (0-17) |
| Pts with at least 1 AE | 6 (100%) | 17 (89%) | 23 (92%) |
| Pt with AE related to Glofit + Pola | 5 (83%) | 13 (68%) | 18 (72%) |
| | 5 (83%) | 11 (59%) | 16 (64%) |
| Pt with Grade 3-4 AE (1 Gr 4 reported to date) | 4 (67%) | 8 (42%) | 12 (48%) |
| Pt with Grade 5 AE | 0 | 1 (5%) | 1 (4%) |
| Pt with Serious AE | 3 (50%) | 11 (59%) | 14 (56%) |
| SAE related to Glofit + Pola | 2 (33%) | 9 (47%) | 11 (44%) |
| | 1 (17%) | 2 (11%) | 3 (12%) |
| AE leading to any treatment withdrawal | 0 | 0 | 0 |

Of the 4 R/R DLBCL patients from Cohort 1 (n=6) who exhibited Grade 3 AEs, 3 patients (50%) exhibited neutropenia, and 1 patient (17%) exhibited febrile neutropenia. Of the 4 R/R DLBCL patients from Cohort 2 & Expansion (n=8), 3 patients (37.5%) exhibited neutropenia and 1 patient (12.5%) exhibited anemia. Notably, to date, there have been no serious neutropenia or anemia, nor have there been any neurologic AEs or peripheral neuropathy of any grade. There have additionally been 2 cases of infections (1 Staph and 1 device-related), but both events were not deemed to be related to any study drug.

CRS events (Lee et al. ASTCT 2019 criteria) experienced by R/R DLBCL patients treated with glofitamab+polatuzumab vedotin are reported below in Table 16.

TABLE 16

All CRS Events (ASTCT) Experienced by R/R DLBCL Patients Treated with Glofitamab + Polatuzumab Vedotin

| | Cohort 1 (2.5/10/10 mg) N = 6 | | | Cohort 2 & Expansion (2.5/10/30 mg) N = 17 | | | | All Glofit-Pola Cohorts SUD N = 25 |
|---|---|---|---|---|---|---|---|---|
| | 2.5 mg N = 6 | 10 mg N = 6 | Any dose N = 6 | 2.5 mg N = 17 | 10 mg N = 15 | 30 mg N = 15 | Any dose N = 17 | Any dose N = 23 |
| # of pts with highest CRS grade of any grade (%) | 2 (33%) | 1 (17%) | 2 (33%) | 8 (47%) | 5 (33%) | 4 (27%) | 10 (59%) | 12 (46%) |
| Grade 1 | 0 | 1 (17%) | 1 (17%) | 6 (35%) | 4 (27%) | 3 (20%) | 7 (41%) | 7 (30%) |
| Grade 2 | 2 (33%) | 0 | 2 (33%) | 2 (12%) | 1 (7%) | 1 (7%) | 3 (18%) | 5 (22%) |
| Grade ≥3 | 0 | 0 | 0 | 0 | 0 | 0 | 0 | 0 |

Of the 12 patients who experienced at least one CRS event, the majority (10/12) experienced the first CRS event at the 2.5 mg dose (C1D1 dose). Two patients experienced the first CRS event at the 30 mg dose (C2D1). No CRS events Grade ≥3 were observed in any of the 25 R/R DLBCL patients in Cohort 1 (2.5/10/10 mg dosing) and Cohort 2 & Expansion (2.5/10/30 mg dosing) treated with glofitamab+polatuzumab vedotin.

Efficacy

Efficacy results for efficacy-evaluable R/R DLBCL patients in Cohort 1 (and Cohort 2 & Expansion are reported below in Table 17.

TABLE 17

Efficacy Results for Glofitamab + Polatuzumab Vedotin Dose Escalation Treatment in Efficacy-Evaluable Patients with R/R DLBCL

|  | Cohort 1 N = 7 | Cohort 2 N = 3 | Expansion Cohort N = 8 | All Glofit-Pola treated R/R DLBCL Patients N = 18 |
|---|---|---|---|---|
| Objective Response Rate (ORR), N (%) | 6 (86%) | — | 6 (75%) | 12 (67%) |
| Complete Response (CR), N (%) | 5 (71%) | — | 6 (75%) | 11 (61%) |
| Partial Response (PR), N (%) | 1 (17%) | — | — | 1 (5.5%) |
| Stable Disease (SD), N (%) | — | — | 1 (9%) | 1 (5.5%) |
| Progressive Disease (PD), N (%) | 1 (17%) | 3 | — | 4 (36%) |
| Indeterminate Response 2 (IR2)* | — | — | 1 (9%) | 1 (5.5%) |

*Indeterminate response 2 per LYRIC criteria: Appearance of new lesions or growth of one or more existing lesion(s) ≥50% at any time during treatment; occurring in the context of lack of overall progression (SPD ≤50% increase) of overall tumor burden, as measured by SPD of up to 6 lesions at any time during the treatment.

R/R DLBCL patients who achieved CR in the 2.5/10/10 mg dosing cohort (Cohort 1) exhibited durable responses up to 6 months post end of treatment (EOT) assessment. Of the 3 R/R DLBCL patients in Cohort 2 who received 2.5/10/30 mg dosing and exhibited progressive disease, 2 were refractory to 3 previous lines of therapy ($1^{st}$: R-CHOP, BR, R-ESHAP; $2^{nd}$: R-CHOP, R-ESHA, CAR-T), and 1 was refractory to 2 previous lines of therapy, including CAR-T. Of the 8 patients evaluable for efficacy in the expansion cohort, 6/8 exhibited complete response (CR).

Conclusions

Anti-CD20/anti-CD3 TCB (glofitamab)+Pola combination treatment showed encouraging efficacy and safety in R/R DLBCL patients. None of the safety-evaluable R/R DLBCL patients experienced Grade ≥3 CRS events after receiving treatment with glofitamab+polatuzumab vedotin. Glofitamab+polatuzumab vedotin treatment also elicited high ORR and CR rates, as well as durable responses in patients with R/R DLBCL.

Example 5. Glofitamab in Combination with Polatuzumab Vedotin: Phase Ib/II Preliminary Data Support Manageable Safety and Encouraging Efficacy in Relapsed/Refractory (R/R) Diffuse Large B-Cell Lymphoma (DLBCL)

The present analysis provides a further update on NP39488 (NCT03533283). Reported here are preliminary results of safety and efficacy for the anti-CD20/anti-CD3 TCB (glofitamab)+polatuzumab vedotin (pola) in patients with R/R DLBCL during dose escalation (DE) and expansion at recommended Phase II dose (RP2D).

Methods

Patients were aged ≥18 years with CD20+DLBCL that was R/R to ≥1 prior therapy; ≥1 measurable target lesion; and an Eastern Cooperative Oncology Group performance status of 0-2. To mitigate the risk of cytokine release syndrome (CRS), a single 1000 mg dose of obinutuzumab pre-treatment (Gpt) was administered on Day 1 of Cycle 1. Step-up dosing (SUD) of glofitamab was administered on Day 8 of Cycle 1 (C1D1 dose) and Day 15 of Cycle 1 (C1D2 dose). Glofitamab was then given at the target dose from Day 1 of Cycle 2 (C2D1 dose), every 3 weeks up to Cycle 12. Pola was administered at 1.8 mg/kg on Day 2 of Cycle 1 and then on Day 1 of each subsequent dosing cycle up to Cycle 6. The primary objective was to establish the RP2D of glofitamab in combination with polatuzumab vedotin.

Results

As of Jun. 10, 2021 (clinical cut-off date (CCOD)), 44 patients were treated with ≥1 dosing cycle; median follow-up was 3.2 months (95% CI: 1.4-3.5). In the first dose escalation (DE) cohort, 7 patients had received glofitamab (Glofit) at 2.5 mg (C1D1 Dose on Day 8 of Cycle 1)/10 mg (C1D2 dose on Day 15 of Cycle 1)/10 mg (C2D1+doses on Day 1 of Cycle 2 and onwards) plus polatuzumab vedotin (Pola). In the second DE cohort, 4 patients received the glofitamab target dose of 30 mg on Day 15 of Cycle 1 (C1D2 dose) and this was established as the recommended Phase II dose (RP2D). During the expansion phase at RP2D, an additional 34 patients were treated with ≥1 cycle of treatment. Of 44 patients, 29 (66%) had histology of relapsed/refractory (R/R) diffuse large B cell lymphoma (DLBCL), 8 (18%) had R/R high grade B cell lymphoma (HGBCL; 2 HGBCL not otherwise specified (NOS); 5 double-hit (DH) DLBCL; 1 triple-hit (TH) DLBCL), and 7 (16%) had R/R transformed follicular lymphoma (trFL). Patients (61% male) had a median age of 65.5 years (range: 29-82) and received a median of 2 prior lines (range: 1-5). Twenty-eight (64%) patients were refractory to their last therapy; 2 patients had not been treated with glofitamab at the CCOD. The most frequent adverse event (AE) was cytokine release syndrome (CRS; 55%; 23/42 patients): Grade (Gr) 1 (n=18); Gr 2 (n=7); and no Gr 3 CRS events were observed (Lee et al. 2019 ASTCT criteria). Of the 7 patients with Gr 2 CRS, 5 were treated with tocilizumab and fluids for hypotension, and 4 patients were treated with low-flow oxygen due to hypoxia. None of the patients required vasopressors or intensive care unit admission. Gr>3 AEs occurred in 52% (n=23) of patients; most commonly, neutropenia (27%) and anemia (23%). For neurological AEs (NAEs), 13 events were reported in 13 patients (29.5%, 13/44 patients), all were limited to Gr 1-2. The most common NAEs were headache and (11%, 5/44 patients) and insomnia (4.5%, 2/44 patients). No immune effector cell-associated neurotoxicity syndromes-like AEs were reported. Peripheral neuropathy due to Pola was reported in 5/44 patients (11%); all events were Gr 1. Serious AEs occurred in 22 patients (52%); none were CNS or neurological events. One patient experienced a fatal COVID-19 pneumonia (not related). Study treatment was discontinued in 2 patients due to AEs (Gr 4 thrombocytopenia, and Gr 3 worsening of pre-existing renal impairment; both events were related to glofitamab and Pola). At CCOD 33/44 patients were evaluable for interim (after 2 dosing cycles, 1 target dose of glofitamab) or primary (after 8 dosing cycles) response; 6/33 patients had experienced progressive disease and discontinued study treatment. Overall response (OR) rate for both dosing cohorts was 73% (24/33) and complete response (CR) rate, per investigator was 51.5% (17/33). Of 7 patients treated with 2.5/10/10 mg SUD Glofit, OR and CR rates were both 86% (6/7); durable responses at ≥6 months post-end of treatment were observed. Of 26 patients treated with 2.5/10/30 mg SUD Glofit, OR rate was 73% (19/26) and CR rate was 46% (12/26); 11.5% (3/26) patients had stable disease after 2 cycles of therapy:

Conclusion

Glofitamab in combination with polatuzumab vedotin showed manageable safety and encouraging preliminary efficacy in R/R DLBCL patients. CRS events were limited to Gr 1 or 2, no new safety signals were detected for this combination, and the safety profile was consistent with that of the individual drugs.

Example 6. Glofitamab in Combination with Polatuzumab Vedotin: Phase Ib/II Preliminary Data Support Manageable Safety and Encouraging Efficacy in Relapsed/Refractory (R/R) Diffuse Large B-Cell Lymphoma (DLBCL)—Updated Data The present analysis provides a further update on NP39488 (NCT03533283). Reported here are preliminary results of safety and efficacy for the anti-CD20/anti-CD3 TCB (glofitamab)+polatuzumab vedotin (pola) in patients with R/R DLBCL during dose escalation (DE) and expansion at recommended Phase II dose (RP2D).

Methods

Patients were aged ≥18 years with CD20+DLBCL that was R/R to ≥1 prior therapy; ≥1 measurable target lesion; and an Eastern Cooperative Oncology Group performance status of 0-2. To mitigate the risk of cytokine release syndrome (CRS), a single 1000 mg dose of obinutuzumab pre-treatment (Gpt) was administered on Day 1 of Cycle 1. Step-up dosing (SUD) of glofitamab was administered on Day 8 of Cycle 1 (C1D1 dose, 2.5 mg) and Day 15 of Cycle 1 (C1D2 dose, 10 mg). Glofitamab was then given at the target dose from Day 1 of Cycle 2 (C2D1 dose, 10 mg in Cohort 1 and 30 mg in Cohort 2 and Expansion cohort), every 3 weeks up to Cycle 12. Polatuzumab vedotin was administered at 1.8 mg/kg on Day 2 of Cycle 1 and then on Day 1 of each subsequent dosing cycle up to Cycle 6. The primary objective was to establish the RP2D of glofitamab in combination with polatuzumab vedotin.

Glofitamab at a final dose of 30 mg was established as the recommended Phase II Dose (RP2D), i.e., the RP2D step-up dosing (SUD) of glofitamab is 2.5 mg on Day 8 of Cycle 1 (C1D8 dose) and 10 mg on Day 15 of Cycle 1 (C1D2 dose), and target dose of 30 mg Glofitamab from Day 1 of Cycle 2 (C2D1 dose), every 3 weeks up to Cycle 12.

Tables 18-20 provide updated results of study NP39488. Patients in the Dose escalation Cohort 1 (DE1) have been treated with Glofitamab 2.5/10/10 mg SUD+Pola (n=6), patients in the Dose escalation Cohort 2 (DE2) have been treated with Glofitamab 2.5/10/30 mg SUD+Pola (n=4) and patients in the Expansion phase at RP2D have been treated with Glofitamab 2.5/10/30 mg SUD+Pola (n=49).

TABLE 18

Patient baseline demographics and disease characteristics, updated data. Abbreviations: DE, dose escalation; HGBCL, high-grade B-cell lymphoma; trFL, transformed follicular lymphoma

| | | DE 1 (2.5/10/10 mg) N = 6 | DE 2 (2.5/10/30 mg) N = 4 | Expansion (2.5/10/30 mg) N = 49 | All patients N = 59 |
|---|---|---|---|---|---|
| Median age, years (range) | | 65.5 (55-76) | 61.8 (47-79) | 63.9 (29-82) | 59 (29-82) |
| Sex, n (%) | Male | 3 (50) | 3 (75) | 30 (61.2) | 36 (61) |
| ECOG | 0-1 | 6 (100) | 4 (100) | 45 (93.7) | 55 (94.9) |
| NHL histology, n (%) | DLBCL | 5 (83.3) | 2 (50) | 29 (59.2) | 36 (61) |
| | HGBCL | 0 | 0 | 9 (18.4) | 9 (15.3) |
| | Tr FL | 1 (16.7) | 2 (50) | 11 (22.4) | 14 (23.7) |
| Prior lines of therapy, Median (range) | | 3 (1-4) | 2.5 (1-3) | 2 (1-5) | 2 (1-5) |
| Refractory Status, n (%) | Refractory to any prior therapy | 3 (50) | 4 (100) | 41 (83.7) | 48 (81) |
| | Refractory to most recent therapy line | 3 (50) | 4 (100) | 34 (69.4) | 41 (69.5) |
| | Refractory to any prior anti-CD20 | 3 (50) | 3 (75) | 39 (79.2) | 45 (76-3) |

Most common Grade 3-4 AEs were neutropenia (27%) and thrombocytopenia (11.9%)

Peripheral neuropathy events (18.6%) were limited to Grade 1 (15.3%) and 2 (3.4%)

Two patients experienced fatal AEs (COVID-19 pneumonia, not related to study treatment; and CRS Cr S related to glofitamab). Study treatment was discontinued in four patients due to AEs (both events related to glofitamab and polatuzumab vedotin):

Grade 4 thrombocytopenia; Grade 3 worsening of pre-existing renal impairment; Grade 5 CRS, Cr 3 CRS and TLS with clinical deterioration; Jejunal perforation Grade 4, summarized in Table 19.

The majority of CRS were Grade 1 and occurred after 2.5 mg Glofitamab dose (Table 20). Of the seven patients with Grade 2 CRS:

Five patients were treated with tocilizumab and fluids for hypotension

Four patients were treated with low-flow oxygen due to hypoxia

None of the patients with Grade 2 CRS required vasopressors or admission to an intensive care unit Neurological adverse events (NAEs): The most common NAEs was headache (n=5, 8.4%). None of the serious AEs reported were CNS or neurological events. No immune effector cell-associated neurotoxicity syndromes were reported at the time of the clinical cut off date.

TABLE 19

Adverse events summary, updated data. Abbreviations: AE, adverse events; Gr, Grade; NCI-CTCAE, National Cancer Institute - Common Terminology Criteria for Adverse Events; Glofit, glofitamab

| N (%) of patients with ≥1 AE | DE 1 2.5/10/10 mg N = 6 | DE 2 and Expansion 2.5/10/30 mg N = 53 | All patients N = 59 |
|---|---|---|---|
| AE | 6 (100) | 48 (90.6) | 54 (91.5) |
| Glofit related | 5 (83.3) | 36 (67.9) | 41 (69.5) |
| Gr 3-4 AE | 4 (66.7) | 30 (56.6) | 34 (57.6) |
| Glofit related | 3 (75) | 17 (32) | 20 (33.8) |
| Gr 5 (fatal) AE | 0 | 2 (3.8) | 2 (3.4) |
| Glofit related | 0 | 1 (1.9) | 1 (1-7) |
| Serious AE | 3 (50) | 24 (54.3) | 27 (45.8) |
| Glofit related | 2 (33.3) | 18 (34) | 20 (33.9) |
| AE leading to Glofit discontinuation | 0 | 4 (7.5) | 4 (6.8) |
| Glofit related | 0 | 4 (7.5) | 4 (6.8) |

TABLE 20

CRS events, updated data. ASTCT criteria: Lee D W et al. Biol Blood Marrow Transplant 2019; 25: 625-38. Abbreviations: ASTCT, American Society for Transplantation and Cellular Therapy; CRS, cytokine release syndrome

| N (%) of patients with ≥1 CRS* | DE 1 (2.5/10/10 mg) N = 6 | DE 2 and Expansion (2.5/10/30 mg) N = 53 | All patients N = 59 |
|---|---|---|---|
| Any Grade CRS | 2 (33.3) | 23 (43.4) | 25 (42.4) |
| Grade 1 CRS | 1 (16.7) | 18 (34) | 19 (32.2) |
| Grade 2 CRS | 2 (33.3) | 5 (9.4) | 7 (11.9) |
| Grade 3-5 CRS | 0 | 1 (1.8) | 1 (1-7) |

Efficacy:

At the clinical cut-off date (6 Sep. 2021):

49/59 patients were evaluable for interim response (after 2 dosing cycles, 1 target dose of glofitamab) or later response (after 8 dosing cycles)

7/49 (14.3%) patients had experienced progressive disease (PD) and discontinued study treatment In Expansion, 11 patients were assessed beyond C3, of which 8 have achieved a complete response (CR)

The glofitamab+polatuzumab vedotin combination resulted in high response rates

Figure 7:
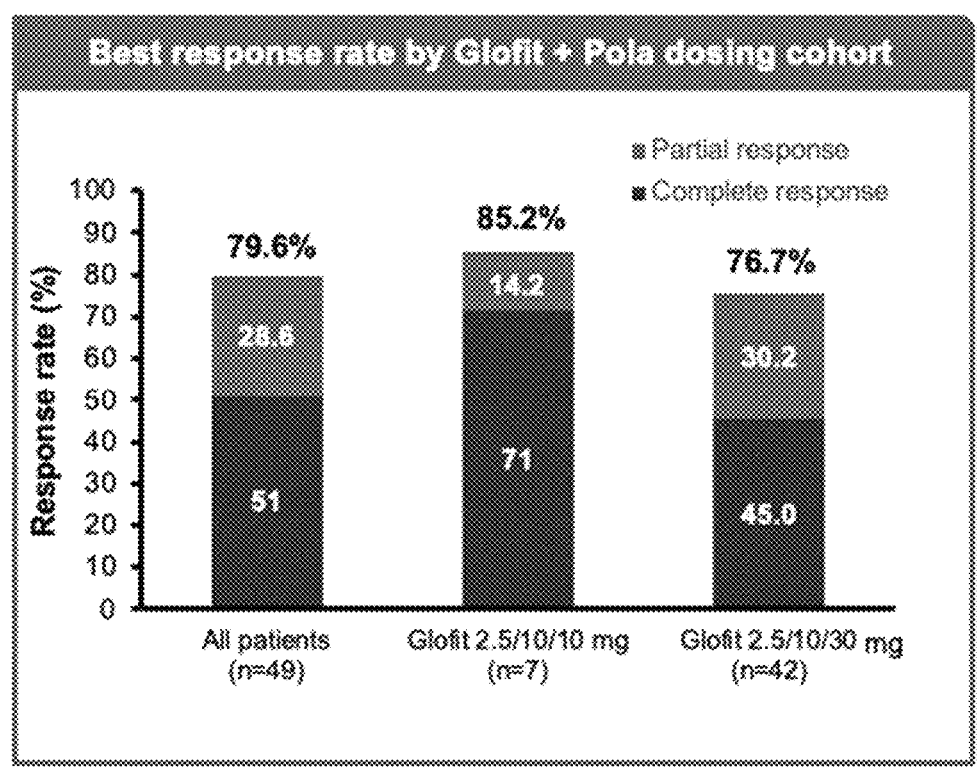
FIG. 7 provides updated efficacy data as of the Clinical Cut-Off Date for Dose Escalation Cohorts 1 and 2 and the Expansion cohort at RP2D. Glofit=glofitamab. Pola=polatuzumab vedotin.

The updated efficacy data is provided in FIG. 7.

Duration of Response

At the clinical cut-off date (6 Sep. 2021):

Median follow-up after first response (months): 2.6 (range: 0-16)

Median DOR (months): NE (95% CI: 4.2-NE)

Median DOR in patients achieving CR (months): NE (95% CI: NE-NE)

Most of the CRs to date were durable

TABLE 21

Best response rates by histology, PET-CT based on Lugano 2014, updated data.

| n (%) | R/R DLBCL (N = 30) | trFL (N = 11) | HGBCL (N = 8) | All DLBCL (N = 49) |
|---|---|---|---|---|
| ORR | 26 (76.7) | 8 (72.7) | 5 (62.5) | 39 (79.6) |
| CR | 14 (46.7) | 7 (63.6) | 4 (50) | 25 (51) |
| PR | 12 (40) | 1 (9-1) | 1 (12.5) | 14 (28.6) |
| SD | 1 (3.3) | 1 (9-1) | 1 (12.5) | 3 (6.1) |
| PD | 3 (10) | 2 (18.2) | 2 (25) | 7 (14.3) |

Conclusions:

Glofitamab in combination with polatuzumab vedotin showed tolerable safety and promising preliminary efficacy in patients with R/R DLBCL. CRS and NAEs were mostly limited to Grade 1 or 2 and no new safety signals were detected for this combination. The safety profile of glofitamab in combination with Pola was consistent with that of the individual drugs.

Example 7. Glofitamab in Combination with Polatuzumab Vedotin: Phase Ib/II Preliminary Data Support Manageable Safety and Encouraging Efficacy in Patients with Relapsed/Refractory (R/R) Diffuse Large B-Cell Lymphoma (DLBCL)

The present analysis provides a further update on NP39488 (NCT03533283). Reported here are preliminary results of safety and efficacy for the anti-CD20/anti-CD3 TCB (glofitamab)+polatuzumab vedotin (pola) in patients with R/R DLBCL during dose escalation (DE) and expansion at recommended Phase II dose (RP2D).

Methods

Patients were aged ≥18 years with CD20+DLBCL that was R/R to ≥1 prior therapy; ≥1 measurable target lesion; and an Eastern Cooperative Oncology Group performance status of 0-2. To mitigate the risk of cytokine release syndrome (CRS), a single 1000 mg dose of obinutuzumab pre-treatment (Gpt) was administered on Day 1 of Cycle 1. Step-up dosing (SUD) of glofitamab was administered on Day 8 of Cycle 1 (C1D1 dose, 2.5 mg) and Day 15 of Cycle 1 (C1D2 dose, 10 mg). Glofitamab was then given at the target dose from Day 1 of Cycle 2 (C2D1 dose, 10 mg in Cohort 1 and 30 mg in Cohort 2 and Expansion cohorts), every 3 weeks up to Cycle 12. Pola was administered at 1.8 mg/kg on Day 2 of Cycle 1 and then on Day 1 of each subsequent dosing cycle up to Cycle 6.

Glofitamab at a final dose of 30 mg was established as the recommended Phase II Dose (RP2D), i.e., the RP2D step-up dosing (SUD) of glofitamab is 2.5 mg on Day 8 of Cycle 1 (C1D1 dose) and 10 mg on Day 15 of Cycle 1 (C1D2 dose), and target dose of 30 mg glofitamab from Day 1 of Cycle 2 (C2D1 dose), every 3 weeks up to Cycle 12.

Tables 22-26 provide updated results of study NP39488. Patients in the Dose escalation Cohort 1 (DE1) were treated with glofitamab 2.5/10/10 mg SUD+Pola (n=6), patients in the Dose escalation Cohort 2 (DE2) were treated with glofitamab 2.5/10/30 mg SUD+Pola (n=4), and patients in the Expansion phase at RP2D were treated with glofitamab 2.5/10/30 mg SUD+Pola (n=86). As of Jan. 9, 2022 (clinical cut-off date (CCOD)), 89 patients were safety-evaluable and 70 patients were efficacy-evaluable.

TABLE 22

Patient baseline demographics and disease characteristics, updated data. Abbreviations: DE, dose escalation; HGBCL, high-grade B-cell lymphoma; trFL, transformed follicular lymphoma; IPI, International Prognostic Index (for DLBCL; see: Ruppert et al., Blood, 135(23): 2041-2048, 2020)

| | | All Safety Evaluable Patients N = 89 |
|---|---|---|
| Median age, years (range) | | 68 (29-82) |
| Sex, n (%) | Male | 53 (59.6%) |
| ECOG | 0-1 | 84 (94.4%) |
| | 2 | 5 (5.6%) |
| NHL histology, n (%) | DLBCL | 50 (56.2%) |
| | HGBCL | 17 (19.1%) |
| | trFL | 22 (24.7%) |
| Prior lines of therapy | Median (range) | 2 (1-7) |
| | 1 | 25 (28.1%) |
| | 2+ | 64 (71.9%) |
| Prior CAR-T therapy | | 25 (28.1%) |
| Refractory Status, n (%) (Refractory to most recent therapy line) | | 62 (69.7%) |
| IPI Score, n (%) | 0-1 | 17 (19.1%) |
| | 2 | 21 (23.6%) |
| | 3 | 27 (30.3%) |
| | 4-5 | 24 (27.0%) |
| Ann Arbor stage at entry | I-II | 19 (21.3%) |
| | III-IV | 70 (78.7%) |
| Bulky disease (≥10 cm), n (%) | | 14 (15.7%) |

Adverse events are summarized in Table 23. CRS events are summarized in Table 24.

TABLE 23

Adverse events summary, updated data. Abbreviations: AE, adverse events; Gr, Grade; NCI-CTCAE, National Cancer Institute - Common Terminology Criteria for Adverse Events

| N (%) of patients with ≥1 AE | All Safety Evaluable Pts (DLBCL/trFL/HGBCL) N = 89 |
|---|---|
| AE | 83 (93.3%) |
| Glofitamab related | 66 (74.2%) |
| Polatuzumab vedotin related | 57 (64.0%) |
| Gr 3-4 AE | 49 (55.1%) |
| Glofitamab related | 29 (32.6%) |
| Pola related | 33 (37.1%) |
| Gr 5 (fatal) AE | 2 (2.2%) |
| Glofitamab related | 1 (1.1%) |
| Polatuzumab vedotin related | 0 (0.0%) |
| Serious AE | 44 (49.4%) |
| Glofitamab related | 31 (34.8%) |
| Polatuzumab vedotin related | 9 (10.1%) |
| AE leading to treatment discontinuation | 5 (5.6%) |
| Glofitamab related | 4 (4.5%) |
| Polatuzumab vedotin related | 5 (5.6%) |

Two patients experienced fatal AEs (COVID-19 pneumonia, not related to study treatment; and CRS Grade 5 related to glofitamab). Study treatment was discontinued in four patients due to AEs (all four events related to glofitamab and polatuzumab vedotin): Grade 4 thrombocytopenia; Grade 3 worsening of pre-existing renal impairment; Grade 5 CRS (Grade 3 CRS and TLS with clinical deterioration); Jejunal perforation Grade 4.

AEs of interest included 27 patients (30.3%) with neutropenia (including 17 patients (19.1%) with Grade 3-4 neutropenia), one patient (1.1%) with febrile neutropenia, 11 patients (12.4%) with thrombocytopenia all Grade (including two patients (2.2%) with Grade 3-4 thrombocytopenia), 30 patients (33.7%) with infection all Grade (including 14 patients (15.7%) with Grade 3-5 infections), 15 patients (16.9%) with peripheral neuropathy all Grade (including none with Grade 3 peripheral neuropathy), and two patients (2.2%) with tumor flare.

TABLE 24

CRS events, updated data. ASTCT criteria: Lee D W et al. Biol Blood Marrow Transplant 2019; 25: 625-38. Abbreviations: ASTCT, American Society for Transplantation and Cellular Therapy; CRS, cytokine release syndrome

| N (%) of patients with ≥1 CRS* | All patients N = 89 |
|---|---|
| Any Grade CRS | 36 (40.4%) |
| Grade 1 CRS | 24 (27.0%) |
| Grade 2 CRS | 11 (12.4%) |
| Grade 5 CRS | 1 (1.1%) |
| Serious AE of CRS (any grade) | 23 (25.8%) |
| Median time to CRS onset after glofitamab dose, hours (range) | |
| 2.5 mg | 16.13 (6.7-37.9) |
| 10 mg | 34.61 (8.9-129.5) |
| 30 mg | 36.15 (18.5-55.9) |
| Duration of CRS hours (range) | |
| 2.5 mg | 30.65 (0-115.9) |
| 10 mg | 30.64 (3-99.7) |
| 30 mg | 11.77 (0.0-65.2) |
| Tocilizumab use in patients with CRS | 10 (27.8%) |

The majority of CRS were Grade 1 and occurred after 2.5 mg Glofitamab dose (Table 25). Occurrence of Grade ≥2 CRS was marginal after day 8 of dosing cycle 1. No Grade 3 or 4 CRS events were reported.

TABLE 25

CRS Events by Dosing Cycle and Day

| | Cycle 1 | | Cycle 2 | |
|---|---|---|---|---|
| N (%) | After day 1 of dosing cycle 1 2.5 mg N = 84 | After day 1 of dosing cycle 1 10 mg N = 80 | After day 1 of dosing cycle 1 30 mg N = 76 | All patients N = 89 |
| Any Grade CRS | 29 (34.5%) | 14 (17.5%) | 9 (11.8%) | 36 (40.4%) |
| Grade 1 CRS | 20 (23.8%) | 12 (15.0%) | 8 (10.5%) | 24 (27.0%) |
| Grade 2 CRS | 8 (9.5%) | 2 (2.5%) | 1 (1.3%) | 11 (12.4%) |
| Grade 5 CRS | 1 (1.2%) | 0 | 0 | 1 (1.1%) |

Figure 8A:
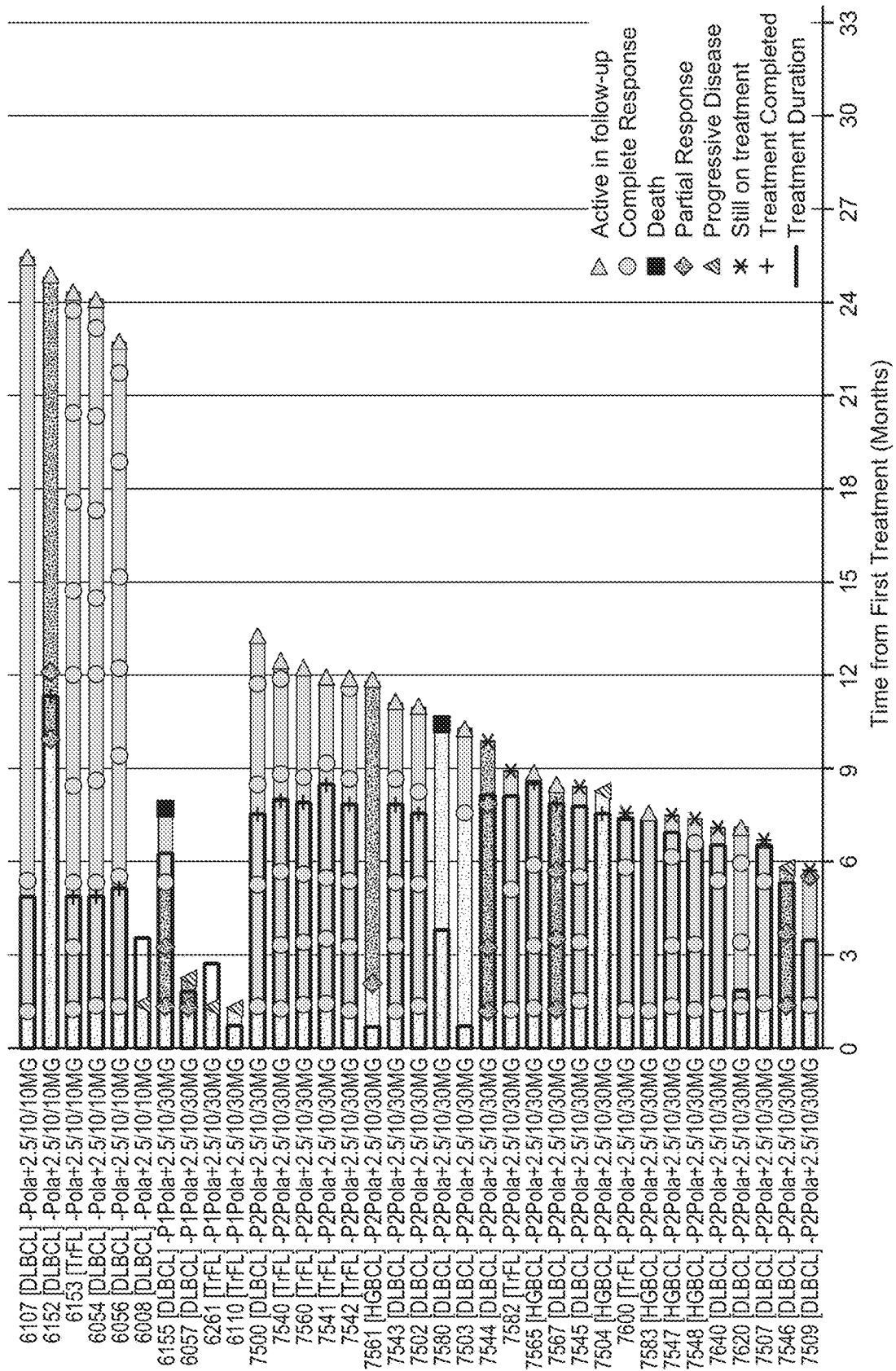
FIG. 8A and FIG. 8B are charts showing response duration of patients treated with glofitamab SUD (2.5/10/10 and 2.5/10/30 mg)+pola.
Figure 8B:
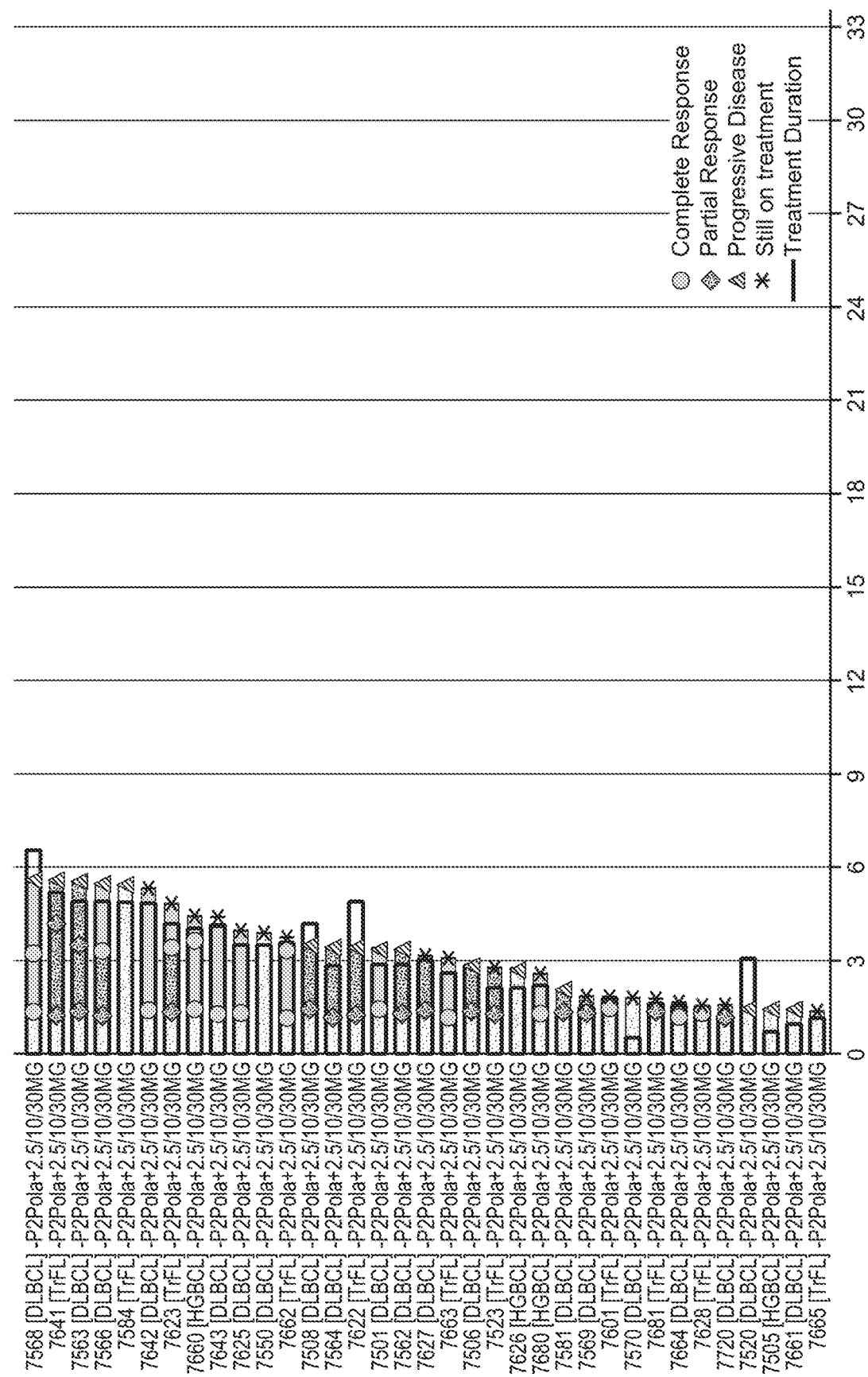

Efficacy:
At CCOD (9 Jan. 2022):
  70/89 patients were evaluable for interim response
  12/70 (17.1%) patients had experienced progressive disease (PD)
  The glofitamab+polatuzumab vedotin combination resulted in high response rates
  See Table 26 below
Duration of Response:
At CCOD (9 Jan. 2022):
  Most of the CRs to date were durable
  See FIG. 8A and FIG. 8B, which summarize duration of response in patients treated with glofitamab SUD+ polatuzumab vedotin as of CCOD

TABLE 26

Best overall response by histology, PET-CT based on Lugano 2014 criteria; or best overall response by prior therapy with or without CAR-T; updated data.

| | Grouped by Histology (Total Patient Number = 70) | | | Grouped by Prior Therapy (Total Patient Number = 70) | | |
|---|---|---|---|---|---|---|
| N (%) | R/R DLBCL (N = 40) | trFL (N = 17) | HGBCL (N = 13) | No Prior CAR-T (N = 55) | Prior CAR-T (N = 15) | All DLBCL (N = 70) |
| ORR | 31 (77.5%) | 13 (76.5%) | 7 (53.8%) | 39 (70.9%) | 12 (80%) | 51 (72.9%) |
| CR | 19 (47.5%) | 10 (58.8%) | 6 (46.2%) | 29 (52.7%) | 6 (40%) | 35 (50%) |
| PR | 12 (30%) | 3 (17.6%) | 1 (7.7%) | 10 (18.2%) | 6 (40%) | 16 (22.9%) |
| SD | 2 (5%) | 2 (11.8%) | 2 (15.4%) | 5 (9.1%) | 1 (6.7%) | 6 (8.6%) |
| PD | 7 (17.5%) | 2 (11.8%) | 3 (23.1%) | 10 (18.2%) | 2 (13.3%) | 12 (17.1%) |
| NA | — | — | 1 (7.7%) | 1 (1.8%) | — | 1 (1.4%) |

Conclusions:

Glofitamab in combination with polatuzumab vedotin showed tolerable safety and promising efficacy in patients with R/R DLBCL, R/R trFL, and R/R HGBCL. The safety profile of glofitamab in combination with pola was consistent with that of the individual drugs. Glofit-pola showed positive results for patients with R/R HGBCL, which typically have worse outcomes within the DLBCL population.

OTHER EMBODIMENTS

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

The invention claimed is:

1. A method of treating a subject having a CD20-positive cell proliferative disorder comprising administering to the subject polatuzumab vedotin and glofitamab in a dosing regimen comprising at least a first dosing cycle and a second dosing cycle, wherein:
   (a) the first dosing cycle comprises:
      (i) a single dose (C1D1) of polatuzumab vedotin administered on Day 2 of the first dosing cycle; and
      (ii) a first dose (C1D1) of glofitamab administered on Day 8 of the first dosing cycle and a second dose (C1D2) of glofitamab administered on Day 15 of the first dosing cycle, wherein the C1D1 of glofitamab is about 2.5 mg, and the C1D2 of glofitamab is about 10 mg; and
   (b) the second dosing cycle comprises:
      (i) a single dose (C2D1) of polatuzumab vedotin administered on Day 1 of the second dosing cycle; and
      (ii) a single dose (C2D1) of glofitamab administered on Day 1 of the second dosing cycle, wherein the C2D1 of glofitamab is about 30 mg, and the C1D1 and C2D1 of polatuzumab vedotin are each about 1.8 mg/kg.

2. A method of treating a subject having a CD20-positive cell proliferative disorder comprising administering to the subject polatuzumab vedotin and glofitamab in a dosing regimen comprising 12 dosing cycles, wherein:
  (a) the first dosing cycle comprises a first dose (C1D1) of glofitamab administered on Day 8 of the first dosing cycle, a second dose (C1D2) of glofitamab administered on Day 15 of the first dosing cycle, and a single dose (C1D1) of polatuzumab vedotin administered on Day 2 of the first dosing cycle, wherein the C1D1 of glofitamab is about 2.5 mg, and the C1D2 of glofitamab is about 10 mg;
  (b) the second to sixth dosing cycles each comprises a single dose (C2D1-C6D1) of glofitamab and a single dose (C2D1-C6D1) of polatuzumab vedotin; and
  (c) the seventh to 12th dosing cycles each comprises a single dose (C7D1-C12D1) of glofitamab and does not comprise administration of polatuzumab vedotin,
  wherein each single dose C2D1-C12D1 of glofitamab is administered on Day 1 of each dosing cycle, and each single dose C2D1-C6D1 of polatuzumab vedotin is administered on Day 1 of each dosing cycle, and wherein each single dose C2D1-C12D1 of glofitamab is about 30 mg and each single dose C1D1-C6D1 of polatuzumab vedotin is about 1.8 mg/kg.

3. The method of claim 2, wherein:
  (a) the dosing cycles are 21-day dosing cycles;
  (b) glofitamab is administered intravenously; and/or
  (c) polatuzumab vedotin is administered intravenously.

4. The method of claim 2, wherein the method further comprises administering to the subject obinutuzumab.

5. The method of claim 4, wherein obinutuzumab is administered:
  (a) prior to administration of glofitamab; and/or
  (b) as a single dose of about 1000 mg.

6. The method of claim 5, wherein obinutuzumab is administered about seven days prior to administration of glofitamab.

7. The method of claim 2, wherein the CD20-positive cell proliferative disorder is a B cell proliferative disorder.

8. The method of claim 7, wherein the B cell proliferative disorder is a non-Hodgkin's lymphoma (NHL) or a central nervous system lymphoma (CNSL).

9. The method of claim 8, wherein the NHL is:
  (a) relapsed and/or refractory; and/or
  (b) a diffuse-large B cell lymphoma (DLBCL), a follicular lymphoma (FL), a mantle cell lymphoma (MCL), a marginal zone lymphoma (MZL), a high-grade B cell lymphoma, a primary mediastinal (thymic) large B cell lymphoma (PMLBCL), a diffuse B cell lymphoma, or a small lymphocytic lymphoma.

10. The method of claim 7, wherein the B cell proliferative disorder is relapsed and/or refractory.

11. A method of treating a population of subjects having a relapsed and/or refractory NHL comprising administering to the subjects polatuzumab vedotin and glofitamab in a dosing regimen comprising 12 dosing cycles, wherein:
  (a) the first dosing cycle comprises:
    (i) a first dose (C1D1) of glofitamab administered on Day 8 of the first dosing cycle and a second dose (C1D2) of glofitamab administered on Day 15 of the first dosing cycle, wherein the C1D1 of glofitamab is about 2.5 mg, and the C1D2 of glofitamab is about 10 mg; and
    (ii) a single dose (C1D1) of polatuzumab vedotin administered on Day 2 of the first dosing cycle;
  (b) the second to sixth dosing cycles each comprises a single dose (C2D1-C6D1) of glofitamab and a single dose (C2D1-C6D1) of polatuzumab vedotin; and
  (c) the seventh to 12th dosing cycles each comprises a single dose (C7D1) of glofitamab and does not comprise administration of polatuzumab vedotin, and
  wherein each single dose C2D1-C12D1 of glofitamab is administered on Day 1 of each dosing cycle, and each single dose C2D1-C6D1 of polatuzumab vedotin is administered on Day 1 of each dosing cycle, and wherein each single dose C2D1-C12D1 of glofitamab is about 30 mg and each single dose C1D1-C6D1 of polatuzumab vedotin is about 1.8 mg/kg.

12. The method of claim 11, wherein:
  (a) the complete response rate is at least 20%; and/or
  (b) the overall response rate is at least 30%.

13. The method of claim 11, wherein:
  (a) the relapsed and/or refractory NHL is a relapsed and/or refractory MCL; and wherein:
    (i) the complete response rate is at least 60%; and/or
    (ii) the overall response rate is at least 60%; or
  (b) the NHL is a relapsed and/or refractory DLBCL; and wherein:
    (i) the complete response rate is at least 35%; and/or
    (ii) the overall response rate is at least 60%.

14. The method of claim 11, wherein:
  (a) the complete response rate is higher than a reference complete response rate in a reference population of subjects treated with a combination therapy comprising glofitamab and atezolizumab and not comprising polatuzumab vedotin; and/or
  (b) the objective response rate is higher than a reference objective response rate in a reference population of subjects treated with a combination therapy comprising glofitamab and atezolizumab and not comprising polatuzumab vedotin.

15. The method of claim 2, wherein the C2D1-C12D1 of glofitamab is administered after the administration of the C2D1-C12D1 of polatuzumab vedotin has completed.

16. The method of claim 2, wherein the subject:
  (a) is human;
  (b) has received at least two prior systemic therapies; and/or
  (c) is ineligible for autologous stem cell transplant (SCT).

17. The method of claim 1, wherein:
  (a) the first and second dosing cycles are 21-day dosing cycles;
  (b) glofitamab is administered intravenously; and/or
  (c) polatuzumab vedotin is administered intravenously.

18. The method of claim 1, wherein the subject:
  (a) is human;
  (b) has received at least two prior systemic therapies; and/or
  (c) is ineligible for autologous stem cell transplant (SCT).

19. The method of claim 1, wherein the method further comprises administering to the subject obinutuzumab.

20. The method of claim 19, wherein obinutuzumab is administered:
  (a) prior to administration of glofitamab; and/or
  (b) as a single dose of about 1000 mg.

21. The method of claim 20, wherein obinutuzumab is administered about seven days prior to administration of glofitamab.

22. The method of claim 1, wherein the CD20-positive cell proliferative disorder is a B cell proliferative disorder.

23. The method of claim 22, wherein the B cell proliferative disorder is a non-Hodgkin's lymphoma (NHL) or a central nervous system lymphoma (CNSL).

24. The method of claim 23, wherein the NHL is:
(a) relapsed and/or refractory; and/or
(b) a diffuse-large B cell lymphoma (DLBCL), a follicular lymphoma (FL), a mantle cell lymphoma (MCL), a marginal zone lymphoma (MZL), a high-grade B cell lymphoma, a primary mediastinal (thymic) large B cell lymphoma (PMLBCL), a diffuse B cell lymphoma, or a small lymphocytic lymphoma.

25. The method of claim 22, wherein the B cell proliferative disorder is relapsed and/or refractory.

26. The method of claim 1, wherein the method further comprises administering to the subject one or more additional therapeutic agents.

27. The method of claim 2, wherein the method further comprises administering to the subject one or more additional therapeutic agents.

28. The method of claim 11, wherein the subjects:
(a) are human;
(b) have received at least two prior systemic therapies; and/or
(c) are ineligible for autologous stem cell transplant (SCT).

* * * * *

SEQUENCE LISTING

```
<160> NUMBER OF SEQ ID NOS: 76

<210> SEQ ID NO 1
<211> LENGTH: 5
<212> TYPE: PRT
<213> ORGANISM: Artificial Sequence
<220> FEATURE:
<223> OTHER INFORMATION: Synthetic Construct

<400> SEQUENCE: 1

Tyr Ser Trp Ile Asn
1               5

<210> SEQ ID NO 2
<211> LENGTH: 17
<212> TYPE: PRT
<213> ORGANISM: Artificial Sequence
<220> FEATURE:
<223> OTHER INFORMATION: Synthetic Construct

<400> SEQUENCE: 2

Arg Ile Phe Pro Gly Asp Gly Asp Thr Asp Tyr Asn Gly Lys Phe Lys
1               5                   10                  15
```

Gly

<210> SEQ ID NO 3
<211> LENGTH: 10
<212> TYPE: PRT
<213> ORGANISM: Artificial Sequence
<220> FEATURE:
<223> OTHER INFORMATION: Synthetic Construct

<400> SEQUENCE: 3

Asn Val Phe Asp Gly Tyr Trp Leu Val Tyr
1               5                   10

<210> SEQ ID NO 4
<211> LENGTH: 16
<212> TYPE: PRT
<213> ORGANISM: Artificial Sequence
<220> FEATURE:
<223> OTHER INFORMATION: Synthetic Construct

<400> SEQUENCE: 4

Arg Ser Ser Lys Ser Leu Leu His Ser Asn Gly Ile Thr Tyr Leu Tyr
1               5                   10                  15

<210> SEQ ID NO 5
<211> LENGTH: 7
<212> TYPE: PRT
<213> ORGANISM: Artificial Sequence
<220> FEATURE:
<223> OTHER INFORMATION: Synthetic Construct

<400> SEQUENCE: 5

Gln Met Ser Asn Leu Val Ser
1               5

<210> SEQ ID NO 6
<211> LENGTH: 9
<212> TYPE: PRT
<213> ORGANISM: Artificial Sequence
<220> FEATURE:
<223> OTHER INFORMATION: Synthetic Construct

<400> SEQUENCE: 6

Ala Gln Asn Leu Glu Leu Pro Tyr Thr
1               5

<210> SEQ ID NO 7
<211> LENGTH: 119
<212> TYPE: PRT
<213> ORGANISM: Artificial Sequence
<220> FEATURE:
<223> OTHER INFORMATION: Synthetic Construct

<400> SEQUENCE: 7

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Tyr Ser
                20                  25                  30

Trp Ile Asn Trp Val Arg Gln Ala Pro Gly Gln Gly Leu Glu Trp Met
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

```
Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
            100                 105                 110

Thr Leu Val Thr Val Ser Ser
        115

<210> SEQ ID NO 8
<211> LENGTH: 112
<212> TYPE: PRT
<213> ORGANISM: Artificial Sequence
<220> FEATURE:
<223> OTHER INFORMATION: Synthetic Construct

<400> SEQUENCE: 8

Asp Ile Val Met Thr Gln Thr Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Leu Val Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Tyr Thr Phe Gly Gly Gly Thr Lys Val Glu Ile Lys
            100                 105                 110

<210> SEQ ID NO 9
<211> LENGTH: 5
<212> TYPE: PRT
<213> ORGANISM: Artificial Sequence
<220> FEATURE:
<223> OTHER INFORMATION: Synthetic Construct

<400> SEQUENCE: 9

Thr Tyr Ala Met Asn
1               5

<210> SEQ ID NO 10
<211> LENGTH: 19
<212> TYPE: PRT
<213> ORGANISM: Artificial Sequence
<220> FEATURE:
<223> OTHER INFORMATION: Synthetic Construct

<400> SEQUENCE: 10

Arg Ile Arg Ser Lys Tyr Asn Asn Tyr Ala Thr Tyr Tyr Ala Asp Ser
1               5                   10                  15

Val Lys Gly

<210> SEQ ID NO 11
<211> LENGTH: 14
<212> TYPE: PRT
<213> ORGANISM: Artificial Sequence
<220> FEATURE:
<223> OTHER INFORMATION: Synthetic Construct

<400> SEQUENCE: 11

His Gly Asn Phe Gly Asn Ser Tyr Val Ser Trp Phe Ala Tyr
```

-continued

```
1               5                   10

<210> SEQ ID NO 12
<211> LENGTH: 14
<212> TYPE: PRT
<213> ORGANISM: Artificial Sequence
<220> FEATURE:
<223> OTHER INFORMATION: Synthetic Construct

<400> SEQUENCE: 12

Gly Ser Ser Thr Gly Ala Val Thr Thr Ser Asn Tyr Ala Asn
1               5                   10

<210> SEQ ID NO 13
<211> LENGTH: 7
<212> TYPE: PRT
<213> ORGANISM: Artificial Sequence
<220> FEATURE:
<223> OTHER INFORMATION: Synthetic Construct

<400> SEQUENCE: 13

Gly Thr Asn Lys Arg Ala Pro
1               5

<210> SEQ ID NO 14
<211> LENGTH: 9
<212> TYPE: PRT
<213> ORGANISM: Artificial Sequence
<220> FEATURE:
<223> OTHER INFORMATION: Synthetic Construct

<400> SEQUENCE: 14

Ala Leu Trp Tyr Ser Asn Leu Trp Val
1               5

<210> SEQ ID NO 15
<211> LENGTH: 127
<212> TYPE: PRT
<213> ORGANISM: Artificial Sequence
<220> FEATURE:
<223> OTHER INFORMATION: Synthetic Construct

<400> SEQUENCE: 15

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ser Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser Ala Ser
        115                 120                 125

<210> SEQ ID NO 16
<211> LENGTH: 111
<212> TYPE: PRT
```

```
<213> ORGANISM: Artificial Sequence
<220> FEATURE:
<223> OTHER INFORMATION: Synthetic Construct

<400> SEQUENCE: 16

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Glu Lys Pro Gly Gln Ala Phe Arg Gly
        35                  40                  45

Leu Ile Gly Gly Thr Asn Lys Arg Ala Pro Gly Thr Pro Ala Arg Phe
    50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu Ser Ser
            100                 105                 110

<210> SEQ ID NO 17
<211> LENGTH: 672
<212> TYPE: PRT
<213> ORGANISM: Artificial Sequence
<220> FEATURE:
<223> OTHER INFORMATION: Synthetic Construct

<400> SEQUENCE: 17

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Tyr Ser
            20                  25                  30

Trp Ile Asn Trp Val Arg Gln Ala Pro Gly Gln Gly Leu Glu Trp Met
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Glu Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Glu Lys Val Glu Pro Lys Ser Cys Asp Gly
    210                 215                 220
```

-continued

```
Gly Gly Gly Ser Gly Gly Gly Ser Gln Ala Val Val Thr Gln Glu
225                 230                 235                 240

Pro Ser Leu Thr Val Ser Pro Gly Gly Thr Val Thr Leu Thr Cys Gly
                245                 250                 255

Ser Ser Thr Gly Ala Val Thr Thr Ser Asn Tyr Ala Asn Trp Val Gln
                260                 265                 270

Glu Lys Pro Gly Gln Ala Phe Arg Gly Leu Ile Gly Gly Thr Asn Lys
                275                 280                 285

Arg Ala Pro Gly Thr Pro Ala Arg Phe Ser Gly Ser Leu Leu Gly Gly
                290                 295                 300

Lys Ala Ala Leu Thr Leu Ser Gly Ala Gln Pro Glu Asp Glu Ala Glu
305                 310                 315                 320

Tyr Tyr Cys Ala Leu Trp Tyr Ser Asn Leu Trp Val Phe Gly Gly Gly
                325                 330                 335

Thr Lys Leu Thr Val Leu Ser Ser Ala Ser Thr Lys Gly Pro Ser Val
                340                 345                 350

Phe Pro Leu Ala Pro Ser Ser Lys Ser Thr Ser Gly Gly Thr Ala Ala
                355                 360                 365

Leu Gly Cys Leu Val Lys Asp Tyr Phe Pro Glu Pro Val Thr Val Ser
370                 375                 380

Trp Asn Ser Gly Ala Leu Thr Ser Gly Val His Thr Phe Pro Ala Val
385                 390                 395                 400

Leu Gln Ser Ser Gly Leu Tyr Ser Leu Ser Ser Val Val Thr Val Pro
                405                 410                 415

Ser Ser Ser Leu Gly Thr Gln Thr Tyr Ile Cys Asn Val Asn His Lys
                420                 425                 430

Pro Ser Asn Thr Lys Val Asp Lys Lys Val Glu Pro Lys Ser Cys Asp
                435                 440                 445

Lys Thr His Thr Cys Pro Pro Cys Pro Ala Pro Glu Ala Ala Gly Gly
450                 455                 460

Pro Ser Val Phe Leu Phe Pro Pro Lys Pro Lys Asp Thr Leu Met Ile
465                 470                 475                 480

Ser Arg Thr Pro Glu Val Thr Cys Val Val Val Asp Val Ser His Glu
                485                 490                 495

Asp Pro Glu Val Lys Phe Asn Trp Tyr Val Asp Gly Val Glu Val His
                500                 505                 510

Asn Ala Lys Thr Lys Pro Arg Glu Glu Gln Tyr Asn Ser Thr Tyr Arg
                515                 520                 525

Val Val Ser Val Leu Thr Val Leu His Gln Asp Trp Leu Asn Gly Lys
                530                 535                 540

Glu Tyr Lys Cys Lys Val Ser Asn Lys Ala Leu Gly Ala Pro Ile Glu
545                 550                 555                 560

Lys Thr Ile Ser Lys Ala Lys Gly Gln Pro Arg Glu Pro Gln Val Tyr
                565                 570                 575

Thr Leu Pro Pro Cys Arg Asp Glu Leu Thr Lys Asn Gln Val Ser Leu
                580                 585                 590

Trp Cys Leu Val Lys Gly Phe Tyr Pro Ser Asp Ile Ala Val Glu Trp
                595                 600                 605

Glu Ser Asn Gly Gln Pro Glu Asn Asn Tyr Lys Thr Thr Pro Pro Val
                610                 615                 620

Leu Asp Ser Asp Gly Ser Phe Phe Leu Tyr Ser Lys Leu Thr Val Asp
625                 630                 635                 640

Lys Ser Arg Trp Gln Gln Gly Asn Val Phe Ser Cys Ser Val Met His
```

```
                    645                 650                 655
Glu Ala Leu His Asn His Tyr Thr Gln Lys Ser Leu Ser Leu Ser Pro
            660                 665                 670

<210> SEQ ID NO 18
<211> LENGTH: 447
<212> TYPE: PRT
<213> ORGANISM: Artificial Sequence
<220> FEATURE:
<223> OTHER INFORMATION: Synthetic Construct

<400> SEQUENCE: 18

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Tyr Ser
            20                  25                  30

Trp Ile Asn Trp Val Arg Gln Ala Pro Gly Gln Gly Leu Glu Trp Met
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Glu Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Glu Lys Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Gly Ala Pro Ile Glu Lys
                325                 330                 335

Thr Ile Ser Lys Ala Lys Gly Gln Pro Arg Glu Pro Gln Val Cys Thr
```

```
                   340                 345                 350
Leu Pro Pro Ser Arg Asp Glu Leu Thr Lys Asn Gln Val Ser Leu Ser
            355                 360                 365

Cys Ala Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Val Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro
            435                 440                 445

<210> SEQ ID NO 19
<211> LENGTH: 232
<212> TYPE: PRT
<213> ORGANISM: Artificial Sequence
<220> FEATURE:
<223> OTHER INFORMATION: Synthetic Construct

<400> SEQUENCE: 19

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ser Arg Ile Arg Ser Lys Tyr Asn Asn Tyr Ala Thr Tyr Tyr Ala Asp
50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser Ala Ser Val
        115                 120                 125

Ala Ala Pro Ser Val Phe Ile Phe Pro Pro Ser Asp Glu Gln Leu Lys
130                 135                 140

Ser Gly Thr Ala Ser Val Val Cys Leu Leu Asn Asn Phe Tyr Pro Arg
145                 150                 155                 160

Glu Ala Lys Val Gln Trp Lys Val Asp Asn Ala Leu Gln Ser Gly Asn
                165                 170                 175

Ser Gln Glu Ser Val Thr Glu Gln Asp Ser Lys Asp Ser Thr Tyr Ser
            180                 185                 190

Leu Ser Ser Thr Leu Thr Leu Ser Lys Ala Asp Tyr Glu Lys His Lys
        195                 200                 205

Val Tyr Ala Cys Glu Val Thr His Gln Gly Leu Ser Ser Pro Val Thr
    210                 215                 220

Lys Ser Phe Asn Arg Gly Glu Cys
225                 230

<210> SEQ ID NO 20
<211> LENGTH: 219
<212> TYPE: PRT
```

```
<213> ORGANISM: Artificial Sequence
<220> FEATURE:
<223> OTHER INFORMATION: Synthetic Construct

<400> SEQUENCE: 20

Asp Ile Val Met Thr Gln Thr Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Leu Val Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Tyr Thr Phe Gly Gly Gly Thr Lys Val Glu Ile Lys
            100                 105                 110

Arg Thr Val Ala Ala Pro Ser Val Phe Ile Phe Pro Pro Ser Asp Arg
        115                 120                 125

Lys Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 21
<211> LENGTH: 10
<212> TYPE: PRT
<213> ORGANISM: Artificial Sequence
<220> FEATURE:
<223> OTHER INFORMATION: Synthetic Construct

<400> SEQUENCE: 21

Gly Tyr Thr Phe Ser Ser Tyr Trp Ile Glu
1               5                   10

<210> SEQ ID NO 22
<211> LENGTH: 18
<212> TYPE: PRT
<213> ORGANISM: Artificial Sequence
<220> FEATURE:
<223> OTHER INFORMATION: Synthetic Construct

<400> SEQUENCE: 22

Gly Glu Ile Leu Pro Gly Gly Gly Asp Thr Asn Tyr Asn Glu Ile Phe
1               5                   10                  15

Lys Gly

<210> SEQ ID NO 23
<211> LENGTH: 10
```

```
<212> TYPE: PRT
<213> ORGANISM: Artificial Sequence
<220> FEATURE:
<223> OTHER INFORMATION: Synthetic Construct

<400> SEQUENCE: 23

Thr Arg Arg Val Pro Ile Arg Leu Asp Tyr
1               5                   10

<210> SEQ ID NO 24
<211> LENGTH: 15
<212> TYPE: PRT
<213> ORGANISM: Artificial Sequence
<220> FEATURE:
<223> OTHER INFORMATION: Synthetic Construct

<400> SEQUENCE: 24

Lys Ala Ser Gln Ser Val Asp Tyr Glu Gly Asp Ser Phe Leu Asn
1               5                   10                  15

<210> SEQ ID NO 25
<211> LENGTH: 7
<212> TYPE: PRT
<213> ORGANISM: Artificial Sequence
<220> FEATURE:
<223> OTHER INFORMATION: Synthetic Construct

<400> SEQUENCE: 25

Ala Ala Ser Asn Leu Glu Ser
1               5

<210> SEQ ID NO 26
<211> LENGTH: 9
<212> TYPE: PRT
<213> ORGANISM: Artificial Sequence
<220> FEATURE:
<223> OTHER INFORMATION: Synthetic Construct

<400> SEQUENCE: 26

Gln Gln Ser Asn Glu Asp Pro Leu Thr
1               5

<210> SEQ ID NO 27
<211> LENGTH: 117
<212> TYPE: PRT
<213> ORGANISM: Artificial Sequence
<220> FEATURE:
<223> OTHER INFORMATION: Synthetic Construct

<400> SEQUENCE: 27

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Ser Ser Tyr
            20                  25                  30

Trp Ile Glu Trp Val Arg Gln Ala Pro Gly Lys Gly Leu Glu Trp Ile
        35                  40                  45

Gly Glu Ile Leu Pro Gly Gly Gly Asp Thr Asn Tyr Asn Glu Ile Phe
    50                  55                  60

Lys Gly Arg Ala Thr Phe Ser Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Thr Arg Arg Val Pro Ile Arg Leu Asp Tyr Trp Gly Gln Gly Thr Leu
            100                 105                 110
```

Val Thr Val Ser Ser
        115

<210> SEQ ID NO 28
<211> LENGTH: 112
<212> TYPE: PRT
<213> ORGANISM: Artificial Sequence
<220> FEATURE:
<223> OTHER INFORMATION: Synthetic Construct

<400> SEQUENCE: 28

Asp Ile Gln Leu Thr Gln Ser Pro Ser Leu Ser Ala Ser Val Gly
1               5                   10                  15

Asp Arg Val Thr Ile Thr Cys Lys Ala Ser Gln Ser Val Asp Tyr Glu
            20                  25                  30

Gly Asp Ser Phe Leu Asn Trp Tyr Gln Gln Lys Pro Gly Lys Ala Pro
        35                  40                  45

Lys Leu Leu Ile Tyr Ala Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser Asn
                85                  90                  95

Glu Asp Pro Leu Thr Phe Gly Gln Gly Thr Lys Val Glu Ile Lys Arg
            100                 105                 110

<210> SEQ ID NO 29
<211> LENGTH: 25
<212> TYPE: PRT
<213> ORGANISM: Artificial Sequence
<220> FEATURE:
<223> OTHER INFORMATION: Synthetic Construct

<400> SEQUENCE: 29

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 30
<211> LENGTH: 13
<212> TYPE: PRT
<213> ORGANISM: Artificial Sequence
<220> FEATURE:
<223> OTHER INFORMATION: Synthetic Construct

<400> SEQUENCE: 30

Trp Val Arg Gln Ala Pro Gly Lys Gly Leu Glu Trp Ile
1               5                   10

<210> SEQ ID NO 31
<211> LENGTH: 30
<212> TYPE: PRT
<213> ORGANISM: Artificial Sequence
<220> FEATURE:
<223> OTHER INFORMATION: Synthetic Construct

<400> SEQUENCE: 31

Arg Ala Thr Phe Ser Ala Asp Thr Ser Lys Asn Thr Ala Tyr Leu Gln
1               5                   10                  15

Met Asn Ser Leu Arg Ala Glu Asp Thr Ala Val Tyr Tyr Cys
            20                  25                  30

<210> SEQ ID NO 32
<211> LENGTH: 11
<212> TYPE: PRT
<213> ORGANISM: Artificial Sequence
<220> FEATURE:
<223> OTHER INFORMATION: Synthetic Construct

<400> SEQUENCE: 32

Trp Gly Gln Gly Thr Leu Val Thr Val Ser Ser
1               5                   10

<210> SEQ ID NO 33
<211> LENGTH: 23
<212> TYPE: PRT
<213> ORGANISM: Artificial Sequence
<220> FEATURE:
<223> OTHER INFORMATION: Synthetic Construct

<400> SEQUENCE: 33

Asp Ile Gln Leu Thr Gln Ser Pro Ser Ser Leu Ser Ala Ser Val Gly
1               5                   10                  15

Asp Arg Val Thr Ile Thr Cys
            20

<210> SEQ ID NO 34
<211> LENGTH: 15
<212> TYPE: PRT
<213> ORGANISM: Artificial Sequence
<220> FEATURE:
<223> OTHER INFORMATION: Synthetic Construct

<400> SEQUENCE: 34

Trp Tyr Gln Gln Lys Pro Gly Lys Ala Pro Lys Leu Leu Ile Tyr
1               5                   10                  15

<210> SEQ ID NO 35
<211> LENGTH: 32
<212> TYPE: PRT
<213> ORGANISM: Artificial Sequence
<220> FEATURE:
<223> OTHER INFORMATION: Synthetic Construct

<400> SEQUENCE: 35

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 36
<211> LENGTH: 11
<212> TYPE: PRT
<213> ORGANISM: Artificial Sequence
<220> FEATURE:
<223> OTHER INFORMATION: Synthetic Construct

<400> SEQUENCE: 36

Phe Gly Gln Gly Thr Lys Val Glu Ile Lys Arg
1               5                   10

<210> SEQ ID NO 37
<211> LENGTH: 447
<212> TYPE: PRT
<213> ORGANISM: Artificial Sequence
<220> FEATURE:
<223> OTHER INFORMATION: Synthetic Construct

<400> SEQUENCE: 37

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Tyr Thr Phe Ser Ser Tyr
            20                  25                  30

Trp Ile Glu Trp Val Arg Gln Ala Pro Gly Lys Gly Leu Glu Trp Ile
        35                  40                  45

Gly Glu Ile Leu Pro Gly Gly Asp Thr Asn Tyr Asn Glu Ile Phe
 50                  55                  60

Lys Gly Arg Ala Thr Phe Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                85                  90                  95

Thr Arg Arg Val Pro Ile Arg Leu Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
```

```
                    405                 410                 415
Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 38
<211> LENGTH: 218
<212> TYPE: PRT
<213> ORGANISM: Artificial Sequence
<220> FEATURE:
<223> OTHER INFORMATION: Synthetic Construct

<400> SEQUENCE: 38

Asp Ile Gln Leu Thr Gln Ser Pro Ser Ser Leu Ser Ala Ser Val Gly
1               5                   10                  15

Asp Arg Val Thr Ile Thr Cys Lys Ala Ser Gln Ser Val Asp Tyr Glu
            20                  25                  30

Gly Asp Ser Phe Leu Asn Trp Tyr Gln Gln Lys Pro Gly Lys Ala Pro
        35                  40                  45

Lys Leu Leu Ile Tyr Ala Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser Asn
                85                  90                  95

Glu Asp Pro Leu Thr Phe Gly Gln Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 39
<211> LENGTH: 5
<212> TYPE: PRT
<213> ORGANISM: Artificial Sequence
<220> FEATURE:
<223> OTHER INFORMATION: Synthetic Construct

<400> SEQUENCE: 39

Gly Gly Gly Gly Ser
1               5

<210> SEQ ID NO 40
<211> LENGTH: 5
<212> TYPE: PRT
<213> ORGANISM: Artificial Sequence
<220> FEATURE:
```

```
<223> OTHER INFORMATION: Synthetic Construct

<400> SEQUENCE: 40

Ser Gly Gly Gly Gly
1               5

<210> SEQ ID NO 41
<211> LENGTH: 9
<212> TYPE: PRT
<213> ORGANISM: Artificial Sequence
<220> FEATURE:
<223> OTHER INFORMATION: Synthetic Construct

<400> SEQUENCE: 41

Gly Gly Gly Gly Ser Gly Gly Gly Gly
1               5

<210> SEQ ID NO 42
<211> LENGTH: 10
<212> TYPE: PRT
<213> ORGANISM: Artificial Sequence
<220> FEATURE:
<223> OTHER INFORMATION: Synthetic Construct

<400> SEQUENCE: 42

Gly Gly Gly Gly Ser Gly Gly Gly Gly Ser
1               5                   10

<210> SEQ ID NO 43
<211> LENGTH: 11
<212> TYPE: PRT
<213> ORGANISM: Artificial Sequence
<220> FEATURE:
<223> OTHER INFORMATION: Synthetic Construct

<400> SEQUENCE: 43

Asp Gly Gly Gly Gly Ser Gly Gly Gly Gly Ser
1               5                   10

<210> SEQ ID NO 44
<211> LENGTH: 20
<212> TYPE: PRT
<213> ORGANISM: Artificial Sequence
<220> FEATURE:
<223> OTHER INFORMATION: Synthetic Construct

<400> SEQUENCE: 44

Gly Gly Gly Gly Ser Gly Gly Gly Gly Ser Gly Gly Gly Gly Ser Gly
1               5                   10                  15

Gly Gly Gly Ser
            20

<210> SEQ ID NO 45
<211> LENGTH: 12
<212> TYPE: PRT
<213> ORGANISM: Artificial Sequence
<220> FEATURE:
<223> OTHER INFORMATION: Synthetic Construct

<400> SEQUENCE: 45

Gly Gly Gly Ser Gly Gly Gly Ser Gly Gly Gly Ser
1               5                   10

<210> SEQ ID NO 46
<211> LENGTH: 16
<212> TYPE: PRT
```

```
<213> ORGANISM: Artificial Sequence
<220> FEATURE:
<223> OTHER INFORMATION: Synthetic Construct

<400> SEQUENCE: 46

Gly Gly Gly Ser Gly Gly Gly Ser Gly Gly Gly Ser Gly Gly Gly Ser
1               5                   10                  15

<210> SEQ ID NO 47
<211> LENGTH: 20
<212> TYPE: PRT
<213> ORGANISM: Artificial Sequence
<220> FEATURE:
<223> OTHER INFORMATION: Synthetic Construct

<400> SEQUENCE: 47

Gly Gly Gly Ser Gly Gly Gly Ser Gly Gly Gly Ser Gly Gly Gly Ser
1               5                   10                  15

Gly Gly Gly Ser
            20

<210> SEQ ID NO 48
<211> LENGTH: 24
<212> TYPE: PRT
<213> ORGANISM: Artificial Sequence
<220> FEATURE:
<223> OTHER INFORMATION: Synthetic Construct

<400> SEQUENCE: 48

Gly Gly Gly Ser Gly Gly Gly Ser Gly Gly Gly Ser Gly Gly Gly Ser
1               5                   10                  15

Gly Gly Gly Ser Gly Gly Gly Ser
            20

<210> SEQ ID NO 49
<211> LENGTH: 10
<212> TYPE: PRT
<213> ORGANISM: Artificial Sequence
<220> FEATURE:
<223> OTHER INFORMATION: Synthetic Construct

<400> SEQUENCE: 49

Gly Gly Gly Gly Ser Gly Gly Gly Gly Ser
1               5                   10

<210> SEQ ID NO 50
<211> LENGTH: 15
<212> TYPE: PRT
<213> ORGANISM: Artificial Sequence
<220> FEATURE:
<223> OTHER INFORMATION: Synthetic Construct

<400> SEQUENCE: 50

Gly Gly Gly Gly Ser Gly Gly Gly Gly Ser Gly Gly Gly Gly Ser
1               5                   10                  15

<210> SEQ ID NO 51
<211> LENGTH: 20
<212> TYPE: PRT
<213> ORGANISM: Artificial Sequence
<220> FEATURE:
<223> OTHER INFORMATION: Synthetic Construct

<400> SEQUENCE: 51

Gly Gly Gly Gly Ser Gly Gly Gly Gly Ser Gly Gly Gly Gly Ser Gly
1               5                   10                  15
```

```
Gly Gly Gly Ser
            20

<210> SEQ ID NO 52
<211> LENGTH: 25
<212> TYPE: PRT
<213> ORGANISM: Artificial Sequence
<220> FEATURE:
<223> OTHER INFORMATION: Synthetic Construct

<400> SEQUENCE: 52

Gly Gly Gly Gly Ser Gly Gly Gly Ser Gly Gly Gly Gly Ser Gly
1               5                   10                  15

Gly Gly Gly Ser Gly Gly Gly Gly Ser
            20                  25

<210> SEQ ID NO 53
<211> LENGTH: 13
<212> TYPE: PRT
<213> ORGANISM: Artificial Sequence
<220> FEATURE:
<223> OTHER INFORMATION: Synthetic Construct

<400> SEQUENCE: 53

Gly Gly Gly Ser Gly Gly Gly Ser Gly Gly Gly Ser Gly
1               5                   10

<210> SEQ ID NO 54
<211> LENGTH: 17
<212> TYPE: PRT
<213> ORGANISM: Artificial Sequence
<220> FEATURE:
<223> OTHER INFORMATION: Synthetic Construct

<400> SEQUENCE: 54

Gly Gly Gly Ser Gly Gly Gly Ser Gly Gly Gly Ser Gly Gly Gly Ser
1               5                   10                  15

Gly

<210> SEQ ID NO 55
<211> LENGTH: 21
<212> TYPE: PRT
<213> ORGANISM: Artificial Sequence
<220> FEATURE:
<223> OTHER INFORMATION: Synthetic Construct

<400> SEQUENCE: 55

Gly Gly Gly Ser Gly Gly Gly Ser Gly Gly Gly Ser Gly Gly Gly Ser
1               5                   10                  15

Gly Gly Gly Ser Gly
            20

<210> SEQ ID NO 56
<211> LENGTH: 25
<212> TYPE: PRT
<213> ORGANISM: Artificial Sequence
<220> FEATURE:
<223> OTHER INFORMATION: Synthetic Construct

<400> SEQUENCE: 56

Gly Gly Gly Ser Gly Gly Gly Ser Gly Gly Gly Ser Gly Gly Gly Ser
1               5                   10                  15

Gly Gly Gly Ser Gly Gly Gly Ser Gly
            20                  25
```

<210> SEQ ID NO 57
<211> LENGTH: 11
<212> TYPE: PRT
<213> ORGANISM: Artificial Sequence
<220> FEATURE:
<223> OTHER INFORMATION: Synthetic Construct

<400> SEQUENCE: 57

Gly Gly Gly Gly Ser Gly Gly Gly Gly Ser Gly
1               5                   10

<210> SEQ ID NO 58
<211> LENGTH: 16
<212> TYPE: PRT
<213> ORGANISM: Artificial Sequence
<220> FEATURE:
<223> OTHER INFORMATION: Synthetic Construct

<400> SEQUENCE: 58

Gly Gly Gly Gly Ser Gly Gly Gly Gly Ser Gly Gly Gly Gly Ser Gly
1               5                   10                  15

<210> SEQ ID NO 59
<211> LENGTH: 21
<212> TYPE: PRT
<213> ORGANISM: Artificial Sequence
<220> FEATURE:
<223> OTHER INFORMATION: Synthetic Construct

<400> SEQUENCE: 59

Gly Gly Gly Gly Ser Gly Gly Gly Gly Ser Gly Gly Gly Gly Ser Gly
1               5                   10                  15

Gly Gly Gly Ser Gly
            20

<210> SEQ ID NO 60
<211> LENGTH: 26
<212> TYPE: PRT
<213> ORGANISM: Artificial Sequence
<220> FEATURE:
<223> OTHER INFORMATION: Synthetic Construct

<400> SEQUENCE: 60

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly
            20                  25

<210> SEQ ID NO 61
<211> LENGTH: 14
<212> TYPE: PRT
<213> ORGANISM: Artificial Sequence
<220> FEATURE:
<223> OTHER INFORMATION: Synthetic Construct

<400> SEQUENCE: 61

Gly Gly Gly Ser Gly Gly Gly Ser Gly Gly Gly Ser Gly Gly
1               5                   10

<210> SEQ ID NO 62
<211> LENGTH: 18
<212> TYPE: PRT
<213> ORGANISM: Artificial Sequence
<220> FEATURE:
<223> OTHER INFORMATION: Synthetic Construct -continued

<400> SEQUENCE: 62

Gly Gly Gly Ser Gly Gly Gly Ser Gly Gly Gly Ser Gly Gly Gly Ser
1               5                   10                  15

Gly Gly

<210> SEQ ID NO 63
<211> LENGTH: 22
<212> TYPE: PRT
<213> ORGANISM: Artificial Sequence
<220> FEATURE:
<223> OTHER INFORMATION: Synthetic Construct

<400> SEQUENCE: 63

Gly Gly Gly Ser Gly Gly Gly Ser Gly Gly Gly Ser Gly Gly Gly Ser
1               5                   10                  15

Gly Gly Gly Ser Gly Gly
            20

<210> SEQ ID NO 64
<211> LENGTH: 26
<212> TYPE: PRT
<213> ORGANISM: Artificial Sequence
<220> FEATURE:
<223> OTHER INFORMATION: Synthetic Construct

<400> SEQUENCE: 64

Gly Gly Gly Ser Gly Gly Gly Ser Gly Gly Gly Ser Gly Gly Gly Ser
1               5                   10                  15

Gly Gly Gly Ser Gly Gly Gly Ser Gly Gly
            20                  25

<210> SEQ ID NO 65
<211> LENGTH: 12
<212> TYPE: PRT
<213> ORGANISM: Artificial Sequence
<220> FEATURE:
<223> OTHER INFORMATION: Synthetic Construct

<400> SEQUENCE: 65

Gly Gly Gly Gly Ser Gly Gly Gly Gly Ser Gly Gly
1               5                   10

<210> SEQ ID NO 66
<211> LENGTH: 17
<212> TYPE: PRT
<213> ORGANISM: Artificial Sequence
<220> FEATURE:
<223> OTHER INFORMATION: Synthetic Construct

<400> SEQUENCE: 66

Gly Gly Gly Gly Ser Gly Gly Gly Gly Ser Gly Gly Gly Gly Ser Gly
1               5                   10                  15

Gly

<210> SEQ ID NO 67
<211> LENGTH: 22
<212> TYPE: PRT
<213> ORGANISM: Artificial Sequence
<220> FEATURE:
<223> OTHER INFORMATION: Synthetic Construct

<400> SEQUENCE: 67

Gly Gly Gly Gly Ser Gly Gly Gly Gly Ser Gly Gly Gly Gly Ser Gly

```
                1               5                  10                 15
Gly Gly Gly Ser Gly Gly
            20

<210> SEQ ID NO 68
<211> LENGTH: 27
<212> TYPE: PRT
<213> ORGANISM: Artificial Sequence
<220> FEATURE:
<223> OTHER INFORMATION: Synthetic Construct

<400> SEQUENCE: 68

Gly Gly Gly Gly Ser Gly Gly Gly Gly Ser Gly Gly Gly Gly Ser Gly
1               5                  10                 15

Gly Gly Gly Ser Gly Gly Gly Gly Ser Gly Gly
            20                  25

<210> SEQ ID NO 69
<211> LENGTH: 15
<212> TYPE: PRT
<213> ORGANISM: Artificial Sequence
<220> FEATURE:
<223> OTHER INFORMATION: Synthetic Construct

<400> SEQUENCE: 69

Gly Gly Gly Ser Gly Gly Gly Ser Gly Gly Gly Ser Gly Gly Gly
1               5                  10                 15

<210> SEQ ID NO 70
<211> LENGTH: 19
<212> TYPE: PRT
<213> ORGANISM: Artificial Sequence
<220> FEATURE:
<223> OTHER INFORMATION: Synthetic Construct

<400> SEQUENCE: 70

Gly Gly Gly Ser Gly Gly Gly Ser Gly Gly Gly Ser Gly Gly Gly Ser
1               5                  10                 15

Gly Gly Gly

<210> SEQ ID NO 71
<211> LENGTH: 23
<212> TYPE: PRT
<213> ORGANISM: Artificial Sequence
<220> FEATURE:
<223> OTHER INFORMATION: Synthetic Construct

<400> SEQUENCE: 71

Gly Gly Gly Ser Gly Gly Gly Ser Gly Gly Gly Ser Gly Gly Gly Ser
1               5                  10                 15

Gly Gly Gly Ser Gly Gly Gly
            20

<210> SEQ ID NO 72
<211> LENGTH: 27
<212> TYPE: PRT
<213> ORGANISM: Artificial Sequence
<220> FEATURE:
<223> OTHER INFORMATION: Synthetic Construct

<400> SEQUENCE: 72

Gly Gly Gly Ser Gly Gly Gly Ser Gly Gly Gly Ser Gly Gly Gly Ser
1               5                  10                 15

Gly Gly Gly Ser Gly Gly Gly Ser Gly Gly Gly
```

<210> SEQ ID NO 73
<211> LENGTH: 13
<212> TYPE: PRT
<213> ORGANISM: Artificial Sequence
<220> FEATURE:
<223> OTHER INFORMATION: Synthetic Construct

<400> SEQUENCE: 73

```
Gly Gly Gly Gly Ser Gly Gly Gly Gly Ser Gly Gly Gly
1               5                   10
```

<210> SEQ ID NO 74
<211> LENGTH: 18
<212> TYPE: PRT
<213> ORGANISM: Artificial Sequence
<220> FEATURE:
<223> OTHER INFORMATION: Synthetic Construct

<400> SEQUENCE: 74

```
Gly Gly Gly Gly Ser Gly Gly Gly Gly Ser Gly Gly Gly Gly Ser Gly
1               5                   10                  15

Gly Gly
```

<210> SEQ ID NO 75
<211> LENGTH: 23
<212> TYPE: PRT
<213> ORGANISM: Artificial Sequence
<220> FEATURE:
<223> OTHER INFORMATION: Synthetic Construct

<400> SEQUENCE: 75

```
Gly Gly Gly Gly Ser Gly Gly Gly Gly Ser Gly Gly Gly Gly Ser Gly
1               5                   10                  15

Gly Gly Gly Ser Gly Gly Gly
                20
```

<210> SEQ ID NO 76
<211> LENGTH: 28
<212> TYPE: PRT
<213> ORGANISM: Artificial Sequence
<220> FEATURE:
<223> OTHER INFORMATION: Synthetic Construct

<400> SEQUENCE: 76

```
Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly
                20                  25
```